US010753941B2

(12) United States Patent
Tang et al.

(10) Patent No.: US 10,753,941 B2
(45) Date of Patent: Aug. 25, 2020

(54) BIOCOMPATIBLE NANOPARTICLES WITH AGGREGATION INDUCED EMISSION CHARACTERISTICS AS FLUORESCENT BIOPROBES AND METHODS OF USING THE SAME FOR IN VITRO AND IN VIVO IMAGING

(75) Inventors: Benzhong Tang, Hong Kong (CN); Wei Qin, Hong Kong (CN); Jianzhao Liu, Hong Kong (CN); Sijie Chen, Hong Kong (CN); Tsz Kin Kwok, Hong Kong (CN); Bin Liu, Singapore (SG); Kai Li, Singapore (SG); Dan Ding, Singapore (SG); Haibin Shi, Singapore (SG); Jun Long Geng, Singapore (SG); Jingzhi Sun, Zhejiang (CN); Anjun Qin, Zhejiang (CN); Qiuli Zhao, Zhejiang (CN)

(73) Assignees: The Hong Kong University of Science and Technology, Hong Kong (CN); National University of Singapore, Singapore (SG)

( * ) Notice: Subject to any disclaimer, the term of this patent is extended or adjusted under 35 U.S.C. 154(b) by 1126 days.

(21) Appl. No.: 14/342,074

(22) PCT Filed: Sep. 3, 2012

(86) PCT No.: PCT/CN2012/001227
§ 371 (c)(1),
(2), (4) Date: Jul. 24, 2014

(87) PCT Pub. No.: WO2013/029340
PCT Pub. Date: Mar. 7, 2013

(65) Prior Publication Data
US 2014/0328764 A1 Nov. 6, 2014

Related U.S. Application Data

(60) Provisional application No. 61/573,097, filed on Sep. 1, 2011, provisional application No. 61/685,227, filed on Mar. 14, 2012.

(51) Int. Cl.
*A61B 5/00* (2006.01)
*A61B 8/00* (2006.01)
*A61B 10/00* (2006.01)
*G01N 33/58* (2006.01)
*A61K 49/00* (2006.01)
*C09K 11/06* (2006.01)
*C12Q 1/37* (2006.01)
*G01N 33/574* (2006.01)

(52) U.S. Cl.
CPC ....... *G01N 33/582* (2013.01); *A61K 49/0021* (2013.01); *A61K 49/0054* (2013.01); *A61K 49/0093* (2013.01); *C09K 11/06* (2013.01); *C12Q 1/37* (2013.01); *G01N 33/574* (2013.01); *G01N 2333/96466* (2013.01)

(58) Field of Classification Search
CPC .. G01N 33/582; C09K 11/06; A61K 49/0021; A61K 49/0093
USPC .......................................................... 424/9.6
See application file for complete search history.

(56) References Cited

U.S. PATENT DOCUMENTS

| 2008/0220407 A1 | 9/2008 | Tang et al. |
| 2012/0237964 A1 | 9/2012 | Tang et al. |
| 2014/0328764 A1 | 11/2014 | Tang et al. |
| 2015/0175747 A1 | 6/2015 | Liu et al. |
| 2016/0356723 A1 | 12/2016 | Liu et al. |
| 2017/0168041 A1 | 6/2017 | Liu et al. |

FOREIGN PATENT DOCUMENTS

| CN | 101712674 | | 5/2010 |
| CN | 101987822 | A | 3/2011 |
| CN | 102153748 | | 8/2011 |
| JP | H0411627 | A | 1/1992 |
| WO | WO 93/06189 | A1 | 1/1993 |
| WO | WO 2011/106990 | A1 | 9/2011 |
| WO | WO 2013/029340 | A1 | 3/2013 |
| WO | WO 2013/176625 | A1 | 11/2013 |
| WO | WO 2014/017983 | A1 | 1/2014 |
| WO | WO 2015/112092 | A2 | 7/2015 |
| WO | WO 2015/163817 | A1 | 10/2015 |

OTHER PUBLICATIONS

Zhao et al. Curr. Org. Chem. 2010, 14, 2109-2132.*
Panthi et al. J. Phys. Chem. A 2010, 114, 4542-4549.*
Li et al. Chem. Commun. 2011, 47, 7323-7325.*
Liu et al. Nat. Nanotech. 2007, 47-52.*
Velusamy et al. Adv. Funct. Mat. 2009, 19, 2388-2397.*
Bringley et al. J. Coll. Interface Sci. 320 (2008) 132-139.*
Adarsh, N. et al., "Tuning Photosensitized Singlet Oxygen Generation Erfficiency of Novel Aza-BODIPY Dyes", Org. Lett., 12(24): 5720-5723 (2010).
Adonai, N. et al., "Ex vivo cell labeling with 64Cu-pyruvaldehyde-bis(N4-methylthiosemicarbazone) for imaging cell trafficking in mice with positron-emission tomography," Proceedings of the National Academy of Sciences, 99, 3030-3035 (2002).
Agostinis, P. et al., "Photodynamic Therapy of Cancer: An Update", Cancer J. Clin., 61(4): 250-281 (2011).
Ali-Osman, F. et al., "Topoisomerase II Inhibition and Altered Kinetics of Formation and Repair of Nitrosourea and Cisplatin-induced DNA Interstrand Cross-Links and Cytotoxicity in Human Glioblastoma Cells", Cancer Res., 53, 5663-5668 (1993).

(Continued)

Primary Examiner — Michael G. Hartley
Assistant Examiner — Sean R Donohue
(74) *Attorney, Agent, or Firm* — Hamilton, Brook, Smith & Reynolds, P.C.

(57) ABSTRACT

The development of fluorescent bioprobes comprising organic fluorescent compounds that exhibit aggregation induced emission (AIE) properties, methods of producing the same, and their practical applications for in vitro and in vivo bioimaging.

15 Claims, 29 Drawing Sheets
(29 of 29 Drawing Sheet(s) Filed in Color)

(56) References Cited

OTHER PUBLICATIONS

Allison, R. R. and C. H. Sibata, "Oncologic photodynamic therapy photosensitizers: A clinical review," Photodiagn. Photodyn. Ther., 7, 61-75 (2010).
Alvarez, M. G. et al. "Photodynamic damages induced by a monocationic porphyrin derivative in a human carcinoma cell line," Int. J. Biochem. Cell Biol., 37, 2504-2512 (2005).
Ang, D. et al., "In vitro studies of magnetically enhanced transfection in COS-7 cells," Materials Science and Engineering: C, 31, 1445-1457 (2011).
Barnes, K.R., et al., "Synthesis, Characterization, and Cytotoxicity of a Series of Estrogen-Tethered Platinum(IV) Complexes", Chemistry & Biology, 11, 557 (2004).
Bennett, L. E. et al., "Singlet oxygen formation in monomeric and aggregated porphyrin c," J. Photochem. Photobiol. B: Biol., 3, 81-89 (1989).
Bertschinger, M. et al., "Disassembly of polyethylenimine-DNA particles in vitro: Implications for polyethylenimine-mediated DNA delivery", J. Control. Release, 116, 96-104 (2006).
Bhuniya, S. et al., "An Activatable Theranostic for Targeted Cancer Therapy and Imaging," Angew. Chem. Int. Edit., 53, 4469-4474 (2014).
Bildstein, L. et al., "Prodrug-based intracellular delivery of anti-cancer agents" Adv. Drug Deliver. Rev., 63, 3-23 (2011).
Bourre, L. et al., "Indirect detection of photosensitizer ex vivo", Journal of Photochemistry and Photobiology B—Biology, 67(1), 23-31 (2002).
Boussif, O. et al., "A versatile vector for gene and oligonucleotide transfer into cells in culture and in vivo: Polyethylenimine", Proc. Natl. Acad. Sci. U.S.A., 92, 7297 (1995).
Brannon-Peppas, L. and J. O. Blanchette, Advanced Drug Delivery Reviews, 56 (11), 1649-1659 (2004).
Brehm, I. et al., "1,4-benzoquinones with styryl substituents," Eur. J. Org. Chem., 3162-3170 (2002).
Breunig, M. et al. "Polymers and nanoparticles: Intelligent tools for intracellular targeting?" Eur. J. Pharm. Biopharm., 68, 112-128 (2008).
Butko, M.T. et al., "Fluorescent and photo-oxidizing TimeSTAMP tags track protein fates in light and electron microscopy," Nat. Neurosci., 15, 1742-1751 (2012).
Cakmak, Y. et al. "Designing Excited States: Theory-Guided Access to Efficient Photosensitizers for Photodynamic Action", Angew. Chem., Int. Ed., 50, 11937-11941 (2011).
Cao, J. et al., Targeted Cancer Therapy with a 2-Deoxyglucose-Based Adriamycin Complex, Cancer Res., 73, 1362-1373 (2013).
Cao, N. et al., "Doxorubicin conjugated to D.α-tocopheryl polyethylene glycol 1000 succinate (TPGS): Conjugation chemistry, characterization, in vitro and in vivo evaluation" Biomaterials, 29, 3856-3865 (2008).
Carlsson, C. et al. "Double bands in DNA gel electrophoresis caused by bis-intercalating dyes", Nucleic Acids Res., 23, 2413 (1995).
Castano, A. P. et al. "Mechanisms in photodynamic therapy: part one—photosensitizers, photochemistry and cellular localization," Photodiagn. Photodyn. Ther., 1, 279-293 (2004).
Castano, A. P. et al., "Photodynamic therapy plus low-dose cyclophosphamide generates antitumor immunity in a mouse model", Proceedings of the National Academy of Sciences, 105 (14), 5495-5500 (2008).
Castano, A. P. et al., "Photodynamic therapy and anti-tumour immunity," Nat. Rev. Cancer, 6, 535-545 (2006).
Celli, J. P. et al., "Imaging and Photodynamic Therapy: Mechanisms, Monitoring and Optimization," Chem. Rev., 110, 2795-2838 (2010).
Chazotte, B., "Labeling the Nucleus with Fluorescent Dyes for Imaging", CHS Protocols; 2008; doi: 10.1101/pdb.prot4950.
Chen, W. et al., "Identification of Bacteria in Water by a Fluorescent Array", Angew. Chem. Int. Ed., 53, 13734-13739 (2014).
Cheng, L., et al., "Functional Nanomaterials for Phototherapies of Cancer," Chem. Rev., 114, 10869-10939 (2014).

Chi, Z. et al. "Recent advances in organic mechanofluorochromic materials," Chem. Soc. Rev., 41, 3878-3896 (2012).
Chithrani, B.D. and W.C.W. Chan, "Elucidating the Mechanism of Cellular Uptake and Removal of Protein-Coated Gold Nanoparticles of Different Sizes and Shapes," Nano Letters, 7, 1542-1550 (2007).
Clennan, E. L. and A. Pace, "Advanced in singlet oxygen chemistry", Tetrahedron, 61 (2005) 6665-6691.
Cló, E. et al., "DNA-Programmed Control of Photosensized Singlet Oxygen Production", J. Am. Chem. Soc., 128, 4200-4201 (2006).
Conti, E. et al., "Crystallographic Analysis of the Recognition of a Nuclear Localization Signal by the Nuclear Import Factor Karyopherin α" Cell, 94, 193-204 (1998).
Corbitt, T. S. et al., "Conjugated Polyelectrolyte Capsules: Light-Activated Antimicrobial Micro "Roach Motels"", ACS Appl. Mater. Interfaces, 1 (1), 48-52 (2009).
Davis, M. E. et al., "Nanoparticle therapeutics: an emerging treatment modality for cancer", Nat. Rev. Drug Discov., 7, 771-782 (2008).
Davis, S. et al., "Mitochondrial and Plasma Membrane Potentials Cause Unusual Accumulation and Retention of Rhodamine 123 by Human Breast Adenocarcinoma-derived MCF-7 Cells", J. Biol. Chem., 260, 13844-13850 (1985).
Decock, J. et al., "Cathepsin B, cathepsin H, Cathepsin X and cystatin C in sera of patients with early-stage and inflammatory breast cancer", Int. J. Biol. Markers, 23(1): 8 pgs. (2008).
Degterev, A. et al., "A decade of caspases," Oncogene, 22, 8543-8567 (2003).
Demas, J. N. et al., "The measurement of photoluminescence Quantum Yields", J. Phys. Chem., 75, 991 (1971).
Demko, Z. and K. Sharpless, "An Intramolecular [2 +3] Cycloaddition Route to Fused 5-Heterosubstituted Tetrazoles", Org. Lett., 3, 4091-4094 (2001).
Denèfle, P., Introduction to Gene Therapy. A Clinical Aftermath, in Viral Vectors for Gene Therapy, O.-W. Merten and M. Al-Rubeai, Editors. 2011, Humana Press. pp. 27-44.
Denning, D.P. et al., "Programmed elimination of cells by caspase-independent cell extrusion in C. elegans," Nature, 488, 226-230 (2012).
Derfus, A. M. et al., "Probing the Cytotoxicity of Semiconductor Quantum Dots", Nano Letters, 4(1): 11-18 (2003).
DeRosa, M., et al., "Photosensitized singlet oxygen and its applications", Coor. Chem. Rev., 233-234, 351-371 (2002).
Dickinson, B. C. and C. J. Chang, "A Targetable Fluorescent Probe for Imaging Hydrogen Peroxide in the Mitochondria of Living Cells," J. Am. Chem. Soc., 130, 9638-9639 (2008).
Ding, D. et al., "Conjugated oligoelectrolyte-polyhedral oligomeric silsesquioxane loaded pH-responsive nanoparticles for targeted fluorescence imaging of cancer cell nucleus", Chem. Comm., 47, 9837-9839 (2011).
Ding, D. et al., "Bioprobes Based on AIE Fluorogens," Accounts of Chemical Research, 46(11): 2441-2453 (2013).
Ding, D. et al., "Light-up bioprobe with aggregation-induced emission characteristics for real-time apoptosis imaging in target cancer cells," Journal of Materials Chemistry B, 2, 231-238 (2014).
Ding, D. et al., "Ultrabright Organic Dots with Aggregation-Induced Emission Characteristics for Real-Time Two-Photon Intravital Vasculature Imaging," Advanced Materials, 25, 6083-6088 (2013).
Dolmans, D. E. et al., "Photodynamic therapy for cancer," Nature Reviews Cancer, 3 (5), 380-387 (2003).
Dombu, C., et al., "Characterization of endocytosis and exocytosis of cationic nanoparticles in airway epithelium cells," Nanotechnology, 21, 355102, 8 pgs. (2010).
Dong, X. et al., "A fluorescent turn-on low dose detection of gamma-radiation based on aggregation-induced emission", Chem. Comm., 51, 3892-3895 (2015).
D'Souza, G. G. M. et al., "Approaches for targeting mitochondria in cancer therapy," Biochim. Biophys. Acta—Bioenerg., 1807, 689-696 (2011).
Du, X. et al., "Efficient Non-doped Near Infrared Organic Light-Emitting Devices Based on Fluorophores with Aggregation-Induced Emission Enhancement", Chemistry of Materials, vol. 24, pp. 2178-2185 (2012).

(56) References Cited

OTHER PUBLICATIONS

Duan, X. et al., "Assemblies of Conjugated Polyelectrolytes with Proteins for Controlled Protein Photoinactivation", Advanced Materials, 22 (14), 1602-1606 (2010).
Duarte, A. et al., "Recent Advances in Conjugated Polyelectrolytes for Emerging Optoelectronic Applications", Chem. Mater., 23, 501-515 (2010).
Duncan, R. et al., "Design of Oligopeptide Side-chains in Poly[N-(2-hydroxypropyl)methacrylamide] Copolymers to Promote Efficient Degradation by Lysosomal Enzymes", Makromol. Chem., 184, 1997-2008 (1983).
Ebert, S.N. et al., "Noninvasive Tracking of Cardiac Embryonic Stem Cells In Vivo Using Magnetic Resonance Imaging Techniques," Stem Cells, 25, 2936-2944 (2007).
Ellenbroek, S. I. J. and J. van Rheenen, "Imaging hallmarks of cancer in living mice," Nat. Rev. Cancer, 14, 406-418 (2014).
Ernster, Lars, et al., "Biochemical, physiological and medical aspects of ubiquinone function", *Biochimica et Biophysica Acta.*, 1271 (1995) 195-204.
Estrela, J. M. et al., "Glutathione in cancer biology and therapy," Crit. Rev. Cl. Lab. Sci., 43, 143-181 (2006).
Esumi, K. et al., "Antioxidant Action by Gold-PAMAM Dendrimer Nanocomposites," Langmuir, 20, 2536-2538 (2004).
Esumi, K. et al., "Antioxidant-potentiality of gold-chitosan nanocomposites," Colloids Surf., B, 32, 117-123 (2003).
Fanara, P. et al., "Quantitative Analysis of Nuclear Localization Signal (NLS)-Importin α Interaction through Fluorescence Depolarization", *Journal of Biological Chemistry*, 275(28): 21218-21223 (2000).
Felsher, D. W., "Cancer revoked: oncogenes as therapeutic targets", *Nat. Rev. Canc.*, 3, 375-380 (2003).
Feng, G. et al. "Ultrabright organic dots with aggregation-induced emission characteristics for cell tracking," Biomaterials, 35, 8669-8677 (2014).
Feng, G. et al., "Fluorescence bioimaging with conjugated polyelectrolytes", Nanoscale, 4 (20), 6150-6165 (2012).
Feng, G. et al., "Bright Single-Chain Conjugated Polymer Dots Embedded Nanoparticles for Long-Term Cell Tracing and Imaging," Small, 10, 1212-1219 (2014).
Feng, L. et al., "Conjugated polymer nanoparticles: preparation, properties, functionalization and biological applications", Chemical Society Reviews, 42 (16), 6620 (2013).
Feng, L. Z. et al., "Smart pH-Responsive Nanocarriers Based on Nano-Graphene Oxide for Combined Chemo-and Photothermal Therapy Overcoming Drug Resistance", Adv. Healthc. Mater., 3, 1261-1271 (2014).
Feng, X. et al., "A Highly Emissive Conjugated Polyelectrolyte Vector for Gene Delivery and Transfection", Adv. Mater., 24, 5428 (2012).
Ferrari, M., "Cancer Nanotechnology: Opportunities and Challenges", *Nat. Rev. Cancer*, 5, 161-171 (2005).
Fischer, D. et al., "A Novel Non-Viral Vector for DNA Delivery Based on Low Molecular Weight, Branched Polyethylenimine: Effect of Molecular Weight on Transfection Efficiency and Cytotoxicity", Pharm. Res., 16, 1273 (1999).
Foote, C. S., "Definition of Type I and Type II Photosensitized Oxidation", Photochem. Photobiol., 54, 659-659 (1991).
Gallo, J. M. et al., "Pharmacokinetic model-predicted anticancer drug concentrations in human tumors," Clin. Cancer Res., 10, 8048-8058 (2004).
Galluzzi, L. et al., "Mitochondria as therapeutic targets for cancer chemotherapy", Oncogene, 25, 4812-4830 (2006).
Ganta, S. et al. "A review of stimuli-responsive nanocarriers for drug and gene delivery," J. Controlled Rel., 126, 187-204 (2008).
Gao, Y. et al., "Stem cell tracking with optically active nanoparticles," American Journal of Nuclear Medicine and Molecular Imaging, 3, 232¬246 (2013).
Ge, J. et al., "A graphene quantum dot photodynamic therapy agent with high singlet oxygen generation", *Nat. Commun.*, 5, 4596 (2014).

Geng, J. et al., "Eccentric Loading of Fluorogen with Aggregation-Induced Emission in PLGA Matrix Increases Nanoparticle Fluorescence Quantum Yield for Targeted Cellular Imaging," Small, 9, 2012-2019 (2013).
Geng, J. et al., "Near-infrared fluorescence amplified organic nanoparticles with aggregation-induced emission characteristics for in vivo imaging," Nanoscale, 6, 939¬945 (2014).
Giepmans, B.N.G. et al., "The Fluorescent Toolbox for Assessing Protein Location and Function," Science, 312, 217-224 (2006).
Gomes, A. et al., "Fluorescence probes used for detection of reactive oxygen species," J. Biochem. Bioph. Meth., 65, 45-80 (2005).
Gong, H. et al., "Near-Infrared absorbing polymeric nanoparticles as a versatile drug carrier for cancer combination therapy", Advanced Functional Materials, 23 (48), 6059-6067 (2013).
Graf, N. and S. J. Lippard, "Redox activation of metal-based prodrugs as a strategy for drug delivery", Advanced Drug Delivery Reviews, 64, 993-1004 (2012).
Gu, X et al., "New Electron-Donor/Acceptor-Substituted Tetraphenylethylenes: Aggregation-Induced Emission with Tunable Emission Color and Optical-Waveguide Behavior", Chemistry—An Asian Journal, vol. 8, pp. 2362-2369 (2013).
Guo, X. and L. Huang, "Recent Advances in Non-viral Vectors for Gene Delivery", Acc. Chem. Res., 45(7), 971-979 (2012).
Guo, Y. et al., "Assessment of the green florescence protein labeling method for tracking implanted mesenchymal stem cells," Cytotechnology, 64, 391-401 (2012).
Hall, M. D. et al., "Basis for Design and Development of Platinum(IV) Anticancer Complexes", J. Med. Chem., 50(15), 3403-3411 (2007).
Hamm, A. et al., "Efficient Transfection Method for Primary Cells", Tissue Engineering, 8(2): 235-245 (2002).
Han, K. et al., "A Tumor Targeted Chimeric Peptide for Synergistic Endosomal Escape and Therapy by Dual-Stage Light Manipulation", Adv. Funct. Mater., 25, 1248 (2015).
Hersel, U. et al., "RGD modified polymers: biomaterials for stimulated cell adhesion and beyond", Biomaterials, 24 (24), 4385-4415 (2003).
Higuchi, M. et al., "Regulation of reactive oxygen species-induced apoptosis and necrosis by caspase 3-like proteases," Oncogene, 17, 2753-2760 (1998).
Hilf, R., "Mitochondria are targets of photodynamic therapy," J. Bioenerg. Biomembr., 39, 85-89 (2007).
Hogset, A. et al., "Light-induced adenovirus gene transfer, an efficient and specific gene delivery technology for cancer gene therapy", *Cancer Gene Ther.*, 9, 365 (2002).
Hogset, A. et al., "Photochemical internalization in drug and gene delivery", Adv. Drug. Deliver. Rev., 56, 95-115 (2004).
Hong, H. et al., "Non-invasive cell tracking in cancer and cancer therapy," Current Topics in Medicinal Chemistry, 10, 1237-1248 (2010).
Hong, Y. et al. "Quantitation, Visualization, and Monitoring of Conformational Transitions of Human Serum Albumin by a Tetraphenylethene Derivative with Aggregation-Induced Emission Characteristics", Analytical Chemistry, 82, 7035-7043 (2010).
Hong, Y. et al., "Aggregation-Induced Emission," Chem. Soc. Rev., 40: 5361-5388 (Jul. 29, 2011).
Hong, Y. et al., "Aggregation-Induced Emission: Phenomenon, Mechanism and Applications," Chem. Comm., pp. 4332-4353 (May 13, 2009).
Horobin, R. W. et al. "Mitochondriotropics: A review of their mode of action, and their applications for drug and DNA delivery to mammalian mitochondria," J. Controlled Rel., 121, 125-136 (2007).
Horobin, R. W. et al., "Fluorescent cationic probes for nuclei of living cells: why are they selective? A quantitative structure-activity relations analysis", Cell Biol., 126: 165-175 (2006).
Hu, C. M. et al., "Nanoparticle-assisted combination therapies for effective cancer treatment", *Ther. Deliv.*, 1 (2), 323-334 (2010).
Hu, F. et al., "Targeted Bioimaging and Photodynamic Therapy of Cancer Cells with an Activatable Red Fluorescent Bioprobe", Analytical Chemistry, vol. 86, pp. 7987-7995 (2014).
Hu, Q. et al. "Mitochondria-Targeted Cancer Therapy Using a Light-Up Probe with Aggregation-Induced-Emission Characteristics," Angew. Chem. Int. Ed., 53, 14225-14229 (2014).

(56) References Cited

OTHER PUBLICATIONS

Hu, R. et al. "AIE macromolecules: syntheses, structures and functionalities," Chem. Soc. Rev., 43, 4494-4562 (2014).
Hu, R. et al., "Twisted Intramolecular Charge Transfer and Aggregation-Induced Emission of Bodipy Derivatives," The Journal of Physical Chemistry C, 113, 15845-15853 (2009).
Hu, X. L. et al., "Cell-Penetrating Hyperbranched Polyprodrug Amphiphiles for Synergistic Reductive Milieu-Triggered Drug Release and Enhanced Magnetic Resonance Signals," Journal of the American Chemical Society, 137, 362-368 (2015).
Huang, Y. et al, "Tetraphenylethylene Conjugated with a Specific Peptide as a Fluorescence Turn-On Bioprobe for the Highly Specific Detection and Tracing of Tumor Markers in Live Cancer Cells", Chemistry—A European Journal, vol. 20, pp. 158-164 (published Jan. 3, 2014; published online Nov. 25, 2013).
Hudson, R. et al. "The development and characterisation of porphyrin isothiocyanate-monoclonal antibody conjugates for photoimmunotherapy," Br. J. Cancer, 92, 1442-1449 (2005).
Hultberg, M. and B. Hultberg, "The effect of different antioxidants on glutathione turnover in human cell lines and their interaction with hydrogen peroxide," Chem-Biol Interact, 163, 192-198 (2006).
Hwang, C., et al., "Oxidized Redox State of Glutathione in the Endoplasmic Reticulum", Science, 257, 1496 (1992).
Ichikawa, Y. et al., "Selective Ablation of β-Galactosidase-Expressing Cells with a Rationally Designed Activatable Photosensitizer", Angew. Chem. Int. Ed., 53(26) 6772-6775 (2014).
Idris, N.M. et al., "Tracking transplanted cells in live animal using upconversion fluorescent nanoparticles," Biomaterials, 30, 5104-5113 (2009).
International Preliminary Report on Patentability for Int'l Application No. PCT/SG2015/000022, titled: Light-Up Probes Based on Fluorogens With Aggregation Induced Emission Characteristics for Cellular Imaging and Drug Screening, dated Aug. 2, 2016.
International Preliminary Report on Patentability for Int'l Application No. PCT/CN2012/001227, titled: Biocompatible Nanoparticles With Aggregation Induced Emission Characteristics as Fluorescent Bioprobes and Methods of Using the Same for In Vitro and In Vivo Imaging, dated Mar. 4, 2014.
International Preliminary Report on Patentability for Int'l Application No. PCT/sg2015/000123, titled: Polymers and Oligomers With Aggregation-Induced Emission Characteristics for Imaging and Image-Guided Therapy, dated Nov. 6, 2016.
International Search Report and Written Opinion for Int'l Application No. PCT/SG2015/000022, titled: Light-Up Probes Based on Fluorogens With Aggregation Induced Emission Characteristics for Cellular Imaging and Drug Screening, dated Sep. 2, 2015.
International Search Report and Written Opinion for Int'l Application No. PCT/SG2015/000123, titled: Polymers and Oligomers With Aggregation-Induced Emission Characteristics for Imaging and Image-Guided Therapy, dated Aug. 26, 2015.
International Search Report and Written Opinion for Int'l Application No. PCT/CN2012/001227, titled: Biocompatible Nanoparticles With Aggregation Induced Emission Characteristics as Fluorescent Bioprobes and Methods of Using the Same for In Vitro and In Vivo Imaging, dated Dec. 13, 2012.
Jabr-Milane, L. et al. "Multi-functional nanocarriers for targeted delivery of drugs and genes," J. Controlled Rel., 130, 121-128 (2008).
Jaiswal, J. K. et al., "Use of quantum dots for live cell imaging", Nat Meth, 1(1): 73-78 (2004).
Jaiswal, J.K. et al., "Long-term multiple color imaging of live cells using quantum dot bioconjugates," Nat Biotech, 21, 47-51 (2003).
Jang, W. D. et al., "Supramolecular Nanocarrier of Anionic Dendrimer Porphyrins Enhance Intracellular with Cationic Block Copolymers Modified with Polyethylene Glycol to Photodynamic Efficacy", Angew. Chem. Int. Ed., 44, 419-423 (2005).
Jia, J. et al., "Mechanisms of drug combinations: interaction and network perspectives" Nat. Rev. Drug Discov ., 8, 111-128 (Feb. 2009).
Jiang, H. et al., "Conjugated Polyelectrolytes: Synthesis, Photophysics, and Application", Angew. Chem. Int. Ed. Engl., 48 (24), 4300-4316 (2009).
Jiang, S. et al., "Optical imaging-guided cancer therapy with fluorescent nanoparticles", Soc. Interface, 7, 3-18 (2010).
Jokerst, J.V. and S.S. Gambhir, :Molecular Imaging with Theranostic Nanoparticles, Acc. Chem. Res., 44(10): 1050-1060 (2011).
Juarranz, Á. et al., "Photodynamic therapy of cancer. Basic principles and applications", Clin. Transl. Oncol., 10, 148-154 (2008).
Kalinowska-Lis, U. et al., "Trans geometry in platinum antitumor complexes", Coordination Chemistry Reviews, 252, 1328-1345 (2008).
Kamaly, Z. et al., "Targeted polymeric therapeutic nanoparticles: design, development and clinical translation", Chem. Soc. Rev., 41, 2971-3010 (2012).
Kandel, P.K. et al., "Incorporating functionalized polyethylene glycol lipids into reprecipitated conjugated polymer nanoparticles for bioconjugation and targeted labeling of cells," Nanoscale, 3, 1037-1045 (2011).
Kang, B.H., et al., "Combinatorial drug design targeting multiple cancer signaling networks controlled by mitochondrial Hsp90", J. Clin. Invest., 119, 454-464 (2009).
Kaplan, I.M. et al. "Cationic TAT peptide transduction domain enters cells by micropinocytosis," Journal of Controlled Release, 102(1): 247-253 (2005).
Kawamura, E. et al. "Intracellular observation of nanocarriers modified with a mitochondrial targeting signal peptide," J. Biosci. Bioeng., 116, 634-637 (2013).
Kelland, L., "The resurgence of platinum-based cancer chemotherapy", Nat. Rev. Cancer, 7, 573-584 (2007).
Kessel, D. and Y. Luo, "Photodynamic therapy: A mitochondrial induced of apoptosis," Cell Death Differ., 6, 28-35 (1999).
Khdair, A. et al., Nanoparticle-mediated combination chemotherapy and photodynamic therapy overcomes tumor drug resistance in vitro, J. Pharm. Biopharm., 71(2): 214-222 (2009).
Khdair, A. et al., "Nanoparticle-mediated combination chemotherapy and photodynamic therapy overcomes tumor drug resistance", Journal of Controlled Release, 141(2): 137-144 (2010).
Kim, S. et al., "Organically modified silica nanoparticles co-encapsulating photosensitizing drug and aggregation-enhanced two-photo absorbing fluorescent dye aggregates for two-photon photodynamic therapy", J. Am. Chem. Soc., 129(9): 2669-2675 (2007).
Kim, S. et al., "Far-Red Fluorescence Probe for Monitoring Singlet Oxygen during Photodynamic Therapy," J. Am. Chem. Soc., 136, 11707-11715 (2014).
Kircher, M.F. et al., "Noninvasive cell-tracking methods," Nat. Rev. Clin. Oncol., 8, 677-688 (2011).
Kondo, Y. et al., "Inhibition of telomerase increases the susceptibility of human malignant glioblastoma cells to cisplatin-induced apoptosis", Oncogene, 16, 2243-2248 (1998).
Kraitchman, D.L. et al., "Dynamic imaging of allogeneic mesenchymal stem cells trafficking to myocardial infarction," Circulation, 112, 1451-1461 (2005).
Králová, J. et al., "Porphyrin-Cyclodextrin Conjugates as a Nanosystem for Versatile Drug Delivery and Multimodal Cancer Therapy", J. Med. Chem., 53, 128-138 (2010).
Krishnamoorthy, G. et al., "Structure and Dynamics of Condensed DNA Probed by 1,1¢ -(4,4,8,8-Tetramethyl-4,8-diazaundecamethylene)bis[4-[[3-methylbenz-1,3-oxazol-2-yl]methylidine]-1,4-dihydroquinolinium] Tetraiodide Fluorescence" Biochemistry, 41, 15277-15287 (2002).
Kuchelmeister, H. Y. et al., "Efficient gene delivery into cells by a surprisingly small three-armed peptide ligand", Chem. Sci., 3, 996 (2012).
Kwok, R. T. et al., "Biosensing by luminogens with aggregation-induced emission characteristics," Chem. Soc. Rev., 2015, 44, 4228-4238.
Lam, M. et al., "Photodynamic Therapy-induced Apoptosis in Epidermoid Carcinoma Cells: Reactive Oxygen Species and Mitochondrial Inner Membrane Permeabilization," J. Biol. Chem., 276, 47379-47386 (2001).

(56) References Cited

OTHER PUBLICATIONS

Lange, A. et al., "Classical Nuclear Localization Signals: Definition, Function, and Interactin with Importin α", Journal of Biological Chemistry, 282(8), 5101-5105 (2007).
Langer, R., "Drug delivery and targeting", Nature, 392 (6679), 5-10 (1998).
Larson, D.R. et al., "Water-Soluble Quantum Dots for Multiphoton Fluorescence Imaging in Vivo," Science, 300, 1434-1436 (2003).
Lau, J. T. F. et al., "A Zinc(II) Phthalocyanine Conjugated with an Oxaliplatin Derivative for Dual Chemo- and Photodynamic Therapy", J. Med. Chem., 55, 5446-5454 (2012).
Lee, D., et al., "Potent and Selective Nonpeptide Inhibitors of Caspases 3 and 7 Inhibit Apoptosis and Maintain Cell Functionality", Journal of Biological Chemistry, 275, 16007 (2000).
Lee, M. H. et al., "Direct Fluorescence Monitoring of the Delivery and Cellular Uptake of a Cancer-Targeted RGD Peptide-Appended Naphthalimide Theragnostic Prodrug", Ant. Chem. Soc., 134, 12668-12674 (2012).
Lee, M. H. et al., "Disulfide-Cleavage-Triggered Chemosensors and Their Biological Applications," Chem. Rev., 113, 5071-5109 (2013).
Lee, S. H. et al., "Current Progress in Reactive Oxygen Species (ROS)-Responsive Materials for Biomedical Applications", Adv. Healthcare. Mater., 2, 908 (2013).
Lee, S. M. et al., "Polymer-Caged Nanobins for Synergistic Cisplatin-Doxorubicin Combination Chemotherapy", J. Am. Chem. Soc., 132 (48), 17130-17138 (2010).
Lee, S.Y., et al., "Luminous Butterflies: Efficient Exciton Harvesting by Benzophenone Derivatives for Full-Color Delayed Fluorescence OLEDs", Angew. Chem, 2014, 126: 6520-6524.
Lei, W. et al. "Mitochondria-targeting properties and photodynamic activities of porphyrin derivatives bearing cationic pendant," J. Photochem. Photobiol. B: Biol., 98, 167-171 (2010).
Leriche, Geoffray, et al., Table 1 from article titled: "Cleavable linkers in chemical biology", Bioorganic & Medicinal Chemistry, vol. 20, Issue 2, pp. 571-582 (2012).
Leung, C. W. T. et al., "A Photostable AIE Luminogen for Specific Mitochondrial Imaging and Tracking", J. Am. Chem. Soc., 135, 62-65 (2013).
Li, C. et al., "A General Strategy to Construct Fluorogenic Probes from Charge-Generation Polymers (CGPs) and AIE-Active Fluorogens through Triggered Complexation", Angew. Chem. Int. Ed., 51, 455-459 (2012.
Li, C. et al., "A Nonemissive Iridium(III) Complex That Specifically Lights-Up the Nuclei of Living Cells", *J. Am. Chem. Soc.*, 133, 11231-11239 (2011).
Li, D. et al. "Synergistic Enhancement of Lung Cancer Therapy Through Nanocarrier-Mediated Sequential Delivery of Superantigen and Tyrosin Kinase Inhibitor", Adv. Funct. Mater., 24, 5482-5492 (2014).
Li, J. et al., "Highly Efficient Organic Light-Emitting Diode Based on a Hidden Thermally Activated Delayed Fluorescence Channel in a Heptazine Derivative", Adv. Mater., 25, 3319-3323 (2013).
Li, J. et al., "Self-assembly of DNA nanohydrogels with controllable size and stimuli-responsive property for targeted gene regulation therapy", *J. Am. Chem. Soc.*, 137, 1412 (2015).
Li, J. et al., "Tuning the singlet-triplet energy gap of AIE luminogens: crystallization-induced room temperature phosphorescence and delay fluorescence, tunable temperature response, highly efficient non-doped organic light-emitting diodes", Phys. Chem. Chem. Phys., 17, 1134-1141 (2015).
Li, J., et al., "Platinum(IV) prodrugs entrapped within multiwalled carbon nanotubes: Selective release by chemical reduction and hydrophobicity reversal", *Chemical Science*, 3, 2083-2087 (2012).
Li, K. and B. Liu, "Polymer-encapsulated organic nanoparticles for fluorescence and photoacoustic imaging," Chem. Soc. Rev., 43, 6570-6597 (2014).
Li, K. et al., "Biocompatible organic dots with aggregation-induced emission for in vitro and in vivo fluorescence imaging," Science China Chemistry, 56, 1228-1233 (2013).
Li, K. et al., "Folic acid-functionalized two-photon absorbing nanoparticles for targeted MCF-7 cancer cell imaging," Chem. Comm., 47, 7323-7325 (2011).
Li, K. et al., "Gadolinium-Functionalized Aggregation-Induced Emission Dots as Dual-Modality Probes for Cancer Metastasis Study", Advanced Healthcare Materials, vol. 2, pp. 1600-1605 (2013).
Li, K. et al., "Organic Dots with Aggregation-Induced Emission (AIE Dots) Characteristics for Dual-Color Cell Tracing," Chem. Mater., 25, 4181-4187 (2013).
Li, K. et al., "Photostable fluorescent organic dots with aggregation-induced emission (AIE dots) for noninvasive long-term cell tracing," Sci. Rep., 3, 1150 (2013).
Li, S. P. Y. et al. "Mitochondria-targeting cyclometalated iridium(III)-PEG complexes with tunable photodynamic activity," Biomaterials, 34, 7519-7532 (2013).
Li, S.-D. and L. Huang, "Non-viral is superior to viral gene delivery," Journal of Controlled Release, 123, 181-183 (2007).
Li, X. et al., "Fluoroscent Aptasensor Based on Aggregation-Induced Emission Probe and Graphene Oxide", Anal. Chem., 86, 298-303 (2014).
Li, Y. et al., "A bioprobe based on aggregation induced emission (AIE) for cell membrane tracking", Chem. Comm., 49, 11335-11337 (2013).
Li, Y. et al., "Amphiphilic Star Copolymer-Based Bimodal Fluorogenic/Magnetic Resonance Probes for Concomitant Bacteria Detection and Inhibition", Adv. Mater., 26, 6734-6741 (2014).
Li, Y. et al., "Increasing the power output of a CdTe solar cell via luminescent down shifting molecules with intramolecular charge transfer and aggregation-induced emission characteristics," Energy & Environmental Science, vol. 6, pp. 2907-2911 (2013).
Liang, J. et al. "Specific light-up bioprobes based on AIEgen conjugates," Chem. Soc. Rev. (2015).
Liu, J. et al., "Aggregation-Induced Emission of Silole Molecules and Polymers: Fundamental and Applications," J. Inorg. Organoment. Polym., 19: 249-285 (2009).
Liu, J.Z. et al., "Acetylenic Polymers: Syntheses, Structures, and Functions," Chem. Rev., 109(11): 5799-5867 (Aug. 13, 2009).
Liu, J.Z. et al., "Hyperbranched Conjugated Polysiloles: Synthesis, Structure, Aggregation-Enhanced Emission, Multicolor Fluorescent Photopatterning, and Superamplified Detection of Explosives," Macromolecules, 43(11): 4921-4936 (May 12, 2010).
Liu, Y. et al., "Tissue Factor-Activated Coagulation Cascade in the Tumor Microenvironment is Critical for Tumor Progression and an Effective Target for Therapy", Cancer Res., 71, 6492-6502 (2011).
Liu, Z., et al., "In vivo biodistribution and highly efficient tumour targeting of carbon nanotubes in mice", *Nat. Nanotech*, 2007, 47-52.
Lopez-Flores, A., et al., "A high-performance liquid chromatographic assay for determination of cisplatin in plasma, cancer cell, and tumor samples", J. Pharmacol. Toxicol. Methods, 52, 366 (2005).
Luhrmann, A. et al., "Inhibition of pathogen-induced apoptosis by a Coxiella burnetii type IV effector protein," *PNAS*, 107, 18997-19001 (2010).
Luo, M. et al, "Synthesis and Properties of Gelators Derived From Tetraphenylethylene and Gallic Acid With Aggregation-Induced Emission", Journal of Molecular and Engineering Materials, vol. 1, pp. 1340007-1 to 1340007-20 (2013).
Marrache, S. and S. Dhar, "Engineering of blended nanoparticle platform for delivery of mitochondria-acting therapeutics," *PNAS* 109, 16288-16293 (2012).
Min, Y., et al., "Near-Infrared Light-Mediated Photoactivation of a Platinum Antitumor Prodrug and Simultaneous Cellular Apoptosis Imaging by Upconversion-Luminescent Nanoparticles", Angew. Chem. Int. Ed., 2014, 53, 1012-1016.
Minotti, G., "Anthracyclines: Molecular Advances and Pharmacologic Developments in Antitumor Activity and Cardiotoxicity", Pharmacol. Rev., 56, 185-229 (2004).
Modica-Napolitano, J. S. et al., "Basis for the Selective Cytotoxicity of Rhodamine 123", Cancer Res., 47, 4361-4365 (1987).
Morris, K.V. et al., "Small Interfering RNA-Induced Transcriptional Gene Silencing in Human Cells," Science, 305, 1289-1292 (2004).

(56) References Cited

OTHER PUBLICATIONS

Moses. B. et al., "Emerging Strategies for Controlling Drug Release by Using Visible/Near IR Light", Med. Chem., 3, 192 (2013).
Nabiev, I. et al., "Nonfunctionalized Nanocrystals Can Exploit a Cell's Active Transport Machinery Delivering Them to Specific Nuclear and Cytoplasmic Compartments", Nano Letters, 7(11): 3452-3461 (2007).
Nakajima, T. et al. "Real-time Monitoring of In Vivo Acute Necrotic Cancer Cell Death Induced by Near Infrared Photoimmunotherapy Using Fluorescence Lifetime Imaging," Cancer Res., 72, 4622-4628 (2012).
Nakajima, T. et al., "Improving the efficacy of Photoimmunotherapy (PIT) using a cocktail of antibody conjugates in a multiple antigen tumor model," Theranostics, 3, 357-365 (2013).
Nakano, S. et al., "Replication-Coupled Chromatin Assembly Generates a Neuronal Bilateral Asymmetry in C. elegans," Cell, 147, 1525-1536 (2011).
Nguyen, J. and F. C. Szoka, "Nucleic acid delivery: the missing pieces of the puzzle?", Acc. Chem. Res., 45(7): 1153-1162 (2012).
Nitiss, J. L., "Targeting DNA topoisomerase II in cancer chemotherapy", Nat. Rev Cancer, 9(5), 338-350 (2009).
Nomoto, T. et al., "Three-layered polyplex micelle as a multifunctional nanocarrier platform for light-induced systemic gene transfer", Nat. Commun., 5: 1-10 (2014).
Olivo, M. et al. "Targeted therapy of cancer using photodynamic therapy in combination with multi-faceted Anti-Tumor Modalities", Pharmaceuticals 3, 1507-1529 (2010).
Ou, M. et al., "A family of bioreducible poly(disulfide amine)s for gene delivery", Biomaterials 30(29): 5804-5814 (2009).
Panti, K., et al., "Aromatic Fumaronitrile Core-Based Donor-Linker-Acceptor-Linker-Donor (D-π-A-π-D) Compounds: synthesis and Photophysical Properties", J. Phys. Chem. A 2010, 114, 4542-4549.
Parrott, E. P. J. et al., "Direct evidence to support the restriction of intramolecular rotation hypothesis for the mechanism of aggregation-induced emission: temperature resolved terahertz spectra of tetraphenylethene," Mater. Horizons, 1, 251-258 (2014).
Paunesku, T. et al. "Intracellular Distribution of TiO2-DNA Oligonucleotide Nanoconjugates Directed to Nucleolus and Mitochondria Indicates Sequence Specificity," Nano Lett., 7, 596-601 (2007).
Perry, S. W. et al., "Mitochondrial membrane potential probes and the proton gradient: a practical usage guide", Biotechniques, 50(2): 98-115 (2011).
Peterson, C. M. et al., "Combination Chemotherapy and Photodynamic Therapy with N-(2-Hydroxypropyl)methacrylamide Copolymer-bound Anticancer Drugs Inhibit Human Ovarian Carcinoma", Cancer Res., 56(17): 3980-3985 (1996).
Petros, R. A. and J. M. DeSimone, "Strategies in the design of nanoparticles for therapeutic applications", Nature Reviews Drug Discovery 9(8): 615-627 (2010).
Piantavigna, S., et al, "A mechanistic investigation of cell-penetrating Tat peptides with supported lipid membranes", Biochimica et Biophysica Acta 1808 (2011) 1811-1817.
Pu, K.Y., et al., "A Molecular Brush Approach to Enhance Quantum Yield and Suppress Nonspecific Interactions of Conjugated Polyelectrolyte for Targeted Far-Red/Near-Infrared Fluorescence Cell Imaging", Adv. Funct. Mater. 2010, 20, 2770-2772.
Pu, K.Y., et al., "Design and Synthesis of Charge-Transfer-Based Conjugated Polyelectrolytes as Multicolor Light-Up Probes", Macromolecules 2009, 42, 5933-5940.
Pu., K.Y., et al., "Fluorescent Single-Molecular Core-Shell Nanospheres of Hyperbranched Conjugated Polyelectrolyte for Live-Cell Imaging", Chem. Mater. 2009, 21, 3816-3822.
Qi, Y. B. et al., "Photo-inducible cell ablation in *Caenorhabditis elegans* using the genetically encoded singlet oxygen generating protein miniSOG", PNAS 109, 7499-7504 (2012).
Qin, W., et al., "Biocompatible Nanoparticles with Aggregation-Induced Emission Characteristics of Far-Red/Near-Infrared Fluorescent Bioprobes for In Vitro and In Vivo Imaging Applications", Adv. Funct. Mater. 2012, 22, 771-779.

Rajendran, L. et al. "Subcellular targeting strategies for drug design and delivery," Nat. Rev. Drug Discov., 9, 29-42 (2010).
Riedl, S. J. and Y. G. Shi, "Molecular mechanisms of caspase regulation during apoptosis," Nat. Rev. Mol. Cell Bio., 5, 897-907 (2004).
Sakhrani, N. M. and H. Padh, "Organelle targeting: third level of drug targeting," Drug Des., Dev. Ther., 7, 585-99 (2013).
Samanta, S. et al., "An aggregation-induced emission (AIE) active probe renders Al(III) sensing and tracking of subsequent interaction with DNA", Chem. Comm., 50, 11833-11836 (2014).
Sambrook, J., et al., "Calcium phosphate-mediated transfection of eukaryotic cells," Nat Meth, 2, 319-320 (2005).
Santra, S. et al., J. "Cell-Specific, Activatable and Theranostic Prodrug for Dual Targeted Cancer Imaging and Therapy", Am. Chem. Soc., 133, 16680-16688 (2011).
Schaffer, D. V. et al., "Vector Unpacking as a Potential Barrier for Receptor-Mediated Polyplex Gene Delivery", Biotechnol. Bioeng., 67, 598 (2000).
Sekkat, N., et al, "Like a Bolt from the Blue Phthalocyanines in Biomedical Optics", Molecules 2012, 17, 98-144.
Shao, A., et al., "Insight into Aggregation-induced emission characteristics of red-emissive quinolone-malononitrile by cell tracking and real-time trypsin detection", Chem. Sc. 2014, 5, 1383-1389.
Sharma, An., et al., "Design and Evaluation of Multi-functional Nanocarriers for Selective Delivery of Coenzyme Q10 to Mitochondria", Biomacromolecules, Jan. 9, 2012; 13(1): 239-252.
Shi, H. et al., "Real-Time Monitoring of Cell Apoptosis and Drug Screening Using Fluorescent Light-Up Probe with Aggregation-Induced Emission Characteristics," J. Am. Chem. Soc., 134(43), 17972-17981 (2012).
Song, Z., et al., "A Ratiometric Fluorescent Probe Based on ESIPT and AIE Processes for Alkaline Phosphatase Activity Assay and Visualization in Living Cells", ACS Appl. Mater. Interfaces 2014, 6, 17245-17254.
Tian, J. et al., "Cell-Specific and pH-Activatable Rubyin-Loaded Nanoparticles for Highly Selective Near-Infrared Photodynamic Therapy against Cancer", J. Am. Chem. Soc., 135, 18850-18858 (2013).
Tsien, R.Y., "Constructing and Exploiting the Fluorescent Protein Paintbox (Nobel Lecture)," Angew. Chem. Int. Ed., 48, 5612-5626 (2009).
Van Dongen, G. A. M. S. et al. "Photosensitizer-antibody conjugates for detection and therapy of cancer," Adv. Drug Delivery Rev., 56, 31-52 (2004).
Van Duijnhoven, F. H. et al., "The immunological consequences of photodynamic treatment of cancer, a literature review," Immunobiology, 207, 105-113 (2003).
Von Eyss, B. et al., "Addicted to Myc—but why?", Cold Spring Harbor Protocols, 2011, 895-897 (2011).
Vrouenraets, M. B. et al. "Development of meta-Tetrahydroxyphenylchlorin-Monoclonal Antibody Conjugates for Photoimmunotherapy," Cancer Res., 59, 1505-1513 (1999).
Wadia, J. S. et al., "Transducible TAT-HA fusogenic peptide enhances escape of TAT-fusion proteins after lipid raft micropinocytosis", Nat. Med., 10, 310 (2004).
Wang, C. et al., "Upconversion Nanoparticles for Photodynamic Therapy and Other Cancer Therapeutics", Theranostics 3 (5), 317-330 (2013).
Wang, F. et al., "Small mitochondria-targeting molecules as anticancer agents", Mol. Aspects Med., 31, 75-92 (2010).
Wang, J.-X. et al, "Sugar-bearing tetraphenylethylene: novel fluorescent probe for studies of carbohydrate-protein interaction based on aggregation-induced emission", Organic & Biomolecular Chemistry vol, 9, pp. 2219-2226 (2011).
Wang, L. and W. Tan, "Multicolor FRET silica nanoparticles by single wavelength excitation," Nano Lett, 6, 84-88 (2006).
Wang, L. et al. "Selective Targeting of Gold Nanorods at the Mitochondria of Cancer Cells: Implications for Cancer Therapy," Nano Len., 11, 772-780 (2010).
Wang, M., et al., "Fluorescent bio/chemosensors based on silole and tetraphenylethene luminogens with aggregation-induced emission feature", J. Mater. Chem., 2010, 20, 1858-1867.

(56) References Cited

OTHER PUBLICATIONS

Wang, X. and Z. Guo, "Targeting and delivery of platinum-based anticancer drugs", Chem. Soc. Rev., 42, 202-224 (2013).

Wang, X. et al, "Highly sensitive and selective fluorometric off-on le probe constructed via host-guest molecular recognition and aggregation-induced emission", Journal of Materials Chemistry vol. 22, pp. 8622-8628 (2012).

Wang, X. et al., "Near-infrared light triggered photodynamic therapy in combination with gene therapy using upconversion nanoparticles for effective cancer cell killing", Nanoscale 6, 9198-9205 (2014).

Wang, X. et al., Chapter Four—Mitochondrial Alterations During Carcinogenesis: A Review of Metabolic Transformation and Targets for Anticancer Treatments. Advances in Cancer Research, Academic Press 119, 127-160 (2013).

Wang, Y. et al., "Multifunctional Mesoporous Silica-Coated Graphene Nanosheet Used for Chemo-Photothermal Synergistic Targeted Therapy of Glioma", J. Am. Chem. Soc., 135 (12), 4799-4804 (2013).

Wang, Y. et al., "Nuclear Targeting Dynamics of Gold Nanoclusters for Enhanced Therapy of HER2+ Breast CancerACS", Nano 5, 9718-9725 (2011).

Wang, Z. et al., "Long-Term Fluorescent Cellular Tracing by the Aggregates of AIE Bioconjugates", J. Am. Chem. Soc., 135, 8238-8245 (2013).

Wei, T.-T. et al, "An efficient fluorescence turn-on probe for Al3+ based on aggregation-induced emission", Analytical Methods, vol. 5, pp. 3909-3914 (2013).

Weigl, S. et al., "Mitochondria and Familial Predisposition to Breast Cancer," Curr. Genomics, 14, 195-203 (2013).

Weinstain, R. et al., "Real-time monitoring of drug release", Commun., 46, 553-555 (2010).

Wiedenmann, J. et al., "Fluorescent proteins for live cell imaging: Opportunities, limitations, and challenges," IUBMB Life, 61, 1029-1042 (2009).

Wilson, D. S. et al., "Orally delivered thioketal-nanoparticles loaded with TNFα-siRNA target inflammation and inhibit gene expression in the intestines", Nat. Mater., 9, 923 (2010).

Wong, K. K. Y. and X. L. Liu, "Nanomedicine: a primer for surgeons," Pediatr. Surg. Int., 28, 943-951 (2012).

Wood, A. C. et al., "Induction of apoptosis by anti-cancer drugs with disparate modes of action: kinetics of cell death and changes in c-myc expression," Br. J. Cancer 71, 937-941 (1995).

Wu, X. et al., "Immunofluorescent labeling of cancer marker Her2 and other cellular targets with semiconductor quantum dots," Nat. Biotech., 21, 41-46 (2003).

Wu, Y. et al., "Exceptional Intersystem Crossing in Di(Perylene bisimede)s: A Structural Platform toward Photosensitizers for Singlet Oxygen Generation", J. Phys. Chem. Lett., 1, 2499-2502 (2010).

Xiao, L. et al., "Porous Silicon Nanoparticle Photosensitizers for Singlet Oxygen and Their Phototoxicity Against Cancer Cells", ACS Nano, 5(5), 3651-3659 (2011).

Xue, X. D. et al., "Spatiotemporal Drug Release Visualized through a Drug Delivery System with Tunable Aggregation-Induced Emission," Adv. Mater., 26, 712-717 (2014).

Yamada, Y. et al. "Dual Function MITO-Porter, a Nano Carrier Integrating Both Efficient Cytoplasmic Delivery and Mitochondrial Macromolecule Delivery," Mol. Ther., 19, 1449-1456 (2011).

Yamada, Y. et al. "Mitochondrial-targeted DNA delivery using a DF-MITO-Porter, an innovative nano carrier with cytoplasmic and mitochondrial fusogenic envelopes," J. Nanopart. Res., 14, 1-15 (2012).

Yang, X. Z. et al., "Rational Design of Polyion Complex Nanoparticles to Overcome Cisplatin Resistance in Cancer Therapy", Adv. Mater., 26, 931-936 (2014).

Yezhelyev, M. V. et al., "Proton-Sponge-Coated Quantum Dots for siRNA Delivery and Intracellular Imaging", J. Am. Chem. Soc., 130, 9006 (2008).

Yin, L. C. et al., "Trigger-Responsive Helical Polypeptides Capable of Toxicity Reduction and DNA Unpacking towards Non-Viral Gene Delivery", Angew. Chem. Int. Ed., 52, 9182 (2013).

Yoshii, H. et al., "CD4-Independent Human Immunodeficiency Virus Infection Involves Participation of Endocytosis and Cathepsin B", PLoS One, 6(4), e19352 (2011), 17 pgs.

Yuan, W. Z. et al. "Changing the Behavior of Chromophores from Aggregation-Caused Quenching to Aggregation-Induced Emission: Development of Highly Efficient Light Emitters in the Solid State," Adv. Mater., 22, 2159-2163 (2010).

Yuan, Y. et al, "A Targeted Theranostic Platinum(IV) Prodrug Containing a Luminogen with Aggregation-induced Emission (AIE) Characteristics for in situ Monitoring of Drug Activation", Chem. Comm., vol. 50, pp. 3868-3870 (2014).

Yuan, Y. et al, "Rational Design of Fluorescent Light-Up Probes Based on an AIE Luminogen for Targeted Intracellular Thiol Imaging", Chem. Comm., 2014, vol. 50, pp. 295-297 (published Jan. 11, 2014; published online Oct. 29, 2013).

Yuan, Y. et al, "Targeted Theranostic Prodrugs Based on an Aggregation-induced Emission (AIE) Luminogen for Real-time Dual-drug Tracking", Chem. Comm., vol. 50, pp. 11465-11468 (2014).

Yuan, Y. et al., "Specific Light-Up Bioprobe with Aggregation-Induced Emission and Activatable Photoactivity for the Targeted and Image-Guided Photodynamic Ablation of Cancer Cells," Angewandte Chemie International Edition, vol. 54, pp. 1780-1786 (Document published online Dec. 11, 2014) (2015).

Yuan, Y., et al., "Targeted Theranostic Platinum(IV) Prodrug with a Built-in AIE Light-up Apoptosis Sensor for Noninvasive Early Evaluation of Its Therapeutic Responses in situ", J. Am. Chem. Soc., 136(6), pp. 2546-2554 (2014).

Zacharias, D.A. et al., "Partitioning of Lipid-Modified Monomeric GFPs into Membrane Microdomains of Live Cells," Science, 296, 913-916 (2002).

Zhang, F. et al., "In Vivo MRI Tracking of Cell Invasion and Migration in a Rat Glioma Model," Molecular Imaging and Biology, 13, 695-701 (2011).

Zhang, J. et al., "Remarkable fluorescence change based on the protonation-deprotonation control in organic crystals", Chem. Comm., 49, 3878-3880 (2013).

Zhang, R, et al., "Fluorogen-Peptide Conjugates with Tunable Aggregation-Induced Emission Characteristics for Bioprobe Design", ACS Appl. Mater. Interfaces 2014, 6, 14302-14310.

Zhang, X. et al. "Aggregation induced emission-based fluorescent nanoparticles: fabrication methodologies and biomedical applications," J. Mater. Chem. B, 2, 4398-4414 (2014).

Zhang, Y. et al., "Panning and Identification of a Colon Tumor Binding Peptide from a Phage Display Peptide Library", Journal of Biomolecular Screening, 12, 429-435 (2007).

Zhao, L. et al., "Evaluation of Combination Chemotherapy: Integration of Nonlinear Regression, Curve Shift, Isobologram and Combination Index Analyses", Clin. Cancer Res., 10, 7994-8004 (2004).

Zhao, Y. S. et al., "Tumor alpha(nu)beta(3) integrin is a therapeutic target for breast cancer bone metastases", Cancer Res, 67, 5821-5830 (2007).

Zhao, Z., "Molecular anchors in the solid state: Restriction of intramolecular rotation boosts emission efficiency of luminogen aggregates to unity", Chem. Sci., 2011, 2, 672-675.

Zhao, Z.J. et al., "Aggregation-Induced Emission of Tetraarylethene Luminogens," Current Organic Chemistry, 14(18): 2109-2132 (2010).

Zhao, Z.J. et al., "Creation of Highly Efficient Solid Emitter by Decorating Pyrene Core with AIE-Active Tetraphenylethene Peripheries," Chem. Comm., 46: 2221-2223 (Feb. 26, 2010).

Zrazhevskiy, P. and X. Gao, "Quantum dot imaging platform for single-cell molecular profiling," Nat. Commun., 4, 1619 (2013).

Zrazhevskiy, P. et al., "Designing multifunctional quantum dots for bioimaging, detection and drug delivery", Chem. Soc. Rev., 39, 4326 (2010).

Zuluaga, M.-F. et al., "Combination of Photodynamic Therapy with Anti-Cancer Agents", Curr. Med. Chem., 15, 1655-1673 (2008).

Anderson, D.H., et al, "Electron spin resonance (E.S.R.) studies of a weakly coupled biradical", Journal Unavailable, 26 pp., Accession No. 1963: 18519—Abstract only.

Boddapati, S. V. et al., "Organelle-Targeted Nanocarriers: Specific Delivery of Liposomal Ceramide to Mitochondria Enhances Its Cytotoxicity in Vitro and in Vivo," Nano Lett., 8, 2559-2563 (2008).

(56) References Cited

OTHER PUBLICATIONS

Burger, H. et al., "Drug Transporters of platinum-based anticancer agents and their clinical significance", Drug Resist. Update, 14, 22-34 (2011).
Buytaert, E. et al., "Molecular effectors of multiple cell death pathways initiated by photodynamic therapy", Biochim. Biophys. Acta, 1776, 86-107 (2007).
CAS Registry No. 143646-22-4; STN Entry Date: Sep. 25, 1992; Phenol, 4-[[442-(4-hydroxyphenyl)-1,2-diphenylethenyl]phenyliphenylamino].
CAS RN 687617-15-8; STN Entry Date: May 31, 2004; 4,4',4'',4'''-(1,2-ethenediylidene)tetrakis[N,N-dimethyl-benzenamine].
Chen, Y. L. et al., "Switching Luminescent Properties in Osmium-Based β-Diketonate Complexes", Chem. Phys. Chem., 6, 2012-2017 (2005).
Copeland, R. A., Enzymes: A Practical Introduction to Structure, Mechanism, and Data Analysis, Wiley-VCH, New York, 2000.
Couleaud, P. et al., "Silica-based nanoparticles for photodynamic therapy applications", Nanoscale, 2 (7), 1083-1095 (2010).
Kay, M. A., "State-of-the-art gene based therapies: the road ahead", Nat. Rev. Genet., 12: 316-328 (May 2011).
Kostiainen, M. A. et al., "Optically triggered release of DNA from multivalent dendrons by degrading and charge-switching multivalency", Angew. Chem. Int. Ed., 46(40): 7600-7604 (2007).
Lee, S. Y. et al. "Luminous Butterflies: Efficient Exciton Harvesting by Benzophenone Derivatives for Full-Color Delayed Fluorescence OLEDs", Angew. Chem., Int. Ed., 53, 6402-6406 (2014).
Liang, J. et al., "Visual sensing with conjugated polyelectrolytes", Chem. Sci., 2013, 4, 1377-1394.
Lichtman, J. W. and J. A. Conchello, "Fluorescence microscopy," Nat Methods, 2, 910-919 (2005).
Lim, C. S., "Organelle-specific targeting in drug delivery and design," Adv. Drug Delivery Rev., 59, 697 (2007).
Lim, S. H. et al., "In Vitro and In Vivo Photocytotoxicity of Boron Dipyrromethene Derivatives for Photodynamic Therapy", J. Med. Chem., 53, 2865-2874 (2010).
Liu, J. N. et al., "Real-Time in Vivo Quantitative Monitoring of Drug Release by Dual-Mode Magnetic Resonance and Upconverted Luminescence Imaging," Angew. Chem. Int. Edit., 53, 4551-4555 (2014).
Liu, J.Z., et al., "Hyperbranched Poly(silylenephenylenes from Polycyclotrimerization of A2-Type Diyne Monomers: Synthesis, Characterization, Structural Modeling, Thermal Stability, and Fluorescent Patterning", Macromolecules, 40,7473-7486 (2007).
Lottner, C. et al., "Combined chemotherapeutic and photodynamic treatment on human bladder cells by hematoporphyrin-platinum(II) conjugates" Cancer Lett., 203, 171-180 (2004).
Lovell, J.F. et al., "Activatable Photosensitizers for Imaging and Therapy", Chem. Rev., 110, 2839-2857 (2010).
Lovell, J.F. et al., "Porphyrin FRET Acceptors for Apoptosis Induction and Monitorning", J. Am. Chem. Soc., 133, 18580-18582 (2011).
Luo, J. et al., "Aggregation-induced emission of 1-methyl-1,2,3,4,5-pentaphenylsilole", Chem. Commun., 37, 1740-1741 (2001).
Luo, K. et al., "Functional and biodegradable dendritic macromolecules with controlled architectures as nontoxic and efficient nanoscale gene vectors", Biotechnology Advances, 32, 818-830 (2014).
Ly, H.Q. et al., "Imaging in cardiac cell-based therapy: in vivo tracking of the biological fate of therapeutic cells," Nat Clin Pract Cardiovasc Med, 5, 96-102 (2008).
Ly, J. D. et al., "The mitochondrial membrane potential (Δψm) in apoptosis; an update" Apoptosis, 8, 115-128 (2003).
Maiti, S. et al., "Gemcitabine-Coumarin-Biotin Conjugates: A Target Specific Theranostic Anticancer Prodrug", J. Am. Chem. Soc., 135(11), pp. 4567-4572 (2013).
Marks, K.M. and G.P. Nolan, "Chemical labeling strategies for cell biology," Nat. Meth., 3, 591-596 (2006).
Marmur, E. S. et al. "A Review of Laser and Photodynamic Therapy for the Treatment of Nonmelanoma Skin Cancer," Dermatol. Surg., 30, 264-271 (2004).

Matsui, K. et al., "Quantitation and visualization of tumor-specific T cells in the secondary lymphoid organs during and after tumor elimination by PET," Nuclear medicine and biology, 31, 1021-1031 (2004).
Mei, J. et al. "Aggregation-Induced Emission: The Whole Is More Brilliant than the Parts," Adv. Mater., 26, 5429-5479 (2014).
Meng, F. H. et al., "Reduction-sensitive polymers and bioconjugates for biomedical applications", Biomaterials, 30, 2180-2198 (2009).
Min, Y. Z. et al., "Combating the Drug Resistance of Cisplatin Using a Platinum Prodrug Based Delivery System", Angew. Chem. Int. Ed., 51, 6742-6747 (2012).
Mintzer, M. A. and E. E. Simanek, "Nonviral Vectors for Gene Delivery", Chem. Rev., 109, 259-302 (2009).
Mo, R. et al. "Multistage pH-Responsive Liposomes for Mitochondrial-Targeted Anticancer Drug Delivery," Adv. Mater., 24, 3659-3665 (2012).
Moan, J. and K. Berg, "The photodegradation of porphyruns in cells can be used to estimate the lifetime of singlet oxygen," Photochem. Photobiol., 53, 549-553 (1991).
Modica-Napolitano, J. S. and J. R. Aprille, "Delocalized lipophilic cations selectively target the mitochondria of carcinoma cells", Advanced Drug Delivery Reviews, 49, 63-70 (2001).
Montagner, D. et al., "A Fluorescent Probe for Investigating the Activation of Anticancer Platinum(IV) Prodrugs Based on the Cisplatin Scaffold", Angew. Chem. Int. Ed., 52, 11785-11789 (2013).
Morgan, J. and A. R. Oseroff, "Mitochondria-based photodynamic anti-cancer therapy," Adv. Drug Delivery Rev., 49, 71-86 (2001).
Ngen, E. J. et al. "Evaluation of delocalized lipophilic cationic dyes as delivery vehicles for photosensitizers to mitochondria," Bioorg. Med. Chem., 17, 6631-6640 (2009).
Ntziachristos, V., "Fluorescence molecular imaging," Annu. Rev. Biomed. Eng., 8, 1-33 (2006).
Ogilby, P. R., "Singlet oxygen: there is indeed something new under the sun," Chemical Society Reviews, 39, 3181-3209 (2010).
Pacardo, D. B. et al., "Programmable nanomedicine" synergistic and sequential drug delivery systems Nanoscale, 7, 3381-3391 (2015).
Pack, D. W. et al., "Design and Development of Polymers for Gene Delivery", Nat. Rev. Drug Discov., 4, 581-593 (2005).
Peer, D. et al. "Nanocarriers as an emerging platform for cancer therapy," Nat. Nanotechnol., 2, 751-760 (2007).
Peng, C. L. et al., "Dual chemotherapy and photodynamic therapy in an HT-29 human colon cancer xenograft model using SN-38-loaded chlorin-core star block copolymer micelles", Biomaterials, 30 (2009): 3614-3625.
Peng, L. et al., "Photoactivatable Aggregation-Induced Emission Fluorophores with Multiple-Color Fluorophores with Multiple-Color Fluorescence and Wavelength-Selective Activation", Chem. Eur. J., 21, 4326-4332 (2015).
Piwnica-Worms, D. et al., "Permeation Peptide Conjugates for In Vivo Molecular Imaging Applications", Molecular Imaging, 5, 1-15 (2006).
Polavarapu, L. et al., "Biocompatible glutathione capped gold clusters as one- and two-photon excitation fluorescence contrast agents for live cells imaging", Nanoscale, 3, 429-434 (2011).
Prabha, S. and V. Labhasetwar, "Critical Determinants in PLGA/PLA Nanoparticle-Mediated Gene Expression", Pharm. Res., 21(2): 354-364 (2004).
Prasad, P. et al. "Mitochondria-Targeting Oxidovanadium(IV) Complex as a Near-IR Light Photocytotoxic Agent," Chem. Eur. J., 19, 17445-17455 (2013).
Pu, K. Y. et al. "Semiconducting Polymer Nanoprobe for In Vivo Imaging of Reactive Oxygen and Nitrogen Species," Angew Chem Int Edit, 52, 10325-10329 (2013).
Pu, K.-Y. and B. Liu, "Fluorescent Conjugated Polyelectrolytes for Bioimaging", Advanced Functional Materials, 21 (18), 3408-3423 (2011).
Pu, K.-Y. et al., "Conjugated Oligoelectrolyte Harnessed Polyhedral Oligomeric Silsesquioxane as Light-Up Hybrid Nanodot for Two-Photon Fluorescence Imaging of Cellular Nucleus", Advanced Materials, 22, 4186-4189 (2010).

(56) References Cited

OTHER PUBLICATIONS

Qin, A. J. et al., "Polytriazoles with Aggregation-Induced Emission Characteristics: Synthesis by Click Polymerization and Application as Explosive Chemosensors", Macromolecules, 42, 1421-1424 (2009).
Qin, W. et al. "Bright and Photostable Organic Fluorescent Dots with Aggregation-Induced Emission Characteristics for Noninvasive Long-Term Cell Imaging," Adv. Funct. Mater., 24, 635-643 (2014).
Rajaputra, P. et al. "Synthesis and in vitro biological evaluation of lipophilic cation conjugated photosensitizers for targeting mitochondria," Bioorg. Med. Chem., 21, 379-387 (2013).
Reinheckel, T. et al., "Towards Specific Functions of Lysosomal Cystein Peptidases: Phenotypes of Mice Deficient for Cathepsin B or Cathepsin L" Biol. Chem., 382, 735-741 (2001).
Rejmanova, P. and J. Kopecek, Polymers Containing Enzymatically Degradable Conds, 8a), Makromol. Chem., 184, 2009-2020 (1983).
Ruoslahti, E., "RGD and Other Recognition Sequences for Integrins", Annu. Rev. Cell Dev. Biol., 12, 697-715 (1996).
Santos, L. et al., "Non-Viral Gene Delivery to Mesenchymal Stem Cells: Methods, Strategies and Application in Bone Tissue Engineering and Regeneration," Current Gene Therapy, 11, 46-57 (2011).
Savić, R. et al. "Nanocontainers Distribute to Defined Cytoplasmic Organelles," Science, 300, 615-618 (2003).
Secret, E. et al., "Anionic porphyrin-grafted porous silicon nanoparticles for photodynamic therapy", Chem. Commun., 49, 4202-4204 (2013).
Shao, P. et al., "A convenient synthetic route to 2,5-dialkoxyterephthalaldehyde," Synthetic. Commun., 35, 49-53 (2005).
Shi, H. et al., "Fluorescent light-up probe with aggregation-induced emission characteristics for in vivo imaging of cell apoptosis", Org. Biomol. Chem. 2013, 11, 7289-7296.
Shi, H. et al., "Specific Detection of Integrin αvβ3 by Light-Up Bioprobe with Aggregation-Induced Emission Characteristics," J. Am. Chem. Soc., 134, 9569-9572 (2012).
Shibu, E. S. et al., "Nanomaterials formulations for photothermal and photodynamic therapy of cancer", Journal of Photochemistry and Photobiology C: Photochemistry Reviews, 15, 53-72 (2013).
Shim, M. S. and Y. J. Kwon, "Stimuli-responsive polymers and nanomaterials for gene delivery and imaging applications", Adv. Drug Deliver. Rev., 64, 1046-1059 (2012).
Shim, M. S. and Y. Xia, "A Reactive Oxygen Species (ROS)-Responsive Polymer for Safe, Efficient, and Targeted Gene Delivery in Cancer Cells", Angew. Chem. Int. Ed., 52, 6926-6929 (2013).
Siggel, U. et al. "Photophysical and photochemical properties of porphyrin aggregates," Ber. Bunseng. Phys. Chem., 100, 2070-2075 (1996).
Simon, H. U. et al., "Role of reactive oxygen species (ROS) in apoptosis induction," Apoptosis, 5, 415-418 (2000).
Skovsen, E. et al., "Lifetime and Diffusion of Singlet Oxygen in a Cell," J. Phys. Chem. B, 109, 8570-8573 (2005).
Smith, A.M. et al., "Bioconjugated quantum dots for in vivo molecular and cellular imaging," Advanced Drug Delivery Reviews, 60, 1226-1240 (2008).
Smith, M. Q. et al., "Multiplexed Fluorescence Imaging of Tumor Biomarkers in Gene Expression and Protein Levels for Personalized and Predictive Medicine," Curr. Mol. Med., 9, 1017-1023 (2009).
Smith, R. a J. et al., "Mitochondria-Targeted Small Molecule Therapeutics and Probes", Antioxidants & Redox Signaling, 15(12), 3021-3038 (2011).
Smith, R. A. J. et al., "Delivery of bioactive molecules to mitochondria in vivo," Proc. Natl. Acad. Sci., 100, 5407-5412 (2003).
Son, K. J. et al., "Photosensitizing Hollow Nanocapsules for Combination Cancer Therapy", Angew. Chem. Int. Ed., 2011, 50, 11968-11971.
Stephens, D.J. & V.J. Allan, "Light Microscopy Techniques for Live Cell Imaging," Science, 300, 82-86 (2003).
Sun, T. M. et al., "Simultaneous Delivery of siRNA and Paclitaxel via a "Two-in-One" Micelleplex Promotes Synergistic Tumor Suppression", ACS Nano, 5 (2), 1483-1494 (2011).
Sutton, E. et al., "Cell tracking with optical imaging," European Radiology, 18, 2021-2032 (2008).
Swedlow, J.R. et al., "Informatics and Quantitative Analysis in Biological Imaging," Science, 300, 100-102 (2003).
Swenson, E.S. et al., "Limitations of Green Fluorescent Protein as a Cell Lineage Marker," Stem Cells, 25, 2593-2600 (2007).
Szakacs, G. et al., "Targeting multidrug resistance in cancer", Nat. Rev. Drug Discov., 5 (3), 219-234 (2006).
Thigpen, J. T., "Phase III Trial of Doxorubicin With or Without Cisplatin in Advanced Endometrial Carcinoma: A Gynecologic Oncology Group Study", J. Clin. Oncol., 22 (19), 3902-3908 (2004).
Torchilin, V. P., "Recent approaches to intracellular delivery of drugs and DNA and organelle targeting," Annu. Rev. Biomed. Eng., 8, 343-375 (2006).
Truant, R. and B. R. Cullen, "The Arginine-Rich Domains Present in Human Immunodeficiency Virus Type 1 Tat and Rev Function as Direct Importin β-Dependent Nuclear Localization Signals", Molecular and Cellular Biology, 19(2), 1210-1217 (1999).
Tsien, R.Y., "The Green Fluorescent Protein," Annt. Rev. Biochem., 67, 509-544 (1998).
Umar, A. et al., "Future directions in cancer prevention", Nat. Rev. Cancer, 12, 835-848 (2012).
Uoyama, H. et al. "Highly efficient organic light-emitting diodes from delayed fluorescence", Nature, 492, 234-238 (2012).
Vaux, D. L. and S.J. Korsmeyer, "Cell death in development," Cell, 96, 245-254 (1999).
Velusamy, et al., "A New Series of Quadrupolar Type Two-Photon Absorption Chromophores Bearing 11, 12-Dibutoxydibenzo[a,c]-phenazine Bridged Amines; Their Applications in Two-Photon Fluorescence Imaging and Two-Photon Photodynamic Therapy", Adv. Funct. Mat., 2009, 19, 2388-2397.
Vuu, K. et al., "Gadolinium-Rhodamine Nanoparticles for Cell Labeling and Tracking via Magnetic Resonance and Optical Imaging," Bioconjugate Chemistry, 16, 995-999 (2005).
Wang, C. et al., "Imaging-Guided pH-Sensitive Photodynamic Therapy Using Charge Reversible Upconversion Nanoparticles under Near-Infrared Light", Advanced Functional Materials, 23 (24), 3077-3086 (2013).
Wang, D. and S. J. Lippard, "Cellular Processing of Platinum Anticancer Drugs", Nat. Rev. Drug Discov., 4, 307-320 (2005).
Wang, M. et al., "Convenient and Continuous Fluorometric Assay Method for Acetylcholinesterase and Inhibitor Screen Based on the Aggregation-Induced Emission", Anal. Chem., 81, 4444-4449 (2009).
Wang, S. and T. Hazelrigg, "Implications for bcd mRNA localization from spatial distribution of exu protein in Drosophila oogenesis," Nature, 369, 400-403 (1994).
Wang, X. R. et al., "Highly Selective Fluorogenic Multianalyte Biosensors Constructed via Enzyme-Catalyzed Coupling and Aggregation-Induced Emission," Journal of the American Chemical Society, 136, 9890-9893 (2014).
Wu, J. et al., "New sensing mechanisms for design of fluorescent chemosensors emerging in recent years", Chem. Soc. Rev., 40, 3483 (2011).
Wu, X. M. et al., "In Vivo and in Situ Tracking Cancer Chemotherapy by Highly Photostable NIR Fluorescent Theranostic Prodrug", J. Am. Chem. Soc., 2014, 136, 3579-3588.
Xiao, H. et al., "Co-delivery of daunomycin and oxaliplatin by biodegradable polymers for safer and more efficacious combination therapy", Journal of Controlled Release, 163 (3): 304-314 (2012).
Xu, J. et al., "Enhanced Photodynamic Efficiency Achieved via a Dual-Targeted Strategy Based on Photosensitizer/Micelle Structure," Biomacromolecules, 15, 4249-4259 (2014).
Xu, S. et al., "An Organic Molecule with Asymmetric Structure Exhibiting Aggregation-Induced Emission, Delayed Fluorescence, and Mechanoluminescence", Angew. Chem., Int. Ed., 54, 874-878 (2015).
Yan, L. et al., "Cell Tracing Techniques in Stern Cell Transplantation," Stem Cell Reviews, 3, 265-269 (2007).
Yde, C. W. and O. G. Issinger, "Enhancing cisplatin sensitivity in MCF-7 human breast cancer cells by down-regulation of Bcl-2 and cyclin D1", Int. J. Oncol., 29, 1397-1404 (2006).

(56) References Cited

OTHER PUBLICATIONS

Yogo, T. et al., "Highly Efficient and Photostable Photosensitizer Based on Bodipy Chromophore", J. Am. Chem. Soc., 127, 12162-12163 (2005).

Yoo, H.S. and T.G. Park, "Folate-receptor-targeted delivery of doxorubicin nano-aggregates stabilized by doxorubicin-PEG_folate conjugate", J. Control. Release, 100, 247-256 (2004).

Yoo, J.-O. and K.-S. Ha, Chapter Four—New Insights into the Mechanisms for Photodynamic Therapy-Induced Cancer Cell Death. International Review of Cell and Molecular Biology. Academic Press: 295, 139-174 (2012).

Yuan, H. et al., "Chemical Molecule-Induced Light-Activated System for Anticancer and Antifungal Activities", Journal of the American Chemical Society, 134 (32), 13184-13187 (2012).

Yuan, Y. et al. "Targeted and image-guided photodynamic cancer therapy based on organic nanoparticles with aggregation-induced emission characteristics," Chem. Commun., 50, 8757-8760 (2014).

Zhang, C. et al., "Imaging Intracellular Anticancer Drug Delivery by Self-Assembly Micelles with Aggregation-Induced Emission (AIE Micelles)", ACS Applied Materials & Interfaces, 6, 5212-5220 (2014).

Zhang, L. et al., "Aggregation-Induced Emission: A Simple Strategy to Improve Chemiluminescence Resonance Energy Transfer", Anal. Chem., 87, 1351-1357 (2015).

Zhang, Q. et al., "Efficient blue organic light-emitting diodes employing thermally activated delayed fluorescence", Nat. Photon., 8, 326-332 (2014).

Zhang, X. et al., "Facile Incorporation of Aggregation-Induced Emission Materials into Mesoporous Silica Nanoparticles for Intracellular Imaging and Cancer Therapy", ACS Appl. Mater. Interfaces, 5, 1943-1947 (2013).

Zhang, Y. et al., Multifunctional Gold Nanorods with Ultrahigh Stability and Tunability for In Vivo Fluorescence Imaging, SERS Detection, and Photodynamic Therapy, Angew. Chem. Int. Ed., 52, 1148-1151 (2013).

Zhao, E. G. et al., "A dual functional AEE fluorogen as a mitochondrial-specific bioprobe and an effective photosensitizer for photodynamic therapy", Chem. Commun., 50, 14451-14454 (2014).

Zhao, J. et al., "Triplet photosensitizers: from molecular design to applications", Chem. Soc. Rev., 42, 5323-5351 (2013).

Zhao, Z. et al., "Full emission color tuning in luminogens constructed from tetraphenylethene, benzo-2,1,3-thiadiazole and thiophene building blocks," Chemical Communications, 47, 8847-8849 (2011).

Zhu, C. et al., "Conjugated Polymer-Coated Bacteria for Multimodal Intracellular and Extracellular Anticancer Activity", Adv. Mater., 25(8): 1203-1208 (2013).

Zhu, C. et al., "Water-Soluble Conjugated Polymers for Imaging, Diagnosis, and Therapy", Chemical Reviews, 112 (8), 4687-4735 (2012).

Zhu, Z. et al., "Platinum(II)-Gadolinium(III) Complexes as Potential Single-Molecular Theranostic Agents for Cancer Treatment", Angew. Chem. Int. Ed., 53(48), 13225-13228 (2014).

Zou, T. T. et al., "Gold(III) Complexes Containing N-Heterocyclic Carbene Ligands: Thiol 'Switch-on' Fluorescent Probes and Anti-Cancer Agents," Angewandte Chemie International Edition, 52, 2930-2933 (2013).

Office Action dated Jul. 6, 2018 for U.S. Appl. No. 15/305,203, "Polymers and Oligomers With Aggregation-Induced Emission Characteristics for Imaging and Image-Guided Therapy".

Plurality, 2018, https://www.google.com/search?rlz=1C1GCEB_enUS775US775&ei=kz86W-LWO5G-zgK1wbywAw&q=plurality+definition&oq=plurality+definition&gs_l=psy-ab.3..016j0i22i30k1l4.14420.17093.0.17325.19.14.4.0.0.0.170.1406.9j5.14.0 .... 0 ... 1.1.64.psy-ab .. 1.18.1423 ... 0i20i264k1j0i 1 0k1 .0.8wIIWSzRr0c.

Plural, 2018, https://www.google.com/search?q=plural+definition&rlz=1C1GCEB_enUS775US775&oq=plural+de&aqs=chrome.0.0j69i57j0l4.2072j0j7&sourceid=chrome&ie=UTF-8.

Song, S., et al., "Microtubes and hollow microspheres formed by winding of nanoribbons from self-assemly of retraphenylethylene amide macrocyles", Chem Commun, 2014, 50, 15212-15215.

Wang, H., et al., "A novel aggregation-induced emission based fluorescent probe for an angiotensin converting enzyme (ACE) assay and inhibitor screenin", Chem. Commun., 2014, 50, 15075-15078.

Yuan, Y. et al, "Targeted Theranostic Prodrugs Based on an Aggregation-induced Emission (AIE) Luminogen for Real-time Dual-drug Tracking", Chemical Communications, vol. 50, pp. 11465-11468 (2014), Abstract only.

Final Office Action dated Feb. 25, 2019 for U.S. Appl. No. 15/305,203, "Polymers and Oligomers With Aggregation-Induced Emission Characteristics for Imaging and Image-Guided Therapy".

Polyethylenimine, 2019, https://en.wikipedia.org/wiki/Polyethylenimine.

\* cited by examiner

BIOCOMPATIBLE NANOPARTICLES WITH AGGREGATION INDUCED EMISSION CHARACTERISTICS AS FLUORESCENT BIOPROBES AND METHODS OF USING THE SAME FOR IN VITRO AND IN VIVO IMAGING

RELATED APPLICATIONS

This is a National Phase Application filed under 35 U.S.C. 371 as a national stage of PCT/CN2012/001227, filed Sep. 3, 2012, and claims priority benefit from U.S. Patent Application No. 61/573,097 filed Sep. 1, 2011 and U.S. Patent Application No. 61/685,227, filed Mar. 14, 2012, the content of each of which is hereby incorporated by reference in its entirety.

TECHNICAL FIELD

The present subject matter relates to the use of fluorescent organic compounds that exhibit aggregation induced emission. The fluorescent compounds can be formulated with a biocompatible polymer matrix resulting in uniformly sized nanoparticles exhibiting high degrees of brightness, low cytotoxicity, and selective uptake by cancer cells. Therefore, the fluorogen-loaded nanoparticles are useful as fluorescent bioprobes for in vitro and in vivo imaging.

BACKGROUND

The emergence of non-invasive live animal fluorescence imaging technology has opened new avenues for the development of cancer diagnosis and therapeutics. Fluorescence imaging probes with intense emission in the far-red/near-infrared (FR/NIR) region (>650 nm) are attracting increasing attention due to their ability to overcome the interferences of optical absorption, light scattering, and auto-fluorescence of biological media.

To date, a large variety of materials, including organic dyes, fluorescent proteins, and inorganic quantum dots (QDs), have been extensively studied for the purpose of FR/NIR fluorescence imaging. Organic dyes and fluorescent proteins, however, suffer from limited molar absorptivity and low photobleaching thresholds, while inorganic QDs are highly cytotoxic in an oxidative environment (A. M. Derfus et al., Nano Lett. 2004, 4, 11). This has greatly limited the application of organic dyes, fluorescent proteins, and QDs for in vitro and in vivo imaging.

Fluorescent nanoparticles, such as organic fluorophore-loaded nanoparticles, have recently emerged as a new generation of nanoprobes for bioimaging. They exhibit advantages such as synthetic versatility, low cytotoxicity, high photostability, and facile surface functionalization for specific targeting. For practical applications, brightly emissive nanoparticles are desirable for high contrast imaging. Ideally, the brightness of fluorophore-doped nanoparticles should be proportional to the number of encapsulated dye molecules. However, at high loading contents, π-conjugated fluorophores are prone to aggregate. The aggregate formation often quenches light emission, a common photophysical phenomenon known as aggregation caused quenching (ACQ). The ACQ effect has prevented the fabrication of nanoparticles with high degrees of brightness. Effort has been made to amplify the fluorescence of dyes with the ACQ property (U.S. Pat. No. 7,883,900). However, even after amplification, the fluorescence signal has been only mildly enhanced.

Most organic fluorophores including ethidium bromide (U.S. Pat. Nos. 4,729,947, 5,346,603, 6,143,151, and 6,143,153), Nile red (U.S. Pat. Nos. 6,897,297 and 6,465,208), fluorescamine (U.S. Pat. No. 4,203,967), o-phthaldialdehyde (U.S. Pat. Nos. 6,969,615 and 6,607,918), and Cyanine dyes (U.S. Pat. Nos. 5,627,027 and 5,410,030) are emissive only in their solution state. Emission is significantly quenched or completely quenched in aggregation states (i.e., high dye concentration state, film state, solid powder state, etc.). Therefore, the loading concentration of dyes in polymer particles can only reach moderate levels, resulting in limited achievable fluorescence intensity. Therefore, the practical applications of organic fluorophore-doped nanoparticles for in vitro and in vivo bioimaging are considerably limited.

Accordingly, there is a great need for the development of fluorescent bioprobes with high biological compatibility, strong photobleaching resistance, and efficient light emission for use in in vitro and in vivo imaging, particularly live animal imaging.

SUMMARY

The present subject matter relates to the development of a novel class of organic fluorogens with aggregation induced emission properties comprising one or more fluorophores and one or more chromophores. Fluorophores are not emissive in dilute solutions but can be induced to luminesce when aggregated via a mechanism of restriction of intramolecular rotation. In contrast, conventional chromophores exhibit aggregation caused quenching in the solid state. The present subject matter relates to the development of a structural design strategy for transforming conventional chromophores that exhibit aggregation caused quenching into efficient solid state emitters by covalent integration with fluorophores that exhibit aggregation induced emission properties. The resultant adducts inherit the aggregation induced emission properties. Due to the extension in the electronic conjugation, the resultant adducts display red-shifted emission, as compared to their parent chromophores, which exhibit aggregation caused quenching.

Therefore, the present subject matter relates to the development and use of a fluorogen that exhibits aggregation induced emission properties through the covalent bonding of conventional chromophores with aggregation induced emission fluorophores.

The present subject matter further relates to the development of fluorescent organic compounds that exhibit aggregation induced emission properties and can be used as fluorescent bioprobes for in vitro and in vivo imaging. Particularly, the present subject matter is directed to the development and use of fluorescent bioprobes comprising fluorogen-loaded nanoparticles comprising a fluorogen that exhibits aggregation induced emission properties, wherein the fluorogen comprises one or more chromophores conjugated with one or more aggregation induced emission fluorophores. The fluorogen-loaded nanoparticles have a fluorescence emission. Furthermore, the fluorogen comprises a backbone structure selected from the group consisting of:

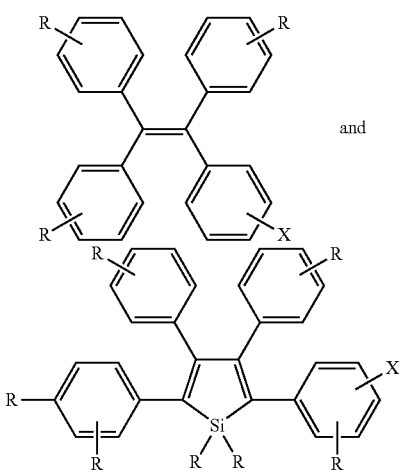

and wherein each R is independently selected from the group consisting of H, alkyl, unsaturated alkyl, heteroalkyl, cycloalkyl, heterocycloalkyl, aryl, heteroaryl, and an alkoxy group; and wherein X is one or more chromophores which can conjugate with one or more fluorophores.

A further aspect of the present subject matter is directed to the development and use of a fluorescent bioprobe comprising fluorogen-loaded nanoparticles comprising a fluorogen that exhibits aggregation induced emission properties and a biocompatible polymer matrix. Formulation of the fluorogens exhibiting aggregation induced emission properties with biocompatible polymer matrices yields uniformly sized nanoparticles with high degrees of brightness and low cytotoxicity.

Another embodiment of the present subject matter is directed to a method for preparing a fluorescent bioprobe comprising fluorogen-loaded nanoparticles comprising a fluorogen that exhibits aggregation induced emission properties and a biocompatible polymer matrix by (a) preparing a solution comprising an organic solvent, such as tetrahydrofuran and the fluorogen, (b) preparing an aqueous solution of a biocompatible polymer, (c) mixing the solution comprising the organic solvent and the fluorogen with the aqueous solution together and sonicating, and (e) removing the organic solvent to form the fluorogen-loaded nanoparticles.

The fluorogen-loaded nanoparticles herein show excellent cancer cell uptake and prominent tumor targeting ability, thereby making the nanoparticles useful as fluorescent bioprobes. The nanoparticles can be used as probes for long term cellular tracking with two-photon fluorescence imaging. Moreover, the fluorescence emission of the nanoparticles can be further amplified by two methods, taken alone or in combination. One method is the application of conjugated polymers as fluorescence resonance energy transfer (FRET) donors. The other method is the application of an arginine-glycine-aspartic acid (RGD) peptide as a biorecognition reagent functionalized on the nanoparticle surface, which can enhance the targeting ability of the nanoparticles to cancer cells. The combined application of the FRET donor and the RGD reagent greatly improves fluorescence contrast (high sensitivity) and selectivity to cancer cells for in vitro and in vivo imaging. Accordingly, the fluorogen-loaded nanoparticles formulated with the biocompatible polymer matrix can be used as fluorescent bioprobes for clinical cancer imaging and diagnostics.

Another embodiment of the present subject matter is directed to a fluorescent bioprobe comprising one or more fluorogens that exhibit aggregation induced emission properties, wherein the fluorogens comprise one or more aggregation induced emission fluorophore conjugated with one or more peptides; wherein the fluorogens have a fluorescence emission; and wherein the fluorogens comprise one or more backbone structures selected from the group consisting of:

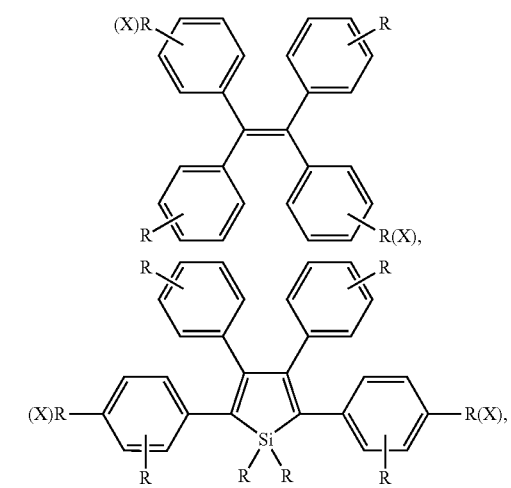

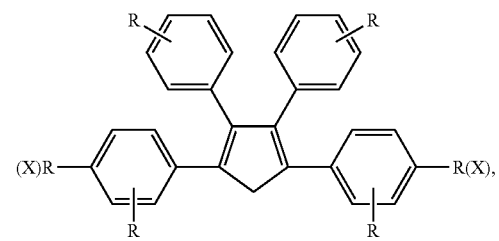

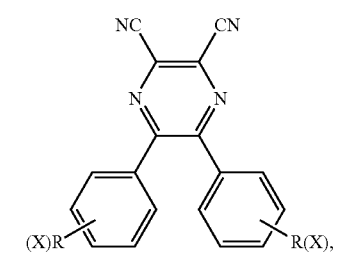

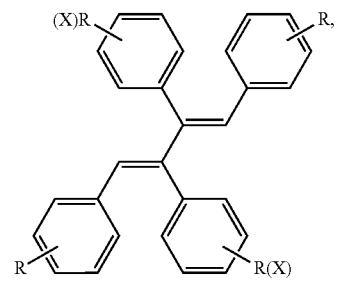

-continued

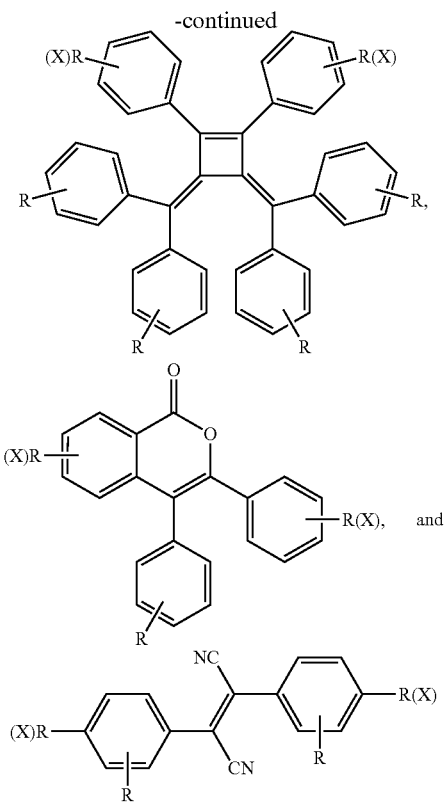

wherein each R is independently selected from the group consisting of H, alkyl, unsaturated alkyl, heteroalkyl, cycloalkyl, heterocycloalkyl, aryl, heteroaryl, a carboxyl group, an amino group, a sulfonic group, and an alkoxy group; wherein R(X) is a terminal functional group independently selected from the group consisting of $N_3$, $NH_2$, COOH, NCS, SH, alkyne, N-Hydroxysuccinimide ester, a maleimide, a hydrazide, a nitrone group, —CHO, —OH, a halide, and a charged ionic group; and wherein one or more peptides is conjugated to R(X).

Another embodiment of the present subject matter is related to a method for preparing the fluorescent bioprobe comprising: (a) preparing a peptide containing a terminal alkyne by solid-phase synthetic method; (b) preparing a DMSO solution of fluorogen azide; (c) mixing the fluorogen azide and the peptide together with $CuSO_4$ and sodium ascorbate; (d) crosslinking the fluorogens and the peptides by click chemistry; and (e) purifying by high performance liquid chromatography (HPLC) to form the fluorescent bioprobes.

The present subject matter is also directed to a method of cellular imaging comprising contacting target cells with the fluorescent bioprobes and detecting cellular imaging. In one embodiment, the target cells are cancer cells. The method of in vitro cellular imaging is conducted using either confocal laser scanning microscopy or two-photon fluorescence spectroscopy. The method of in vivo cellular imaging is conducted using a Maestro in vivo fluorescence imaging system.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

Various embodiments will be described in detail with reference to the accompanying drawings.

FIGS. 14A-B illustrate confocal images of MCF-7 cancer cells after incubation with (A) F37NP0 and (B) F37NP50 for 2 hours at 37° C. ([F37]=2 μM). The fluorescence of F37NPs was recorded under excitation at 543 nm with a 560 nm longpass barrier filter. The cell nuclei were stained by 4′,6-diamidino-2-phenylindole (DAPI). FIG. 14C illustrates a confocal image of MCF-7 cancer cells without incubation with F37NPs. FIG. 14D illustrates a 3D image of MCF-7 cancer cells incubated with F37NP50 for 2 hours at 37° C. The scale bar is the same for all images.

FIGS. 23A-B illustrate confocal images of HT-29 cancer cells after incubation with PFV/TPE-TPA-DCM co-loaded BSA nanoparticles for 2 hours upon excitation at (A) 532 nm and (B) 405 nm. The signals are collected above 650 nm for both (A) and (B). FIG. 23C illustrates a confocal image of HT-29 cancer cells after incubation with RGD-functionalized PFV/TPE-TPA-DCM co-loaded BSA nanoparticles for 2 hours. The imaging conditions for (C) are the same as those for (B).

FIG. 41(a) illustrates a PL spectra of AcDEVDK-TPE (5 µM) treated with caspase-3 and caspase-7 in presence and absence of caspases inhibitor. The amount of caspases is 1 µg in each assay. The concentration of caspase inhibitor is 10 µM. FIG. FIG. 41(b) illustrates the time-dependent emission spectra of AcDEVDK-TPE after adding caspase-3 and caspase-7 from 0 min to 120 min. $\lambda_{ex}$=312 nm.

FIG. 43(b) illustrates a plot of $(I-I_0)/I_0$ with respect to different concentrations of caspase-3/caspase-7 substrates. I=FL intensity at different concentrations of substrate. $I_0$=PL intensity of reactions without enzyme. $\lambda_{ex}$=312 nm.

DETAILED DESCRIPTION

Definitions

Figure 1:
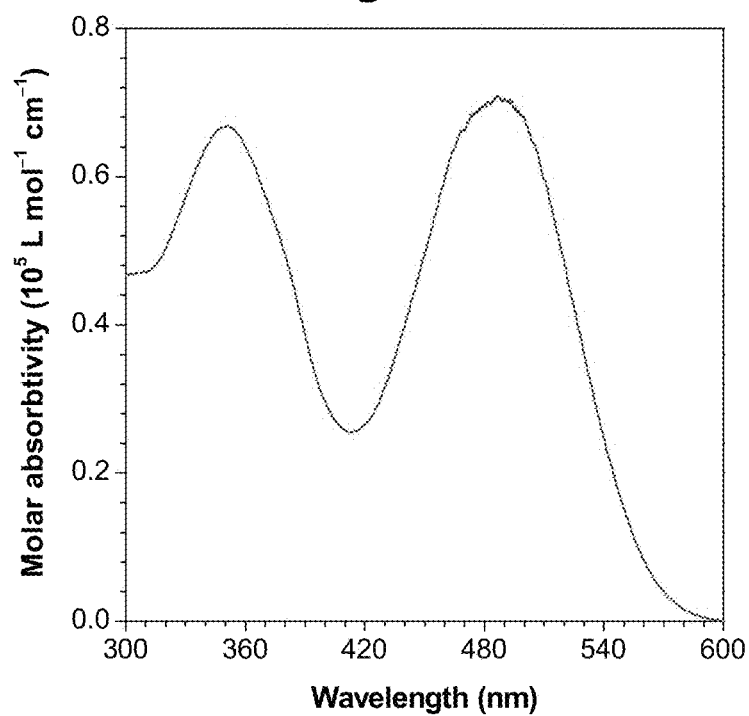
FIG. 1 illustrates the absorption spectrum of TPE-TPA-DCM (10 µM) in THF.

All technical and scientific terms used herein have the same meanings as commonly understood by someone ordinarily skilled in the art to which the present subject matter belongs. The following definitions are provided for clarity.

The phrase "π-conjugated fluorophore" as used herein refers to any fluorophore covalently bonded with alternating single and double bonds in an organic compound.

The term "$\lambda_{ex}$" as used herein refers to excitation wavelength.

The phrase "aggregation caused quenching" or "ACQ" as used herein refers to the phenomenon wherein the aggregation of π-conjugated fluorophores significantly decreases the fluorescence intensity of the fluorophores. The aggregate formation is said to "quench" light emission of the fluorophores.

The phrase "aggregation induced emission" or "AIE" as used herein refers to the phenomenon manifested by compounds exhibiting significant enhancement of light-emission upon aggregation in the amorphous or crystalline (solid) states whereas they exhibit weak or almost no emission in dilute solutions.

The term "alkyl" as used herein refers to a branched or unbranched hydrocarbon chain comprising a designated number of carbon atoms. For example, a $C_1$-$C_6$ straight or branched alkyl hydrocarbon chain contains 1 to 6 carbon atoms, and includes but is not limited to methyl, ethyl, propyl, iso-propyl, butyl, iso-butyl, tert-butyl, n-pentyl, n-hexyl, and the like. In one embodiment, the "alkyl" chain may be unsubstituted or is substituted by one or more substituents. It is also contemplated as with the scope of the present subject matter that "alkyl" may also refer to a hydrocarbon chain wherein any of the carbon atoms of the alkyl are optionally replaced with 0, NH, S, or $SO_2$. For example, carbon 2 of n-pentyl can be replaced with 0 to form propyloxymethyl.

The term "alkoxy group" refers to an alkyl group singularly bonded to an oxygen. The range of alkoxy groups is great, the simplest being methoxy ($CH_3O-$).

The term "aryl" refers to an aromatic carboxcyclic group having a single ring, for example a phenyl ring; multiple rings, for example biphenyl; or multiple condensed rings in which at least one ring is aromatic, for example naphthyl, 1,2,3,4-tetrahydronaphthyl, anthrl, or phenanthryl, which can be unsubstituted or substituted with one or more other substituents.

The phrase "arginine-glycine-aspartic acid" or "RGD" as used here in refers to the use of a RGD peptide as a biorecognition reagent functionalized on the nanoparticle surface, which can enhance the targeting ability of nanoparticles to cancer cells.

The term "biomacromolecule" as used herein refers to a very large molecule, such as a protein, nucleic acid, or polysaccharide of biological origin.

The phrase "bovine serum albumin" or "BSA" as used herein refers to a serum albumin protein derived from cows. It is used herein as a biocompatible polymer matrix.

The term "boc" as used herein refers to tert-Butyloxycarbonyl group which is a protective group for amine. It can be removed by a concentrated, strong acid, such as HCl or $CF_3COOH$.

The term "CHAPS" as used herein refers to 3-[(3-Cholamidopropyl)dimethylammonio]-1-propanesulfonate. It is a zwitterionic detergent used in the laboratory to solubilize biological macromolecules such as proteins.

The term "chromophore" as used herein refers to the part of a molecule responsible for its color.

The term "cycloalkyl" as used herein refers to an organic cyclic substituent comprising a designated number of carbon atoms. For example, a $C_3$-$C_8$ cycloalkyl contains three to eight carbon atoms forming a three, four, five, six, seven, or eight-membered ring, including, for example, a cyclopropyl, cyclobutyl, cyclopentyl, cyclohexyl, cycloheptyl, or cyclooctyl ring, and the like. In one embodiment, the "cycloalkyl" may be unsubstituted or is substituted by one or more substituents.

The term "DEVD" as used herein refers to Asp-Glu-Val-Asp peptide sequence which can be selectively and specifically cleaved by caspase-3/caspase-7.

The term "DEVD-AFC" as used herein refers to (7-amino-4-trifluoromethylcoumarin)-derived caspase substrate which is widely used for the fluorimetric detection of various caspase activities.

The term "DIEA" as used herein refers to N,N-Diisopropylethylamine, or Hünig's base. DIPEA or DIEA, is an organic compound and an amine. It is used in organic chemistry as a base.

The term "DMF" as used herein refers to dimethylformamide which is an organic compound with the formula $(CH_3)_2NC(O)H$. It is a common solvent for chemical reactions.

The term "EDTA" as used herein refers to ethylenediaminetetraacetic acid. It is a polyamino carboxylic acid and a colorless, water-soluble solid.

The phrase "emission intensity" as used herein refers to the magnitude of fluorescence/phosphorescence normally obtained from a fluorescence spectrometer or a fluorescence microscopy measurement.

The term "fluorogen" as used herein refers to a chemical compound that manifests luminescence.

The term "fluorophore" as used herein refers to a fluorescent chemical compound that can re-emit light upon light excitation. Fluorophores typically contain several combined aromatic groups, or plane or cyclic molecules with several π bonds. Fluorophores can be used as tracers in fluids, dyes for staining certain structures, substrates of enzymes, or probes or indicators. Fluorophores absorb light energy of a specific wavelength and re-emit light at a longer wavelength. The absorbed wavelengths, energy transfer efficiency, and time before emission depend on both the fluorophore structure and its chemical environment, as the molecule in its excited state interacts with surrounding molecules.

The phrase "fluorescence resonance energy transfer" or "FRET" as used herein refers to a mechanism describing energy transfer between two chromophores. A donor chromophore, initially in its electronic excited state, may transfer energy to an acceptor chromophore through nonradiative dipole-dipole coupling. The efficiency of this energy transfer is inversely proportional to the sixth power of the distance between donor and acceptor making FRET extremely sensitive to small distances.

The term "Fmoc" as used herein refers to a 9-Fluorenylmethyloxycarbonyl group which is a protective group for amines. It can be removed by a base, such as piperidine.

The term "HBTU" as used herein refers to O-Benzotriazole-N,N,N,N'-tetramethyl-uronium-hexafluoro-phosphate, which is commonly used for coupling reaction between acids and amines.

The term "heteroaryl" as used herein refers to a heterocycle in which at least one ring is aromatic. A heterocycle is a saturated, unsaturated, or aromatic carbocyclic group having a single ring, multiple rings, or multiple condensed rings, and having at least one hetero atom such as nitrogen, oxygen, or sulfur within at least one of the rings. A heteroaryl can also encompass a heteroalkyl or heterocycloakyl. In one embodiment, the "heteroaryl" may be unsubstituted or is substituted by one or more substituents.

The term "HOBt" as used herein refers to hydroxybenzotriazole which is an organic compound that is a derivative of benzotriazole. It is mainly used to suppress racemization and improve the efficiency of peptide synthesis.

The term "nanoparticle" as used herein refers to any microscopic particle or particle population having a mean diameter of about 100 or less nanometers (nm); less than about 90 nm; less than about 80 nm; less than about 70 nm; less than about 60 nm; less than about 50 nm in diameter; or having a mean diameter of from 1 nm to less than 100 nm; from 10 nm to less than 100 nm; from 20 nm to less than 100 nm; from 30 nm to less than 100 nm; from 40 nm to less than 100 nm; from 50 nm to less than 100 nm; from 10 nm to 90 nm; from 20 to 80 nm; or having a mean diameter of from 30 to 70 nm. In an embodiment, greater than 99% of the nanoparticles of a nanoparticle population have a mean diameter falling within a described range; greater than about 90% of the microparticles have a mean diameter falling within a described range; greater than about 80% of the microparticles have a mean diameter falling within a described range; greater than about 70% of the microparticles have a mean diameter falling within a described range; greater than about 60% of the microparticles have a mean diameter falling within a described range; greater than about 50% of the microparticles have a mean diameter falling within a described range; greater than about 40% of the microparticles have a mean diameter falling within a described range; greater than about 30% of the microparticles have a mean diameter falling within a described range; greater than about 20% of the microparticles have a mean diameter falling within a described range; or greater than about 10% of the microparticles have a mean diameter falling within a described range.

The term "NHS" as used herein refers to N-hydroxysuccinimide which is commonly used in organic chemistry or biochemistry as an activating reagent for carboxylic acids.

The phrase "peptide-conjugated fluorophore" as used herein refers to a fluorophore covalently connected with an interested peptide substrate.

The term "PIPES" as used herein refers to means piperazine-N,N'-bis(2-ethanesulfonic acid) which is a frequently used buffering agent in biochemistry.

The phrase "quantum dots" as used herein refers to a type of matter, i.e., a semiconductor, whose excitons are confined in all three spatial dimensions. Quantum dots can be semiconductors whose electronic characteristics are closely related to the size and shape of the individual crystal. Generally, the smaller the size of the crystal, the larger the band gap, i.e., the difference in energy between the highest valence band and the lowest conduction band becomes greater. Therefore more energy is needed to excite the dot, and concurrently, more energy is released when the crystal returns to its resting state.

The term "STS" as used herein refers to staurosporine, an anti-cancer treatment drug, which can induce cell apoptosis.

The term "TFA" as used herein refers to trifluoroacetic acid, a strong carboxylic acid widely used in organic chemistry.

The term "TIS" as used herein refers to triisopropylsilane, which is an organic compound. It is sometimes used for the peptide cleavage from resin in solid-phase synthesis.

The phrase "unsaturated alkyl" as used herein refers to a branched or unbranched unsaturated hydrocarbon chain comprising a designated number of carbon atoms, and may also be referred to as an "alkenyl." For example, a $C_2$-$C_6$ straight or branched alkenyl hydrocarbon chain contains 2 to 6 carbon atoms having at least one double bond, and includes but is not limited to ethenyl, propenyl, iso-propenyl, butenyl, iso-butenyl, tert-butenyl, n-pentenyl, n-hexenyl, and the like. It is also contemplated as within the scope of the present subject matter that "unsaturated alkyl" may also refer to an unsaturated hydrocarbon chain wherein any of the carbon atoms of said unsaturated alkyl are optionally replaced with O, NH, S, or $SO_2$. For example, carbon 2 of 4-pentene can be replaced with O to form (2-propene) oxymethyl. In one embodiment, the "unsaturated alkyl" may be unsubstituted or is substituted by one or more substituents.

The term "a" or "an" as used herein includes the singular and the plural, unless specifically stated otherwise. Therefore, the term "a," "an," or "at least one" can be used interchangeably in this application.

Throughout the application, descriptions of various embodiments use the term "comprising;" however, it will be understood by one of skill in the art, that in some specific instances, an embodiment can alternatively be described using the language "consisting essentially of" or "consisting of."

For the purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Fluorogen-Loaded Nanoparticles as Fluorescent Bioprobes

In one aspect, the present subject matter relates to a fluorescent bioprobe comprising fluorogen-loaded nanoparticles comprising a fluorogen that exhibits aggregation induced emission properties, wherein the fluorogen comprises one or more chromophores conjugated with one or more aggregation induced emission fluorophores; wherein the fluorogen-loaded nanoparticles have a fluorescence emission; and wherein the fluorogen comprises a backbone structure selected from the group consisting of:

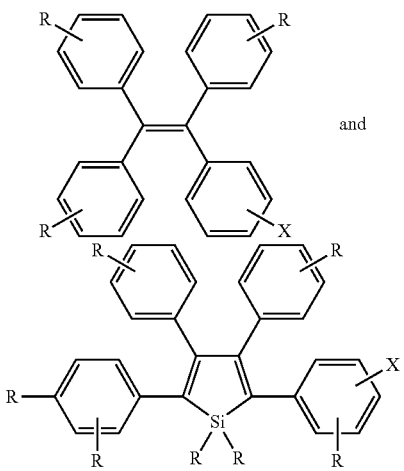

wherein each R is independently selected from the group consisting of H, alkyl, unsaturated alkyl, heteroalkyl, cycloalkyl, heterocycloalkyl, aryl, heteroaryl, and an alkoxy group; and wherein X is one or more chromophore which can conjugate with one or more fluorophores.

The fluorophores, such as tetraphenylethene (TPE), are non-emissive in dilute solutions but are induced to luminesce intensely when aggregated due to their aggregation induced emission properties. Aggregation induced emission of the fluorophores can be carried out via a mechanism of restriction of intramolecular rotation.

The chromophores, such as 2-(4H-pyran-4-ylidene)malononitrile (DCM), exhibit weak to no emission in the solid aggregated state due to aggregation caused quenching.

Through a structural design strategy, conventional chromophores that exhibit aggregation caused quenching are transformed to efficient solid emitters by covalent integration with fluorophores that exhibit aggregation induced emission. Due to extension in the electronic conjugation, the resultant adducts inherit the aggregation induced emission properties and display red-shifted emission, in contrast to their aggregation caused quenching parents.

Therefore, the present subject matter relates to fluorogen-loaded nanoparticles constructed through covalent bonding of conventional chromophores, such as triphenylamine (TPA), 4H-pyrans, and perylene, with an aggregation induced emission fluorophore, such as tetraphenylethene (TPE).

In one embodiment, the fluorogen is TPE-TPA-DCM which comprises the chromophores TPA and DCM and the aggregation induced emission fluorophore TPE. TPE-TPA-DCM has the following chemical structure.

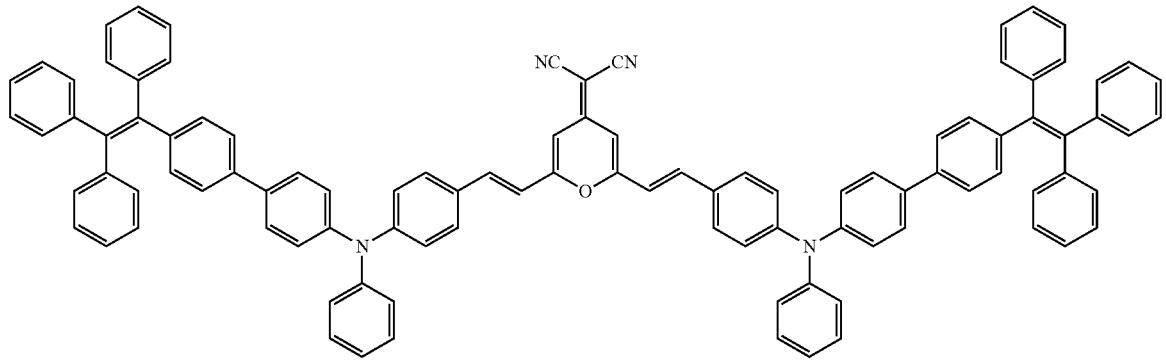

TPE-TPA-DCM

Another aspect of the present subject matter relates to a fluorescent bioprobe comprising fluorogen-loaded nanoparticles comprising a fluorogen that exhibits aggregation induced emission properties, wherein the fluorogen-loaded nanoparticles have a fluorescence emission; and wherein the fluorogen comprises a backbone structure selected from the group consisting of:

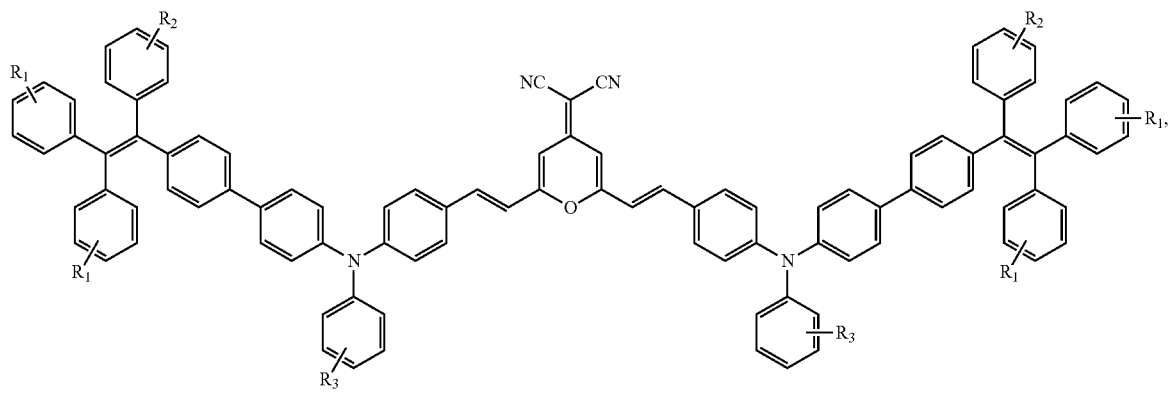

-continued
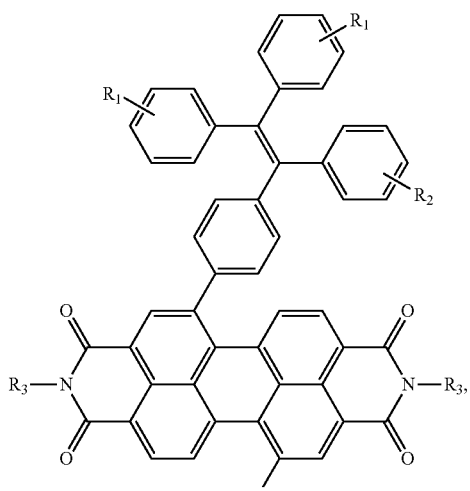
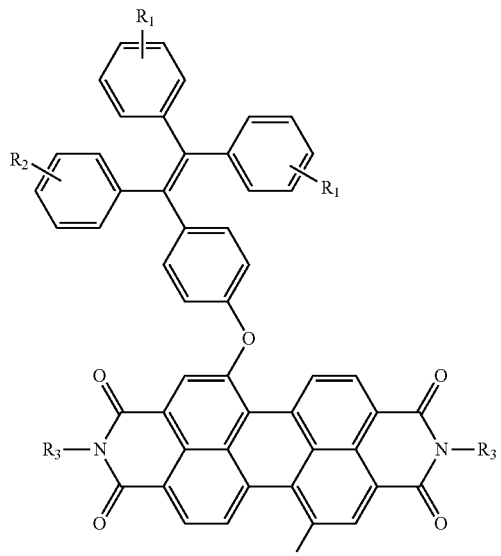
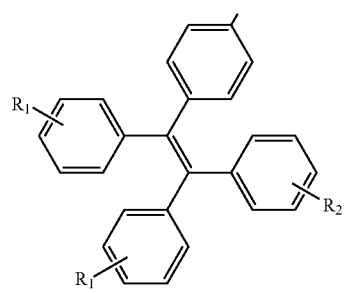
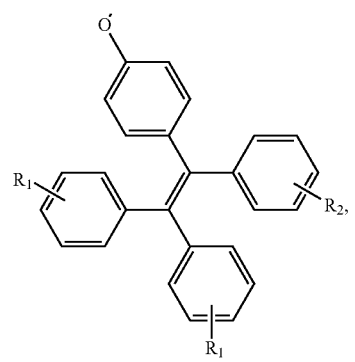
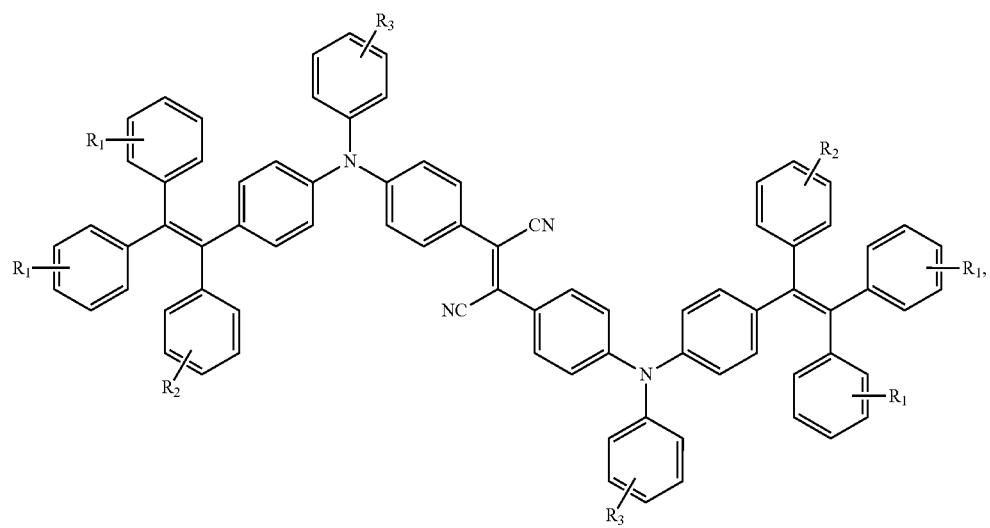

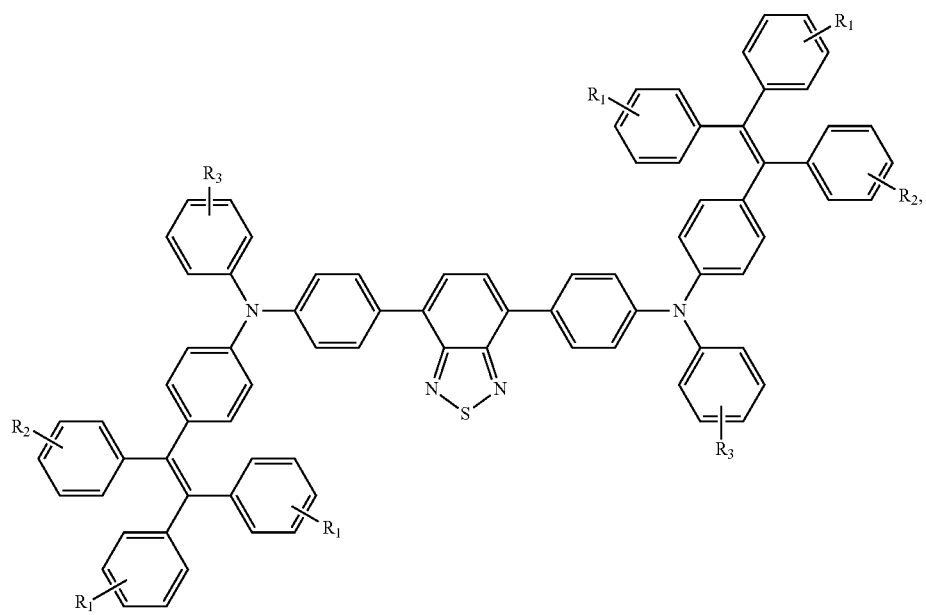
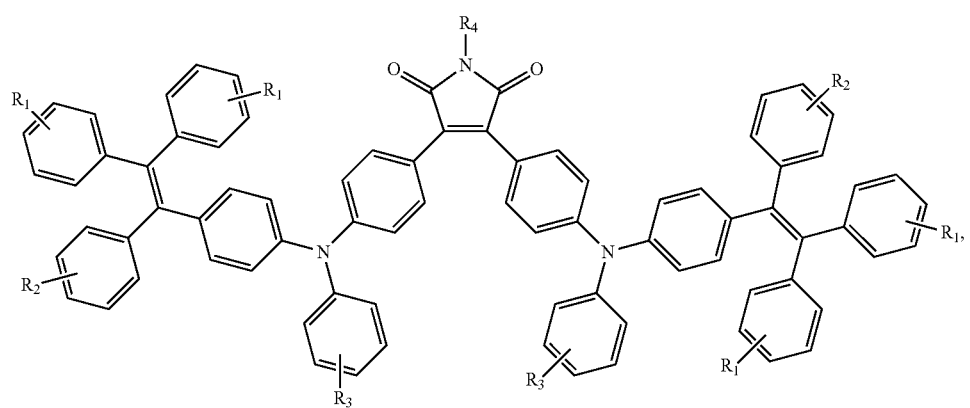
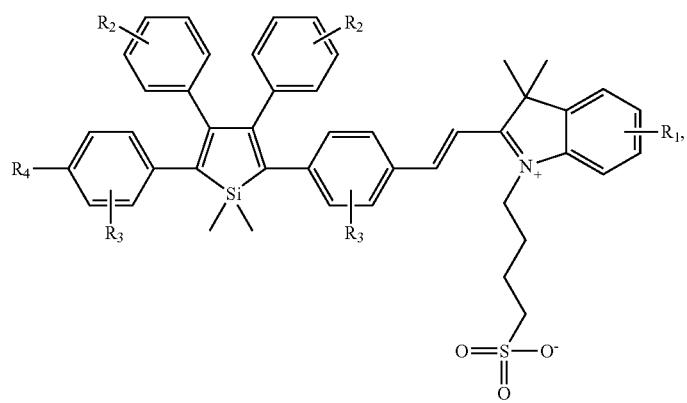

-continued
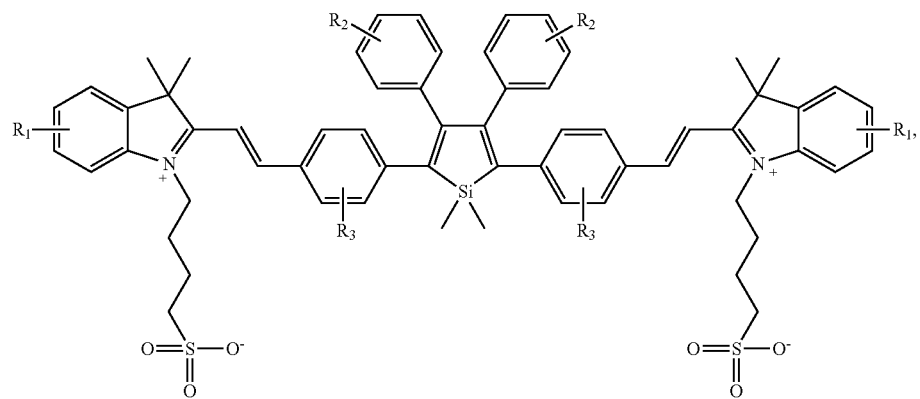
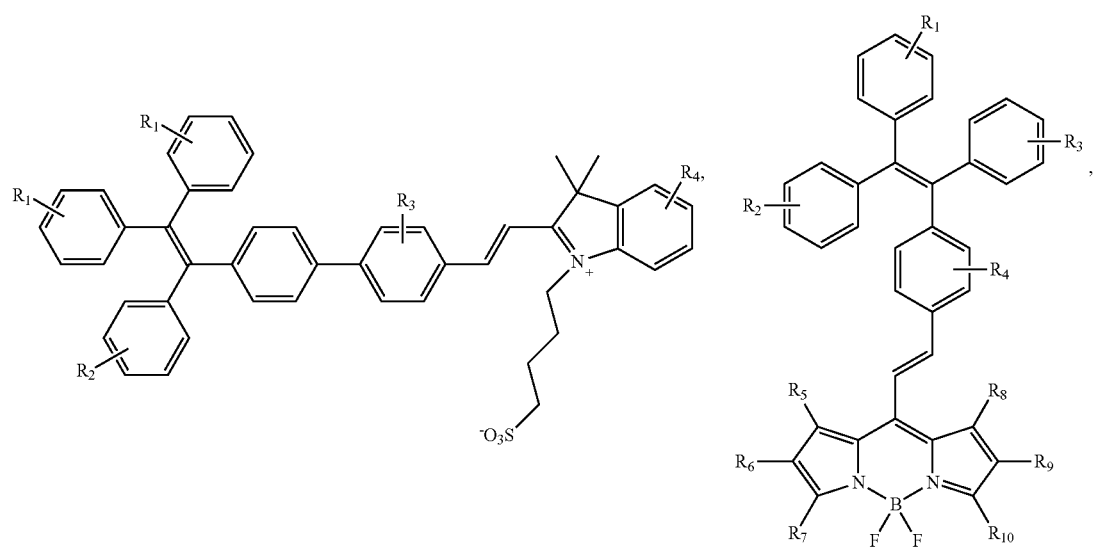
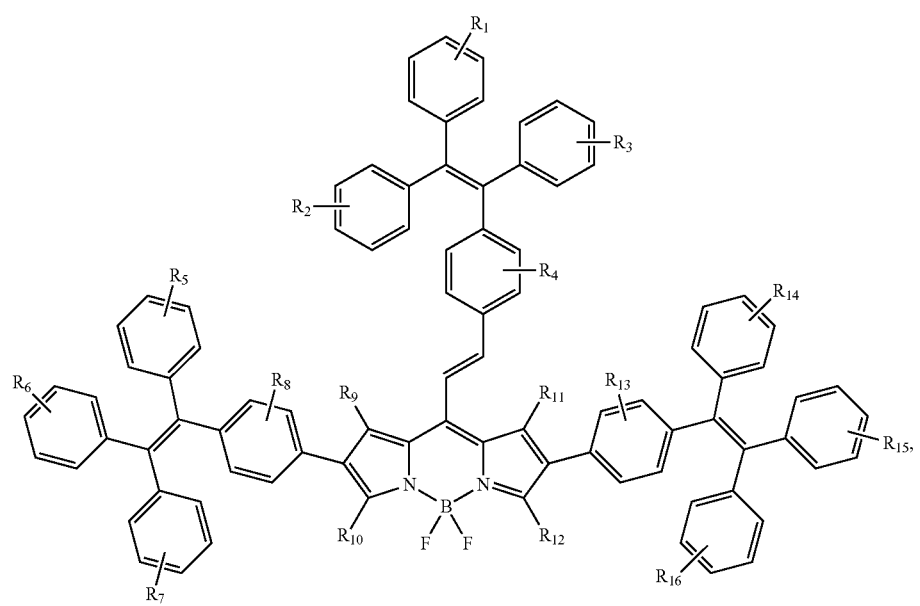

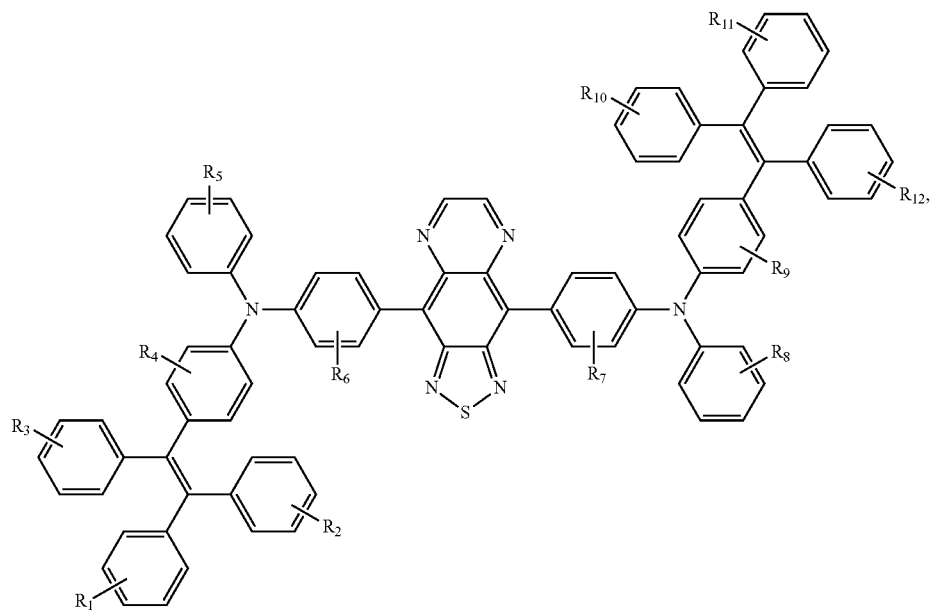
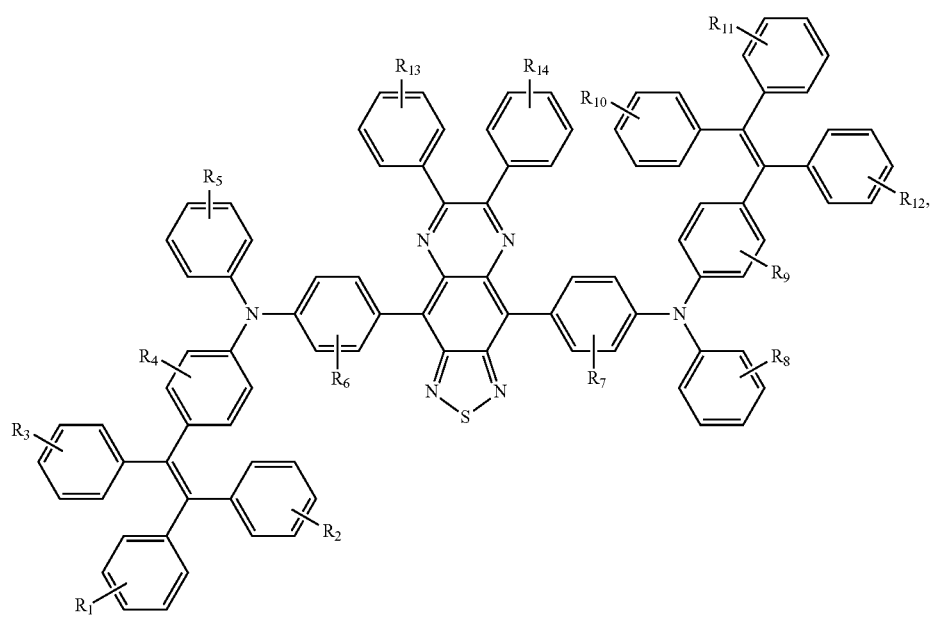

-continued

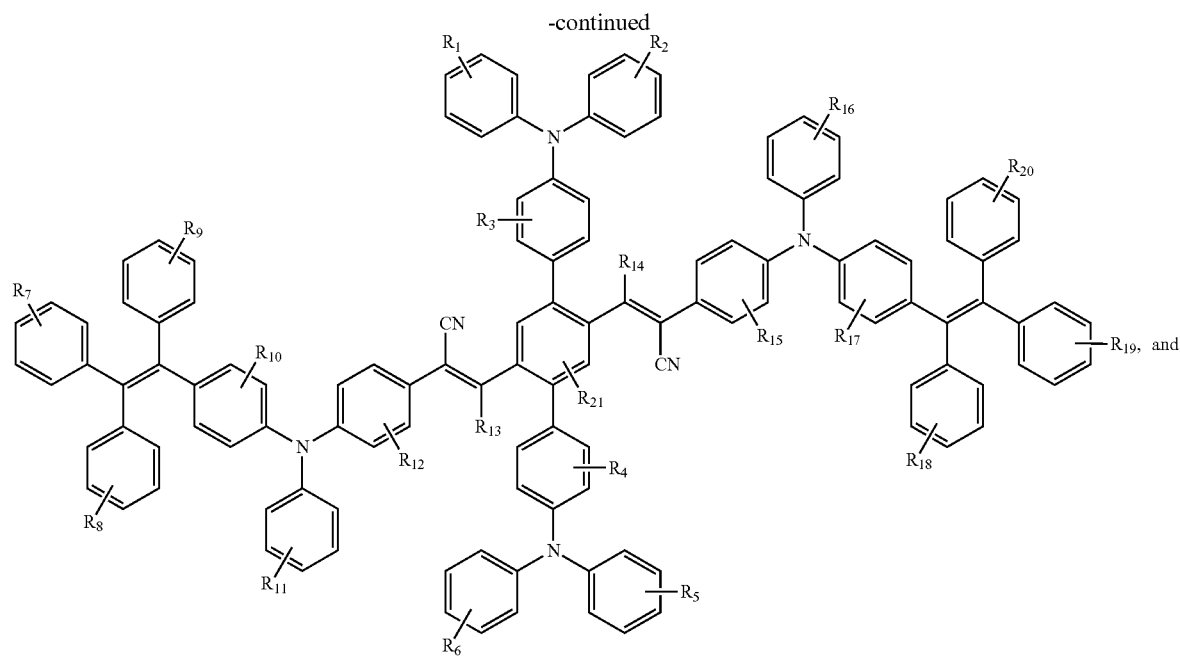

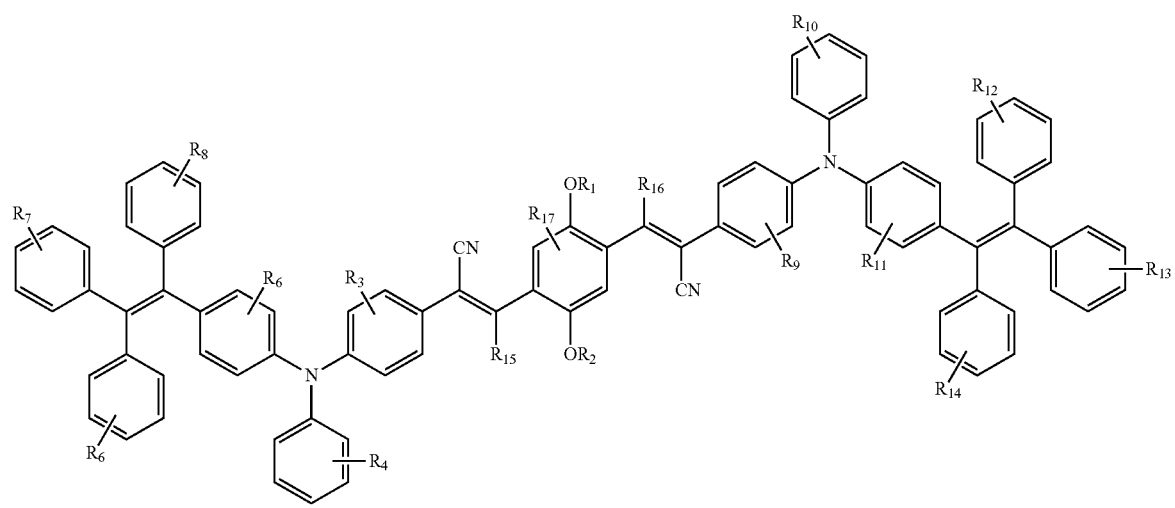

wherein each $R_1$, $R_2$, $R_3$, and $R_4$ is independently selected from the group consisting of H, alkyl, unsaturated alkyl, heteroalkyl, cycloalkyl, heterocycloalkyl, aryl, heteroaryl, and an alkoxy group.

In another aspect of the present subject matter, each $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$, above may be substituted or unsubstituted, and is independently selected from the group consisting of H, $C_nH_{2n+1}$, $OC_nH_{2n+1}$, $C_6H_5$, $C_{10}H_7$, $C_{12}H_9$, $OC_6H_5$, $OC_{10}H_7$, and $OC_{12}H_9$; wherein n=0 to 20, and the compounds exhibit aggregation induced emission.

In another embodiment, anyone of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ further comprises a terminal functional group independently selected from the group consisting of $N_3$, $NH_2$, COOH, NCS, SH, alkyne, N-Hydroxysuccinimide ester, a maleimide, a hydrazide, a nitrone group, —CHO, —OH, a halide, and a charged ionic group; wherein a peptide independently selected from the group consisting of a biorecognition peptide and a cell penetrating peptide is conjugated to the terminal functional group.

In one embodiment, anyone of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ comprises one or more charged ionic groups in order to endow the fluorescent bioprobe with water solubility. In a further embodiment, the charged ionic groups include but are not limited to —COOH, quaternized amine, $SO_3^-$, and $PO_3^-$.

In one embodiment, the biorecognition peptide is selected from the group consisting of a cyclic-RGD peptide and a DEVD peptide substrate. In another embodiment, the cell penetrating peptide is trans-activator of transcription peptide (Tat).

In one embodiment, TPA-DCM and TPE-TPA-DCM were prepared according to the reaction scheme shown below.

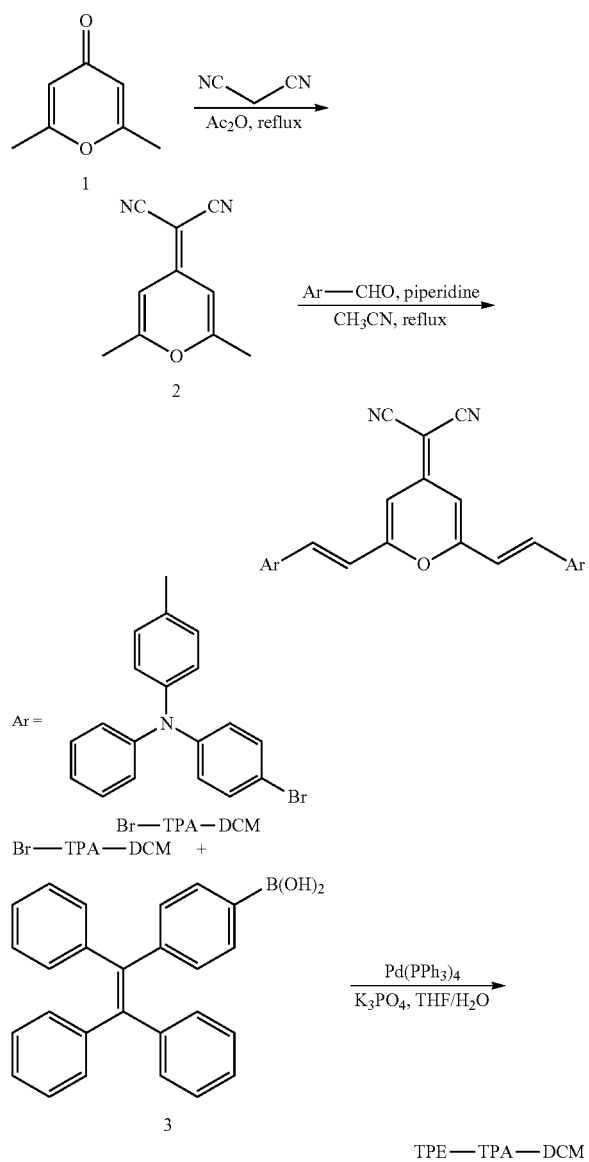

TPE-TPA-DCM was synthesized by Suzuki coupling between Br-TPA-DCM and 4-(1,2,2-triphenylvinyl)phenylboronic acid (3) using Pd(PPh$_3$)$_4$ as a catalyst under basic conditions. Formation of the trans isomer is favored in the reaction due to the thermodynamic stability of the trans conformation and the steric hindrance hampering the formation of the cis structure.

Figure 2:
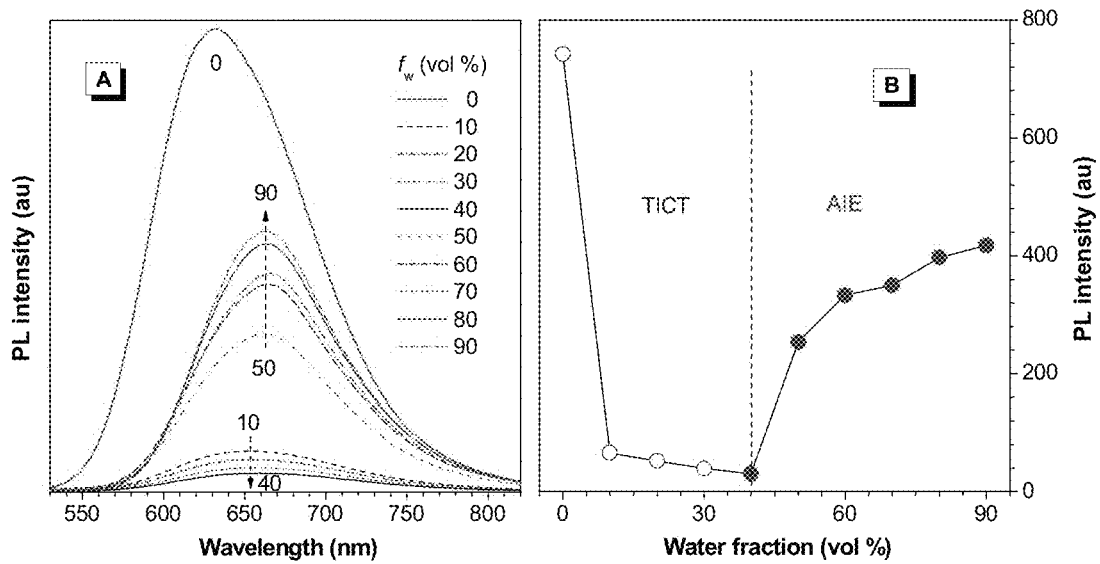
FIG. 2A illustrates a photoluminescence (PL) spectra of TPE-TPA-DCM (10 µM) in THF/water mixtures with different water fractions ($f_w$) (vol %).
FIG. 2B illustrates the photoluminescence (PL) spectra of TPE-TPA-DCM (10 µM) in THF/water mixtures relative to increasing water fractions ($f_w$) (vol %) at a constant wavelength of 480 nm.

TPE is a paradigm of an aggregation induced emission fluorophore. Attaching TPE units to TPA-DCM endows the resultant adduct TPE-TPA-DCM with aggregation induced emission properties, while retaining the twisted intermediate charge transfer (TICT) feature of its parent, TPA-DCM. As shown in FIG. 2A, TPE-TPA-DCM exhibits an emission maximum at 633 nm in THF, which is 13 nm red-shifted from that of TPA-DCM. As shown in FIG. 2B, with the gradual addition of water into THF, the emission of TPE-TPA-DCM is dramatically weakened and the emission color is bathochromically shifted, due to the increase in the solvent polarity and the transformation to the TICT state. Then at f$_w$≈50 vol %, the intensity of the light emission begins to increase and continues to increase as more water is added. Meanwhile, in FIG. 2A, the emission maximum is gradually red-shifted to ~660 nm when f$_w$ reaches 90 vol %. Therefore, in one embodiment, TPE-TPA-DCM is a fluorogen with both TICT and AIE characteristics.

In one aspect, the fluorogen-loaded nanoparticles are 1 nm to 100,000 nm in size. I another aspect, the nanoparticles are uniformly sized with high brightness and low cytotoxicity.

In another embodiment, the present subject matter relates to the fluorogen-loaded nanoparticles further comprising a biocompatible polymer matrix. The biocompatible polymer matrix can comprise animal serum albumin, 1,2-distearoyl-sn-glycero-3-phosphoethanolamine (DSPE), polyethylene glycol (PEG), polyfluorene vinylene (PFV), or mixtures thereof. Preferably, the biocompatible polymer matrix comprises bovine serum albumin (BSA), DSPE-PEG, DSPE-PEG-Folate, PFV, or any combination thereof. DSPE-PEG can include but is not limited to 1,2-distearoyl-sn-glycero-3-phosphoethanolamine-N-[methoxy(polyethylene glycol)-2000] (DSPE-PEG$_{2000}$). DSPE-PEG-Folate can include but is not limited to 1,2-distearoyl-sn-glycero-3-phosphoethanolamine-N-[folate(polyethylene glycol)-5000]-Folate (DSPE-PEG$_{5000}$-Folate).

In one aspect, the fluorogen-loaded nanoparticles further comprising a biocompatible polymer matrix are uniformly sized nanoparticles with high brightness and low cytotoxicity.

In another embodiment, the TPE-TPA-DCM loaded BSA nanoparticles have excellent cancer cell uptake and prominent tumor targeting ability in vivo due to their enhanced permeability and retention effect, as discussed further below.

Method for the Preparation of Fluorogen-Loaded Nanoparticles

Another embodiment of the present subject matter is a method for the preparation of the fluorogen-loaded nanoparticles further comprising a biocompatible polymer matrix. In another embodiment, the fluorogen-loaded nanoparticles are used as fluorescent bioprobes. First, a solution comprising an organic solvent and the fluorogen is prepared. The organic solvent is preferably one with a low boiling point, such as tetrahydrofuran (THF). Then an aqueous solution of a biocompatible polymer is prepared. The THF solution and the aqueous solution are mixed together and sonicated. Then the fluorogen and the biocompatible polymer can be crosslinked. However, if the biocompatible polymer is DSPE-PEG, crosslinking is not required. Finally, THF is removed to form the fluorogen-loaded nanoparticles further comprising a biocompatible polymer matrix.

Figure 3:
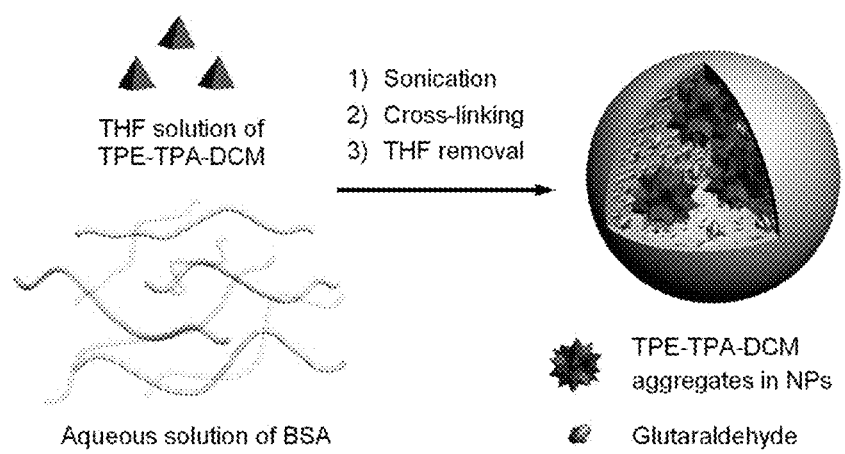
FIG. 3 illustrates the fabrication of bovine serum albumin (BSA) nanoparticles loaded with TPE-TPA-DCM.

FIG. 3 illustrates a method for the preparation of fluorogen-loaded BSA nanoparticles, wherein the fluorogen is TPE-TPA-DCM, and the biocompatible polymer matrix is BSA. Upon addition of the TPE-TPA-DCM solution in THF to the aqueous solution of BSA, the TPE-TPA-DCM molecules aggregate and entangle with the hydrophobic domains of the BSA chains. BSA is gradually phase-separated, accompanying its hybridization with the hydrophobic fluorogen. Fluorogen-loaded BSA nanoparticles are formed instantly upon sonication. The BSA matrix is knitted together by glutaraldehyde, an amine-reactive homobifunctional cross-linker. THF is then removed and the cross-linked nanoparticles are further purified by filtration through a microfilter, followed by washing with Milli-Q water. The zeta potential of the purified Nanoparticles is −29 mV in aqueous suspension, suggesting that the nanoparticles are stabilized by outer layers of ionized carboxylic groups.

In a further aspect the fluorogen-loaded nanoparticles are fabricated with any molecule that can specifically target cancer cells or can amplify the fluorescence imaging. In one embodiment, the fluorescence emission of the nanoparticles is further amplified by two methods, either taken alone or in combination. One method is the application of conjugated polymers as fluorescence resonance energy transfer (FRET) donors. The other method is the application of an arginine-glycine-aspartic acid (RGD) peptide as a biorecognition reagent functionalized on the nanoparticle surface, which can enhance the targeting ability of the nanoparticles to cancer cells. The combined application of the FRET donor and the RGD reagent greatly improves fluorescence contrast (high sensitivity) and selectivity to cancer cells for in vitro and in vivo imaging. Accordingly, the fluorogen-loaded nanoparticles formulated with the biocompatible polymer matrix can be used as fluorescent bioprobes for clinical cancer imaging and diagnostics.

Table 1 shows the encapsulation efficiencies (EE) and average sizes of the AIE-active fluorogen-loaded nanoparticles prepared at different feeding ratios of TPE-TPA-DCM. The fluorogen loading is increased with an increase in the fluorogen feeding. The EE of the fluorogen is >85 wt % when the TPE-TPA-DCM feeding ratio is <1 wt %, while a decrease in the EE is observed when the fluorogen feeding ratio is increased to >1 wt %. The average size of the pure BSA nanoparticles without the AIE fluorogen encapsulation is 97.1 nm with a narrow size distribution or polydispersity (PDI=0.065). The average size of the BSA nanoparticles is increased from 98.8 nm to 148.1 nm when the fluorogen loading is increased from 0.25 wt % to 3.07 wt %. In comparison, the average size of the bare TPE-TPA-DCM nanoparticles prepared from an aqueous mixture with $f_w$=90 vol % is measured to be 307.3 nm by laser light scattering (LLS) with a broad size distribution (PDI=0.279).

TABLE 1

Characteristics of the BSA NPs loaded with TPE-TPA-DCM

| TPE-TPA-DCM feeding ratio [wt %] [a] | TPE-TPA-DCM loading ratio [wt %] [b] | Encapsulation efficiency [wt %] | Size [nm] [c] (PDI [d]) |
|---|---|---|---|
| 0 | 0 | | 97.1 (0.065) |
| 0.25 | 0.25 | 100 | 98.8 (0.089) |
| 0.5 | 0.49 | 98.7 | 124.8 (0.125) |
| 1.0 | 0.86 | 85.6 | 124.7 (0.110) |
| 2.5 | 1.87 | 74.8 | 141.3 (0.180) |
| 5.0 | 3.07 | 61.4 | 148.1 (0.161) |

[a] The ratio of the weight of TPE-TPA-DCM to that of BSA in the feed mixture.
[b] The ratio of the weight of loaded TPE-TPA-DCM to that of BSA matrix in the nanoparticles.
[c] Average diameter of the nanoparticles measured by laser light scattering (LLS).
[d] Polydispersity index (PDI).

Figure 4:
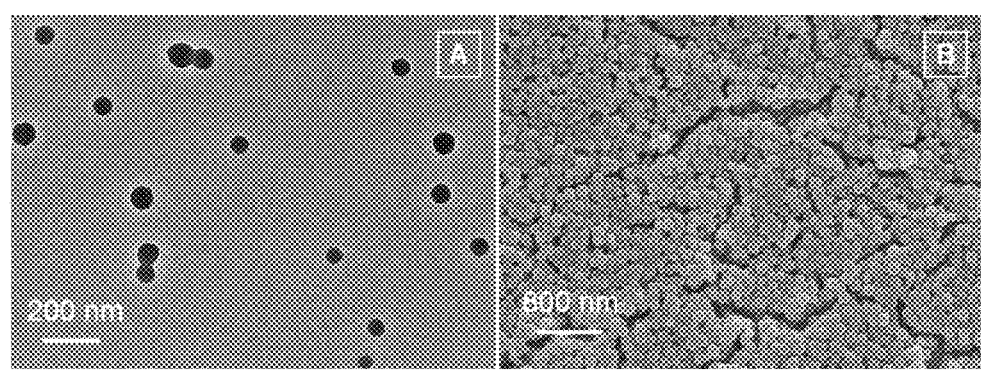
FIG. 4A illustrates transmission electron microscopy (TEM) images of the -TPE-TPA-DCM-loaded BSA nanoparticles.
FIG. 4B illustrates field-emission scanning electron microscopy (FESEM) images of the -TPE-TPA-DCM-loaded BSA nanoparticles.
Figure 5:
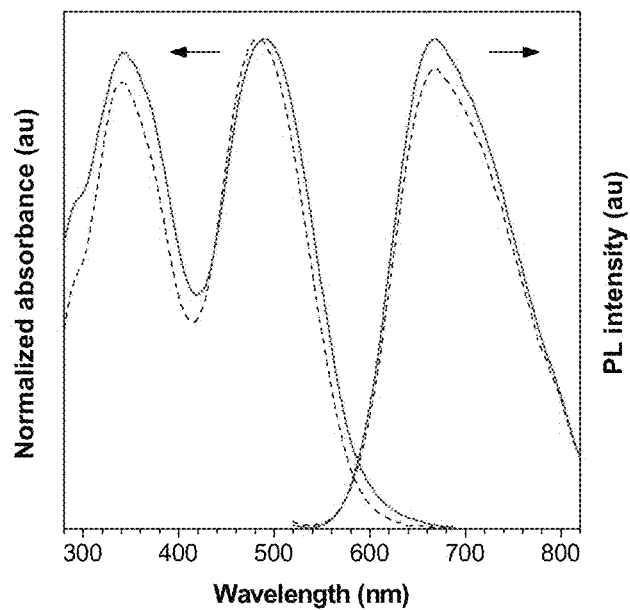
FIG. 5 is a diagram illustrating the normalized UV-vis absorption and photoluminescence (PL) emission spectra of the fluorogen-loaded BSA nanoparticles (with TPE-TPA-DCM loading of 0.86%; -solid line) and the bare TPE-TPA-DCM nanoparticles (dashed line) in water.

The transmission electron microscopy (TEM) and field-emission scanning electron microscopy (FESEM) images of the fluorogen-loaded BSA nanoparticles with 0.86% loading of TPE-TPA-DCM are shown in FIG. 4 as examples. The images indicate that the AIE-active fluorogen-loaded nanoparticles have a spherical shape and smooth surface with an almost uniform size of around 90 nm. The size is smaller than that obtained from the LLS measurement (124.7 nm), due to the shrinkage of the BSA nanoparticles in the ultra-dry state under the high vacuum in the TEM and FESEM chambers. FIG. 5 shows the absorption and emission spectra of the AIE-active fluorogen-loaded BSA nanoparticles with 0.86% fluorogen loading and the bare TPE-TPA-DCM nanoparticles suspended in water. The fluorogen-loaded BSA nanoparticles show two absorption maxima at 360 and 505 nm, while those of the bare TPE-TPA-DCM nanoparticles are slightly blue-shifted, appearing at 359 and 497 nm. The emission maximum of the fluorogen-loaded BSA nanoparticles is located at 668 nm, similar to that of the bare TPE-TPA-DCM nanoparticles in water.

Figure 6:
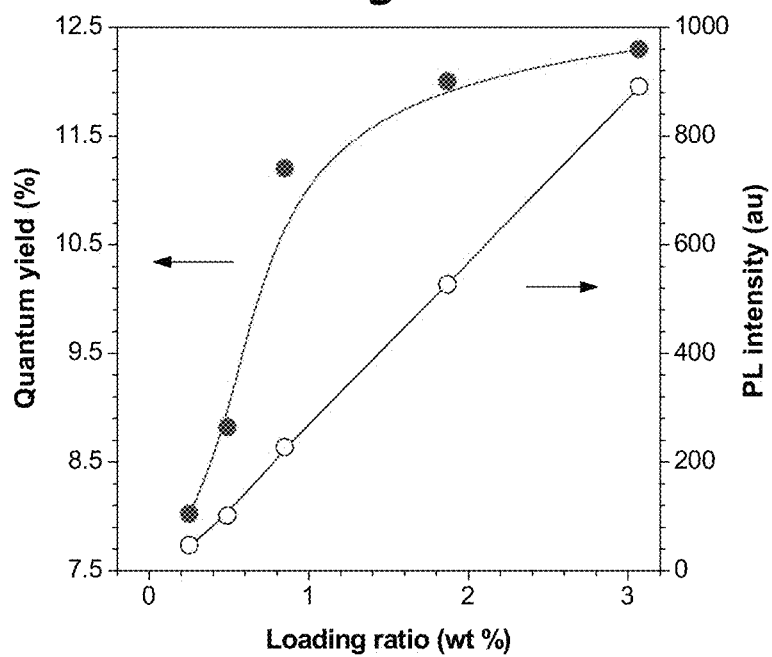
FIG. 6 is a diagram illustrating the changes in the quantum yield and photoluminescence (PL) intensity relative to the weight ratio of TPE-TPA-DCM in the fluorogen-loaded BSA nanoparticles.

The emission intensity of the fluorogen-loaded BSA nanoparticles increases almost linearly with increasing fluorogen loading within the studied range (FIG. 6). The fluorescence quantum yield ($\Phi_F$) values of the fluorogen-loaded BSA nanoparticles in water were measured using Rhodamine 6G in ethanol as the standard. The $\Phi_F$ is initially increased rapidly and then slowly increased relative to the increasing fluorogen loading ratio. The $\Phi_F$ eventually reaches a value of ~12% at a fluorogen loading of 3.07 wt %.

Methods of Cellular Imaging Using Fluorogen-Loaded Nanoparticles

The present subject matter also relates to a method of cellular imaging comprising contacting target cells with the fluorescent bioprobe and detecting cellular imaging. In one embodiment, the target cells are cancer cells or cells that preferentially accumulate in tumors.

The biological imaging samples used were MCF-7 cells or HT-29 cancer cells for in vitro imaging and ICR mice bearing tumors for in vivo imaging. Therefore, the present subject matter also relates to a method for diagnosing a tumor or cancer through in vivo cellular imaging.

Figure 7:
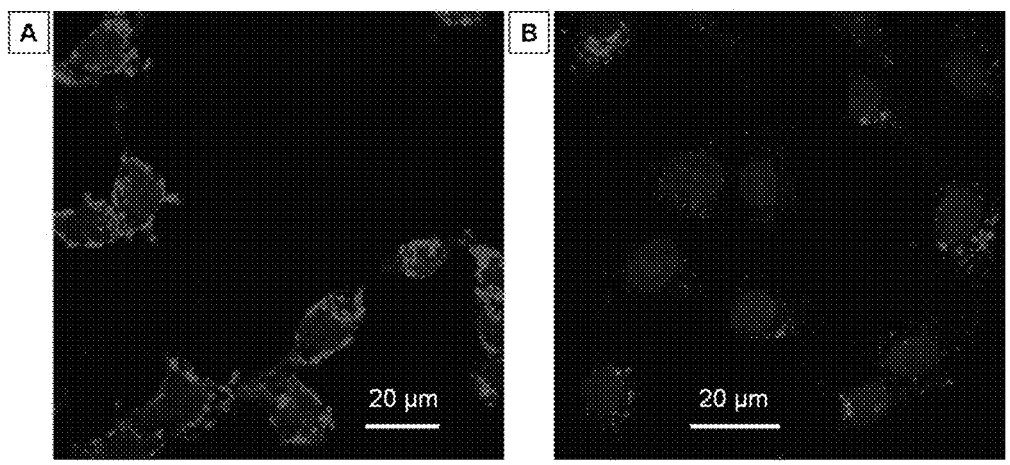
FIG. 7 illustrates confocal laser scanning microscopy (CLSM) images of MCF-7 breast cancer cells after incubation with (A) TPE-TPA-DCM-loaded BSA nanoparticles (with a fluorogen loading of 0.86%) and (B) bare TPE-TPA-DCM nanoparticles (TPE-TPA-DCM=0.4 µM) for 2 hours at 37° C.
Figure 8:
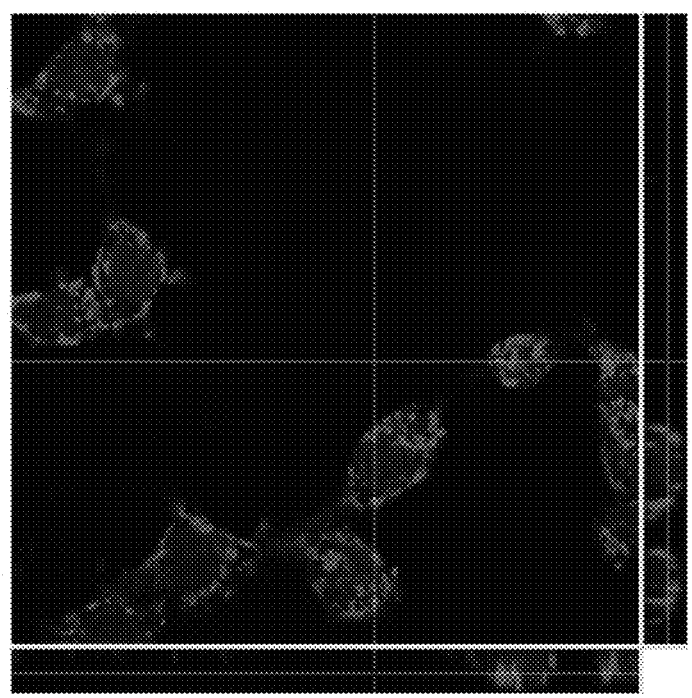
FIG. 8 is a 3D confocal laser scanning microscopy (CLSM) image of the MCF-7 cancer cells after incubation with the fluorogen-loaded BSA nanoparticles (TPE-TPA-DCM=0.4 µM) for 2 hours at 37° C.
Figure 9:
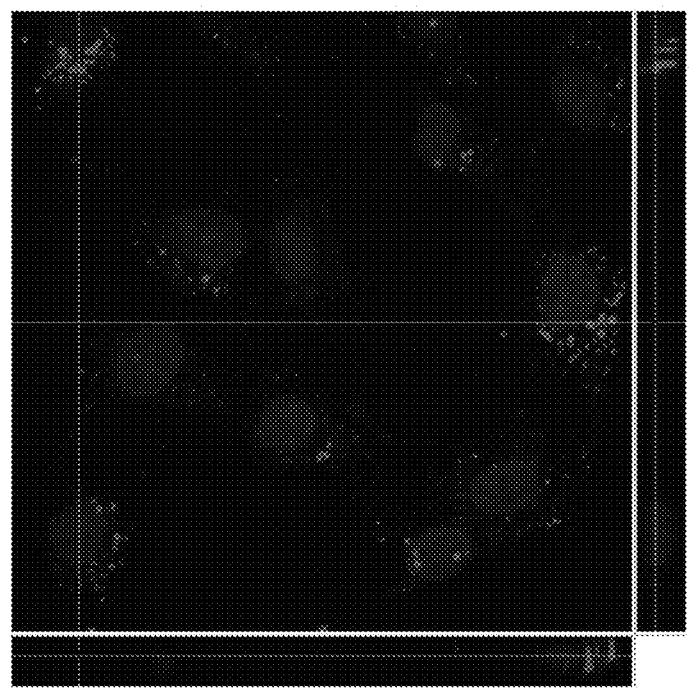
FIG. 9 is a 3D confocal laser scanning microscopy (CLSM) image of the MCF-7 cancer cells after incubation with bare TPE-TPA-DCM nanoparticles (TPE-TPA-DCM=0.4 µM) for 2 hours at 37° C.

A further aspect comprises a method of in vitro cellular imaging. The in vitro cellular imaging can be conducted using confocal laser scanning microscopy or two-photon fluorescence spectroscopy. As shown in FIGS. 7-9, the cellular cytoplasms of MCF-7 breast cancer cells after incubation with either fluorogen-loaded BSA nanoparticles or bare TPE-TPA-DCM nanoparticles exhibit intense red fluorescence.

FIG. 7B shows the confocal laser scanning microscopy (CLSM) image of the MCF-7 cells after incubation with the bare TPE-TPA-DCM nanoparticles. Only a few bare nanoparticles with weak fluorescence can be observed in the cytoplasms. FIG. 9 shows the 3D CLSM image of the MCF-7 cells after incubation with bare TPE-TPA-DCM nanoparticles. Similarly only a few bare nanoparticles with weak fluorescence can be observed in the cytoplasms. This indicates that the bare fluorogen nanoparticles have been internalized into the cytoplasms.

In contrast, FIGS. 7A and 8 show the CLSM image and 3D CLSM image, respectively, of the MCF-7 cells after incubation with fluorogen-loaded BSA nanoparticles. In FIGS. 7A and 8, several of the fluorogen-loaded BSA nanoparticles with strong fluorescence can be observed in the cytoplasms. The homogeneous distribution of the AIE-active fluorogen-loaded BSA nanoparticles exhibiting stronger fluorescence than that of the bare TPE-TPA-DCM nanoparticles indicates that BSA as the encapsulation matrix has efficiently enhanced the intracellular uptake of the formulated nanoparticles. Therefore, fluorogen-loaded BSA nanoparticles can be effective fluorescent bioprobes for cellular imaging with high fluorescence contrast.

Figure 10:
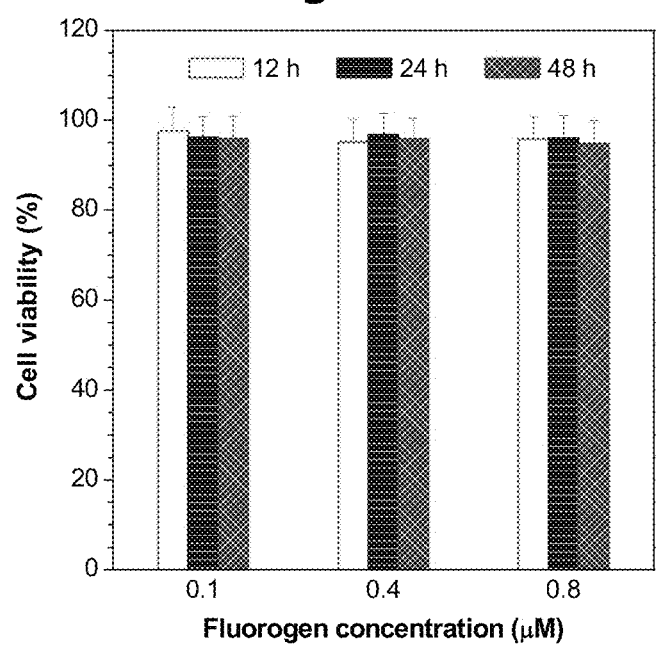
FIG. 10 is a chart illustrating the metabolic viability of MCF-7 breast cancer cells after incubation with TPE-TPA-DCM-loaded BSA nanoparticles at various fluorogen concentrations after 12, 24, and 48 hours.

Furthermore, the fluorogen-loaded BSA nanoparticles exhibit low cytotoxicity, as illustrated in FIG. 10. Cell viabilities of more than 95% are observed for all the fluorogen concentrations within the tested periods of time, indicating that the AIE-active fluorogen-loaded BSA nanoparticles have low cytotoxicity and/or good biocompatibility. The low cytotoxicity makes the nanoparticles effective for bioimaging applications and superior to QDs, which are well-know for their concentration-dependent cytotoxicity.

Figure 11:
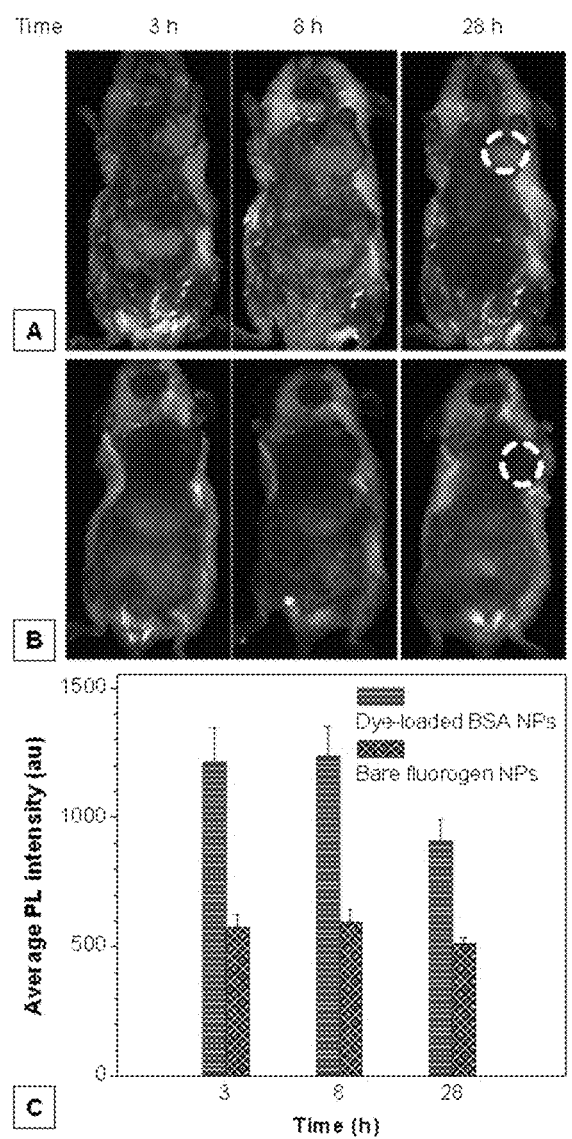
FIGS. 11A-B illustrate in vivo non-invasive fluorescence imaging of $H_{22}$ tumor-bearing mice after intravenous injection of (A) fluorogen-loaded BSA nanoparticles (with TPE-TPA-DCM loading of 0.86%) and (B) bare TPE-TPA-DCM nanoparticles at the same fluorogen concentration. The white circles mark the tumor sites.
FIG. 11C is a chart illustrating the average photoluminescence (PL) intensities for the tumor tissues from the mice treated with the TPE-TPA-DCM-loaded BSA nanoparticles and the bare fluorogen nanoparticles at different times.

Another embodiment of the present subject matter relates to a method of in vivo cellular imaging. In vivo cellular imaging can be conducted using non-invasive live animal fluorescence imaging techniques. For example, in vivo cellular imaging was conducted using a Maestro EX in vivo fluorescence imaging system in FIG. 11. Mice were inoculated with the hepatoma-22 ($H_{22}$) cancer cells in the left axillary. FIG. 11A shows the time-dependent in vivo distribution profile and tumor accumulation of the AIE fluorogen-loaded BSA nanoparticles in the $H_{22}$ tumor-bearing mice.

Clear tumor delineations with intense fluorescence are observed in the left auxiliaries of the mice at all the imaging times, indicating accumulation of the fluorogen-loaded BSA nanoparticles in the tumor tissue.

FIG. 11B shows the in vivo non-invasive fluorescence imaging of mice intravenously injected with bare TPE-TPA-DCM nanoparticles. The fluorescence intensities in the abdomen and liver areas of the mice are much higher than in the tumor tissue at all the tested points. This is due to the fact that bare TPE-TPA-DCM nanoparticles have a relatively large average particle size (~300 nm), most of which cannot escape from the RES uptake. As a consequence, accumulation of the bare fluorogen nanoparticles in the tumor is limited and the tumor imaging shows poor fluorescence contrast.

FIG. 11C summarizes the semi-quantitative analysis data of average TPE-TPA-DCM fluorescence intensities for tumor tissues from mice treated with the fluorogen-loaded BSA nanoparticles and the bare TPE-TPA-DCM nanoparticles. The average fluorescence intensities of the tumor stained by the fluorogen-loaded BSA nanoparticles are nearly twice as high as those for the bare TPE-TPA-DCM nanoparticles at all the imaging time points. Clearly, FIG. 11A shows enhanced accumulation of the AIE-active fluorogen-loaded BSA nanoparticles in the tumor as compared to the accumulation of the bare TPE-TPA-DCM nanoparticles in the tumor, as shown in FIG. 11B. The enhanced accumulation of the AIE-active fluorogen-loaded BSA nanoparticles in the tumor demonstrates clear differentiation of tumor cells from other tissues.

The capability of the fluorogen-loaded BSA nanoparticles to selectively illuminate tumor tissue with high contrast may be associated with two factors. The first is that the AIE-active nanoparticles accumulated in the tumor are highly fluorescent. The second factor is the "passive" tumor-targeting ability due to the enhanced permeability and retention (EPR) effect, which benefits from the uniform nanoparticle size of ~100 nm. Although strong fluorescence is also observed in the abdomen and liver areas of the same mouse at 3 hours post-injection, it almost completely disappears in 28 hours. This suggests that the AIE fluorogen-loaded BSA nanoparticles have undergone uptake by the reticuloendothelial system (RES) organs such as the liver and spleen, followed by facile excretion from the body through the biliary pathway. The clearance rate of the nanoparticles within the tumor, however, is very slow due to the lack of lymphatic drainage in the tumor. At 28 hours post-injection, the uptake of the fluorogen-loaded BSA nanoparticles in the tumor becomes prominent, in sharp contrast to the weak fluorescence signals in other parts of the body, demonstrating the effectiveness of the nanoparticles as fluorescent bioprobes for cancer diagnosis.

F37NP0/F37NP50 and F30NP0/F30NP50 as Fluorescent Bioprobes

In another embodiment, the AIE chromophore-doped nanoparticles were synthesized through a modified nanoprecipitation method, using a mixture of DSPE-PEG$_{2000}$ and DSPE-PEG$_{5000}$-Folate as the encapsulation matrix to yield nanoparticles with good biocompatibility and different surface folic acid densities. F37NP0/F37NP50 and F30NP0/F30NP50 represent ZQL-37 and ZQL-30 based nanoparticles that were formulated with polymers containing the feed ratio of 0% and 50% for DSPE-PEG$_{5000}$-Folate in the polymer matrix. During nanoparticle formation, the hydrophobic DSPE segments tend to be embedded into the hydrophobic core while the hydrophilic PEG-folate chains extend into the aqueous phase. The chemical structures of F37, F30, DSPE-PEG$_{2000}$, and DSPE-PEG$_{5000}$-Folate are show below.

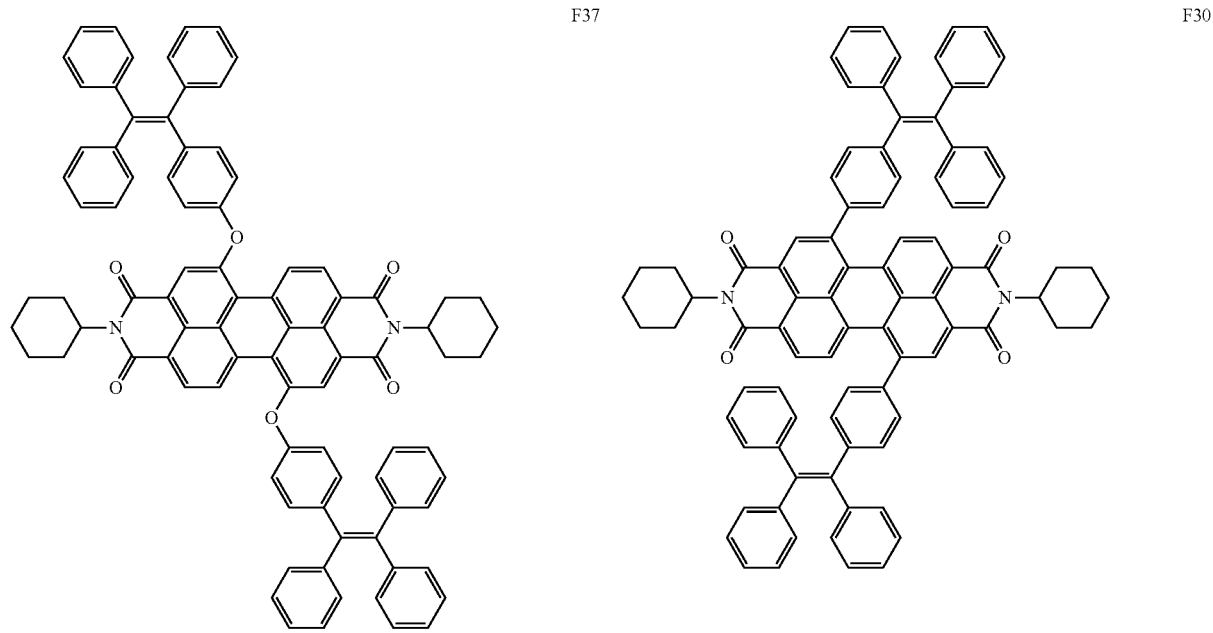

-continued

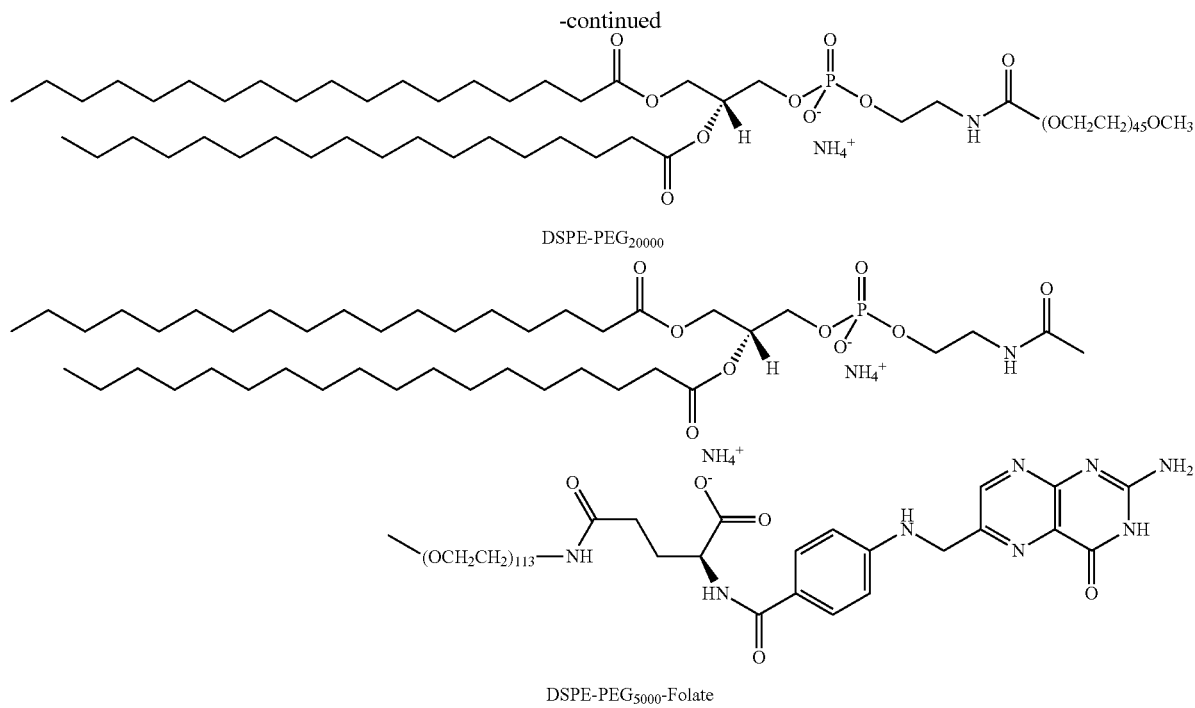

DSPE-PEG$_{20000}$

DSPE-PEG$_{5000}$-Folate

Figure 12:
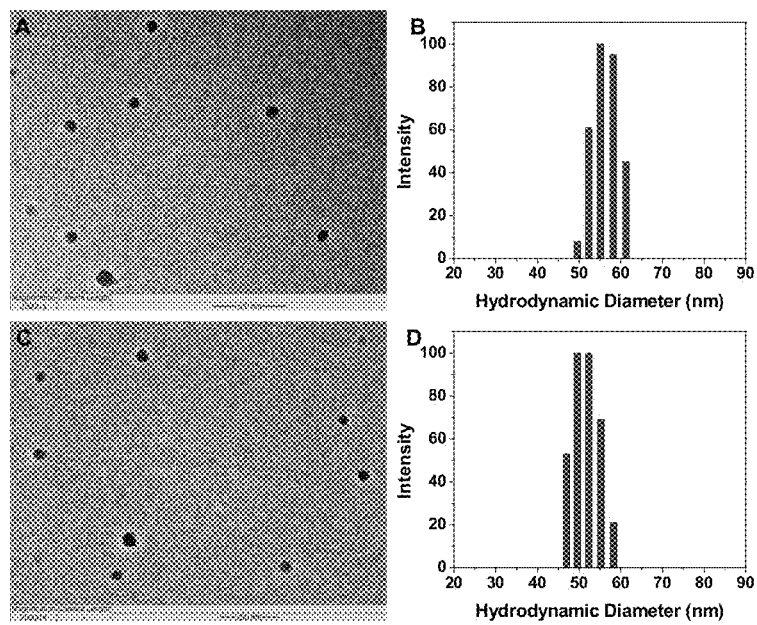
FIG. 12A is a high-resolution transmission electron microscopy (HR-TEM) image of F37NP50.
FIG. 12B is a diagram illustrating the particle size distribution of F37NP50 in water studied via laser light scattering.
FIG. 12C is a high-resolution transmission electron microscopy (HR-TEM) image of F30NP50.
FIG. 12D is a diagram illustrating the particle size distribution of F30NP50 in water studied via laser light scattering.
Figure 13:
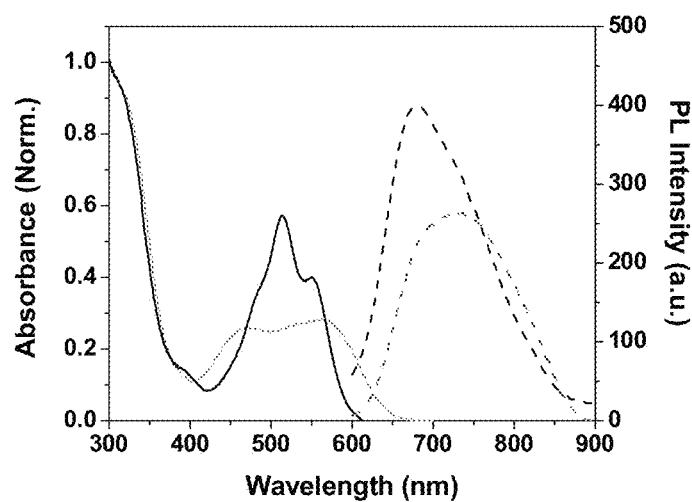
FIG. 13 is a diagram illustrating the UV-vis absorption (solid line) and photoluminescence (PL) spectra (dashed line) of F37NP50 (black) and F30NP50 (gray) in water (excited at 543 nm).

FIG. 12 shows high-resolution transmission electron microscopy (HR-TEM) images of F37NP50 and F30NP50. The spherical shapes of F37NP50 and F30NP50 can be clearly distinguished from the black dots due to the high electron density of F37 and F30 molecules. Laser light scattering (LLS) results suggest that the volume average hydrodynamic diameters of F37NP0, F37NP50, F30NP0 and F30NP50 are 59±2 nm, 57±1 nm, 51±2 nm and 52±3 nm respectively. FIG. 13 shows the UV-vis absorption and photoluminescence (PL) spectra of F37NP50 and F30NP50 in water. The emission maxima of F37NP50 and F30NP50 are 680 nm and 734 nm, respectively, which are similar to those of F37NP0 and F30NP0 in water. The quantum yields of F37NP50 and F30NP50 in water are measured to be 8% and 3%, respectively, using Rhodamine 6G in ethanol as the standard.

Methods of Cellular Imaging Using F37NP0/F37NP50 and F30NP0/F30NP50

Figure 14:
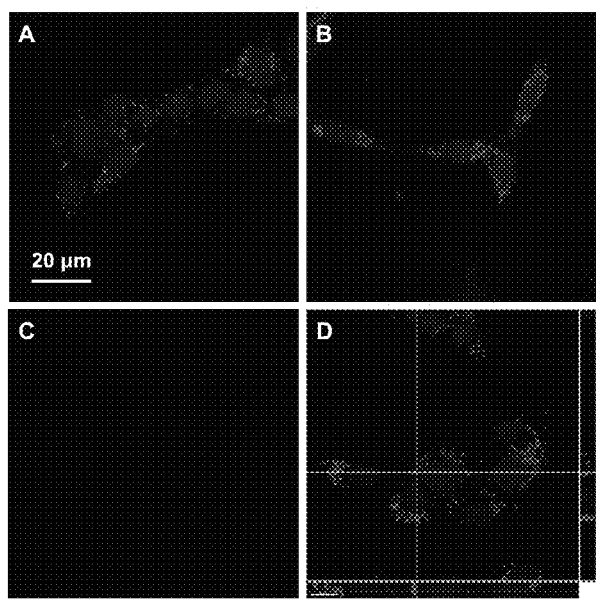
FIGS. 14A-D illustrate images of MCF-7 cancer cells.

A further aspect comprises a method of in vitro cellular imaging using confocal laser scanning microscopy or two-photon fluorescence spectroscopy. MCF-7 breast cancer cells with a high folate receptor expression level in cell membrane were used to evaluate the targeting ability of F37NP50 over F37NP0. The effect of nanoparticle surface folic acid on MCF-7 breast cancer cell uptake was investigated by confocal laser scanning microscopy. FIGS. 14A and 14B show the confocal images of MCF-7 breast cancer cells after incubation with F37NP0 and F37NP50 suspension in culture medium. It should be noted that in FIG. 14C, no auto fluorescence from the cell itself can be detected under the same experimental conditions. In addition, the fluorescence intensity from cell cytoplasm after incubation with F37NP50 (FIG. 14B) is higher than that after incubation with F37NP0 (FIG. 14A). Quantitative studies using Image-Pro Plus 5.0 software indicate that the average fluorescence intensity of red signal in FIG. 14B is ~1.7 times higher than that in FIG. 14A. The confocal image of the corresponding cells incubated with F37NP50 shows that the intense fluorescence is mainly from nanoparticles internalized in the MCF-7 cell cytoplasm (FIG. 14D). The higher fluorescence intensity of MCF-7 cancer cells in FIG. 14B as compared to that in FIG. 14A suggests that more nanoparticles are internalized into the cells due to specific interactions between folic acid on the nanoparticle surface and folate receptors in the cancer cell membrane, which should favor folate receptor-mediated endocytosis.

Figure 15:
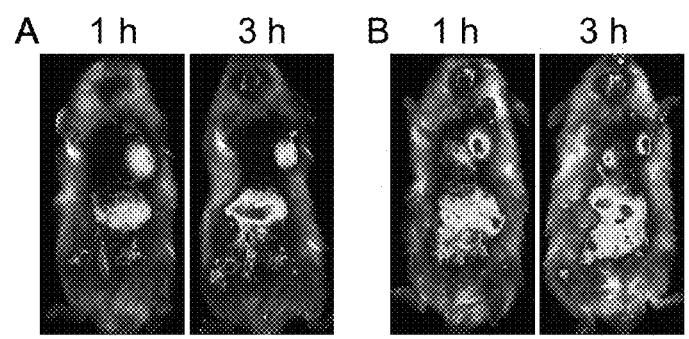
FIG. 15 illustrates in vivo fluorescence imaging of $H_{22}$ tumor-bearing mice after intravenous injection of (A) F37NP0 and (B) F37NP50. The circle in the left axillary indicates the tumor site.

A further aspect comprises a method of in vivo cellular imaging. In vivo imaging based on F37NP50 and F37NP0 was studied on a tumor-bearing mouse model. Mice were subcutaneously inoculated with murine hepatic H$_{22}$ cancer cells in the left axillary of each mouse. Then the mice were intravenously injected with either F37NP50 or F37NP0. The mice were subsequently imaged by a Maestro EX in vivo fluorescence imaging system. FIG. 15A shows the tumor accumulation and in vivo distribution of F37NP0 in the tumor-bearing mouse at 1 hour and 3 hours post-injection. The different fluorescence intensities are shown by different colors, and the order of red, orange, yellow, green, and blue refers to a successive decrease in intensity.

Obvious fluorescence is observed in the area of tumor tissue at 1 hour and 3 hours, indicating that F37NP0 are efficiently accumulated in the tumor through enhanced permeability and retention (EPR) effect. In addition, strong fluorescence from the liver region is also observed. This is due to the fact that nanoparticles with a size of 50-60 nm have a tendency to undergo reticuloendothelial system (RES) uptake to be enriched in different organs including liver.

The specific tumor targeting ability of F37NP50 was also evaluated on the same tumor-bearing mouse model, as displayed in FIG. 15B. Much higher fluorescence intensity is shown in the tumor tissue of a F37NP50-treated mouse as compared to that of F37NP0-treated mouse at both 1 hour and 3 hours post injection, demonstrating that F37NP50 has specific targeting ability for tumors that contain folate receptors over expressed in cancer cells in a living body. These results illustrate that F37NP50 is an effective fluorescent probe for in vivo tumor diagnosis with high specificity and fluorescence contrast.

Figure 16:
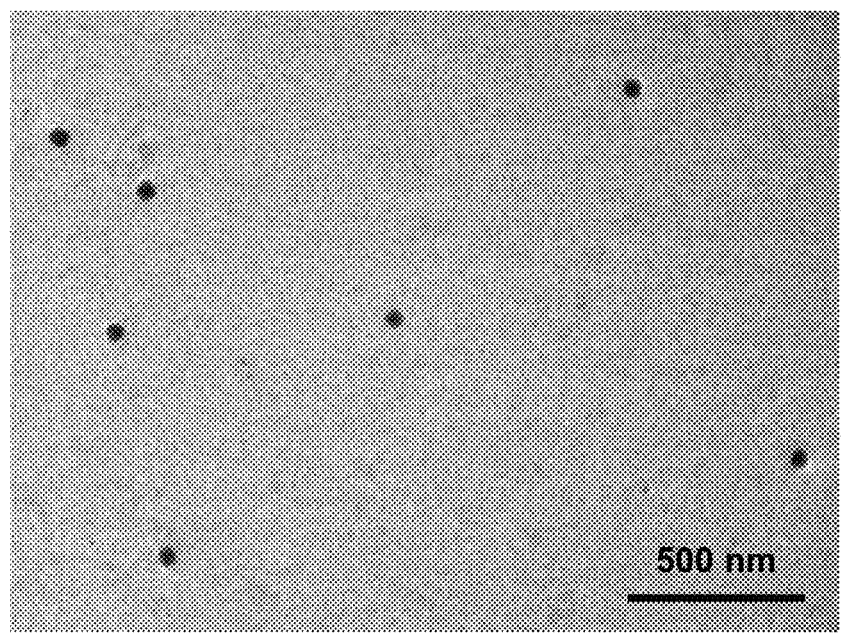
FIG. 16 is a high-resolution transmission electron microscopy (HR-TEM) image of FTNPs with DSPE-PEG$_{2000}$ and DSPE-PEG$_{5000}$-Folate as the biocompatible polymer matrix.
Figure 17:
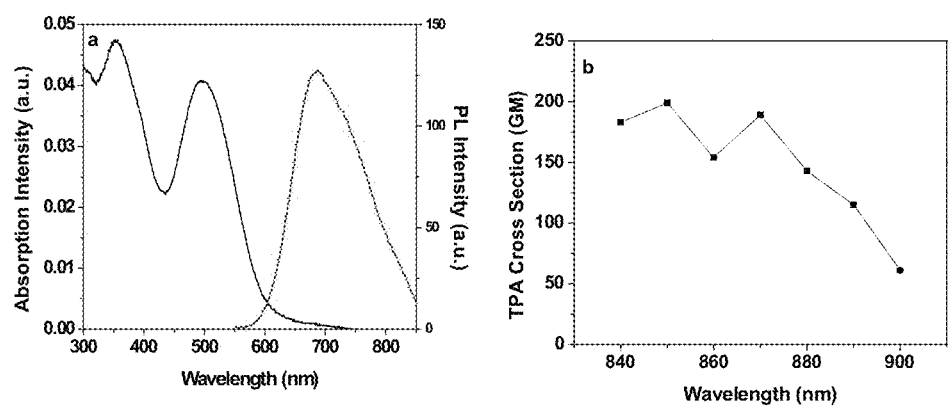
FIG. 17A illustrates the linear absorption (black) and emission spectra (gray) of FTNPs in water.
FIG. 17B illustrates the two-photon absorption spectrum of FTNPs in water.

FIG. 16 shows HR-TEM images of folate-targeted nanoparticles (FTNPs) with DSPE-PEG$_{2000}$ and DSPE-PEG$_{5000}$-Folate as the biocompatible polymer matrix. The spherical shape of FTNPs with an average size of 45 nm can be clearly distinguished from the black dots due to the high electron density of TPE-TPA-DCM molecules. Laser light scattering (LLS) results suggest that the volume average hydrodynamic diameter of FTNPs is 52±2 nm. FIG. 17A shows the linear absorption and emission spectra of FTNPs in water. The FTNP suspension in water has two maximum absorption peaks at 353 and 496 nm. The emission peak of FTNPs in water is 687 nm, demonstrating the effectiveness of these nanoparticles in fluorescence imaging.

The quantum yield (η) of FTNP suspension was determined to be 0.12, using rhodamine 6G in ethanol as a standard. The two-photon absorption (TPA) spectra of FTNP water suspension were studied using the two-photon-induced fluorescence (TPIF) technique with a femtosecond pulsed laser source. As shown in FIG. 17B, the maximum TPA cross-section (δ) is 199 GM at 850 nm, which is sufficient for two-photon fluorescence imaging application.

In a further embodiment, the present subject matter relates to folate-targeted nanoparticles (FTNPs) that can be used for living cell tracking and tissue imaging with two-photon microscopy.

Figure 18:
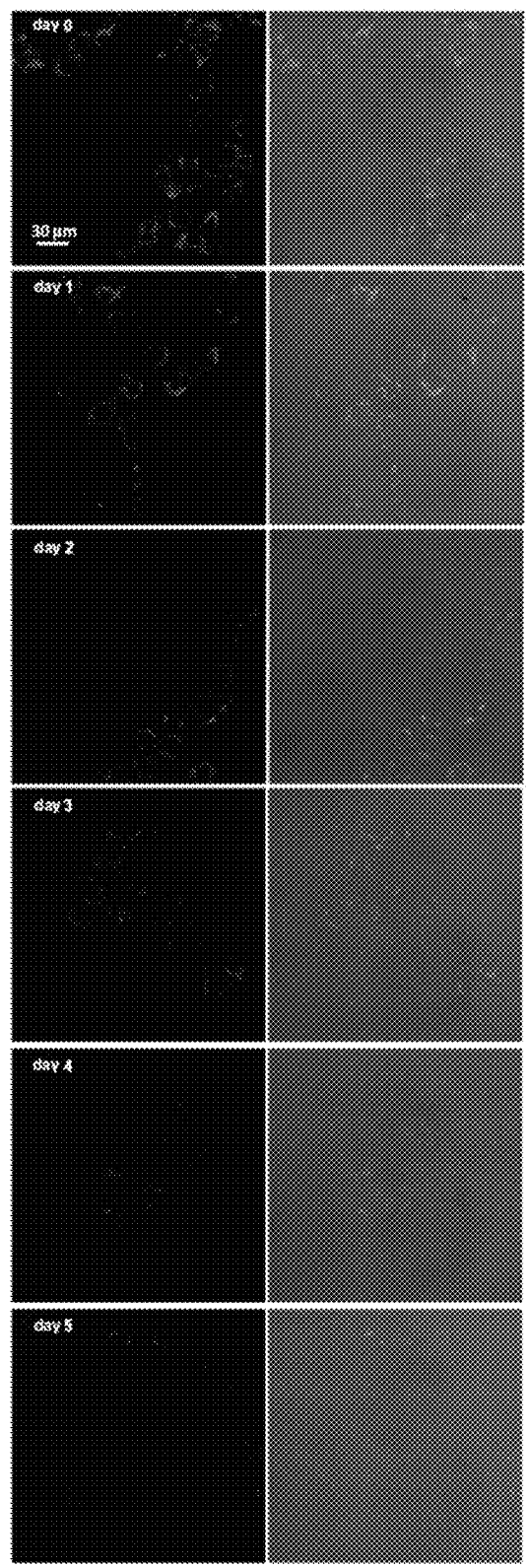
FIG. 18 illustrates two-photon fluorescence images of FTNP-treated MCF-7 cancer cells after incubation for designated time intervals. The two photon fluorescence of FTNPs was collected by a 600-800 nm bandpass filter upon excitation at 800 nm.

The two-photon fluorescence images of FTNP-treated MCF-7 cancer cells after designated incubation time intervals of 0, 1, 2, 3, 4, and 5 days are shown in FIG. 18. The profile of FTNP-treated cells can be clearly distinguished after 4 days of incubation and the fluorescence from FTNPs which internalized into cells remains detectable even after 5 days. These results suggest that FTNPs can be used for living cell tracking and tissue imaging with two-photon microscopy for a period up to 96 hours under the experimental conditions, which corresponds to more than six cell generations.

Figure 19:
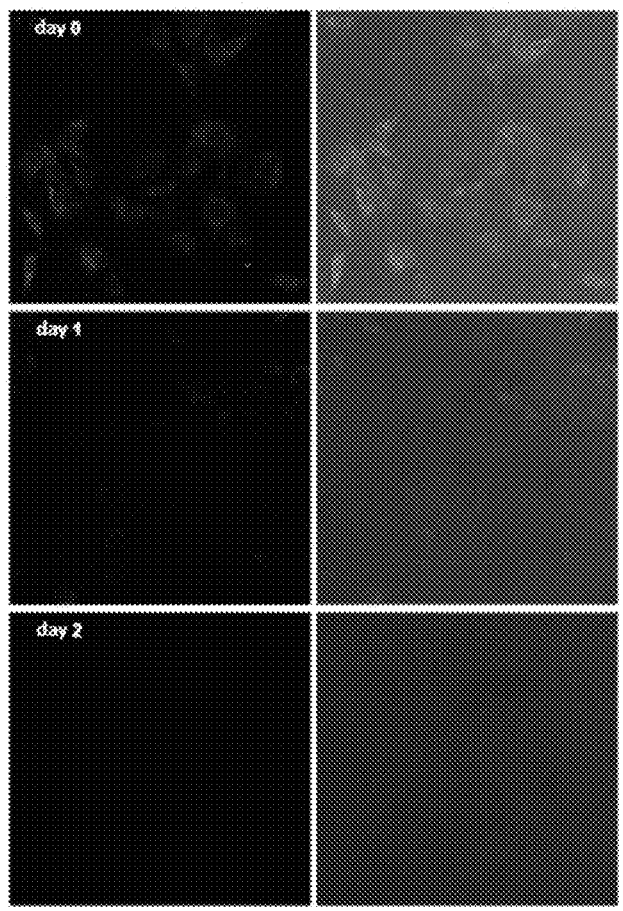
FIG. 19 illustrates confocal images of MTR-treated MCF-7 cancer cells after incubation for designated time intervals. The fluorescence of MTR was collected by a 600-800 nm bandpass filter upon excitation at 560 nm.

In contrast, the fluorescence from MTR-treated MCF-7 cancer cells only sustained 1 day and became undetectable after 2 days. The confocal images of MTR-treated MCF-7 cancer cells after designated incubation time intervals of 0, 1, and 2 days are show in FIG. 19. It should be noted that the concentration of MTR in this experiment (1 μM) is much higher than the recommended highest working concentration of 200 μM.

PFV/TPE-TPA-DCM Co-Loaded Nanoparticles as Fluorescent Bioprobes

In another embodiment, the AIE chromophore-doped nanoparticles further comprise PFV. The chemical structures of PFV and TPE-TPA-DCM are shown below.

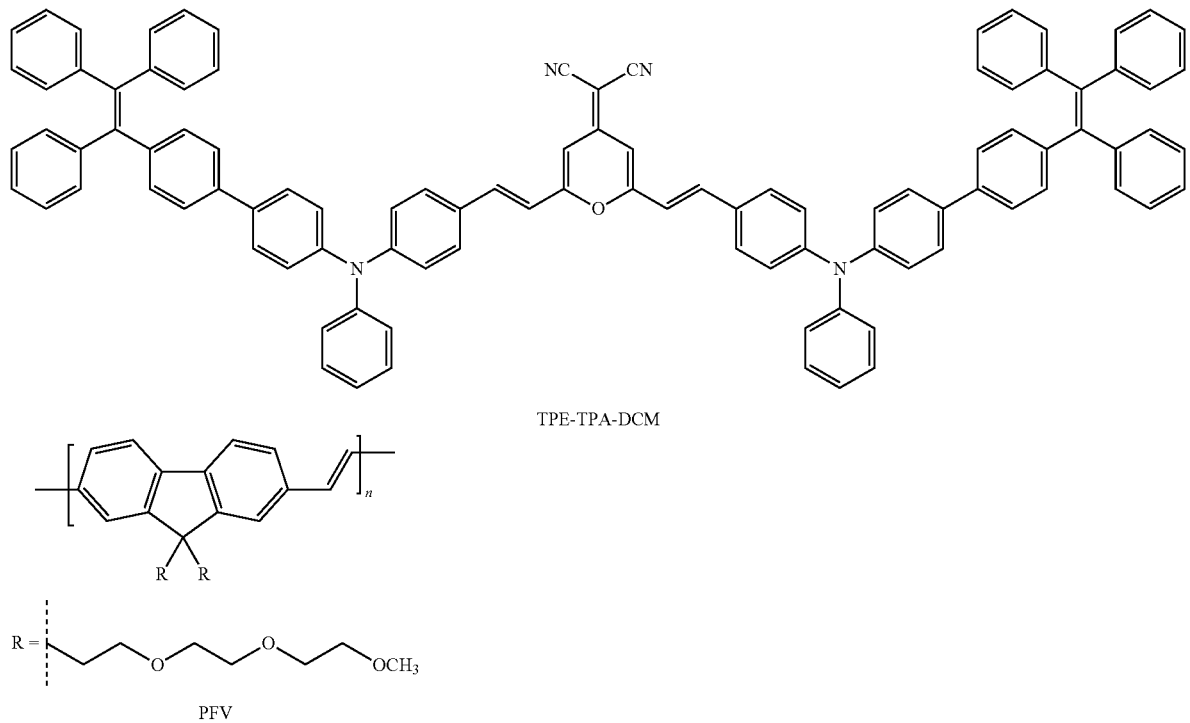

Figure 20:
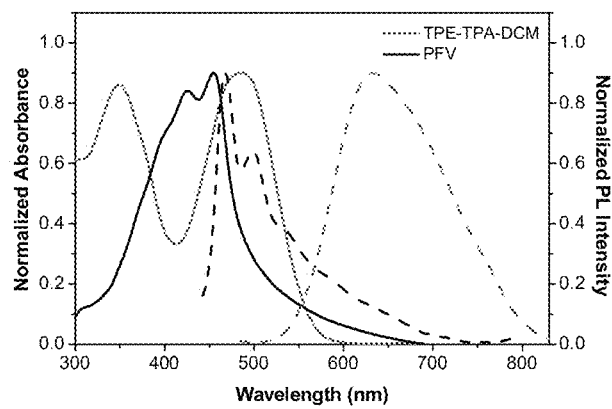
FIG. 20 illustrates the normalized UV-vis absorption (solid line) and photoluminescence (PL) spectra (dashed line) of PFV (black) and TPE-TPA-DCM (gray) in THF.

FIG. 20 shows the absorption and emission spectra of PFV and TPE-TPA-DCM in tetrahydrofuran (THF). As shown in FIG. 20, PFV has two absorption maxima at 425 and 455 nm. The emission maxima of PFV are located at 467 and 498 nm. On the other hand, TPE-TPA-DCM shows two absorption bands centered at 350 and 486 nm with an emission maximum at 633 nm. The emission spectrum of PFV overlaps with the absorption spectrum of TPE-TPA-DCM.

Because the emission spectrum of PFV overlaps well with the absorption spectrum of TPE-TPA-DCM, these two molecules are well suited as donor-acceptor pairs for fluorescence resonance energy transfer (FRET). In a further aspect, FRET occurs when PFV (donor) and TPE-TPA-DCM (acceptor) are co-encapsulated into the nanoparticles.

In an embodiment, bovine serum albumin (BSA) is the polymer matrix to formulate nanoparticles loaded with both TPE-TPA-DCM and PFV. The PFV/TPE-TPA-DCM co-loaded BSA nanoparticles can be synthesized through a modified desolvation method with cross-linking by glutaraldehyde.

One embodiment comprises RGD-functionalized PFV/TPE-TPA-DCM co-loaded BSA nanoparticles that can target integrin receptors over expressed in many tumor cells serving as effective probes for in vivo fluorescence imaging in a high contrast manner, by virtue of the efficient FRET from PFV donor to the TPE-TPA-DCM acceptor.

Methods of Cellular Imaging Using PFV/TPE-TPA-DCM Co-Loaded Nanoparticles

A further aspect comprises a method of cellular imaging using PFV/TPE-TPA-DCM co-loaded BSA nanoparticles. In addition, since arginine-glycine-aspartic acid (RGD) peptide can target integrin receptors over expressed in many tumor cells, the PFV/TPE-TPA-DCM co-loaded BSA nanoparticles are preferably modified with positively charged RGDKKKKKK peptide.

Figure 23:
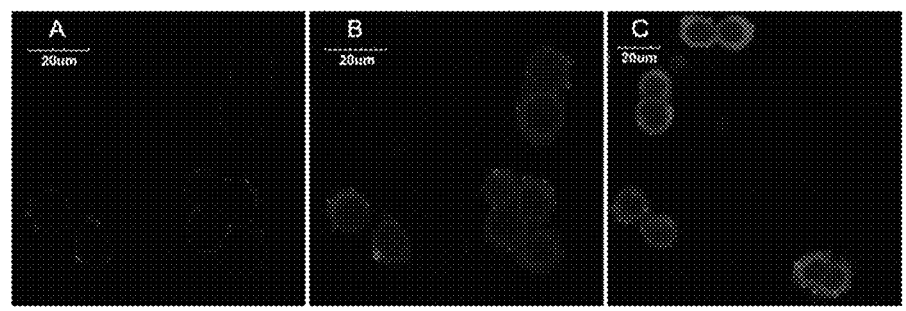
FIGS. 23A-C illustrate confocal images of HT-29 cancer cells.

FIG. 23 shows the confocal images of HT-29 cancer cells after incubation with PFV/TPE-TPA-DCM co-loaded BSA nanoparticles without RGD functionalization for 2 hours.

Another embodiment comprises a method of in vivo live animal imaging using PFV/TPE-TPA-DCM co-loaded BSA nanoparticles with and without RGD functionalization.

Figure 24:
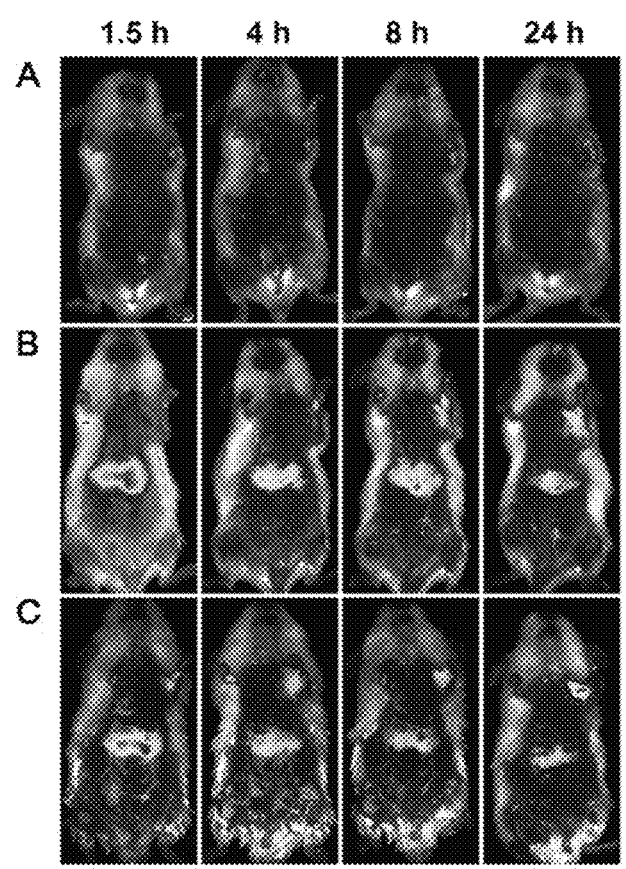
FIGS. 24A-C illustrate in vivo non-invasive fluorescence imaging of $H_{22}$ tumor-bearing mice after intravenous injection of (A) TPE-TPA-DCM loaded BSA nanoparticles, (B) PFV/TPE-TPA-DCM co-loaded BSA nanoparticles, and (C) RGD-functionalized PFV/TPE-TPA-DCM co-loaded BSA nanoparticles. The red circles mark the tumor sites.

FIGS. 24A and B show the time-dependent in vivo distribution profile as well as tumor accumulation of TPE-DAM-TPA loaded BSA nanoparticles and PFV/TPE-TPA-DCM co-loaded BSA nanoparticles, respectively. Under the same experimental conditions, a much higher degree of fluorescence from the tumor-bearing mouse is observed in FIG. 24B as compared to that in FIG. 24A, suggesting that the PFV/TPE-TPA-DCM co-loaded BSA nanoparticles can also serve as an effective probe for in vivo fluorescence imaging in a high contrast manner, by virtue of the efficient FRET from PFV donor to TPE-TPA-DCM acceptor. As shown in FIG. 24B, a clear tumor delineation is observed in the area of left axillary of the mouse after 8 hours post-injection (p.i.), indicating the accumulation of the nanoparticles in tumor tissue by the enhanced permeability and retention (EPR) effect. Moreover, strong fluorescent signals are also observed in the liver area of the mouse at 1.5 hours p.i., which then decreases over time. This suggests that some nanoparticles undergo the uptake of reticuloendothelial system (RES) organs such as the liver and spleen, followed by facile excretion form the body through the biliary pathway.

FIG. 24C shows the time-dependent in vivo distribution profile and tumor accumulation of RGD-functionalized PFV/TPE-TPA-DCM co-loaded BSA nanoparticles in a $H_{22}$ tumor-bearing mouse. It is noteworthy that the fluorescence intensity from the tumor site in FIG. 24C is higher as compared to that in FIG. 24B at all tested time points, revealing that RGD-functionalized PFV/TPE-TPA-DCM co-loaded BSA nanoparticles can achieve efficient tumor targeting through specific RGD-integrin $\alpha_v\beta_3$ recognition.

The present subject matter also relates to methods for preparing the fluorescent bioprobes and methods of in vitro and in vivo cellular imaging using the fluorescent bioprobes. In particular, the fluorescent bioprobes exhibit excellent tumor targeting ability can be used for long-term cellular tracking with two-photon fluorescence imaging. Furthermore, the present subject matter relates to diagnostic methods for determining whether a tumor or cancer cells are present.

TPETPAFN as a Fluorescent Bioprobe

In another aspect, 2,3-bis[4-(diphenylamino)phenyl]fumaronitrile (TPAFN), which is an adduct of triphenylamine (TPA) and fumaronitrile (FN), was attached to tetraphenylethene (TPE) to produce 2,3-bis(4(phenyl(4-(1,2,2-triphenylvinyl)phenyl)amino)phenyl)fumaronitrile (TPETPAFN), shown below.

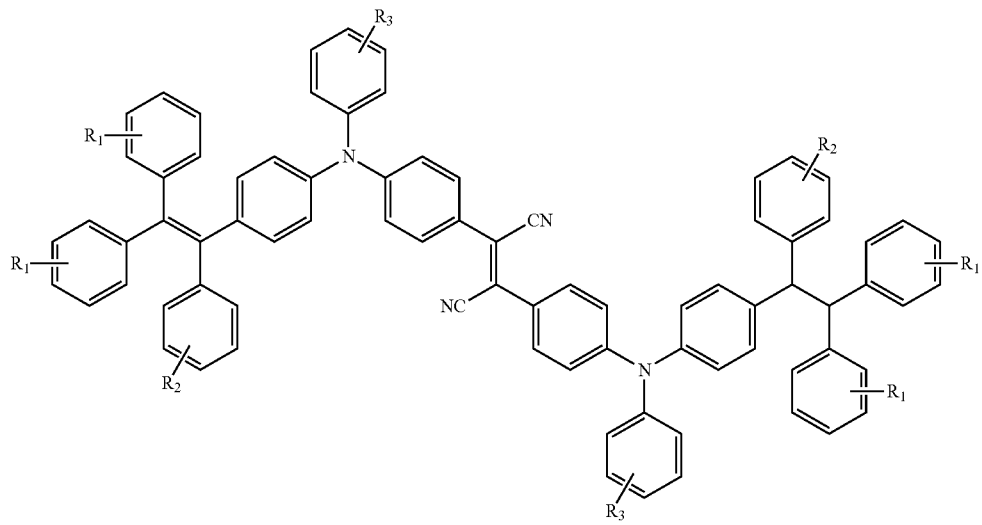

The molecular fusion of two types of AIE units (TPE+TPAFN) resulted in the generation of a new fluorogen with extended electronic conjugation, long absorption wavelength and large molar absorptivity. Its nanoaggregates exhibit strong AIE activity, bright red emission, high fluorescence quantum efficiency, superb cytocompatability, and excellent resistance to photobleaching. This makes it ideal for use as a long-term cell tracer.

Figure 25:
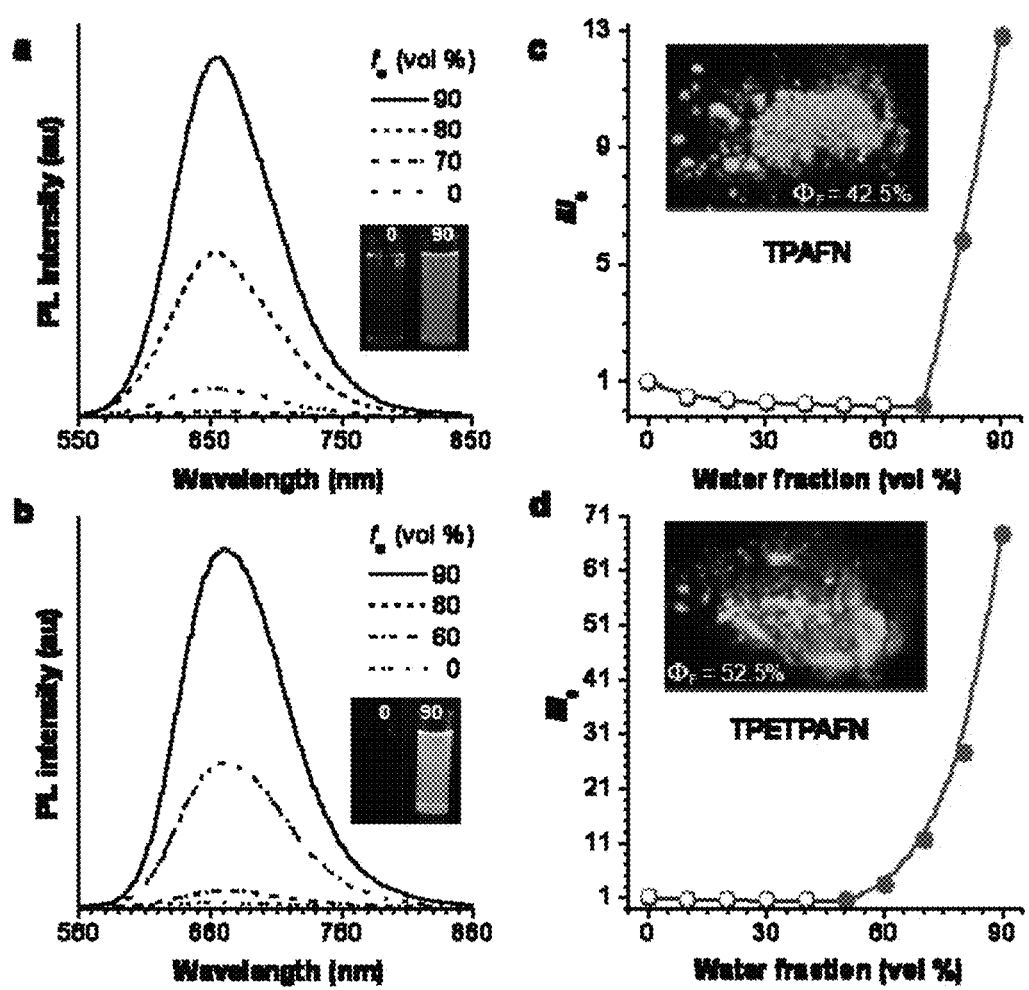
FIG. 25 illustrates (a) TPAFN and (b) TPETPAFN in THF/water mixtures with different water fractions ($f_w$); concentration=1 μM; excitation wavelength ($\lambda_{ex}$): (a) 485 nm, (b) 500 nm. Insets: fluorescent photographs of (a) TPAFN and (b) TPETPAFN in THF ($f_w$=0%) and a THF/water mixture with $f_w$=90%. Variations in $I/I_0$ of (c) TPAFN and (d) TPETPAFN with $f_w$. $I_0$ and I are the PL intensities in THF ($f_w$=0%) and a THF/water mixture with a specific $f_w$, respectively. Insets: fluorescent photographs of powders of (c) TPAFN and (d) TPETPAFN; $\Phi_F$=fluorescence quantum yield.

FIG. 25 shows the photoluminescence (PL) spectra of TPAFN and TPETPAFN in THF/water mixtures with different water fractions ($f_w$) The pure THF solution of TPAFN shows weak red fluorescence with an emission maximum at 652 nm. With gradual addition of water into THF ($f_w \leq 70$ vol %), the emission of TPAFN is weakened and is bathochromically shifted from 652 to 665 nm, possibly due to the increase in the solvent polarity and hence the transformation to the twisted intramolecular charge transfer (TICT) state. The TICT phenomenon is often observed in D-A fluorophores that are featured with red-shifted emission and decreased emission intensity with increasing solvent polarity. In polar solvents, the excited molecule can be relaxed from the locally excited state or the Franck-Condon state with partial charge separation to a TICT state with full charge separation through intramolecular rotation of its donor or acceptor unit along the molecular backbone. When more water ($f_w$>70 vol %) is added, TPAFN molecules cluster into nanoaggregates due to the poor solubility and the emission is dramatically enhanced with an increase in $f_w$, showing an obvious AIE effect. In addition, the emission maximum is shifted back to 655 nm which is similar to that in pure THF. The emission intensity at $f_w$, =90 vol % is 12-fold higher than that in pure THF solution.

In a typical AIE fluorophore (e.g., TPE), intramolecular rotations play a crucial role to populate the nonradiative decay channels (e.g., internal conversion) for the excited states and thus effectively quench the light emission. Bearing two extra TPE units to TPAFN, TPETPAFN has more freely rotated rotors and is expected to have a more pronounced AIE effect. As shown in FIG. 25, TPETPAFN is almost nonluminescent in THF under a hand-held UV lamp. The magnified PL spectrum reveals an emission peak located at 660 nm, which is 8 nm red-shifted from that of TPAFN. With gradual addition of water into THF at $f_w$50 vol %, the emission keeps silent and is almost unchanged in profile. At $f_w$>50 vol %, the light emission is turned on and exponentially intensified with $f_w$. At $f_w$=90 vol %, a 70-fold enhancement of emission has been observed as compared to that in THF. This demonstrates that TPETPAFN is a fluorogen having a stronger AIE effect but a negligible TICT effect relative to TPAFN.

The fluorescence quantum yield ($\Phi_F$) gives a quantitative measure of the AIE effect. The $\Phi_{F,s}$'s of TPAFN and TPETPAFN in THF are as low as 2.32 and 0.59%, while their $\Phi_{F,f}$'s in the solid state reach 42.5 and 52.5%, respectively. After covalent integration of TPE, TPETPAFN enjoys ~24% enhancement in solid state emission efficiency compared to its parent TPAFN. Their corresponding AIE factors $\alpha_{AIE's}$ defined by $\Phi_{F,f}/\Phi_{F,s}$ are ~18 and ~89, demonstrating the larger AIE effect of TPETPAFN. Meanwhile, no obvious PL spectral shifts were observed from solution to solid thin film state, ruling out the possibility of π-π stacking interactions involved in the aggregate state. As a result, TPETPAFN is highly suitable as a fluorophore for constructing AIE dots to satisfy sophisticated bioimaging applications.

Figure 26:
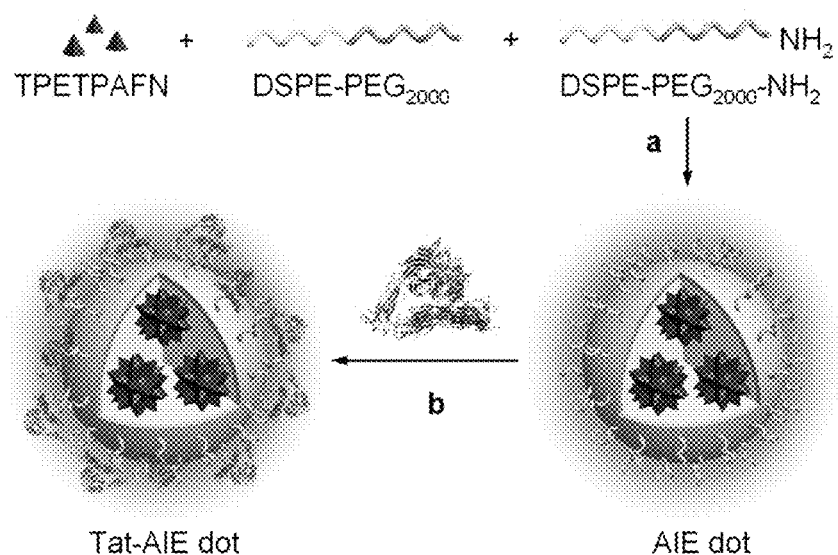
FIG. 26 illustrates the fabrication of biocompatible organic dots. (a) Addition of a THF solution of TPETPAFN, 1,2-distearoyl-sn-glycero-3-phosphoethanolamine-N-[methoxy(polyethylene glycol)-2000] (DSPE-PEG$_{2000}$) and its derivative end-capped by amino group (DSPE-PEG$_{2000}$-NH$_2$) into water under sonication affords amino-decorated core-shell organic dots with AIE characteristics (AIE dots). (b) Coupling of the amino-functionalized AIE dots with trans-activator of transcription (Tat) peptide yields Tat-AIE dots.

FIG. 26 shows the synthesis of AIE dots with surface amine groups. They were synthesized through a modified nanoprecipitation method. 1,2-Distearoyl-sn-glycero-3-phosphoethanolamine-N-[methoxy(polyethylene glycol)-2000] (DSPE-PEG$_{2000}$) and its amine end-capped DSPE-PEG$_{2000}$-NH$_2$ were used to encapsulate TPETPAFN to afford AIE dots with surface amine groups. The synthesis starts with the preparation of a THF solution containing TPETPAFN, DSPE-PEG$_{2000}$ and DSPE-PEG$_{2000}$-NH$_2$. Upon mixing the THF solution with water under continuous sonication, the hydrophobic lipid segments tend to be embedded in the aggregated hydrophobic TPETPAFN core while the hydrophilic PEG chains extend into the aqueous phase to produce the dots with abundant surface amine groups for subsequent bioconjugation. Then the water suspension of AIE dots was reacted with a cell-penetrating peptide HIV 1 trans-activator of transcription (Tat) (RK-KRRQRRRC) through carbodiimide-mediated coupling. This resulted in Tat-AIE dots.

Methods of Cellular Imaging with TPETPAFN

Figure 27:
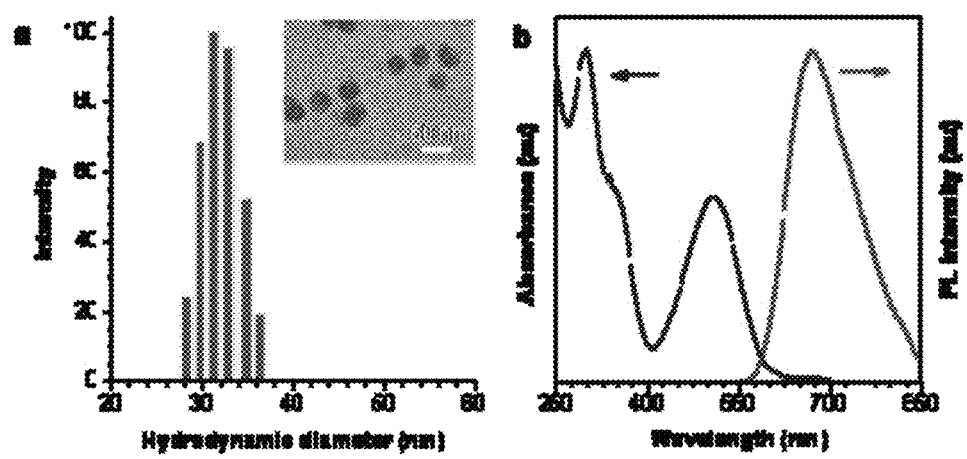
FIG. 27 illustrates the morphology and fluorescence of Tat-AIE dots. (a) Particle size distribution and morphological structure of Tat-AIE dots studied by laser light scattering and (inset) high-resolution transmission electron microscopy (HR-TEM). (b) Absorption and emission spectra of Tat-AIE dots suspended in water; $\lambda_{ex}$=510 nm.

In another embodiment, TPETPAFN can be used as a fluorescent bioprobe for in vitro and in vivo fluorescence imaging. FIG. 27(a) shows the size distribution of Tat-AIE dots in water. High-resolution transmission electron microscopy (HR-TEM) indicated that the dots are spherically shaped with an average size of 29±3 nm. The dark dots are due to the high electron density of TPETPAFN. As shown in the UV-vis absorption and PL spectra (FIG. 27(b)), Tat-AIE dots have an intense absorption peak at 511 nm, which matches well with the confocal laser excitation at 514 nm. The emission maximum appears at 671 nm with an emission tail extending to 900 nm, which is beneficial to both in vitro and in vivo fluorescence imaging.

Figure 28:
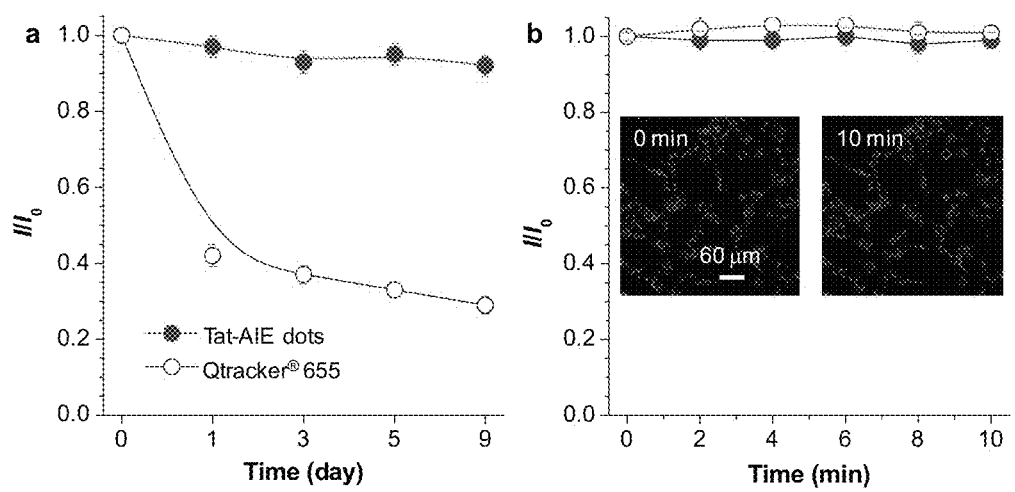
FIG. 28 illustrates the stability of Tat-AIE dots. (a) Time courses of PL intensity change of 2 nM Tat-AIE dots in DMEM with 10% FBS at 37° C.; data for inorganic semiconductor quantum dots of Qtracker® (Invitrogen Corporation, 1600 Faraday, Carlsbad Calif. 92008) 655 are shown for comparison. (b) Photobleaching resistance of Tat-AIE dots and Qtracker® 655 to the continuous irradiation by a laser beam (2 mW) at 514 nm. Insets: confocal images of the Tat-AIE dot-stained cells before (0 min) and after the laser irradiation for 10 min. $I_0$ is the initial PL intensity, while I is that of the corresponding sample after a designated time interval.

For long-term tracing in a biological environment, excellent fluorescence stability of the probes is essential to ensure accurate deciphering of the obtained optical information. The Tat-AIE dots in the cell culture medium (Dulbecco's Modified Eagle Medium, DMEM, supplemented with 10% fetal bovine serum, FBS) showed excellent fluorescence stability, as illustrated in FIG. 28. FIG. 28(a) shows that the fluorescence intensity of the Tat-AIE dots retains 93% of its initial value after a 9-day incubation period in DMEM at 37° C. FIG. 28(b) shows that, overall, the outstanding fluorescence stability in biological media and excellent photostability of Tat-AIE dots will greatly benefit both in vitro and in vivo cell tracing experiments.

Figure 29:
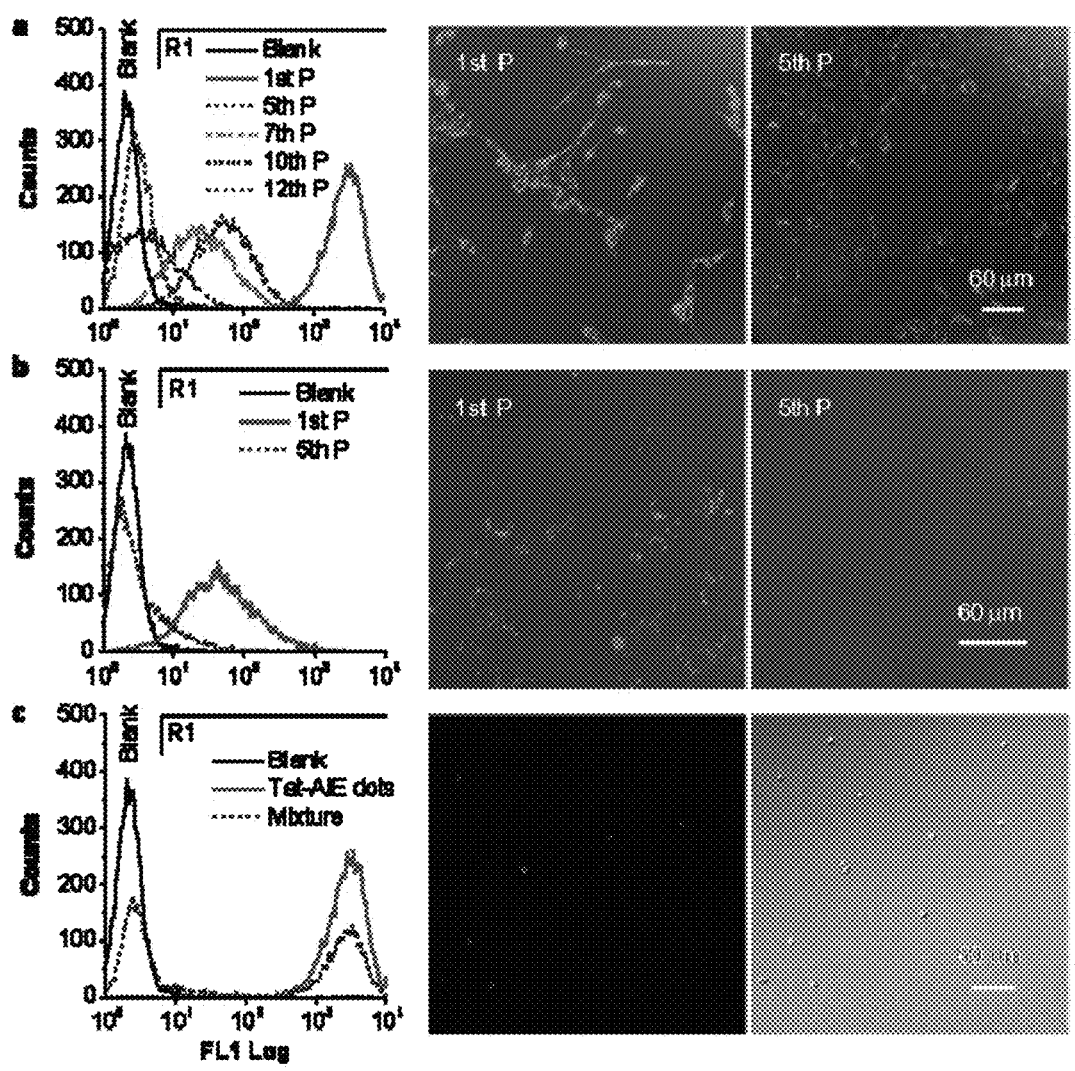
FIG. 29 illustrates long-term tracing of living cells by Tat-AIE dots. On the left: Flow cytometry histograms of MCF-7 breast cancer cells after incubation with 2 nM (a) Tat-AIE dots and (b) Qtracker® 655 at 37° C. for 4 h and then subcultured for designated passages (P). The untreated MCF-7 cells were used as the control (blank solid line). The corresponding confocal images shown on the right were taken under excitation at 514 nm (~1 mW) with a 550-750 nm bandpass filter. (c) Flow cytometry histograms of the MCF-7 cells stained by 2 nM of Tat-AIE dots at 37° C. for 4 h (gray solid line) and a mixture of Tat-AIE dot-stained MCF-7 cells and unstained cells (1:1; gray dashed line). The histograms were recorded after subculture for 1 day. The fluorescence image and fluorescence/transmission overlay image of the cell mixture are shown on the right.

FIG. 29 shows the superior cell tracing ability of Tat-AIE dots. FIG. 29(a) shows that the labeling rate of MCF-7 cells is 99.65% at the first passage and remains above 95% at the seventh passage as compared to the untreated cells. The labeling rate is 16.28% after continuous culture till the tenth passage. On the contrary, only 18.13% of Qtracker® 655-treated cells are labeled at the fifth passage (FIG. 29(b)). The results clearly indicate the superior cell tracing ability of Tat-AIE dots over Qtracker® 655, which is able to trace 5-6 generations as indicated in the protocol.

These results were further confirmed by confocal images. Only very weak fluorescence is detectable in Qtracker® 655-labeled cells while the Tat-AIE dot-labeled cells show a high fluorescence signal at the fifth passage (FIG. 29). The fluorescence signal in the confocal images in FIG. 29(a) is from the Tat-AIE dots since cell autofluorescence is not detectable under the same experimental conditions. The high-resolution fluorescence image indicates that the Tat-AIE dots are internalized into cell cytoplasm and distributed surrounding the nuclei due to their relatively larger size than the nuclear pore.

MCF-7 cells incubated with 2 nM dots for 4 hours were mixed with untreated cells at a 1:1 ratio and further incubated for 1 day in a fresh culture medium. Flow cytometry histogram of the mixture indicates that the ratio of cells with and without fluorescence is almost 1:1 (FIG. 29(c)), indicating that Tat-AIE dots are hardly transferred from the labeled cells to adjacent untreated cells during the co-culture process. The good intracellular retention of Tat-AIE dots in living cells is ideal in tracing the migration, spread, invasion and morphology change of cancer cells. In addition, when Tat-AIE dots were incubated with MCF-7 cells, 99.10% and 10.56% of the cells were efficiently labeled at the first and seventh passages, respectively, which are comparable to the data obtained using Qtracker® 655, indicating the superior cell tracing ability of the as-prepared Tat-AIE dots. As Qtracker® labeling kits are the most commonly used long-term fluorescent tracing probes, the superior performance of Tat-AIE dots clearly demonstrates their great potential in practice.

As a critical issue in fluorescence imaging of living biosubstrates, the toxicity of Tat-AIE dots was evaluated through methylthiazolyldiphenyltetrazolium bromide (MTT) assays to determine the metabolic viability of both MCF-7 breast cancer cells and C6 glioma cells after incubation with Tat-AIE dots. The cell viability remains above 95% after being treated with 1, 2 and 8 nM Tat-AIE dots for 72 h, indicating low cytotoxicity in the test, which is essential for in vitro and in vivo long-term tracing applications.

Figure 30:
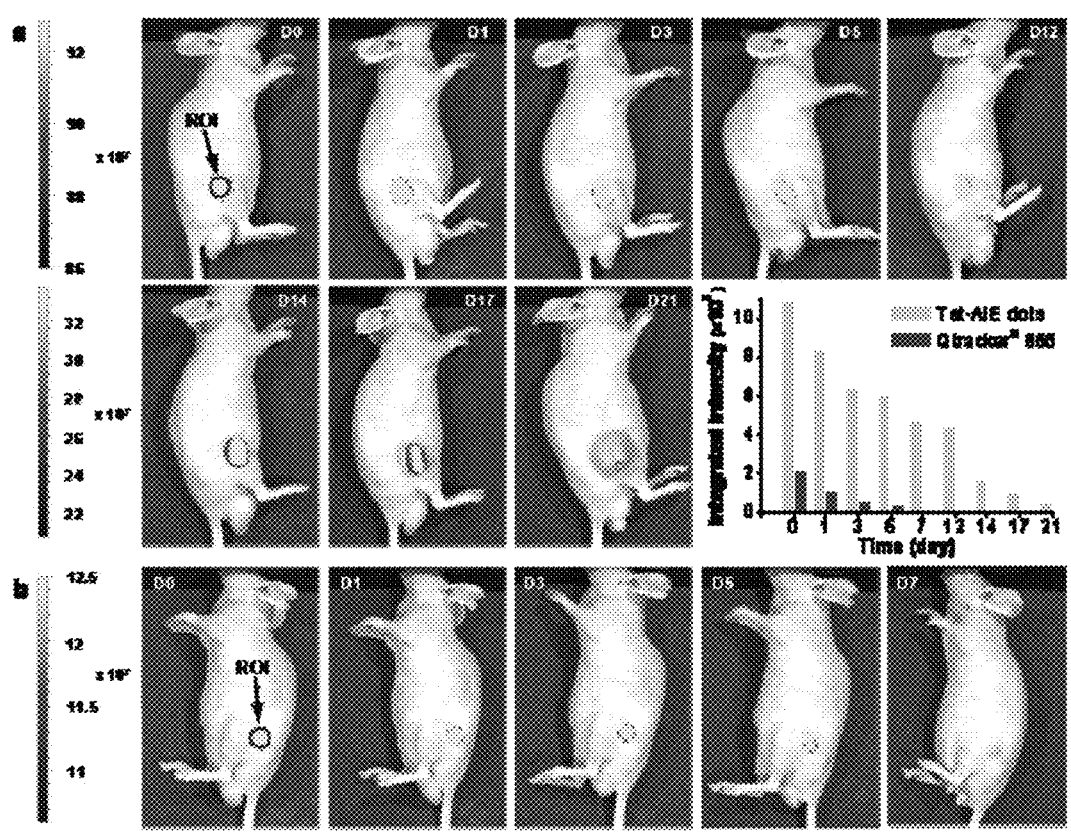
FIG. 30 illustrates the fluorescence imaging of tumor cells by Tat-AIE dots. (a) Representative in vivo fluorescence images of the mouse subcutaneously injected with 1×10$^6$ of C6 glioma cells after staining by 2 nM Tat-AIE dots. (b) Data for Qtracker® 655 obtained under similar conditions. The images were taken on designated days post cell injection. The inset in the middle panel shows the integrated PL intensities of the regions of interest (-dark gray circles) at the tumor sites from the corresponding images.

As shown in FIG. 30(a), C6 glioma cells after incubation with Tat-AIE dots or Qtracker® 655 were subcutaneously injected into the flank of mice. The intense fluorescence from the injected site can be clearly distinguished at 1 h post injection (day 0). As the cells grow, the whole injected site emits obvious fluorescence signals after tracing for 21 days. On the contrary, no fluorescence from the Qtracker® 655-labeled cells can be detected at 7 days post injection, but the excrement shows QD fluorescence (FIG. 30(b)). Quantitative evaluation of the integrated fluorescence intensity in the region of interest (ROI, marked with blue circles of the same size in FIG. 30) upon injection of Tat-AIE dot-labeled or Qtracker® 655-labeled C6 cells was conducted using IVIS Spectrum imaging software after subtraction of autofluorescence (inset of FIG. 30). The fluorescence intensity ($1.08 \times 10^{10}$) of Tat-AIE dot-labeled cells is ~5-fold higher than that of Qtracker® 655-labeled ones ($2.05 \times 10^9$) upon 1 h post injection. It is noteworthy that the intensity of Tat-AIE dot-labeled cells 12 days after injection ($4.35 \times 10^9$) is still two times higher than the initial value of Qtracker® 655-labeled ones. At 21 days post injection, the integrated fluorescence intensity is $4.5 \times 10^8$ at the tumor site. Therefore, Tat-AIE dots can be used in long-term cell tracing in a living body.

Figure 31:
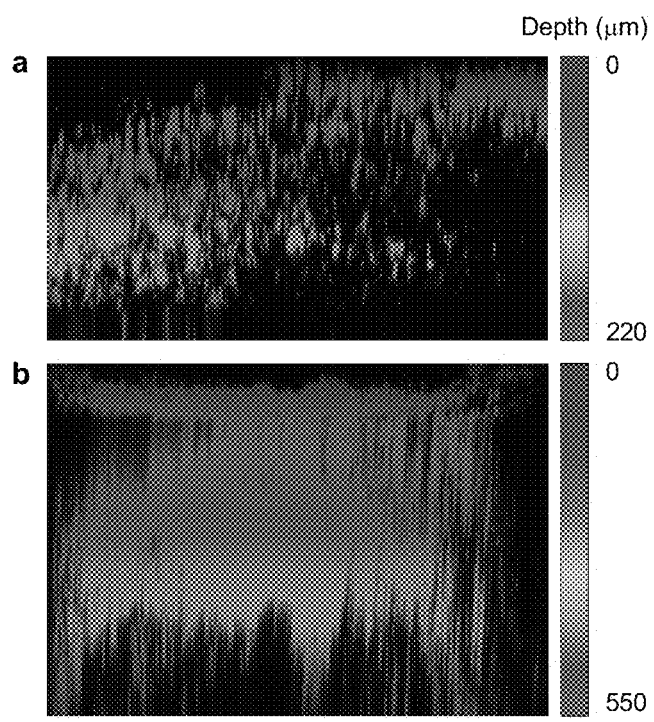
FIG. 31 illustrates depth profiles of fluorescence images of the tumor stained by Tat-AIE dots. Projections of z-stacks of (a) one- and (b) two-photon excited fluorescence of the tumor; (a) $\lambda_{ex}$=560 nm, (b) $\lambda_{ex}$=800 nm. The solid tumor was collected from the mouse after 9-day injection of the Tat-AIE dot-stained cells. The fluorescence signals were collected with a 550-780 nm bandpass filter.

Upon 9 days post injection of Tat-AIE dot-labeled C6 glioma cells, one mouse was sacrificed to collect the tumor. The whole tumor was then mounted and imaged upon excitation at 560 nm using one-photon excited fluorescence microscope. The images were taken layer-by-layer at 3 μm interval to monitor the efficient penetration depth of fluorescence from Tat-AIE dots in tumor tissue. As shown in FIG. 31(a), the 3D color-coded projection of deep tissue image reveals that the fluorescence signal can be detected at 220 μm depth in the tumor upon excitation at 560 nm. The outstanding one-photon excited deep tumor imaging performance can be ascribed to the high brightness of the Tat-AIE dots in the region. The sectioned tumor image was also obtained, showing clear accumulation of the dots inside cells of the solid tumor.

AIE Fluorogens Conjugated with Peptides as Fluorescent Bioprobes

Another embodiment of the present subject matter relates to a fluorescent bioprobe comprising one or more fluorogens that exhibit aggregation induced emission properties, wherein the fluorogens comprise one or more aggregation induced emission fluorophores conjugated with one or more peptides; wherein the fluorogens have a fluorescence emission; and wherein the fluorogens comprise one or more backbone structures selected from the group consisting of:

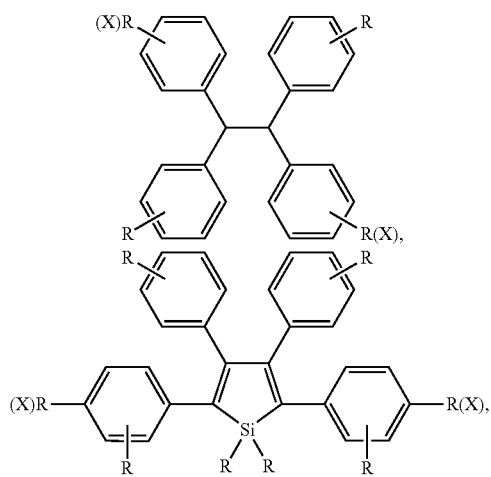

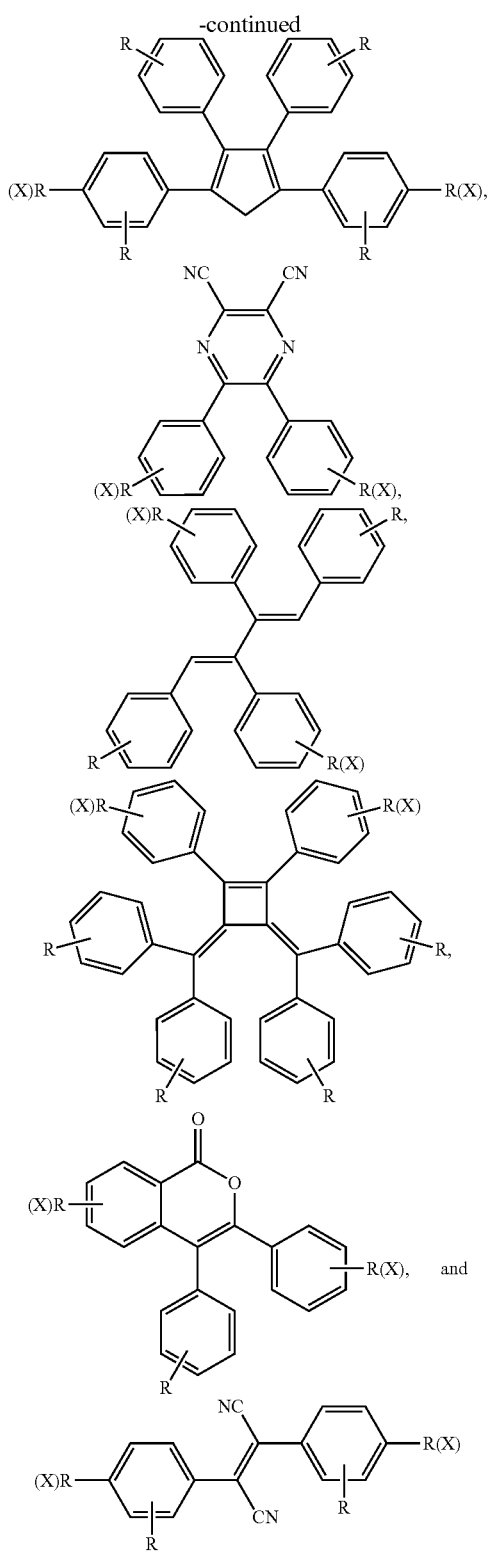

wherein each R is independently selected from the group consisting of H, alkyl, unsaturated alkyl, heteroalkyl, cycloalkyl, heterocycloalkyl, aryl, heteroaryl, a carboxyl group, an amino group, a sulfonic group, and an alkoxy group; wherein R(X) is a terminal functional group independently selected from the group consisting of $N_3$, $NH_2$, COOH, NCS, SH, alkyne, N-Hydroxysuccinimide ester, a maleimide, a hydrazide, a nitrone group, —CHO, —OH, a halide, and a charged ionic group; and wherein one or more peptides is conjugated to R(X).

In one embodiment, R(X) comprises one or more charged ionic groups in order to endow the fluorescent bioprobe with water solubility. In a further embodiment, the charged ionic groups include but are not limited to —COOH, quaternized amine, $SO_3^-$, and $PO_3^-$.

In another embodiment of the present subject matter, the fluorescent bioprobe comprises fluorogens having a chemical structure selected from the group consisting of:

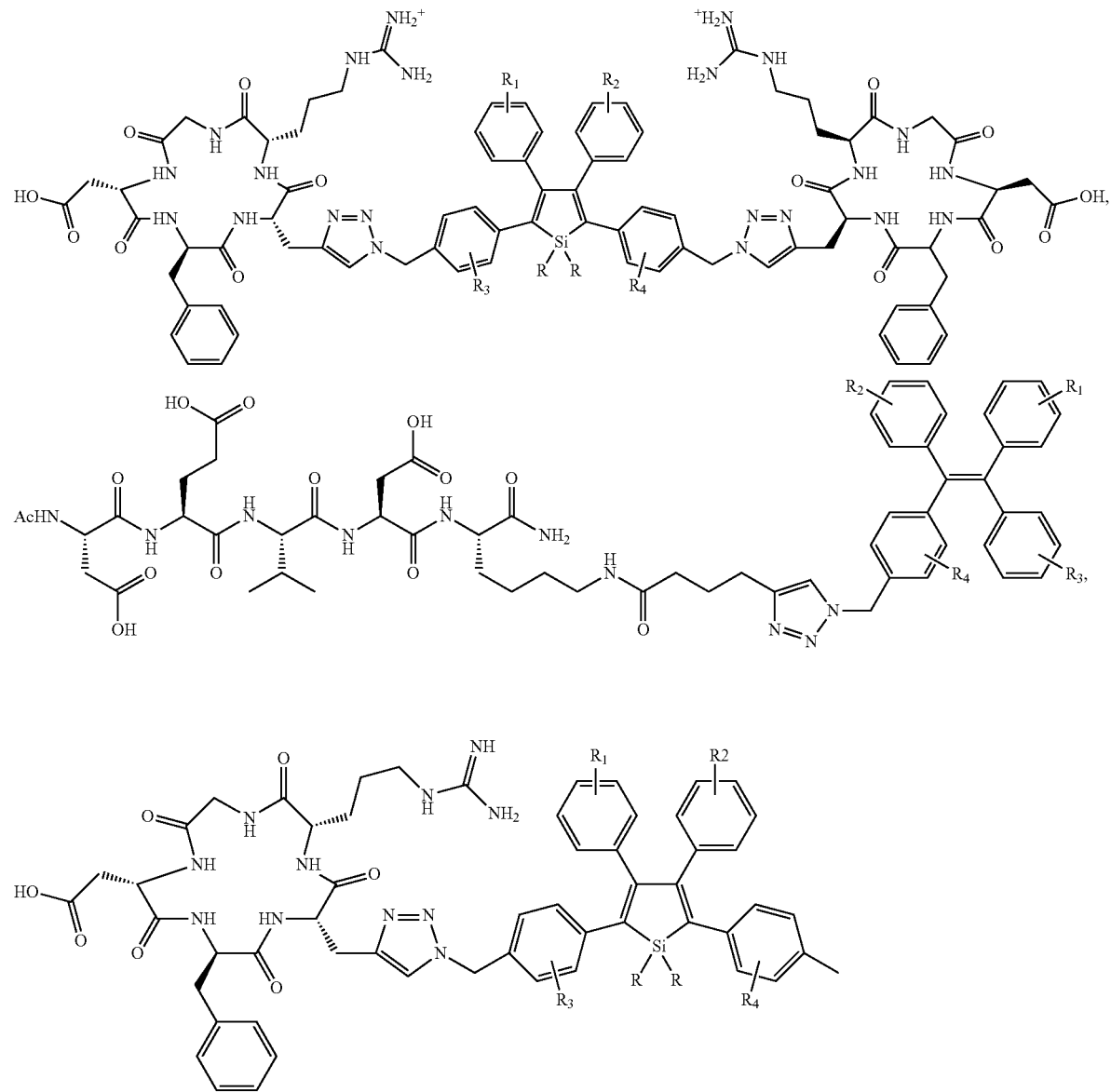

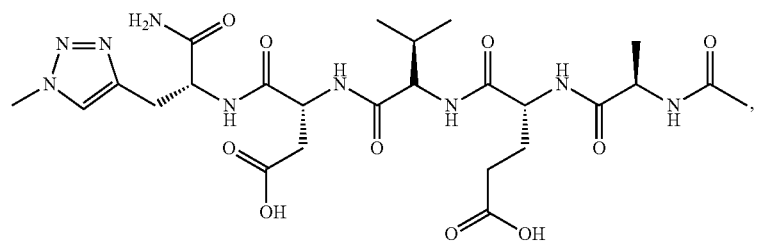

-continued

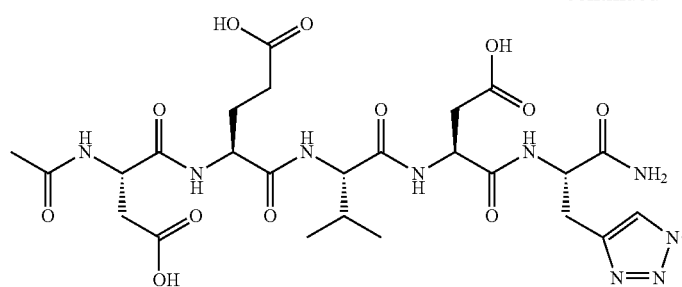
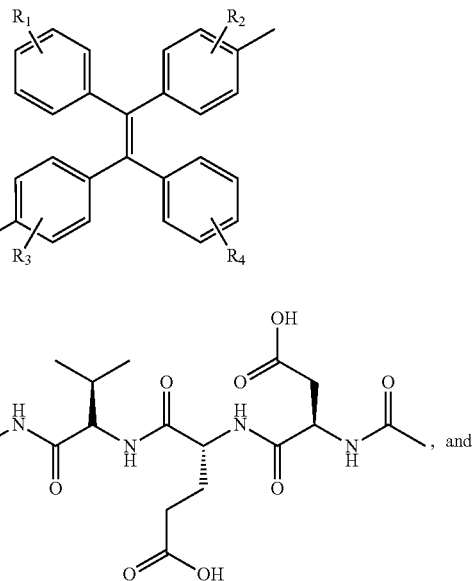
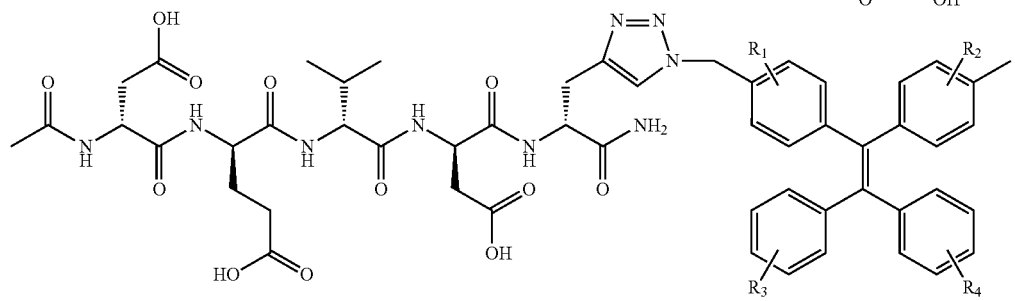
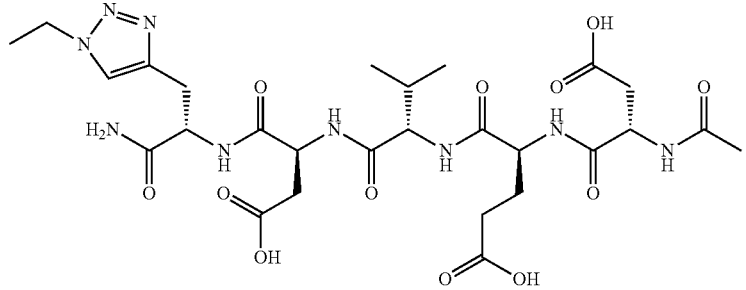

wherein each $R_1$, $R_2$, $R_3$, and $R_4$ is independently selected from the group consisting of H, alkyl, unsaturated alkyl, heteroalkyl, cycloalkyl, heterocycloalkyl, aryl, heteroaryl, a carboxyl group, an amino group, a sulfonic group, and an alkoxy group.

In one embodiment, the peptide is independently selected from the group consisting of a biorecognition peptide and a cell penetrating peptide.

In another embodiment, the fluorescent bioprobe comprises one or more biorecognition peptides selected from the group consisting of a cyclic-RGD peptide and a DEVD peptide substrate. In yet another embodiment, the cell penetrating peptide is trans-activator of transcription peptide (Tat).

Method for Preparing Fluorescent Bioprobes with Peptides

In another embodiment, the method for preparing the fluorescent bioprobe with peptides comprises: (a) preparing a peptide containing a terminal alkyne by solid-phase synthesis; (b) preparing a DMSO solution of fluorogen azide; (c) mixing the fluorogen azide and the peptide together with $CuSO_4$ and sodium ascorbate; (d) crosslinking the fluorogens and the peptides by click chemistry; and (e) purifying by high performance liquid chromatography to form the fluorescent bioprobes.

TPS-2cRGD as a Fluorescent Bioprobe

In another embodiment, AIE-active bioprobe TPS-2cRGD was synthesized as a fluorescent bioprobe. In one aspect 1,1-dimethyl-2,5-bis[4-(azidomethyl)phenyl]-3,4-diphenylsilole (5, BATPS) was synthesized via the following reaction scheme.

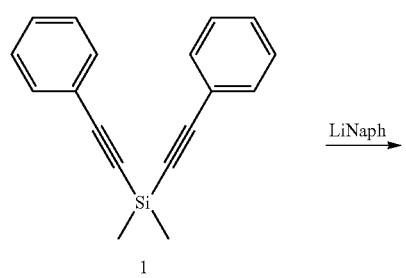
1
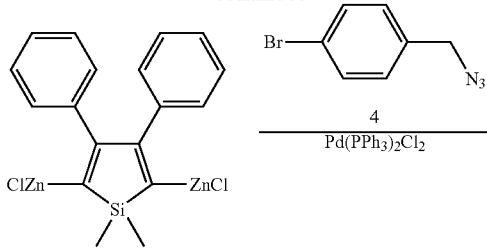
5
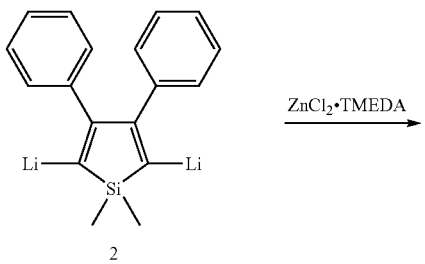
2
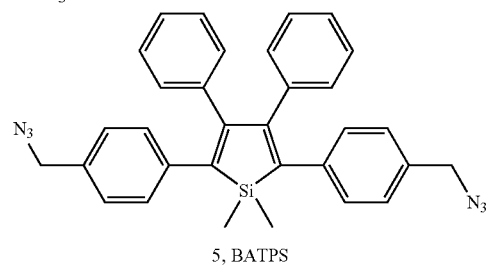
3
5, BATPS
In another aspect, TPS-2cRGD was synthesized, using BATPS (5), via the following reaction scheme.
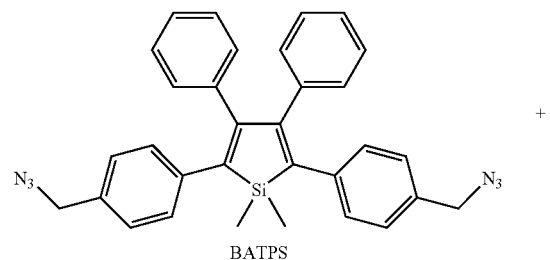
BATPS
+
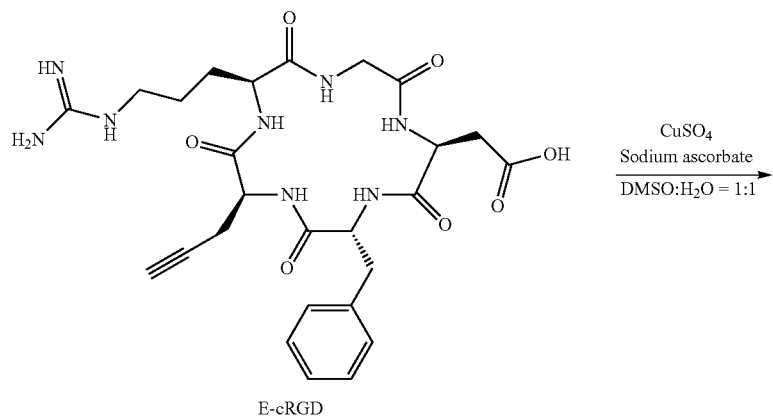
E-cRGD

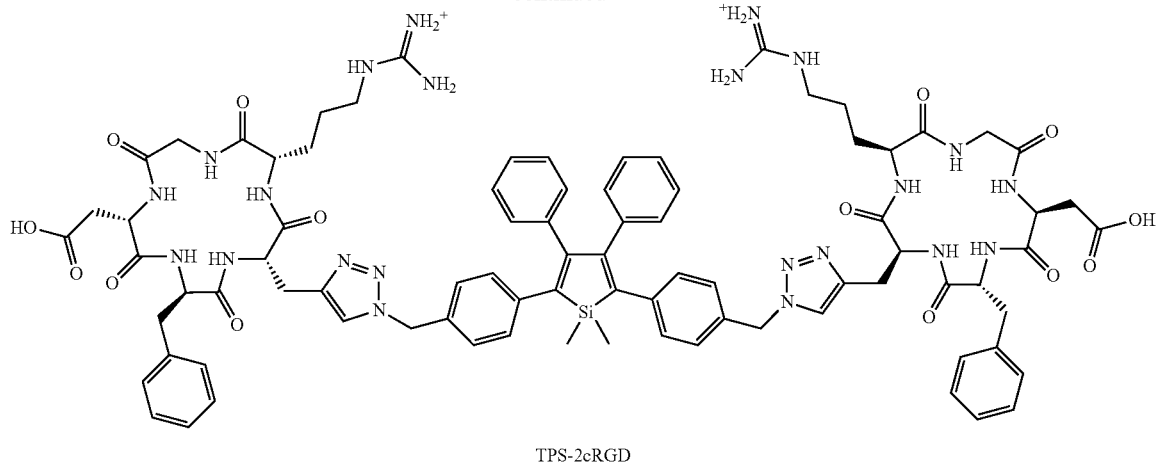 [SMILES: C[Si]1(C)C(c2ccc(Cn3cc(C[C@@H]4NC(=O)[C@@H](Cc5ccccc5)NC(=O)[C@H](CC(=O)O)NC(=O)CNC(=O)[C@H](CCCNC(N)=[NH2+])NC4=O)nn3)cc2)=C(c2ccccc2)C(c2ccccc2)=C1c1ccc(Cn2cc(C[C@@H]3NC(=O)[C@@H](Cc4ccccc4)NC(=O)[C@H](CC(=O)O)NC(=O)CNC(=O)[C@H](CCCNC(N)=[NH2+])NC3=O)nn2)cc1]

TPS-2cRGD

Figure 32:
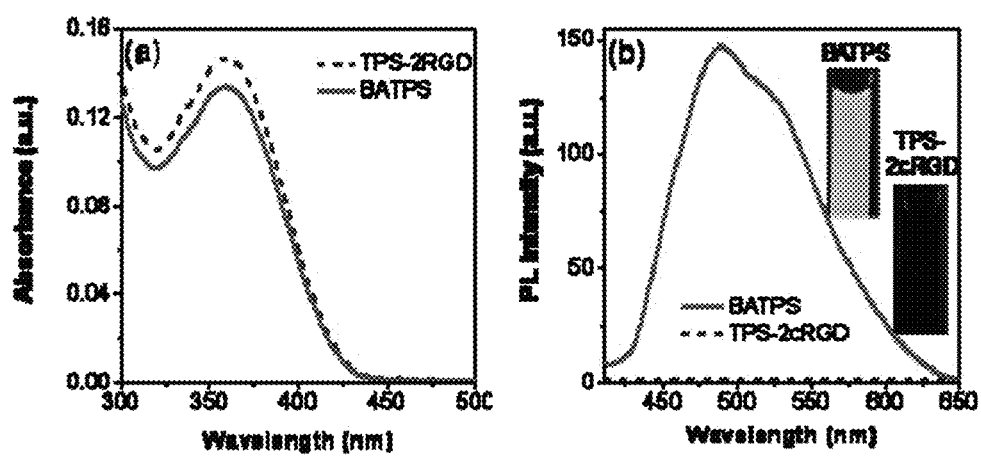
FIG. 32A illustrates an absorption spectrum of BATPS (solid line) and TPS-2cRGD (dashed line) in DMSO/water (v/v=1/199) where [BATPS]=[TPS-2cRGD]=10 µM.
FIG. 32B illustrates a PL spectra of BATPS (solid line) and TPS-2cRGD (dashed line) in DMSO/water (v/v=1/199) where [BATPS]=[TPS-2cRGD]=10 µM.
Figure 33:
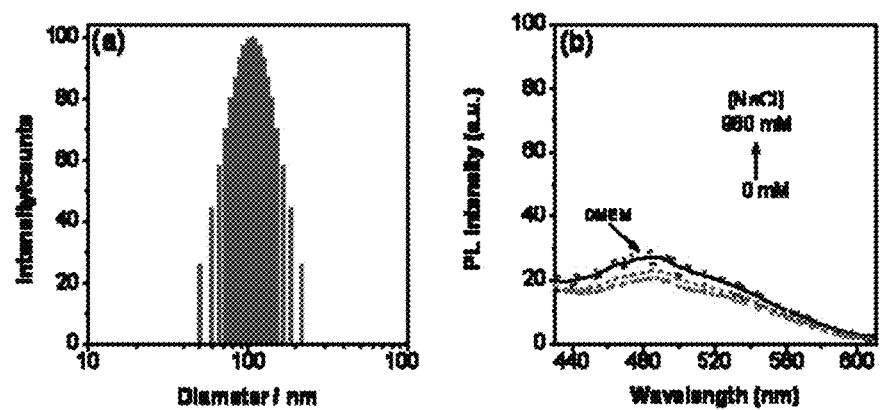
FIG. 33A illustrates the hydrodynamic diameters of BATPS in DMSO/water (v/v=1:199) obtained from laser light scattering.
FIG. 33B illustrates the PL spectra of TPS-2cRGD in $H_2O$ with varied concentrations of NaCl (0, 30, 60, 120, 240, 480, and 960 mM) and in cell culture medium (DMEM). [BATPS]=[TPS-2cRGD]=10 µM; $\lambda_{ex}$=356 nm.
Figure 34:
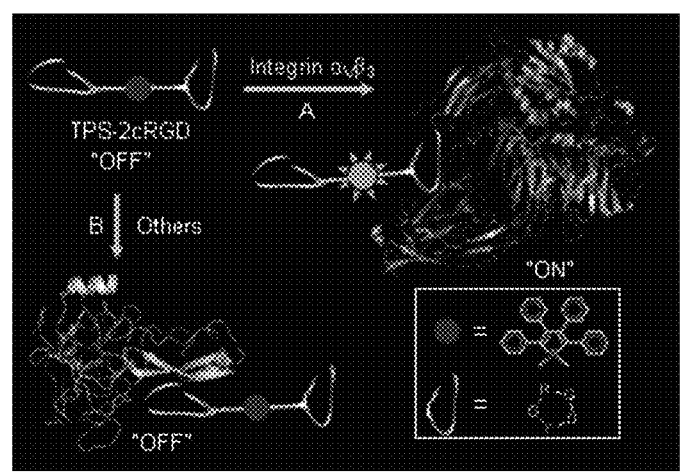
FIG. 34 illustrates the determination of (A) Integrin $\alpha_v\beta_3$ from (B) other proteins through specific cRGD-Integrin interaction.

FIG. 32A illustrates the UV-vis absorption spectra of BATPS (5) and TPS-2cRGD. Both have a similar absorption profile with the maximum at 356 nm. The corresponding photoluminescence (PL) spectra are shown in FIG. 32B, along with the photographs taken under UV irradiation. It is known that AIE fluorogens are virtually non-fluorescent in good solvents but emit intensely when aggregated in poor solvents. BATPS is a hydrophobic AIE fluorogen, which shows intense fluorescence as nanoaggregates in water, while its conjugate TPS-2cRGD is almost non-fluorescent. This indicates that TPS-2cRGD has good solubility in water, which is further supported by the laser light scattering (LLS) data. As shown in FIG. 33A, BATPS forms nanoaggregates in water with an average diameter of 103 nm, while no detectable signal is observed for TPS-2cRGD.

In a further embodiment, the effect of ionic strength on the fluorescence intensity of TPS-2cRGD was tested. The fluorescence spectra are show in FIG. 33B. With increasing concentration of sodium chloride from 0 to 960 mM, there is no obvious change in the emission profile of TPS-2cRGD. In addition, the PL intensity remains almost the same. This indicates that ionic strength does not affect the fluorescent properties of the probe. It is also important to note that the fluorescence spectrum of TPS-2cRGD does not change in the presence of cell culture medium DMEM, which contains amino acids, salts, glucose, and vitamins. These studies demonstrate that the probe maintains low fluorescence in a complex environment, making it an ideal probe for specific fluorescence turn-on sensing and imaging applications.

Figure 41:
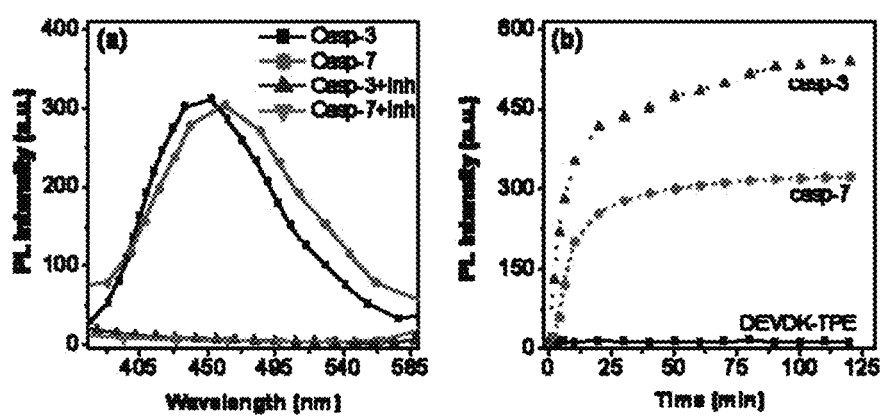
FIG. 41 illustrates enzymatic screening of AcDEVDK-TPE against pure caspase-3 and caspase-7.

As shown in FIG. 41, when the bioprobe is well-dissolved in water, the excited states are readily annihilated by intramolecular rotations of phenyl rings to yield very weak fluorescence. Upon the addition of an analyte protein, two situations can occur. One situation involves the addition of a specific protein, e.g. integrin αVβ3. According to the AIE mechanism, specific binding between TPS-2cRGD and integrin αVβ3 can significantly restrict the molecular rotations of the silole core, leading to fluorescence turn-on of the probe. On the other hand, when the protein has non-specific interaction with TPS-2cRGD, the solution remains dark.

Figure 35:
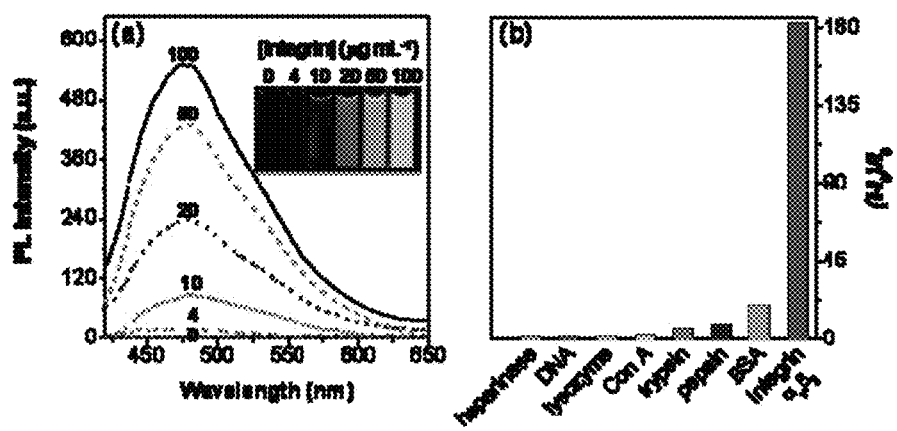
FIG. 35A illustrates the PL spectra of TPS-2cRGD in the presence of different amounts of integrin $\alpha_v\beta_3$ (0, 4, 10, 20, 50 and 100 µg mL$^{-1}$). The inset in FIG. 35A shows the corresponding photograph taken under the illumination of a handheld UV lamp.
FIG. 35B illustrates plot of $I/I_0$ with respect to different proteins, where I and $I_0$ are probe PL intensities at 50 µg mL$^{-1}$ and 0 µg mL$^{-1}$ proteins, respectively. [TPS-2cRGD]=10 µM; $\lambda_{ex}$ 356 nm.

FIG. 35A shows the changes in PL spectra of TPS-2cRGD upon addition of integrin $\alpha_v\beta_3$ with the concentration ranging from 0 to 100 μg mL$^{-1}$. With increasing concentration of integrin $\alpha_v\beta_3$, TPS-2cRGD exhibits a progressive intensity increase. As compared to its intrinsic fluorescence, up to a seven-fold fluorescence enhancement was observed when the probe was incubated with integrin $\alpha_v\beta_3$. As each integrin $\alpha_v\beta_3$ only has one binding site for cRGD in between the a and 0 domain and the probe size is much smaller as compared to that for the protein, each probe can only bind to one integrin $\alpha_v\beta_3$. As such, the fluorescence enhancement is mainly caused by restricted intramolecular rotation of phenyl groups after complex formation between the probe and integrin $\alpha_v\beta_3$.

Figure 36:
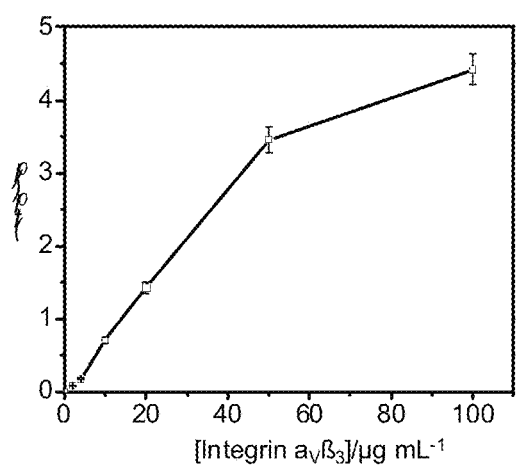
FIG. 36 illustrates the plot of $(I-I_0)/I_0$ with respect to different concentration of integrin $\alpha_v\beta_3$ in PBS buffer. I and $I_0$ are PL intensities of TPS-2cRGD in the presence and in the absence of integrin $\alpha_v\beta_3$.

The specificity and selectivity of the probe for human integrin $\alpha_v\beta_3$ was tested. TPS-2cRGD was treated with several other proteins which are widely present in cells, such as lysozyme (isoelectric point, pI=11.0), papain (pI=8.7), trypsin (pI=10.1) and BSA (pI=4.9) under the same experimental conditions. As shown in FIG. 35B, I and $I_0$ represent the peak intensities of the probe in the presence of 100 μg mL$^{-1}$ protein and in the absence of protein, respectively. Except for integrin $\alpha_v\beta_3$, very little change of PL intensity is observed for the other four proteins. This indicates that TPS-2cRGD has high specificity and selectivity for human integrin $\alpha_v\beta_3$. Plotting the changes in fluorescence intensity over the protein concentration yielded a linear curve followed by saturation (FIG. 36). The limit of detection for integrin $\alpha_v\beta_3$ in solution is 4 μg/mL, estimated using three times the standard deviation.

Figure 37:
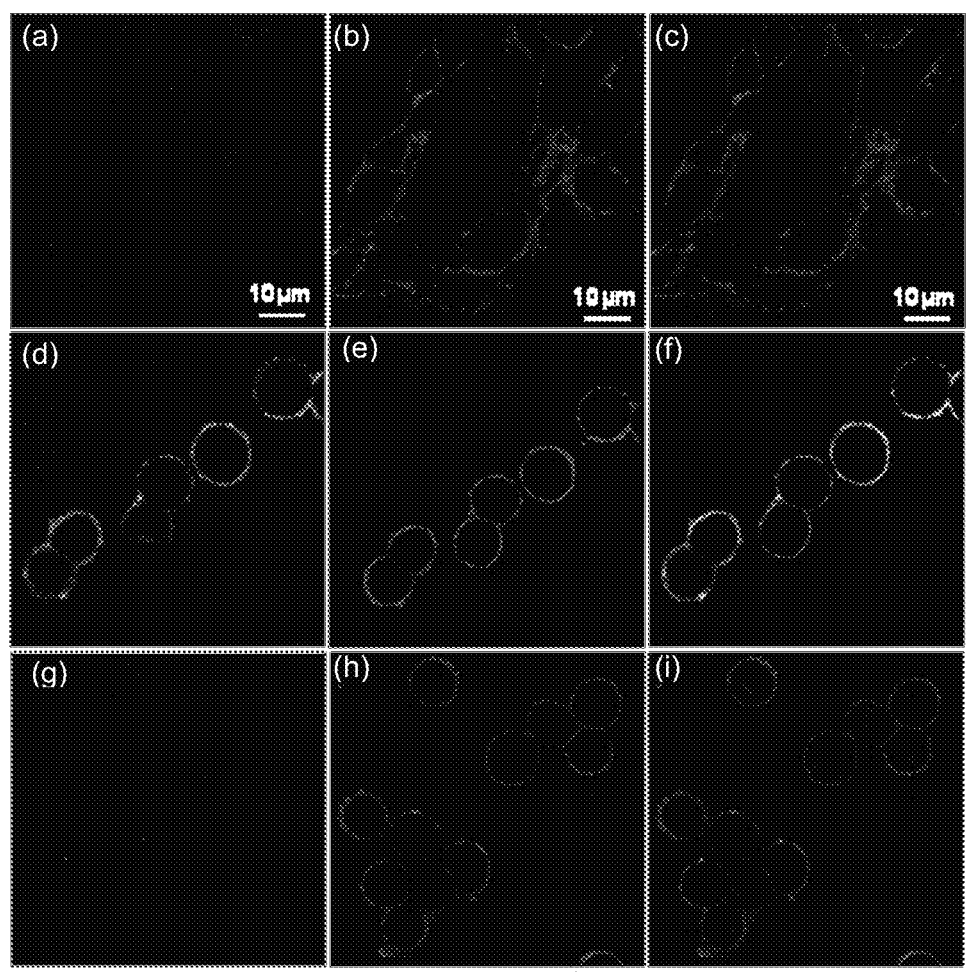
FIG. 37 illustrates CLSM images of live cells after 30 min incubation with 2 µM TPS-2cRGD in the absence and presence of membrane tracker at 4° C. Fluorescent images of MCF7 cells stained with (a) TPS-2cRGD, (b) membrane tracker, and (c) overlapped image; Fluorescent images of HT-29 cells stained with (d) TPS-2cRGD, (e) membrane tracker, and (f) overlapped image; Fluorescent images of HT-29 cells pre-treated with 10 µM cyclic RGD peptide followed by staining with (g) TPS-2cRGD, (h) membrane tracker, and (i) overlapped image. The confocal images were collected under excitation at 405 nm (5% laser power) with a band pass 505-525 nm filter (a, d, g), and 543 nm (5% laser power) with a band pass 575-635 nm filter (b, e, h). All images share the same bar.

TPS-2cRGD can act as a specific probe for in vitro integrin $\alpha_v\beta_3$ detection. The receptor-mediated binding of TPS-2cRGD to integrin $\alpha_v\beta_3$ was tested in mammalian cells. Colon cancer cells HT-29 with overexpressed integrin $\alpha_v\beta_3$ on cellular membrane were used as integrin $\alpha_v\beta_3$-positive cancer cells while breast cancer cells MCF7 with low integrin $\alpha_v\beta_3$ expression were used as a negative control. FIG. 30 shows the confocal laser scanning microscopy (CLSM) images of HT-29 and MCF7 live cells after incubation with TPS-2cRGD. A commercial membrane tracker is also used to indicate the location of the cell membrane (FIGS. 37 (b), (e), and (h)). As shown in FIG. 37(a), very weak fluorescence was detected from MCF-7 cells. However, under the same experimental conditions, a strong fluorescent signal was observed for HT-29 colon cancer cells (FIG. 37(d)). In addition, the signal can be significantly reduced when the cells were pre-treated with free cyclic RGD peptide (FIG. 37(g)), indicating that the fluorescence originated from specific binding between TPS-2cRGD and integrin $\alpha_v\beta_3$. In addition, the well overlapped images between the probe and membrane tracker in FIG. 37(f) clearly demonstrates that the specific binding occurs on cellular membrane. The specific interaction between TPS-2cRGD and integrin $\alpha_v\beta_3$ allows clear determination of integrin $\alpha_v\beta_3$-positive cancer cells (FIG. 37(d) vs. FIG. 37(a)).

Figure 38:
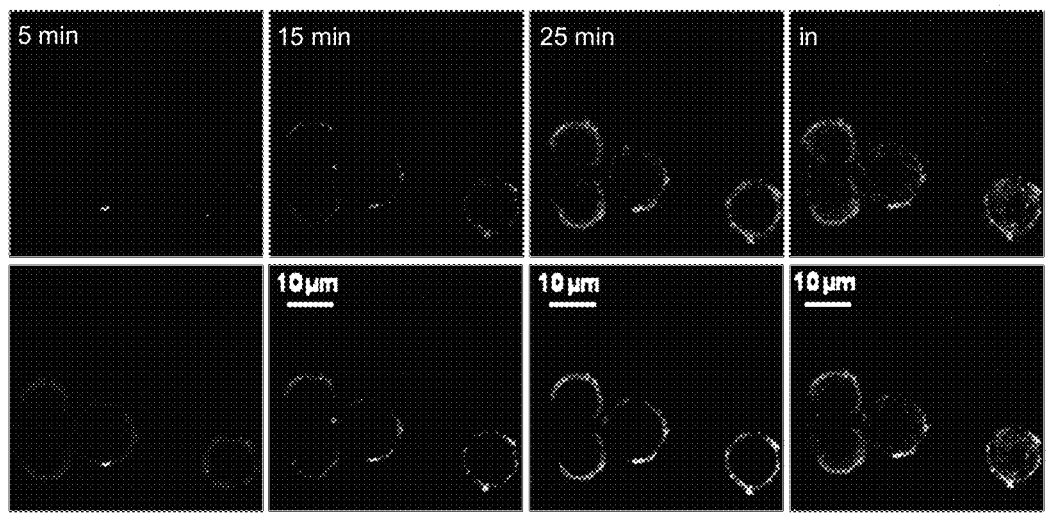
FIG. 38 illustrates real-time fluorescence imaging of TPS-2cRGD uptake into HT-29 cells at room temperature (top panel) and overlapped images of cells stained with TPS-2cRGD and membrane tracker (bottom panel). All images have the same scale bar of 10 µm.

In a further aspect, the internalization of integrin $\alpha_v\beta_3$ was monitored using the bioprobe, and real time imaging was conducted with HT-29 live cells. TPS-2cRGD was added to the cell culture chamber and fluorescence images were acquired at different time points. As shown in FIG. 38, the very dark background in each image indicates that the probe is virtually non-fluorescent in cell growth media. Within the first 25 min, as time elapses, the fluorescence intensity increases as the probe binds to integrin $α_vβ_3$. The green fluorescence from the probe overlaps well with that from the membrane tracker, indicating that during this period most of the bound probes are localized on the cell membrane. Longer incubation times (>25 min) results in the probe being gradually internalized within cells (FIG. 38, 30 min). Collectively, these results demonstrate that TPS-2cRGD can not only be used for detection of integrin $α_vβ_3$-positive cancer cells but also can trace the internalization of integrin $α_vβ_3$ in real-time manner.

Figure 39:
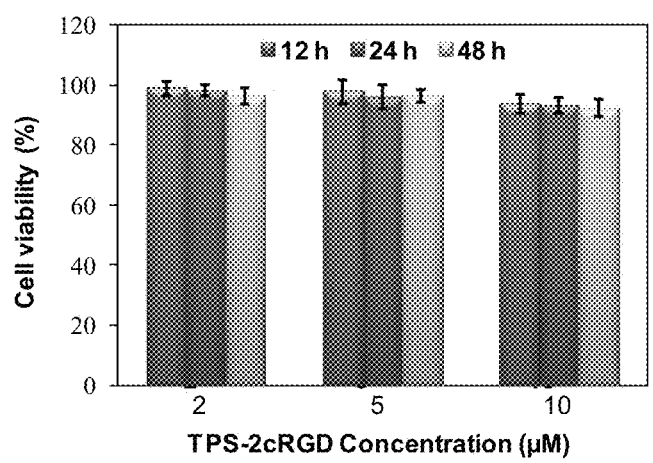
FIG. 39 illustrates the metabolic viability of HT-29 cancer cells after incubation with TPS-2cRGD at concentrations of 2, 5 and 10 µM for 12, 24 and 48 h, respectively.

In another aspect, TPS-2cRGD has a very low cytotoxicity. This is shown in FIG. 39, where the cytotoxicity of TPS-2cRGD was evaluated by the metabolic viability of HT-29 cancer cells. FIG. 39 shows the cell metabolic viability after incubation with TPS-2cRGD at increasing concentrations over increasing periods of time. The metabolic viability of HT-29 cells remained ~100% after incubation with TPS-2cRGD under the studied conditions, demonstrating low cytotoxicity of TPS-2cRGD.

AcDEVDK-TPE as a Fluorescent Bioprobe

In another embodiment, AIE-active bioprobe AcDEVDK-TPE was synthesized for detecting caspase-3/caspase-7 activity. The synthesis of AcDEVDK-TPE involves both solution- and solid-phase chemistry.

First, the TPE-containing azide TPE-$N_3$ (6) was synthesized according to the reaction scheme, below.

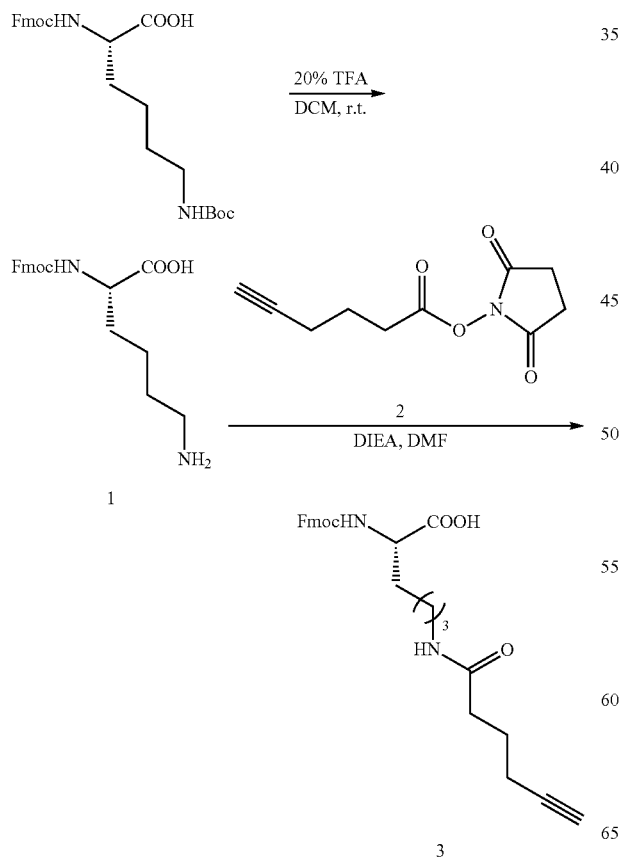

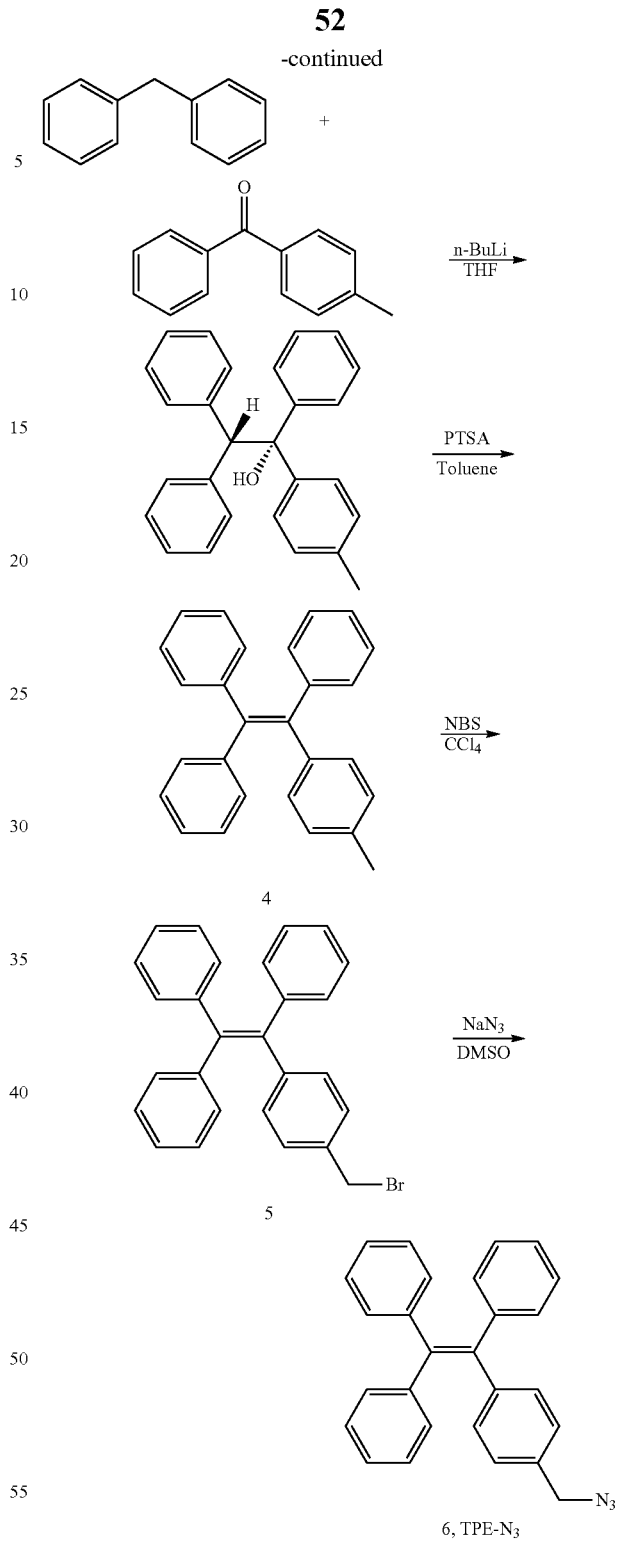

Then, the DEVD peptide is synthesized following standard solid-phase peptide synthesis with Fmoc chemistry. Then, the DEVD peptide is coupled with TPE-$N_3$ via Cu(I)-catalyzed click chemistry using $CuSO_4$/sodium ascorbate as the catalyst and DMSO/$H_2O$ as the solvent. The reaction scheme for the synthesis of AcDEVDK-TPE is shown below.

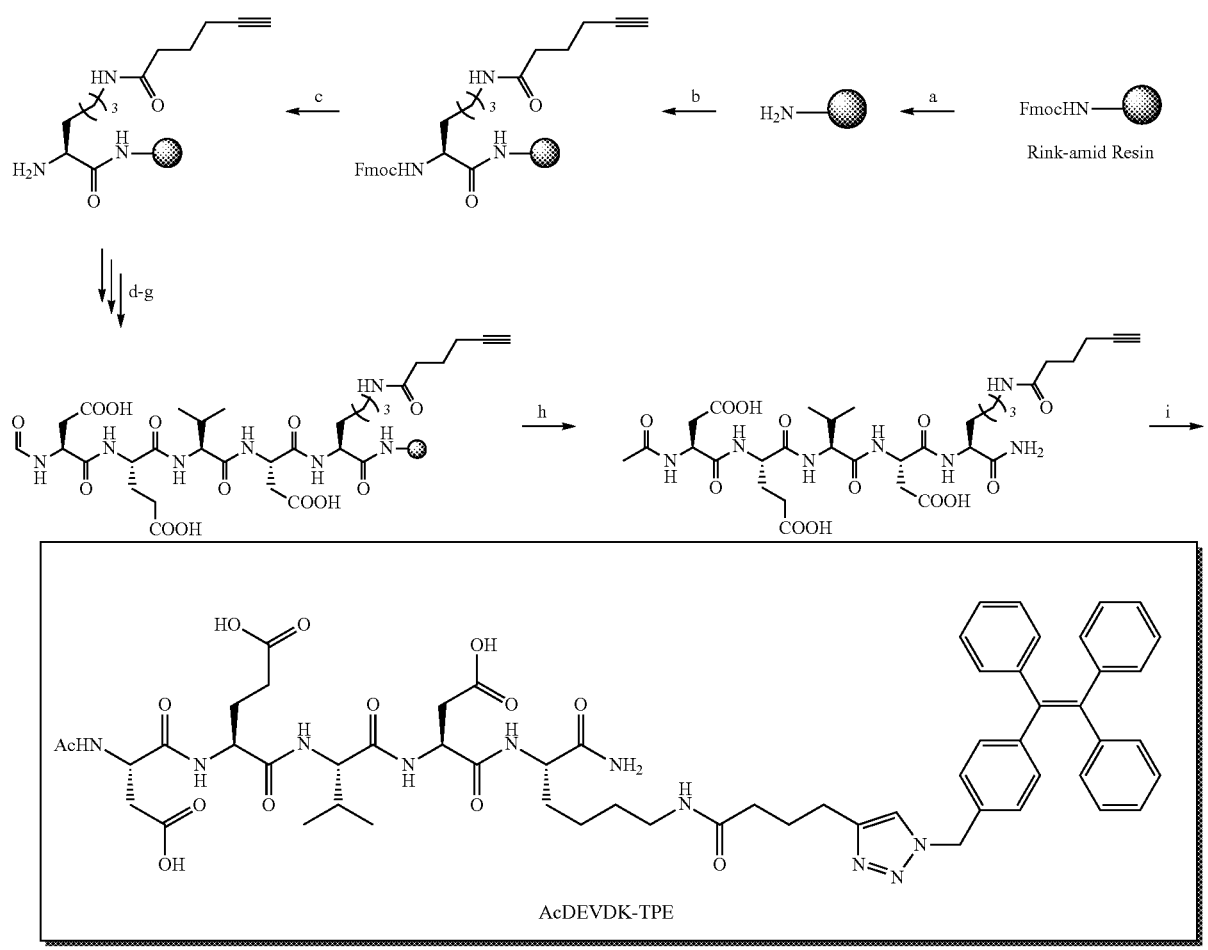

Another embodiment of the present subject matter relates to a method for preparing a fluorescent bioprobe comprising: (a) preparing a biorecognition peptide containing terminal alkyne by solid-phase synthesis; (b) preparing a DMSO solution of fluorogen azide; (c) mixing the fluorogen azide and the biorecognition together with $CuSO_4$ and sodium ascorbate; (d) crosslinking the fluorogens and the biorecognition peptides by click chemistry; and (e) purifying by HPLC to form the fluorescent bioprobes.

Figure 40:
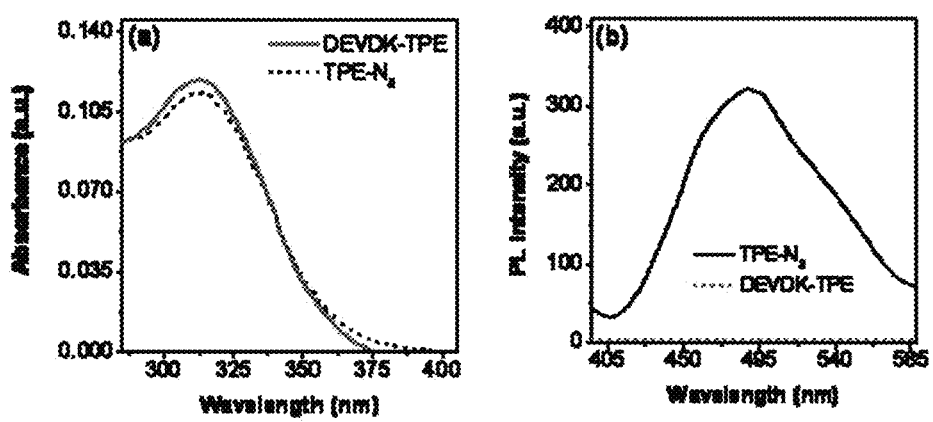
FIG. 40(a) illustrates UV-vis absorption-spectra of TPE-$N_3$ (dashed line) and AcDEVDK-TPE (solid line) in DMSO/water (v/v=2:98).
FIG. 40(b) illustrates photoluminescence (PL) spectra of TPE-$N_3$ (solid line) and AcDEVDK-TPE (dashed line) in DMSO/water (v/v=2:98). [TPE-$N_3$]=[AcDEVDK-TPE]=8 µM; $\lambda_{ex}$=312 nm.

FIG. 40A shows the UV-vis absorption and photoluminescence (PL) spectra of both TPE and AcDEVDK-TPE. Both showed similar absorption profiles with the maximum at 312 nm. It is well known that AIE dye is virtually non-luminescent in good solvents but emits intensely when aggregated in its poor solvents. FIG. 40B shows the PL spectra of TPE-$N_3$ and AcDEVDK-TPE in water. TPE-$N_3$ is a hydrophobic AIE fluorophore and therefore shows intense fluorescence as nanoaggregates in water, while DEVD conjugated AcDEVDK-TPE is almost non-fluorescent. This demonstrates that after conjugation of the DEVD peptide, AcDEVDK-TPE has a good solubility in water. The excited states are readily annihilated by the intramolecular rotations of phenyl rings. Therefore, very low fluorescence was observed.

In a further aspect, cleavage of the amide bond by a protease releases the organic soluble TPE fluorogen in aqueous solution, and the formation of nanoaggregates leads to fluorescence turn-on. Due to this the AcDEVDK-TPE fluorescent peptide can be used to study the protease activity. As shown in FIG. 41A, upon addition of active caspase-3/caspase-7, the peptide sequence DEVD is selectively cleaved from TPE dye resulting in fluorescence turn-on in solution. In addition, no fluorescence turn-on was observed when the enzymes are pretreated with known caspase-3/caspase-7 inhibitors, demonstrating that AcDEVDK-TPE was specifically cleaved by caspase-3/caspase-7.

The bioprobe can also be used for real-time monitoring of enzyme activity. The PL spectra of a solution containing AcDEVDK-TPE and caspase-3/caspase-7 were monitored at different time points. As shown in FIG. 41B, AcDEVDK-TPE was initially not fluorescent. Upon incubation with caspase-3 or caspase-7, there was a time-dependent increase in fluorescence, demonstrating that AcDEVDK-TPE can be used for continuous monitoring of protease activities.

Figure 42:
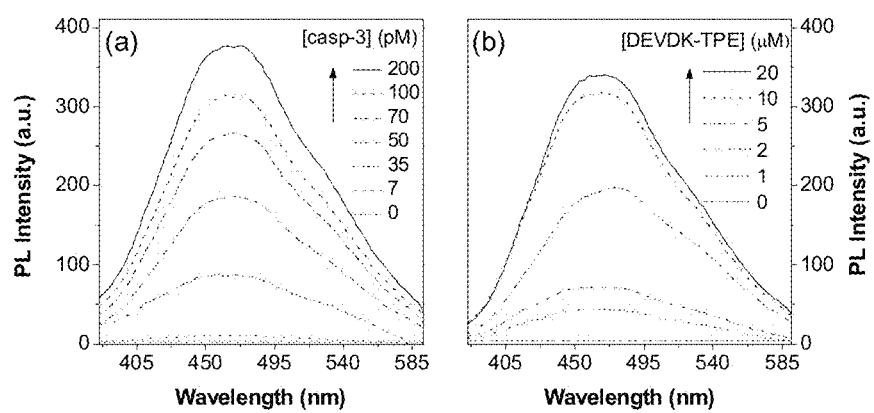
FIG. 42 illustrates (a) PL spectra of AcDEVDK-TPE (5 µM) in presence of different concentrations of caspase-3 (0, 7, 35, 50, 70, 100 and 200 pM) and (b) PL spectra of different concentrations of AcDEVDK-TPE (0, 1, 2, 5, 10 and 20 µM) in presence of 70 pM caspase-3. $\lambda_{ex}$=312 nm.

FIG. 42A shows the changes in PL spectra of AcDEVDK-TPE upon addition of caspase-3 with the concentration ranging from 0 to 200 pM. With increasing concentration of enzymes, AcDEVDK-TPE exhibits a progressive intensity increase. Compared with its intrinsic fluorescence, up to ten-fold fluorescence enhancement was observed when the probe was incubated with 200 pM of caspase-3. FIG. 42B shows the PL spectra for different concentrations of AcDEVDK-TPE ranging from 0 to 20 μM after addition of the same amount of caspase-3. With increasing concentration of AcDEVDK-TPE, the fluorescence exhibits a progressive intensity increase.

Figure 43:
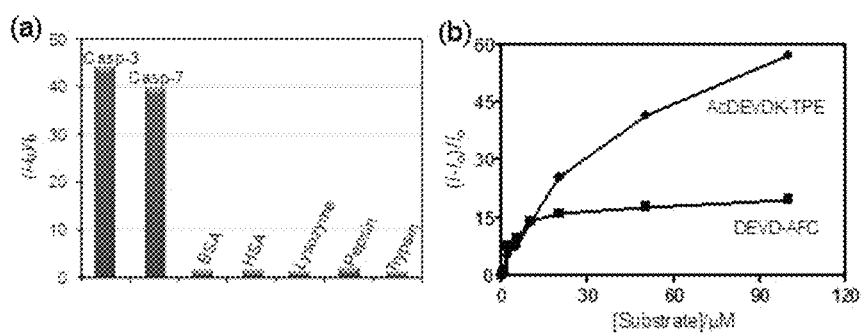
FIG. 43 illustrates (a) a plot of $(I-I_0)/I_0$ with respect to different proteins, where I=FL intensity and $I_0$=FL intensity at 20 and 0 µg mL$^{-1}$ proteins, respectively. Concentration of Ac-DEVDK-TPE=5 µM.

The specificity and selectivity of AcDEVDK-TPE for caspase-3 and caspase-7 is demonstrated in FIG. 43. AcDEVDK-TPE was treated with five other enzymes which are widely present in cells, such as BSA, HSA, Lysozyme, Pepsin and Trypsin under the same conditions. As shown in FIG. 43A, I and $I_0$ represent the peak intensities of the probe in the presence of 20 μg mL$^{-1}$ protein and in the absence of protein, respectively. Except for caspase-3 and caspase-7, very little change of PL intensity is observed for the other five proteins. Furthermore, the addition of fresh cellular lysate also did not lead to any obvious fluorescence change in solution. This demonstrates that AcDEVDK-TPE has high specificity and selectivity for caspase-3 and caspase-7.

FIG. 43B shows the plot of the changes in fluorescence intensity over the substrate concentration yielded a linear curve. As compared to the commercially available coumarin-based caspase-3/caspase-7 substrate DEVD-AFC, the AcDEVDK-TPE bioprobe shows a wider linear response in the substrate concentration range from 0 to 20 μM. This further demonstrates the ability of the AcDEVDK-TPE bioprobe can act as a reasonably efficient substrate for studying enzyme activity.

Figure 44:
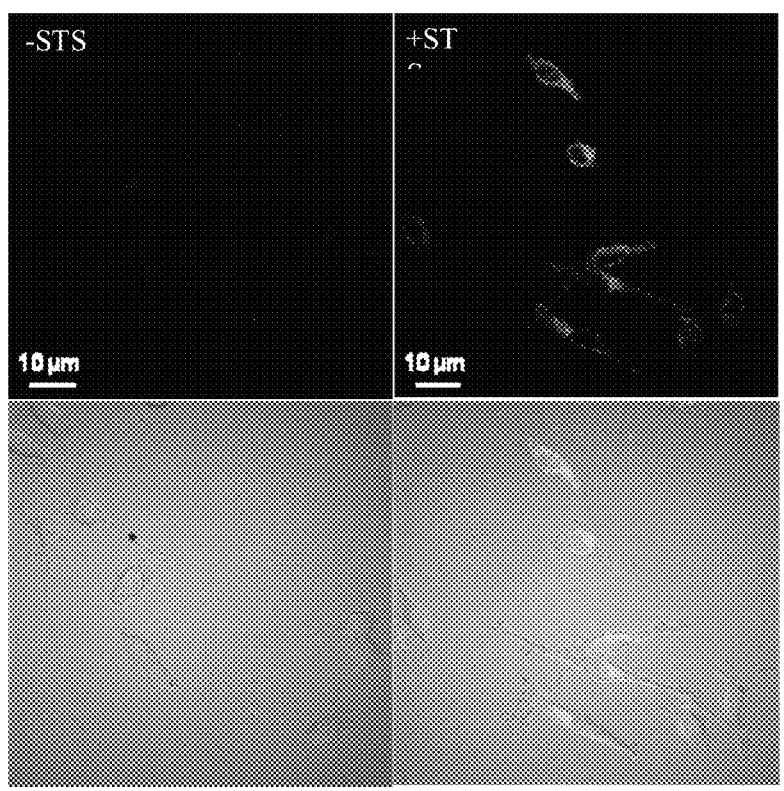
FIG. 44 illustrates confocal microscope images of caspase-3/caspase-7 activities using AcDEVDK-TPE in apoptotic HeLa cells. Left panel: Normal HeLa cells incubated with AcDEVDK-TPE. Right panel: apoptotic HeLa cells incubated with AcDEVDK-TPE. [AcDEVDK-TPE]=5 µM. All images were acquired under excitation at 405 nm (5% laser power) with a band pass 505-525 nm filter. STS represents staurosporine, an anti-cancer treatment drug.

It is well known in the art that caspase-3 and caspase-7 are key mediators of cell apoptosis where improper regulation of caspase activity has detrimental pathological and physiological effects. FIG. 44 demonstrates that the AcDEVDK-TPE bioprobe can be used for live cell enzyme activity study. FIG. 44 shows the ability of AcDEVDK-TPE to image apoptosis in live cells. As shown in FIG. 44, cells treated with AcDEVDK-TPE showed a strong green fluorescence upon apoptosis induction with staurosporine (STS, an anti-cancer drug, right panel). In contrast, only very weak green fluorescence was observed in nonapoptotic cells. AcDEVDK-TPE can serve as a useful probe for fluorescence turn-on imaging of protease activities in live cells.

A c-RGD conjugated tetraphenylsilole (TPS-2cRGD) probe and a DEVD peptide-conjugated tetraphenylethene (TPE) probe, two peptide-conjugated AIE fluorogen probes were synthesized, which are initially non-fluorescent due to their good water solubility. Upon addition of the corresponding proteins, specific binding between TPS-2cRGD and integrin $\alpha_v\beta_3$ can significantly restrict the molecular rotations of the silole core, leading to fluorescence turn-on of the probe. However, for the probe AcDEVDK-TPE, specific cleavage of the DEVD peptide substrate by caspase-3/caspase-7 releases the organic soluble AIE fluorogen, leading to nanoaggregates with intense fluorescence in water. These fluorescence turn-on features allow the study of protein activity both in solution and cells. The preliminary results showed that a TPS-2cRGD probe could not only be used for detection of integrin $\alpha_v\beta_3$-positive cancer cells but also can be used to trace the internalization of integrin $\alpha_v\beta_3$ in real-time manner. Additionally, a DEVD peptide-conjugated TPE probe was not only capable of monitoring the activities of caspase-3/caspase-7 but also cell apoptosis. Both of these probes can be used as AIE-active biocompatible probes for clinical cancer imaging and diagnostics.

c-RGD-TPS-DEVD

Another embodiment of the present subject matter relates to the asymmetric fluorescent bioprobe c-RGD-TPS-DEVD, the chemical structure of which is shown below.

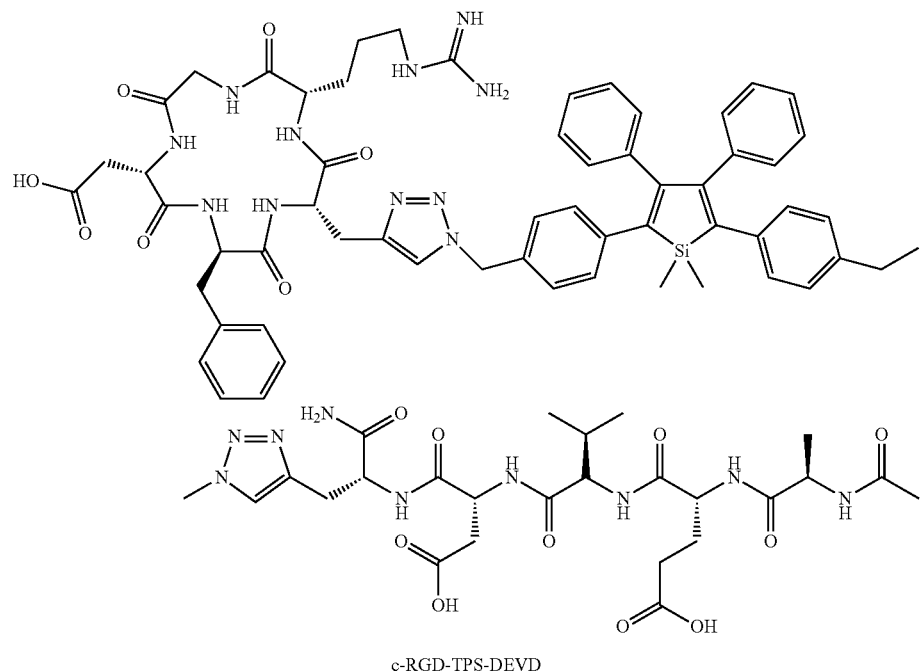

c-RGD-TPS-DEVD

C-RGD-TPS-DEVD can be used as a fluorescent bioprobe in living apoptotic cell imaging. Furthermore, it is able to specifically target the integrin receptor-overexpressed in cancer cells.

E/Z-TPE-2DEVD as Fluorescent Bioprobes

In another embodiment of the present subject matter, two pure stereoisomers of Asp-Glu-Val-Asp (DEVD) peptide-conjugated TPE probe (TPE-2DEVD) can be used as fluorescent bioprobes. Bother isomers are initially non-fluorescent due to their good water solubility. Upon addition of caspase-3/-7, specific cleavage of DEVD peptide substrate induces aggregation of the hydrophobic TPE residues and thus enhances the fluorescence output signal. This fluorescence turn-on feature allows detection of the activities of caspase-3/-7.

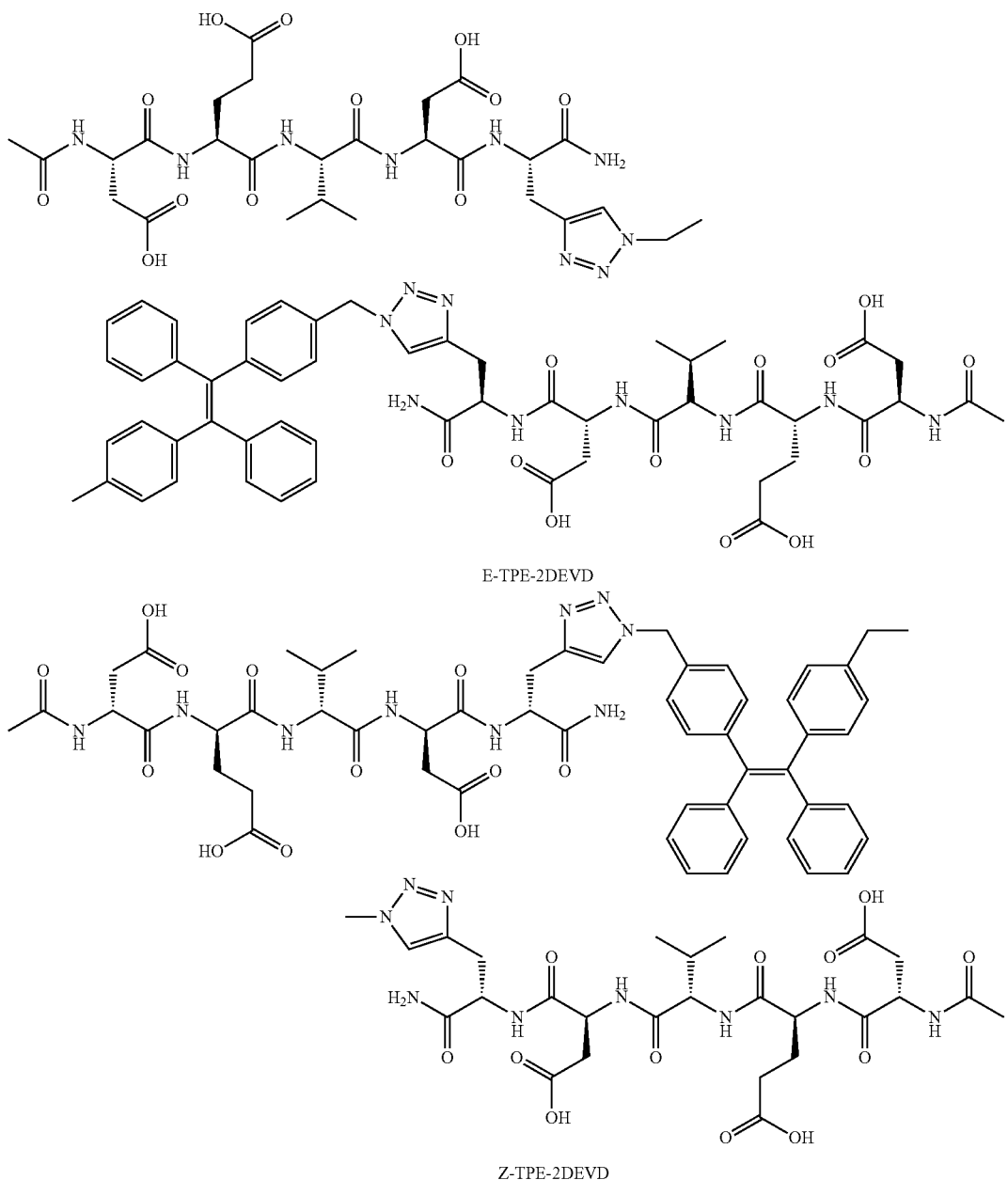

E-TPE-2DEVD

Z-TPE-2DEVD

Of particularly importance is that upon treatment with caspase-3, the two isomer probes show differences in the degree of fluorescence "turn-on." Z-TPE-2DEVD has a stronger fluorescence emission than E-TPE-2DEVD. However, Z-TPE-2DEVD has a slower hydrolysis rate, which was confirmed by HPLC analysis and molecular docking experiments.

Methods of Cellular Imaging with Fluorescent Bioprobes with Peptides

Accordingly, in one embodiment, the present subject matter relates to a method of cellular imaging comprising contacting target cells with the fluorescent bioprobes discussed above and detecting cellular imaging. In a further embodiment, the cellular imagining is in vitro cellular imaging using confocal laser scanning microscopy or two-photon fluorescence spectroscopy; or is in vivo cellular imaging using a Maestro in vivo fluorescence imaging system. In an even further aspect, the two-photon fluorescence spectroscopy can be used for living cell tracking and tissue imaging.

In another embodiment, the target cells are cancer cells or cells that can preferentially accumulate in tumors. In a further aspect, the bioprobes can specifically target integrin $\alpha_v\beta_3$ in cancer cells. In addition, the methods of cellular imaging can be used to determine whether a tumor or cancer cells are present.

In a further aspect, the in vitro cellular imaging is conducted using biological imaging samples selected from the group consisting of MCF-7 cells, HT-29 cancer cells, or HeLa cancer cells. Alternatively, in vivo cellular imaging is conducted using ICR mice bearing tumors as the biological imaging sample.

Another embodiment of the present subject matter relates to a method of detecting caspase-3/caspase-7 activity comprising contacting a solution containing cells with a fluorescent bioprobe and detecting fluorescence. In a further aspect, the fluorescent bioprobe is specifically cleaved by caspase-3/caspase-7.

In an additional embodiment, the present subject matter further relates to a method of detecting caspase-3/caspase-7 activity further comprising real-time fluorescence turn-on monitoring of an interaction between the fluorescent bioprobe and the cells, and cell apoptosis. Furthermore, the method of detecting caspase-3/caspase-7 activity further comprises in vitro screening of drugs that can induce cell apoptosis.

EXAMPLES

The examples below demonstrate various embodiments of the present subject matter.

BSA, glutaraldehyde, penicillin-streptomycin solution, trypsin-ethylenediaminetetraacetic acid (EDTA) solution, 3-(4,5-dimethylthiazol-2-yl)-2,5-diphenyl tetrazolium bromide (MTT), and 4',6-diamidino-2-phenylindole (DAPI) were purchased from Sigma-Aldrich (St. Louis, USA). Fetal bovine serum (FBS) was purchased from Gibco (Lige Technologies, Switzerland). Acetonitrile was distilled over $P_2O_5$. THF was distilled from sodium benzophenone ketyl under dry nitrogen immediately prior to use. Milli-Q water was supplied by a Milli-Q Plus System (Millipore Corp., Breford, USA). MCF-7 breast cancer cells were obtained from American Type Culture Collection. Murine hepatic $H_{22}$ cancer cells were obtained from Shanghai Institute of Cell Biology (Shanghai, China). Male ICR mice (6-8 weeks old) were provided by the animal center of Drum-Tower Hospital (Nanjing, China).

$^1H$ and $^{13}C$ NMR spectra were measured on a Bruker AV 300 spectrometer in $CDCl_3$ using tetramethylsilane (TMS, δ=0) as internal reference. High resolution mass spectra (HRMS) were recorded on a GCT premier CAB048 mass spectrometer operating in MALDI-TOF mode. Absorption spectra were recorded on a Shimadzu UV-1700 spectrometer. Emission spectra were recorded on a Perkin-Elmer LS 55 spectrofluorometer. Average particle size and size distribution of the nanoparticles were measured by LLS with a 90Plus particle size analyzer (Brookhaven Instruments Co., USA) at a fixed angle of 90° at room temperature. Zeta potential of the nanoparticles was measured using a Brookhaven ZetaPlus zeta potential analyzer at room temperature. Morphology of the nanoparticles was studied by FESEM (JSM-6700F, JEOL, Japan) at an accelerating voltage of 10 kV. Sample was fixed on a stub with a double-sided sticky tape and then coated with a platinum layer using an autofine coater (JEOL, Tokyo, Japan) for 60 s in a vacuum at a current intensity of 10 mA. Morphology of the nanoparticles was also investigated by TEM (JEM-2010F, JEOL, Japan) and HR-TEM (JEM-2010F, JEOL, Japan).

1,2-distearoyl-sn-glycero-3-phosphoethanolamine-N-[methoxy(polyethylene glycol)-2000] (DSPE-PEG$_{2000}$) was obtained from Lipoid GmbH (Ludwigshafen, Germany). DSPE-PEG$_{5000}$-Folate was obtained from Avanti Polar Lipids, Inc. Tetrahydrofuran (THF) was purchased from Sigma-Aldrich.

PFV and TPE-TPA-DCM were prepared according to the literature. (Adv. Func. Mater. 2011, 21, 287-294.; W. Qin et al. Adv. Funct. Mater. 2012, 22, 771-779)

All animal studies were performed in compliance with guidelines set by the Animal Care Committee at Drum-Tower Hospital.

Example 1

Synthesis of TPE-TPA-DCM

The reaction scheme for the synthesis of TPE-TPA-DCM is shown below.

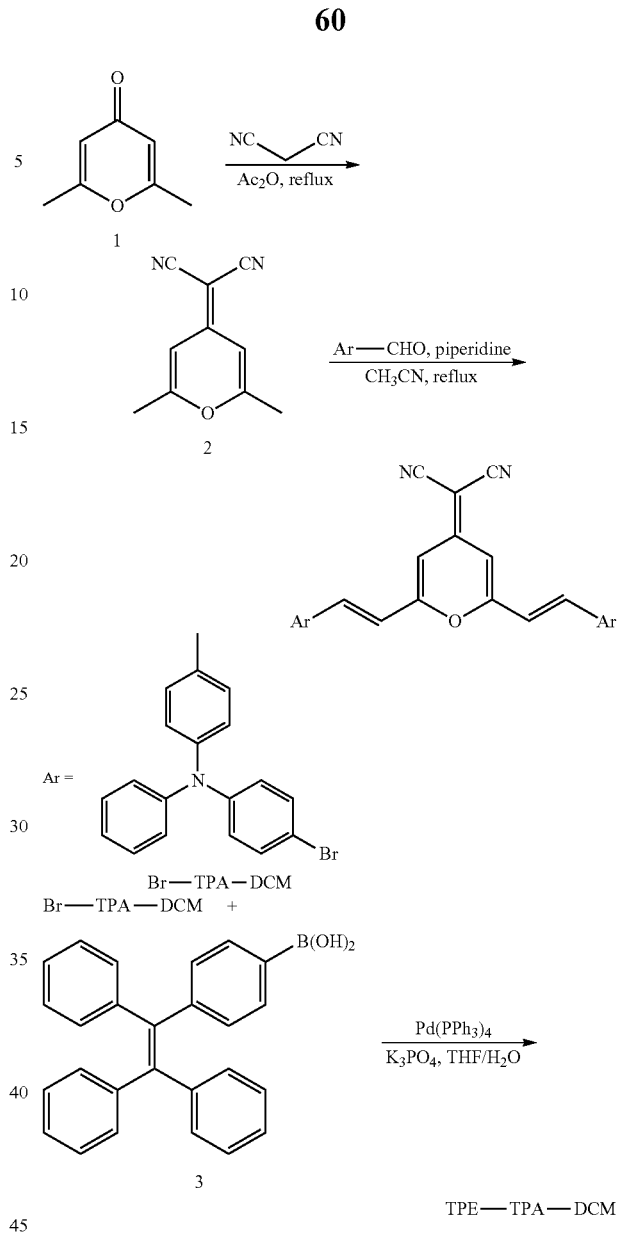

2-(2,6-Dimethyl-4H-pyran-4-ylidene)malononitrile (2) was prepared in 73% yield from 2,6-dimethyl-4-pyrone (1). Knoevenagel condensations of 2-(2,6-Dimethyl-4H-pyran-4-ylidene)malononitrile with TPA-containing aldehydes gave TPA-DCM and Br-TPA-DCM adducts in over 70% yields. TPE-TPA-DCM was obtained in 60% yield by Suzuki coupling between Br-TPA-DCM and 4-(1,2,2-triphenylvinyl)phenylboronic acid (3) using Pd(PPh$_3$)$_4$ as catalyst under basic conditions. TPE-TPA-DCM was isolated by column chromatography followed by recrystallization.

The following are detailed experimental procedures for the dye synthesis. 526 mg (1.4 mmol) of 4-(1,2,2-triphenylvinyl)phenylboronic acid (3) and 1060 mg of K$_3$PO$_4$ (5 mmol) in 50 mL of THF and 8 mL of water was added into a stirred mixture of 336 mg (0.4 mmol) of Br-TPA-DCM along with 36 mg of Pd(PPh$_3$)$_4$ under nitrogen. The mixture was heated to 70° C. for 36 hours. After cooling to room temperature, the solution was extracted with dichloromethane (100 mL) twice, washed with water, and dried over Na$_2$SO$_4$. After filtration and solvent evaporation under reduced pressure, the product was purified by silica-gel column chromatography using hexane/dichloromethane as the eluent. TPE-TPA-DCM was obtained in 60% yield (322 mg) as red powder after recrystallization from a mixture of chloroform/isopropyl alcohol.

The purified product was characterized by standard spectroscopic methods. The coupling constant of its vinyl protons in the $^1$H NMR spectrum is 16 Hz, proving that it possesses a trans conformation. Formation of the trans isomer is favored in the reaction due to the thermodynamic stability of the trans conformation and the steric hindrance hampering the formation of the cis structure. The absence of the NMR peaks of the minor cis isomer is possibly because it was removed by the recrystallization process during product purification.

$^1$H NMR (300 MHz, CDCl$_3$, δ): 7.51-7.40 (m, 10H), 7.35-7.29 (m, 8H), 7.17-7.01 (m, 48H), 6.63 (s, 2H; pyran H), 6.60 (d, J=16 Hz, 2H; pyran-CH=). $^{13}$C NMR (75 MHz, CDCl$_3$, δ): 159.39, 156.53, 150.50, 147.26, 146.54, 144.41, 144.39, 144.37, 143.40, 141.83, 141.15, 138.59, 138.07, 136.97, 132.55, 132.03, 130.29, 129.75, 128.34, 127.16, 126.44, 126.27, 126.14, 125.08, 122.50, 116.51, 116.35, 107.07. HRMS (MALDI-TOF, m/z): M$^+$, calcd. for C$_{100}$H$_{70}$N$_4$O, 1343.5583. found, 1343.5820. Anal. calcd for C$_{100}$H$_{70}$N$_4$O: C, 89.39, H, 5.25, N, 4.17. found: C, 89.66, H, 5.23, N, 4.22

Example 2

Fabrication of Fluorogen-Loaded BSA Nanoparticles

The BSA nanoparticles loaded with TPE-TPA-DCM were prepared by a modified desolvation method (FIG. 3). The nanoparticles were prepared with varied feeding ratios ranging from 0.25 to 5 wt %, defined as the ratio of the weight of the fluorogen to that of BSA in the feed mixture. In brief, 13 mg of BSA was dissolved in 5 mL of Milli-Q water. Subsequently, 8 mL of THF (desolvation agent) containing a predetermined amount of TPE-TPA-DCM was added dropwise into the aqueous solution of BSA at room temperature under sonication using a microtip probe sonicator with a 18 W output (XL2000, Misonix Incorp., USA), leading to the formation of the fluorogen-loaded BSA Nanoparticles. A small amount (5 µL) of a glutaraldehyde solution (50%) was then added to cross-link the nanoparticles at room temperature for 4 h. THF was removed by rotary evaporation under vacuum. The cross-linked fluorogen-loaded BSA nanoparticle suspension was filtered through a 0.45 µm microfilter and was then washed with Milli-Q water. The amounts of the fluorogen aggregates successfully encapsulated into the BSA nanoparticles were determined by the absorption spectra with reference to a calibration curve established from DMSO solutions of TPE-TPA-DCM. The EE is defined as the ratio of the amount of the fluorogen aggregates loaded in the nanoparticles to the total amount of the fluorogen in the feed mixture. To prepare the bare TPE-TPA-DCM nanoparticles, 60 µL of a THF solution of the fluorogen (0.5 mg/mL) was added into 3 ml, of a water/THF (9:1 v/v) mixture, followed by sonication of the fluorogen mixture for 60 s at an 18 W output. The emulsion was then stirred at room temperature overnight to evaporate THF solvent.

Example 3

Cell Culture

MCF-7 breast cancer cells and murine hepatic H22 cancer cells were cultured in Dulbecco's Modified Eagel's Medium (DMEM) containing 10% fetal bovine serum and 1% penicillin streptomycin at a constant temperature of 37° C. in a humidified environment containing 5% CO$_2$. Prior to the imaging experiments, the cells were precultured until confluence was reached.

Example 4

Cell Imaging

MCF-7 cells were cultured in a LAB-TEK chamber (Chambered Coverglass System, Rochester, USA) at 37° C. After 80% confluence, the medium was removed and the adherent cells were washed twice with 1×PBS buffer. The AIE-active fluorogen-loaded BSA nanoparticles (with a fluorogen loading of 0.86%) or the bare TPE-TPA-DCM nanoparticles (0.4 µM) in FBS-free DMEM medium were then added to the chamber. After incubation for 2 h, the cells were washed three times with 1×PBS buffer and then fixed with 75% ethanol for 20 min, which were further washed twice with 1×PBS buffer. The nuclei were stained by DAPI for 10 min. The cell monolayer was then washed twice with 1×PBS buffer and imaged by CLSM (Zeiss LSM 410, Jena, Germany) with imaging software Olympus Fluoview FV1000 (FIGS. 7-9). The fluorescent signals from the nanoparticles were collected upon excitation at 488 nm (1.25 mW) with a 650 nm longpass barrier filter.

Example 5

Cytotoxicity of Fluorogen-Loaded BSA Nanoparticles

Cytotoxicity of the nanoparticles against MCF-7 breast cancer cells was assessed by 3-(4,5-dimethylthiazol-2-yl)-2,5-diphenyltetrazolium bromide (MTT) cell-viability assay. FIG. 10 illustrates the cell viability after incubation with the nanoparticle suspension at the fluorogen concentrations of 0.1, 0.4, and 0.8 µM for 12, 24, and 48 h.

MCF-7 cells were seeded in 96-well plates (Costar, Ill., USA) at a density of 4×104 cells/mL. After 24 h incubation, the cells were exposed to a series of doses of fluorogen-loaded BSA nanoparticles at 37° C. To eliminate the UV absorption interference of the fluorogen-loaded nanoparticles at 570 nm, the cells were incubated with the same series of doses of the fluorogen-loaded nanoparticles as the control. After the designated time intervals, the sample wells were washed twice with 1×PBS buffer and 100 µL of freshly prepared MTT solution (0.5 mg/mL) in culture medium was added into each sample well. The MTT medium solution was carefully removed after 3 h incubation in the incubator for the sample wells, whereas the control wells without addition of MTT solution were washed twice with 1×PBS buffer. DMSO (100 µL) was then added into each well and the plate was gently shaken for 10 min at room temperature to dissolve all the precipitates formed. The absorbance of individual wells at 570 nm was then monitored by Tecan GENios Microplate Reader. The absorbance of MTT in the sample well was determined by the differentiation between the absorbance of the sample well and that of the corresponding control well. Cell viability was expressed by the ratio of the absorbance of MTT in the sample wells to that of the cells incubated with culture medium only.

Example 6

In Vivo Real-Time Fluorescence Imaging

The fluorogen-loaded BSA nanoparticles were examined for in vivo bioimaging applications, employing the non-invasive live animal fluorescence imaging technique. Murine hepatoma-22 (H$_{22}$) transplanted tumor-bearing ICR mice were used as the model animals.

H22 cell suspension containing 5-6×106 cells (0.1 mL) were injected subcutaneously to ICR mice (average body weight of 25 g) at the left axilla. When the tumor volume reached a mean size of about 400 mm$^3$, the mice were intravenously injected with 250 μL of the fluorogen-loaded BSA nanoparticles (with a fluorogen loading of 0.86%) at a nanoparticle concentration of 1 mg/mL. The same experiment was conducted with the bare TPE-TPA-DCM nanoparticles at the same fluorogen concentration. The mice were anesthetized and placed on an animal plate heated to 37° C. The time-dependent bio-distribution in mice was imaged using a Maestro in vivo fluorescence imaging system (CRi, Inc., Woburn, USA). The light with a central wavelength of 523 nm was selected as the excitation source. In vivo spectral imaging from 560 to 900 nm (with 10 nm step) was conducted with an exposure time of 150 ms for each image frame. The auto-fluorescence was removed using spectral unmixing software. Scans were carried out at 3 h, 8 h and 28 h post-injection.

FIGS. 11A-B illustrate the in vivo non-invasive fluorescence imaging of $H_{22}$ tumor-bearing mice after intravenous injection of (A) fluorogen-loaded BSA nanoparticles and (B) bare TPE-TPA-DCM nanoparticles. FIG. 11C illustrates the average PL intensities for the tumor tissues from the mice treated with the fluorogen-loaded BSA nanoparticles and the bare fluorogen nanoparticles at the specified time intervals.

Example 7

Synthesis of F37 and F30 Based Nanoparticles

A THF solution (0.5 mL) containing 1 mg of F37/F30 and 2 mg of the mixture of DSPE-PEG$_{2000}$ and DSPE-PEG$_{5000}$-Folate (molar ratio of 1:0 and 1:1, respectively) was poured into 10 mL of 90% (v/v) water/THF solution. This was followed by sonicating the mixture for 60 seconds at 12 W output using a microtip probe sonicator (XL2000, Misonix Incorporated, N.Y.). The emulsion was then stirred at room temperature overnight to evaporate THF. F37NP0 and F37NP50 are assigned to F37 based nanoparticles prepared with 0% and 50% of the DSPE-PEG$_{5000}$-Folate at the feed. Similarly, F30 based nanoparticles prepared with 0% and 50% of DSPE-PEG$_{5000}$-Folate at the feed are defined as F30NP0 and F30NP50, respectively. The obtained solution was filtered over a 0.22 μm syringe-driven filter to collect the products.

Example 8

Cell Culture

MCF-7 breast cancer cells and murine hepatic $H_{22}$ cancer cells were cultured in folate-free Dulbecco's Modified Eagle Medium (DMEM) containing 10% fetal bovine serum and 1% penicillin streptomycin at 37° C. in a humidified environment containing 5% $CO_2$, respectively. Before experiment, the cells were pre-cultured until confluence was reached.

Example 9

Cell Imaging

MCF-7 breast cancer cells with high folate receptor expression level in cell membrane were used to evaluate the targeting ability of F37NP50 over F37NP0. MCF-7 breast cancer cells were cultured in the confocal imaging chambers (LAB-TEK, Chambered Coverglass System) at 37° C. After 80% confluence, the medium was removed and the adherent cells were washed twice with 1×PBS buffer. The F37NP0 and F37NP50 in FBS-free DMEM medium at 2 μM of F37 were then added to the chambers, respectively. After incubation for 2 h, the cells were washed three times with 1×PBS buffer and then fixed by 75% ethanol for 20 minutes, which were further washed twice with 1×PBS buffer. The cell nuclei were stained with 4',6-diamidino-2-phenylindole (DAPI) for 10 min. The cell monolayer was then washed twice with 1×PBS buffer and imaged by confocal laser scanning microscope (CLSM, Zeiss LSM 410, Jena, Germany) with imaging software (Olympus Fluoview FV1000) under the same experimental condition. The fluorescence signal from FTNPs was collected at 543 nm excitation with a 560 nm longpass barrier filter. The images were analyzed using Image-Pro Plus 5.0 software to obtain the average fluorescence intensity of red signal for MCF-7 cells.

FIGS. 14A and 14B show the confocal images of MCF-7 breast cancer cells after incubation with F37NP0 and F37NP50 suspension for 2 hours in culture medium containing 2 μM ZQL-37. It should be noted that in FIG. 14C, no auto fluorescence from the cell itself can be detected under the same experimental conditions. In addition, the fluorescence intensity from cell cytoplasm after incubation with F37NP50 (FIG. 14B) is higher than that after incubation with F37NP0 (FIG. 14A). Quantitative studies using Image-Pro Plus 5.0 software indicate that the average fluorescence intensity of red signal in FIG. 14B is ~1.7 times higher than that in FIG. 14A. The confocal image of the corresponding cells incubated with F37NP50 shows that the intense fluorescence is mainly from nanoparticles internalized in the MCF-7 cell cytoplasm (FIG. 14D). The higher fluorescence intensity of MCF-7 cancer cells in FIG. 14B as compared to that in FIG. 17A suggests that more nanoparticles are internalized into the cells due to specific interactions between folic acid on nanoparticle surface and folate receptors in the cancer cell membrane, which should favor folate receptor-mediated endocytosis.

Example 10

In Vivo Fluorescence Imaging 0.1 mL of $H_{22}$ cell suspension containing 5-6×10$^6$ cells was injected subcutaneously into ICR mice (average body weight of 25 g) at the left axilla. When the tumor volume reached a mean size of about 300 mm$^3$, the mice were intravenously injected with 250 μL of F37NP50 and F37NP0, respectively, at the dye concentration of 4 mg/kg animal. Subsequently, the mice were anesthetized and placed on an animal plate heated to 37° C. The bio distribution in mice was imaged using the Maestro in vivo fluorescence imaging system (CRi, Inc.). The light with a central wavelength at 523 nm was selected as the excitation source. In vivo spectral imaging from 560 nm to 900 nm (10 nm step) was conducted with an exposure time of 150 ms for each image frame. Auto-fluorescence was removed by using the spectral unmixing software. Scans were carried out at 1 h and 3 h post-injection.

FIG. 15A shows the tumor accumulation and in vivo distribution of F37NP0 in the tumor-bearing mouse at 1 hour and 3 hours post-injection. The different fluorescence intensities are shown by different colors, and the order of red, orange, yellow, green, and blue refers to a successive decrease in intensity. Obvious fluorescence is observed in the area of tumor tissue at 1 hour and 3 hours, indicating that F37NP0 are efficiently accumulated in the tumor through enhanced permeability and retention (EPR) effect. In addition, strong fluorescence from the liver region is also observed, which suggests that some nanoparticles in the blood circulation tend to be enriched in the liver. This comports with the previous results demonstrating that nanoparticles with a size of 50-60 nm have a tendency to undergo reticuloendothelial system (RES) uptake to be enriched in different organs including liver.

The specific tumor targeting ability of F37NP50 was also evaluated on the same tumor-bearing mouse model, as displayed in FIG. 15B. Much higher fluorescence intensity is shown in the tumor tissue of F37NP50-treated mouse as compared to that of F37NP0-treated mouse at both 1 hour and 3 hours post injection, demonstrating that F37NP50 has specific targeting ability for tumors that contain folate receptors over expressed in cancer cells in a living body.

Example 11

Synthesis of TPE-TPA-DCM Doped Nanoparticles (FTNPs)

A THF solution (0.5 mL) containing 1 mg of TPE-TPA-DCM and 2 mg of mixture of DSPE-PEG$_{2000}$ and DSPE-PEG$_{5000}$-Folate (molar percentage ratio of DSPE-PEG$_{5000}$-Folate was 50%) was poured into 10 mL of 90% (v/v) water/THF solution. This was followed by sonicating the mixture for 60 seconds at 12 W output using a microtip probe sonicator (XL2000, Misonix Incorporated, N.Y.). The emulsion was then stirred at room temperature overnight to evaporate THF to obtain FTNP suspension in water.

FIG. 16 shows HR-TEM images of folate-targeted nanoparticles (FTNPs) with DSPE-PEG$_{2000}$ and DSPE-PEG$_{5000}$-Folate as the biocompatible polymer matrix. The spherical shape of FTNPs with an average size of 45 nm can be clearly distinguished from the black dots due to the high electron density of TPE-TPA-DCM molecules. Laser light scattering (LLS) results suggest that the volume average hydrodynamic diameter of FTNPs is 52±2 nm. FIG. 17A shows the linear absorption and emission spectra of FTNPs in water. The FTNP suspension in water has two maximum absorption peaks at 353 and 496 nm.

Example 12

Two-photon Absorption Measurements

Two-photon absorbing (TPA) spectra were measured using two-photon induced fluorescence (TPIF) spectroscopy. The samples were excited with laser pulses of 100 fs produced by the mode-locked Ti:Sapphire laser (Spectraphysics Tsunami) with a repetition rate of 82 MHz, and a femtosecond optical parametric amplifier (OPA) was used within the spectral range 840-900 nm at a 10 nm interval. The suspension was degassed before measurement, and no obvious photodegradation was observed during the experiment. The emission from FTNP aqueous suspension was collected at a 90° angle by a high numerical aperture lens and directed to a spectrometer's entrance slit. The concentration of T1 in the aqueous suspensions was 10 μM. Rhodamine B in methanol was used as a standard. TPA cross section was calculated from the following equation:

$$\frac{\delta_2}{\delta_1} = \frac{F_2 \eta_1 c_1 n_1}{F_1 \eta_2 c_2 n_2}$$

Where $\delta_1$ and $\delta_2$ are the TPA cross section, $F_1$ and $F_2$ are the TPIF intensities, $\eta_1$ and $\eta_2$ are the fluorescence quantum yields, $c_1$ and $c_2$ are the concentrations, $n_1$ and $n_2$ are the refractive indexes of solvents (1 corresponds to Rhodamine B, 2 is used for FTNPs). As shown in FIG. 17B, the maximum TPA cross-section (δ) is 199 GM at 850 nm, which is sufficient for two-photon fluorescence imaging application.

Example 13

Long Term Cellular Tracking with Two-Photon Fluorescence Imaging

The performance of FTNPs in MCF-7 cancer cell tracking was investigated and compared with that of commercial Mitotracker red (MTR).

MCF-7 breast cancer cells were cultured in Dulbecco's Modified Eagle Medium (DMEM) containing 10% fetal bovine serum and 1% penicillin streptomycin at 37° C. in a humidified environment containing 5% $CO_2$.

Prior to the experiment, MCF-7 breast cancer cells were pre-cultured until confluence was reached. After incubation with FTNPs and Mitotracker red (MTR) in DMEM medium (FBS-free) at 1 μM T1 and MTR for 4 h at 37° C., respectively, the corresponding cells were detached by 1× trypsin and suspended in culture medium with different cell densities. The cells were then cultured on round coverslip in 35 mm petri dishes for 0, 1, 2, 3, 4 and 5 days, respectively. After designated time intervals, the medium was removed and the adherent cells were washed twice with 1×PBS buffer, followed by fixation using 75% ethanol for 20 minutes. The cells were further washed twice with 1×PBS buffer and the coverslips were then mounted on glass slides using mounting medium in purpose of long-term storage. The samples were imaged by confocal laser scanning microscope (Leica TCS SP5 X) equipped with multi-photon laser. The detection of two-photon excited fluorescence of FTNPs was achieved by excitation at 800 nm with a 600-800 nm bandpass filter. On the other hand, the one-photon excited fluorescence signal from MTR was collected with a 600-800 nm bandpass filter upon 560 nm excitation.

The two-photon fluorescence images of FTNP-treated MCF-7 cancer cells after designated incubation time intervals of 0, 1, 2, 3, 4, and 5 days are shown in FIG. 18. The profile of FTNP-treated cells can be clearly distinguished after 4 days of incubation and the fluorescence from FTNPs which internalized into cells remains detectable even after 5 days. These results suggest that FTNPs can be used for living cell tracking and tissue imaging with two-photon microscopy for a period up to 96 hours under the experimental conditions, which corresponds to more than six cell generations.

In contrast, the fluorescence from MTR-treated MCF-7 cancer cells only sustained 1 day and became undetectable after 2 days. The confocal images of MTR-treated MCF-7 cancer cells after designated incubation time intervals of 0, 1, and 2 days are show in FIG. 19. It should be noted that the concentration of MTR in this experiment (1 μM) is much higher than the recommended highest working concentration of 200 μM.

Example 14

Preparation of PFV/TPE-TPA-DCM Co-Loaded BSA Nanoparticles

The PFV/TPE-TPA-DCM co-loaded BSA nanoparticles were prepared through a modified desolvation method. In brief, 13 mg of BSA was dissolved in 5 mL of MilliQ water. Subsequently, 8 mL of THF (desolvation agent) containing PFV and TPE-TPA-DCM with varied molar ratio was added dropwise into the BSA aqueous solution at room temperature under sonication using a microtip probe sonicator (XL2000, Misonix Incorporated, N.Y., 18 W output), resulting in the formation of PFV/TPE-TPA-DCM co-loaded BSA Nanoparticles. 5 μL of glutaraldehyde solution (50%) was subsequently added to cross-link the obtained nanoparticles at room temperature for 4 h. THF was removed by rotary evaporation under vacuum. The cross-linked nanoparticle suspension was filtered through 0.45 μm microfilter, which was subsequently washed and centrifuged with MilliQ water to remove free TPE-TPA-DCM that was not encapsulated in the nanoparticles. To synthesize RGD functionalized PFV/TPE-TPA-DCM co-loaded BSA nanoparticles, RGDKKK-KKK solution ($10^{-3}$ M) was added into the PFV/TPE-TPA-DCM co-loaded BSA nanoparticle aqueous suspension and gently mixed for 2 h. After centrifugation to remove the excess RGD, the RGD functionalized nanoparticles were collected for further study.

Figure 21:
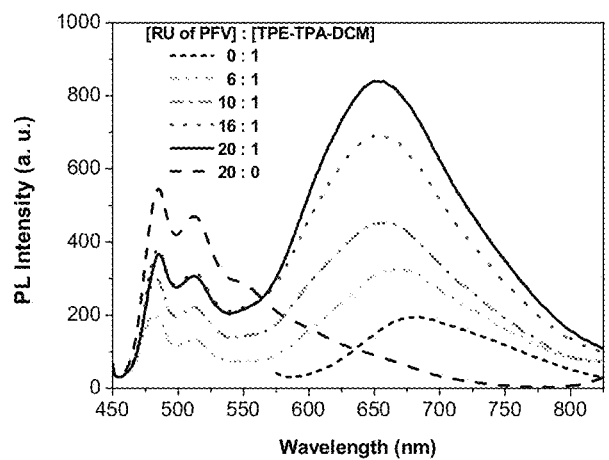
FIG. 21 illustrates a photoluminescence (PL) spectra of PFV/TPE-TPA-DCM co-loaded BSA nanoparticles in water with [RU of PFV]/[TPE-TPA-DCM] ranging from 6:1 to 20:0 upon excitation at 435 nm. The TPE-TPA-DCM loading ratio was fixed at 0.86%. The PL spectrum of TPE-TPA-DCM loaded nanoparticles (0:1) was excited at 505 nm.

To optimize the donor/acceptor ratio for in vitro and in vivo fluorescence imaging in a high contrast manner, PL spectra of PFV/TPE-TPA-DCM co-encapsulated BSA nanoparticles with various donor/acceptor molar ratios were collected upon excitation of PFV at 435 nm (FIG. 20). In these experiments, the molar ratios between the repeat unit (RU) of PFV and TPE-TPA-DCM in the co-encapsulated nanoparticles were varied from 6:1 to 20:1 at a fixed TPE-TPA-DCM loading ratio of 0.86%. As shown in FIG. 21, with the increased ratio of [RU of PFV]/[TPE-TPA-DCM], the acceptor emission band ranging from 550 nm to 825 nm increases at the expense of the donor emission intensity at 485 nm. The amplification of acceptor emission is evaluated by comparing the fluorescence of PFV/TPE-TPA-DCM co-loaded BSA nanoparticles upon excitation at 435 nm with that of TPE-TPA-DCM loaded nanoparticles upon direct excitation at 505 nm ([RU of PFV]/[TPE-TPA-DCM]=0:1). The emission of acceptor can be amplified for ~5-fold at [RU of PFV]/[TPE-TPA-DCM]=20:1, demonstrating efficient FRET between PFV and TPE-TPA-DCM in the nanoparticles. In addition, the PFV/TPE-TPA-DCM co-loaded BSA nanoparticles show a large Stokes shift of ~215 nm, which indicates effective bioimaging with minimal background interferences.

Figure 22:
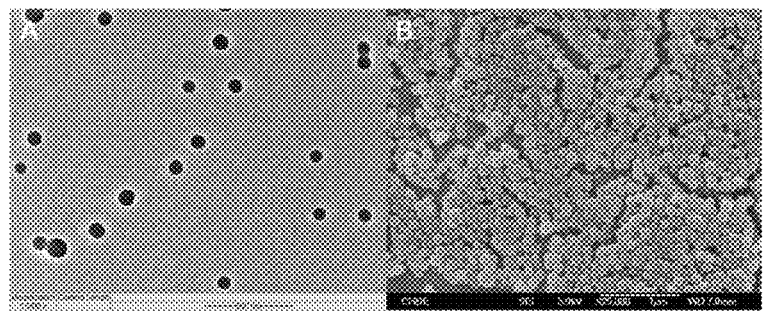
FIGS. 22A-B illustrate (A) a transmission electron microscopy (TEM) image and (B) a field-emission scanning electron microscopy (FESEM) image of the PFV/TPE-TPA-DCM co-loaded BSA nanoparticles with [RU of PFV]/[TPE-TPA-DCM]=20:1.

Laser light scattering (LLS) results indicate that the volume average hydrodynamic diameter of PFV/TPE-TPA-DCM co-loaded BSA nanoparticles with [RU of PFV]/[TPE-TPA-DCM]=20:1 is ~159 nm, which is larger than that of TPE-TPA-DCM loaded BSA nanoparticles (~125 nm) due to the concurrent encapsulation of PFV in the nanoparticles. The morphology of the co-loaded nanoparticles was also studied by transmission electron microscopy (TEM) and field-emission scanning electron microscopy (FESEM). As shown in FIG. 22, the nanoparticles are spherical in shape with an average size of around 100 nm, which is smaller than the LLS result because of the dry sample state.

Example 15

Cell Culture

HT-29 cancer cells and murine hepatic $H_{22}$ cancer cells were cultured in Dulbecco's Modified Eagle's Medium (DMEM) containing 10% fetal bovine serum and 1% penicillin streptomycin at 37° C. in a humidified environment containing 5% $CO_2$, respectively. Prior to experiments, the cells were pre-cultured until confluence was reached.

Example 16

Cell Imaging

HT-29 colon cancer cells that have over expressed integrin receptors were used as target cells. HT-29 cells were cultured in chamber (LAB-TEK, Chambered Coverglass System) at 37° C. After 80% confluence, the medium was removed and the adherent cells were washed twice with 1×PBS buffer. The PFV/TPE-TPA-DCM co-loaded BSA nanoparticles and RGD-functionalized PFV/TPE-TPA-DCM co-loaded BSA nanoparticles with [RU of PFV]/[TPE-TPA-DCM]=20:1 at 0.2 μM TPE-TPA-DCM in FBS-free DMEM medium were then added to the chamber, respectively. PFV/TPE-TPA-DCM co-loaded BSA nanoparticles with [RU of PFV]/[TPE-TPA-DCM]=20:1 were used because of their high fluorescence in far-red/near-infrared (FR/NIR) region (>650 nm) by FRET. In addition, as arginine-glycine-aspartic acid (RGD) peptide can target integrin receptors over expressed in many tumor cells, the PFV/TPE-TPA-DCM co-loaded BSA nanoparticles were further modified with positively charged RGD peptide (isoelectric point (PI)~11.2) at pH 7.4 through electrostatic interaction.

After incubation for 2 h, the cells were washed three times with 1×PBS buffer and then fixed with 75% ethanol for 20 min, which were further washed twice with 1×PBS buffer. The cells were imaged by confocal laser scanning microscope (CLSM, Zeiss LSM 410, Jena, Germany) with imaging software (Olympus Fluoview FV1000). As shown in FIG. 23, the fluorescent signal from the PFV/TPE-TPA-DCM co-loaded BSA nanoparticles was collected upon excitation at 405 and 532 nm, with a 650 nm longpass barrier filter. The fluorescent signal from the RGD-functionalized PFV/TPE-TPA-DCM co-loaded BSA nanoparticles was collected upon excitation at 405 nm with a 650 nm longpass barrier filter.

FIG. 23 shows the confocal images of HT-29 cancer cells after incubation with PFV/TPE-TPA-DCM co-loaded BSA nanoparticles without RGD functionalization for 2 hours. The images were taken by collecting the signals above 650 nm upon excitation at 532 nm for FIG. 23A and 405 nm for FIG. 23B. Red fluorescence from the cytoplasm is observed from both images, indicating that the PFV/TPE-TPA-DCM co-loaded nanoparticles are internalized by the cells.

Additionally, the higher fluorescence intensity of HT-29 cancer cells shown in FIG. 23B as compared to that in FIG. 23A demonstrates the polymer amplified TPE-TPA-DCM emission is maintained in cells. FIG. 23C shows the confocal image of HT-29 cancer cells after incubation with RGD-functionalized PFV/TPE-TPA-DCM co-loaded BSA nanoparticles for 2 hours. Under the same imaging conditions as those for FIG. 23B, FIG. 23C shows further enhanced fluorescence from the cellular cytoplasm, which suggests that more RGD-functionalized nanoparticles are internalized by HT-29 cancer cells. This is due to the specific binding between RGD and integrin receptors over expressed in HT-29 cells.

Example 17

Conjugated Polymer Amplified AIE Emission Application in In Vivo Real-Time Fluorescence Imaging The application of PFV/TPE-TPA-DCM co-loaded BSA nanoparticles with and without RGD functionalization in in vivo fluorescence imaging on a tumor-bearing mouse model was investigated using the non-invasive live animal fluorescence imaging technique. Murine hepatic $H_{22}$ transplanted tumor-bearing ICR mice were used as model animals. In addition, as $H_{22}$ tumor is demonstrated to be integrin $α_vβ_3$ positive, $H_{22}$ tumor-bearing mice can also be used to evaluate the utility of RGD-functionalized PFV/TPE-TPA-DCM co-loaded BSA nanoparticles in in vivo targeted imaging of integrin $α_vβ_3$ positive tumors.

0.1 mL of $H_{22}$ cell suspension containing 5-6×$10^6$ cells were injected subcutaneously to ICR mice (average body weight of 25 g) at the left axilla. When the tumor volume reached a mean size of about 400 $mm^3$, the mice were intravenously injected with 250 μL of PFV/TPE-TPA-DCM co-loaded BSA nanoparticles with [RU of PFV]/[TPE-TPA-DCM]=20:1. The same experiments were also conducted for TPE-TPA-DCM loaded BSA nanoparticles and RGD-functionalized PFV/TPE-TPA-DCM co-loaded BSA nanoparticles, respectively, at the same TPE-TPA-DCM concentration. Subsequently, the mice were anesthetized and placed on an animal plate heated to 37° C. The time-dependent bio-distribution in mice was imaged using a Maestro in vivo fluorescence imaging system (CRi, Inc.). The light with a central wavelength at 457 nm was selected as the excitation source. In vivo spectral imaging from 500 nm to 900 nm (10 nm step) was conducted with an exposure time of 150 ms for each image frame. The auto-fluorescence was removed using spectral unmixing software. Scans were carried out at 1.5 h, 4 h, 8 h and 24 h post-injection.

FIGS. 24A and B show the time-dependent in vivo distribution profile as well as tumor accumulation of TPE-DAM-TPA loaded BSA nanoparticles and PFV/TPE-TPA-DCM co-loaded BSA nanoparticles, respectively. Under the same experimental conditions, much higher fluorescence from the tumor-bearing mouse is observed in FIG. 24B as compared to that in FIG. 24A, suggesting that the PFV/TPE-TPA-DCM co-loaded BSA nanoparticles can also serve as an effective probe for in vivo fluorescence imaging in a high contrast manner, by virtue of the efficient FRET from PFV donor to TPE-TPA-DCM acceptor. As shown in FIG. 24B, a clear tumor delineation is observed in the area of left axillary of the mouse after 8 hours post-injection (p.i.), indicating the accumulation of the nanoparticles in tumor tissue by the enhanced permeability and retention (EPR) effect. Moreover, strong fluorescent signals are also observed in the liver area of mouse at 1.5 hours p.i., which then decrease over time. This suggests that some nanoparticles undergo the uptake of reticuloendothelial system (RES) organs such as liver and spleen, followed by facile excretion form the body through biliary pathway.

FIG. 24C shows the time-dependent in vivo distribution profile and tumor accumulation of RGD-functionalized PFV/TPE-TPA-DCM co-loaded BSA nanoparticles in $H_{22}$ tumor-bearing mouse. It is noteworthy that the fluorescence intensity from the tumor site in FIG. 24C is higher as compared to that in FIG. 24B at all tested time points, revealing that RGD-functionalized PFV/TPE-TPA-DCM co-loaded BSA nanoparticles can achieve efficient tumor targeting through specific RGD-integrin $\alpha_v\beta_3$ recognition.

Example 18

Synthesis of TPETPAFN

A mixture of bis(4-bromophenyl)fumaronitrile (194 mg, 0.5 mmol), N-(4-(1,2,2-triphenylvinyl)phenyl)benzenamine (635 mg, 1.5 mmol), $Cs_2CO_3$ (1.14 g, 3.5 mmol), $Pd(OAc)_2$ (11.2 mg, 0.05 mmol), tri-tert-butylphosphine (30.3 mg, 0.15 mmol) and toluene (30 mL) was heated at 40° C. for 2 h. The reaction mixture was then heated at 110° C. for 24 h. After the mixture was cooled to room temperature, water (80 mL) and chloroform (200 mL) were added. The organic layer was separated and washed with brine, dried over anhydrous $MgSO_4$ and evaporated to dryness under reduced pressure. The crude product was purified by column chromatography on silica gel using hexane/toluene as eluent to afford 9 as a red solid in 61% yield (327 mg). $^1$H NMR (300 MHz, $CDCl_3$), δ (TMS, ppm): 7.66 (d, J=8.9 Hz, 4H), 7.31 (t, J=7.9 Hz, 4H). 7.16-7.02 (m, 36H), 6.98 (t, J=9.0 Hz, 8H), 6.87 (d, J=8.6 Hz, 4H). $^{13}$C NMR (75 MHz, $CDCl_3$), δ (TMS, ppm): 150.92, 146.83, 145.08, 144.49, 144.19, 143.95, 141.90, 141.05, 140.90, 133.22, 132.01, 130.49, 130.40, 130.25, 128.34, 127.24, 126.50, 125.46, 125.23, 121.46, 121.22, 121.13, 118.44. HRMS (MALDI-TOF, m/z): $M^+$, calcd. for $C_{80}H_{56}N_4$, 1072.4505. found, 1072.4502. Elemental Anal. calcd for $C_{80}H_{56}N_4$: C, 89.52; H, 5.26; N, 5.22. found: C, 89.20; H, 5.23; N, 5.18.

Example 19

Synthesis of Tat Peptide-Functionalized AIE Dots

A THF solution (1 mL) containing 1 mg of TPETPAFN and 1.5 mg of a mixture of $DSPE-PEG_{2000}$ and $DSPE-PEG_{2000}-NH_2$ (molar percentage ratio of $DSPE-PEG_{2000}-NH_2$ is 50%) was poured into water (9 mL). The mixture was sonicated for 60 seconds using a microtip probe sonicator at 12 W output (XL2000, Misonix Incorporated, N.Y.). After filtration using a 0.2 μm syringe driven filter, the suspension was then stirred vigorously at room temperature overnight to yield TPETPAFN-loaded AIE dots in water (8 mL). The AIE dots (1.8 mL) were further mixed with borate buffer (0.2 M, pH=8.5, 0.2 mL) and reacted with HIV1-Tat peptide ($3\times10^{-5}$ M) in the presence of EDAC (1 mM). After reaction for 4 h at room temperature, the solution was dialysed against MilliQ water for 2 days to eliminate the excess peptide and EDAC. The Tat-AIE dots were collected for further use.

Example 20

In Vitro Cell Tracing

MCF-7 breast cancer cells were cultured in 6-well plates (Costar, Ill., USA) to achieve 80% confluence. After medium removal and washing with 1×PBS buffer, 2 nM Tat-AIE dots or Qtracker® 655 in DMEM medium were then added to the wells. After 4 h incubation at 37° C., the cells were washed twice with 1×PBS buffer and detached by 1× tripsin and resuspended in culture medium. Upon dilution, the cells were subcultured in 6-well plates containing cell culture coverslips for 1, 5, 7, 10 and 12 passages, respectively. After designated time intervals, the cells were washed twice with 1×PBS buffer and then trypsinalized to suspend in 1×PBS buffer. The fluorescence intensities of cells were then analyzed by flow cytometry measurements using Cyan-LX (DakoCytomation) and the histogram of each sample was obtained by counting 10,000 events ($\lambda_{ex}$=488 nm, 680/20 nm bandpass filter). To study cell retention of Tat-AIE dots, two groups of cells were used. The sample group was incubated with 2 nM Tat-AIE dots for 4 h at 37° C. while the control group remained untreated. After incubation and detachment, 2 mL of Tat-AIE dot-treated cells and 2 mL of control cells with the same density (300,000 cells/mL) were mixed and subcultured in culture flasks for 1 day. Meanwhile, the control and sample cells were also subcultured for 1 day. The three batches of cells were then trypsinalized and tested using flow cytometry. In all flow cytometry tests, blank cells without any treatment were used as the control. For confocal image studies, the cells were first labeled by 2 nM Tat-AIE dots or Qtracker® 655. The labeled cells were then washed twice with 1×PBS buffer and detached by 1× tripsin to resuspend in culture medium. Upon dilution, the cells were subcultured in 6-well plates containing cell culture coverslips for designated passages, washed twice with 1×PBS buffer and then fixed by 75% ethanol for 20 minutes. The coverslips were sealed with mounting medium and the two-photon excited fluorescence images were studied by Leica TCS SP 5X. The laser at 514 nm (1 mW) was adopted to obtain the one-photon excited fluorescence images with a 550-780 nm bandpass filter.

Example 21

In Vivo Cell Tracing

All animal experiments were performed in compliance with guidelines set by the Institutional Animal Care and Use Committee (IACUC), Sigapore General Hospital. After 4 h incubation with 2 nM Tat-AIE dots or Qtracker® 655 at 37° C., C6 glioma cells (1×10⁶ cells in 0.1 mL of culture medium) were subcutaneously injected into the flank of mice. Three mice were used for each group. After designated time intervals post injection, the mice were imaged using an IVIS Spectrum imaging system (Caliper Life Sciences) while under anesthesia. The fluorescence images were recorded with 1 second exposure using a filter 660/20 nm upon excitation at 535 nm. Scans were carried out on 0 d (1 h), 1 d, 3 d, 5 d, 7 d, 12 d, 14 d, 17 d and 21 d. The autofluorescence was removed using the software of IVIS Spectrum imaging system.

Example 22

Synthesis of TPS-2cRGD

Hexane and tetrahydrofuran (THF) were distilled from sodium benzophenone ketyl immediately prior to use. Dichloromethane (DCM) was distilled over calcium hydride. Dichlorobis(triphenylphosphine)palladium(II), ZnCl$_2$.TMEDA, copper(I) iodide, triphenylphosphine, and other chemicals and solvents were all purchased from Aldrich and used as received without further purification. Copper (II) sulfate, Sodium ascorbate, Dimethyl sulfoxide (DMSO), 3-(4,5-dimethylthiazol-2-yl)-2,5-diphenyl tetrazolium bromide (MTT), bovine serum albumin (BSA), Human serum albumin (HSA), lysozyme, papsin, trypsin were purchased from Sigma-Aldrich. Alkyne-functionalized cyclic RGD peptide was customized from GL Biochem Ltd. Recombinant human integrin $\alpha_v\beta_3$ was purchased from ImmunoCell. Recombinant human caspase-3 and caspase-7, DEVD-AFC substrate and known caspase-3/caspase-7 inhibitor were purchased from R&D Systems. Fetal bovine serum (FBS) and trypsin-EDTA solution were purchased from Gibco (Lige Technologies, Ag, Switzerland). Milli-Q water was supplied by Milli-Q Plus System (Millipore Corporation, Breford, USA). HeLa cancer cell was provided by American Type Culture Collection.

Characterization:

$^1$H and $^{13}$C NMR spectra were measured on a Bruker AV 300 spectrometer or Bruker ARX 400 NMR in CDCl$_3$ using tetramethylsilane (TMS, δ=0) as internal reference. UV absorption spectra were taken on a Milton Ray Spectronic 3000 array spectrophotometer. Photoluminescence (PL) spectra were recorded on a Perkin-Elmer LS 55 spectrofluorometer (USA) with an excitation wavelength of 312 nm. High-resolution mass spectra (HRMS) were recorded on a Finnigan MAT TSQ 7000 Mass Spectrometer System operating in a MALDI-TOF mode. The HPLC profiles and ESI mass spectra were acquired using a Shimadzu IT-TOF.

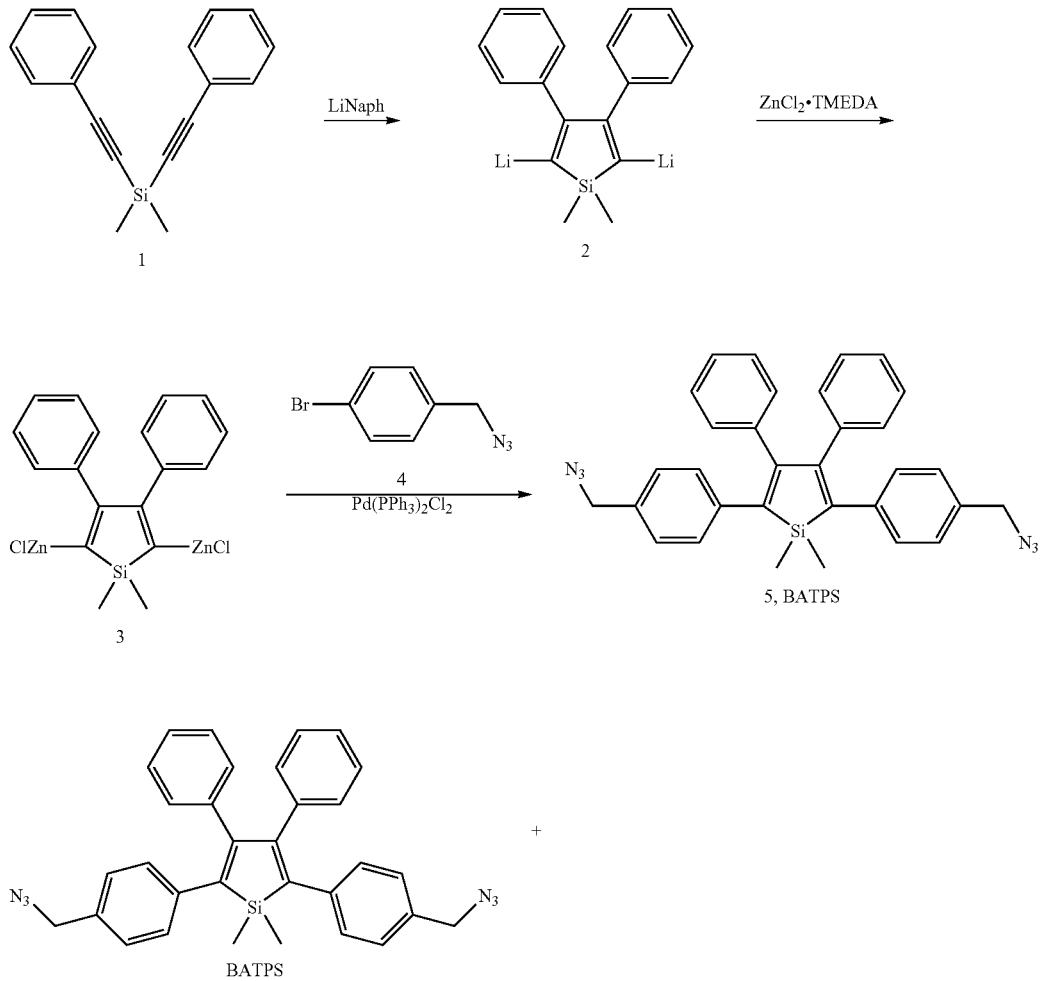

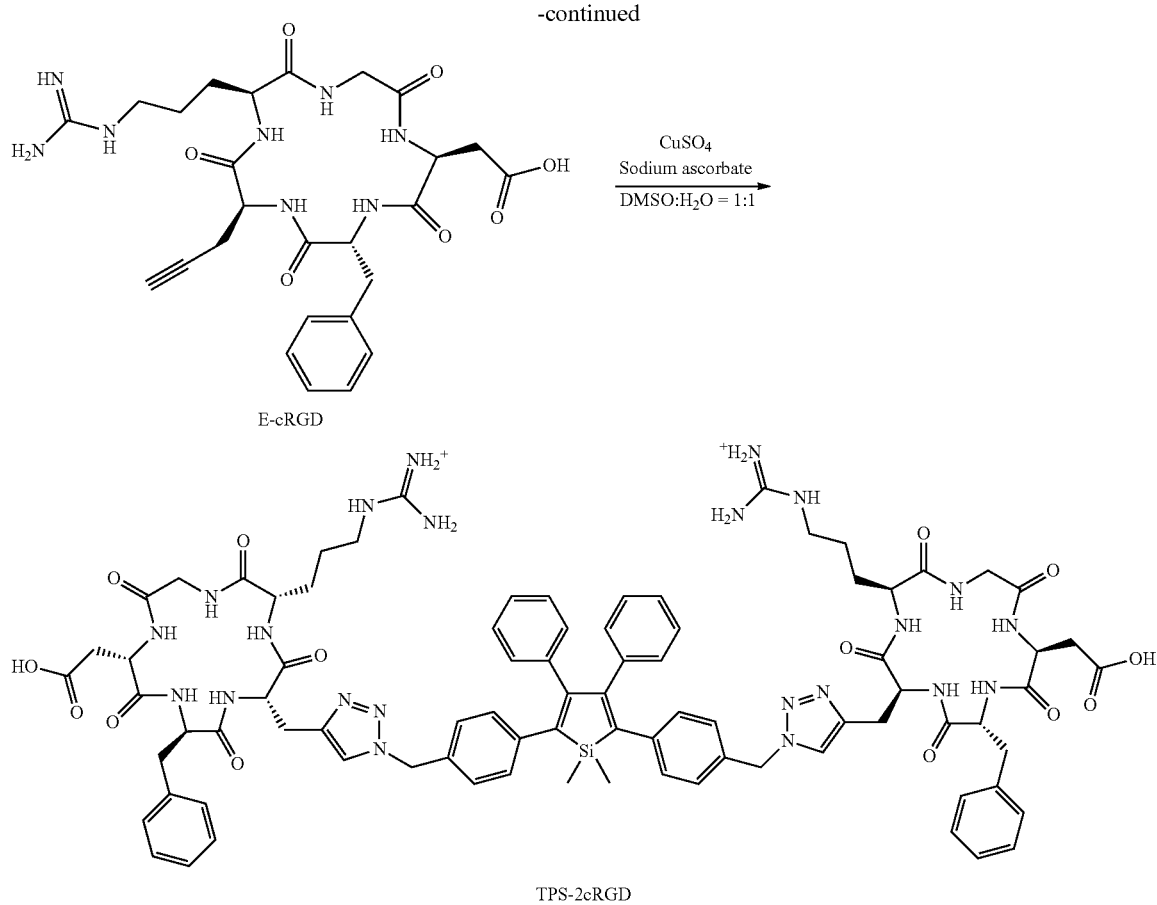

Preparation of dimethylbis(phenylethynyl)silane (1)

n-BuLi (25.0 mL, 40.1 mmol, 1.6 M solution in hexane) was added to a THF solution of phenylacetylene (4.0 mL, 36.4 mmol) at −78° C. After stirring at −78° C. for 4 h, dichlorodimethylsilane (2.2 mL, 18.2 mmol) was added. The mixture was warmed to room temperature and stirred overnight. The solvent was removed under reduced pressure. The mixture was dissolved in DCM and washed with brine and water. The organic layer was dried over magnesium sulfate. The crude product was purified by a silica-gel column using hexane as eluent. A colorless solid was obtained in 86.1% yield. $^1$H NMR (400 MHz, CDCl$_3$), δ (ppm): 7.57 (m, 4H), 7.36 (m, 6H), 0.55 (s, 6H). $^{13}$C NMR (100 MHz, CDCl$_3$), δ (ppm): 132.1, 128.9, 128.2, 122.6, 105.9, 90.6, 0.45. HRMS (MALDI-TOF), m/z 260.1013 (M$^+$, calcd 260.1021).

Preparation of 4-bromobenzylazide (4)

Into a flask equipped with a magnetic stirrer were added 4-bromobenzyl bromide (7.5 g, 30 mmol), sodium azide (7.8 g, 120 mmol), and 40 mL of DMSO. After stirred at 70° C. for 12 h, the solution was poured into 150 mL of water and extracted with CH$_2$Cl$_2$. The crude product was purified by silica-gel chromatography to give a colorless viscous liquid in 96.2% yield (6.12 g). $^1$HNMR (CDCl$_3$, 400 MHz), δ (TMS, ppm): 7.47 (d, J=8.2 Hz, 2H), 7.15 (d, J=8.2 Hz, 2H), 4.26 (s, 2H). $^{13}$C NMR (CDCl$_3$, 100 MHz), δ (TMS, ppm): 134.3, 131.8, 129.6, 122.1, 53.9. HRMS (MALDI-TOF): m/z 210.9640 (M$^+$, calcd 210.9745).

Preparation of 1,1-dimethyl-2,5-bis[4-(azidomethyl)phenyl]-3,4-diphenylsilole (5)

A mixture of lithium (0.056 g, 8 mmol) and naphthalene (1.04 g, 8 mmol) in 8 mL of THF was stirred at room temperature under nitrogen for 3 h to form a deep dark green solution of LiNaph. The viscous solution was then added dropwise to a solution of dimethylbis(phenylethynyl)silane (1) (0.52 g, 2 mmol) in 5 mL of THF over 4 min at room temperature. After stirring for 1 h, the mixture was cooled to 0° C. and then diluted with 25 mL THF. A black suspension was formed upon addition of ZnCl$_2$.TMEDA (2 g, 8 mmol). After stirring for an additional hour at room temperature, a solution of 4-bromobenzylazide (4) (0.89 g, 4.2 mmol) and PdCl$_2$(PPh$_3$)$_2$ (0.08 g, 0.1 mmol) in 25 mL of THF was added. The mixture was refluxed overnight. After cooled to room temperature, 100 mL of 1 M HCl solution was added and the mixture was extracted with DCM. The combined organic layer was washed with brine and water and then dried over magnesium sulfate. After solvent evaporation under reduced pressure, the residue was purified by a silica-gel column using hexane as eluent. The product was obtained as a yellow solid in 57.3% yield. $^1$H NMR (400 MHz, CDCl$_3$), δ (TMS, ppm): 7.06 (d, J=8.1 Hz, 4H), 7.01 (m, 6H), 6.92 (d, J=8.1 Hz, 4H), 6.78 (m, 4H), 4.24 (s, 4H), 0.47 (s, 6H). $^{13}$C NMR (100 MHz, CDCl$_3$), δ (TMS, ppm): 154.3, 141.3, 139.9, 138.5, 132.4, 129.9, 129.1, 127.9, 127.5, 126.3, 54.6, 3.9. HRMS (MALDI-TOF): m/z 524.2200 (M$^+$, calcd 524.2145).

Synthesis of TPS-2cRGD

The alkyne-containing cyclic RGD peptide (2.5 mg, 4.4 μmol) and azide-functionalized tetraphenylsilole (5, BATPS) (1 mg, 2 µmol) were dissolved in 50 µL DMSO. A mixture of DMSO/H₂O solution (1:1; 0.5 mL) was subsequently added and the reaction was shaken for a few minutes to obtain a clear solution. The "click" reaction was initiated by sequential addition of catalytic amounts of sodium ascorbate (0.16 mg, 0.8 µmol) and CuSO₄ (0.64 mg, 0.4 µmol). The reaction was continued with shaking at room temperature for another 12 h. The final product was purified by prep-HPLC and further characterized/confirmed by LC-MS. IT-TOF m/z [(M+H)/2]⁺ calcd: 833.445. found 833.846.

Example 23

Solution-Phase Synthesis of Alkyne-Containing Amino Acid and TPE-N₃

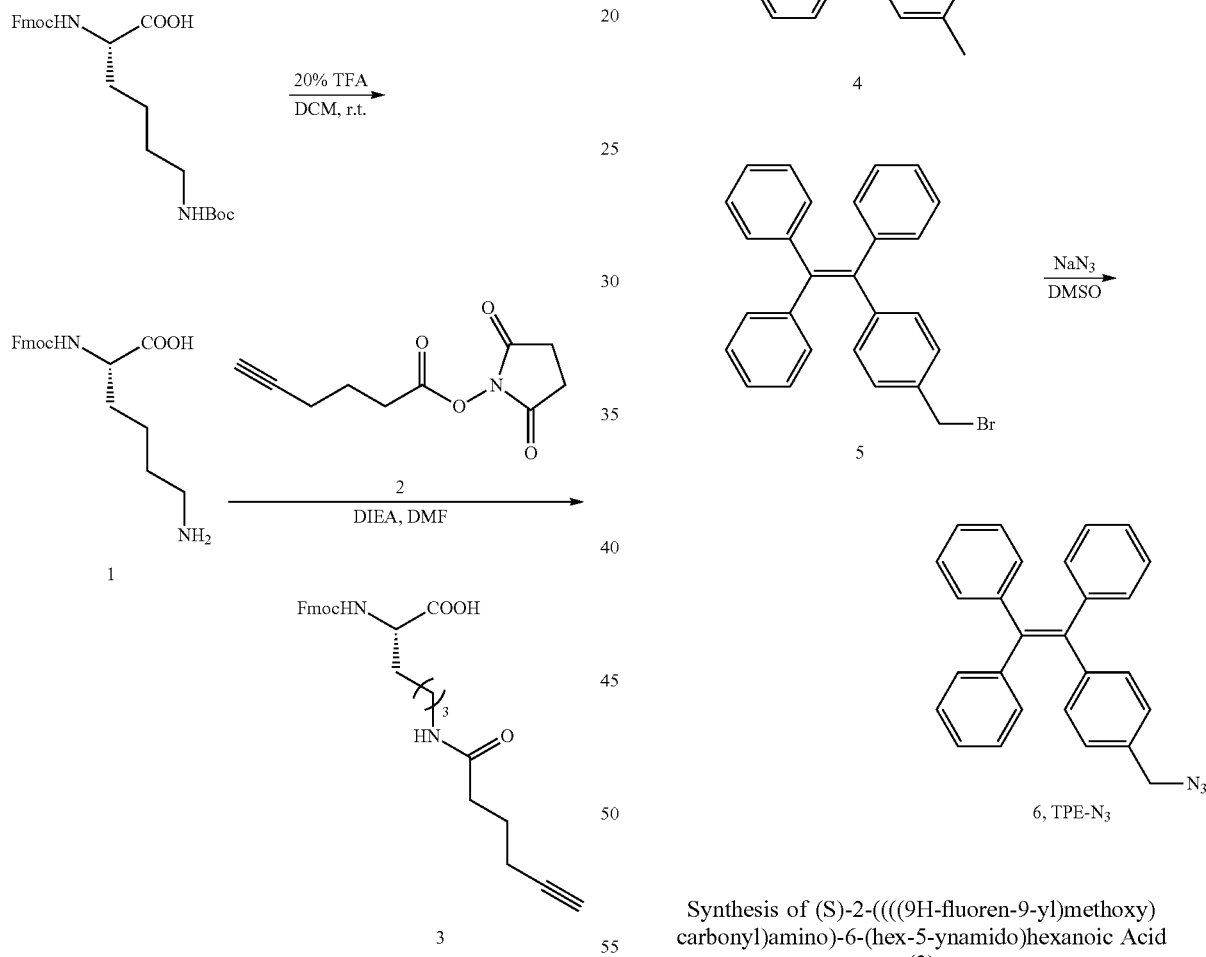

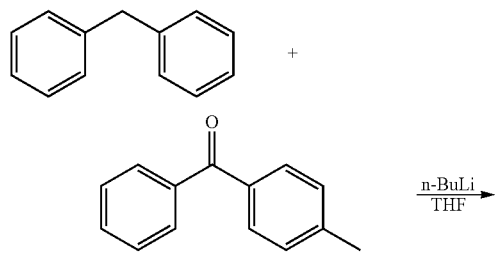

Synthesis of (S)-2-((((9H-fluoren-9-yl)methoxy) carbonyl)amino)-6-(hex-5-ynamido)hexanoic Acid (3)

Fmoc-Lys (Boc)-COOH (0.48 g, 1.0 mmol) was vigorously stirred in 20% TFA/DCM solution for around 3 hrs. The reaction solution was concentrated and dried in vacuo to afford intermediate (S)-2-((((9H-fluoren-9-yl)methoxy)carbonyl)amino)-6-aminohexanoic acid (1). 1 (0.37 g, 1.0 mmol) was further reacted with NHS-ester of acid (0.25 g, 1.2 mmol) and DIEA (0.15 g, 1.2 mmol) in DMF. After 12 h, the reaction was acidified with 3 M HCl, and then extracted with DCM. Solvents were removed in vacuum and the crude product was purified by purified by flash chromatography (hexane/EtOAc=10/1 to 5/1 v/v) to give the product 3 (9.17 g, 78.4%). $^1$H NMR (CDCl$_3$, 300 MHz), δ (TMS, ppm): 1.16̃1.21 (m, 2H), 1.23̃1.84 (m, 6H), 2.08 (t, J=6.0 Hz, 2H), 2.18 (t, J=7.5 Hz, 2H), 2.85 (s, 1H), 3.10 (s, 2H), 4.06 (t, J=9.0 Hz, 2H), 4.25 (d, J=6.0 Hz, 2H), 5.82 (s, 1H), 6.02 (s, 1H), 7.18 (t, J=7.0 Hz, 2H), 7.28 (t, J=7.5 Hz, 2H), 7.49 (t, J=6.0 Hz, 2H), 7.64 (d, J=6.0 Hz, 2H). $^{13}$C NMR (CDCl$_3$, 75 MHz), δ (TMS, ppm): 14.15, 17.69, 21.02, 22.16, 24.11, 27.34, 28.69, 31.63, 33.96, 34.95, 36.03, 39.06, 45.19, 47.02, 50.19, 53.56, 60.42, 65.22, 67.06, 69.35, 74.18, 83.36, 120.13, 125.08, 127.06, 127.69, 141.19, 142.85, 143.62, 156.43, 173.50, 175.55. HRMS (IT-TOF): m/z 462.5400 [(M+1)$^+$, calcd. 463.2080].

Synthesis of 1-(4-methylphenyl)-1,2,2-triphenylethene (4)

In a 250 mL two necked round bottom flask, 5.047 g (30 mmol) of diphenylmethane was dissolved in 100 mL distilled THF under N$_2$. After the mixture was cooled to 0° C., 15 mL (2.5 M in hexane, 37.5 mmol) of n-butyllithium was slowly added by a syringe. The mixture was stirred at 0° C. for 1 hr. 4.906 g (25 mmol) of 4-methylbenzophenone was then added into the reaction mixture. The mixture was warmed to room temperature and stirred overnight. The reaction mixture was quenched with saturated NH$_4$Cl solution and then extracted with DCM. The organic layer was collected and concentrated. The crude product and 0.2 g of p-toluenesulfonic acid were dissolved into 100 mL toluene. The mixture was heated to reflux for 4 hrs. After cooled to room temperature, the reaction mixture was extracted with DCM. The organic layer was collected and concentrated. The crude product was purified by silica-gel chromatography using hexane as eluent to give white solid in 78% yield. $^1$H NMR (CDCl$_3$, 400 MHz), δ (TMS, ppm): 2.24 (s, 3H), 6.90 (s, 4H), 6.99-7.12 (m, 15H). $^{13}$C NMR (CDCl$_3$, 100 MHz), δ (TMS, ppm): 21.87, 126.95, 127.00, 128.27, 128.33, 129.05, 129.61, 131.89, 131.98, 132.02, 136.71, 141.14, 141.40, 141.56, 144.60. HRMS (MALDI-TOF): m/z 346.1701 (M$^+$, calcd. 346.1722).

Synthesis of 1-[(4-bromomethyl)phenyl]-1,2,2-triphenylethene (5)

In a 250 mL round bottom flask, a solution of 5.197 g (15 mmol) of 1, 2.937 g (16 mmol) of N-bromosuccinimide, 0.036 g of benzoyl peroxide in 80 mL CCl$_4$ was refluxed for 12 hrs. After reaction completed, the reaction mixture was extracted with DCM and water. The organic layers were combined, dried over magnesium sulfate, and removed under reduced pressure. The crude product was purified by silica-gel chromatography using hexane as eluent to give white solid in 60% yield. $^1$H NMR (CDCl$_3$, 400 MHz), δ (TMS, ppm): 4.42 (s, 2H), 6.93-7.05 (m, 8H), 7.09-7.14 (m, 11H). $^{13}$C NMR (CDCl$_3$, 100 MHz), δ (TMS, ppm): 34.31, 127.22, 127.27, 128.33, 128.42, 129.09, 131.96, 132.01, 132.35, 136.36, 140.88, 142.20, 144.09, 144.15, 144.64. HRMS (MALDI-TOF): m/z 426.0819 [(M+2)$^+$, calcd. 426.0827].

Synthesis of 1-((4-azidomethyl)phenyl)-1,2,2-triphenylethene (6)

In a 250 mL two necked round bottom flask, 1.701 g (4 mmol) of 2,5-dioxopyrrolidin-1-yl hex-5-ynoate (2) and 0.39 g (6 mmol) of sodium azide were dissolved in DMSO under N$_2$. The mixture was stirred at room temperature overnight. A large amount (100 mL) of water was then added and the solution was extracted three times with diethyl ether. The organic layers were combined, dried over magnesium sulfate and concentrated. The crude product was purified by silica-gel chromatography using hexane/chloroform as eluent to give white solid in 97% yield. $^1$H NMR (CDCl$_3$, 400 MHz), δ (TMS, ppm): 4.24 (s, 2H), 6.98, 7.06 (m, 10H), 7.06, 7.13 (m, 9H). $^{13}$C NMR (CDCl$_3$, 100 MHz), δ (TMS, ppm): 53.91, 125.90, 126.02, 126.99, 127.04, 127.09, 130.67, 131.11, 131.22, 132.61, 139.62, 140.82, 142.83, 142.90, 143.27. HRMS (MALDI-TOF): m/z 387.1342 (M$^+$, calcd. 387.1735).

Example 24

Preparation of Solid-Phase Synthesis of DEVD Peptide

General Procedure for Fmoc Deprotection:

The Fmoc-protected amino-functionalized resin was treated with 20% piperidine/DMF for 1 h at room temperature. The resin was washed with DMF (3×), DCM (3×), DMF (2×) and DCM (1×) and dried in vacuum. The completeness of the reaction was monitored by ninhydrin test. Blue beads indicate the presence of primary amine and the completeness of the reaction.

General Procedure for Coupling of Fmoc-Amino Acids onto Resin:

Fmoc-amino acid (4 eq), HBTU (4 eq) and HOBt (4 eq) were dissolved in DMF (2 mL) and DIEA (8 eq) was added and agitated for 10 min. This pre-activated Fmoc amino acid solution was added to the amino-functionalized resin and shaken for overnight at room temperature. The resin was filtered and washed with DMF (3×), DCM (3×), DMF (2×) and DCM (1×). Finally, the free amine of Asp amino acid was capped with acetic anhydride.

Cleavage of Peptide from Resin:

After capping the free amine of Asp amino acid, the resin was washed with DMF (3×), DCM (3×), DMF (2×) and DCM (1×) and dried thoroughly under vacuum. A solution of TFA/TIS/H$_2$O (95/2.5/2.5, 2 mL) was added to the resin at room temperature and shaken for 3 hrs. The resin was filtered off and washed with DCM (2×). The combined DCM and cleavage solutions were concentrated to ~0.3 mL, cold diethyl ether (3 mL) was subsequently added to precipitate the peptide. The peptide was then collected by centrifugation, washed with cold diethyl ether and dried in vacuum.

Example 25

Synthesis of AcDEVDk-TPE

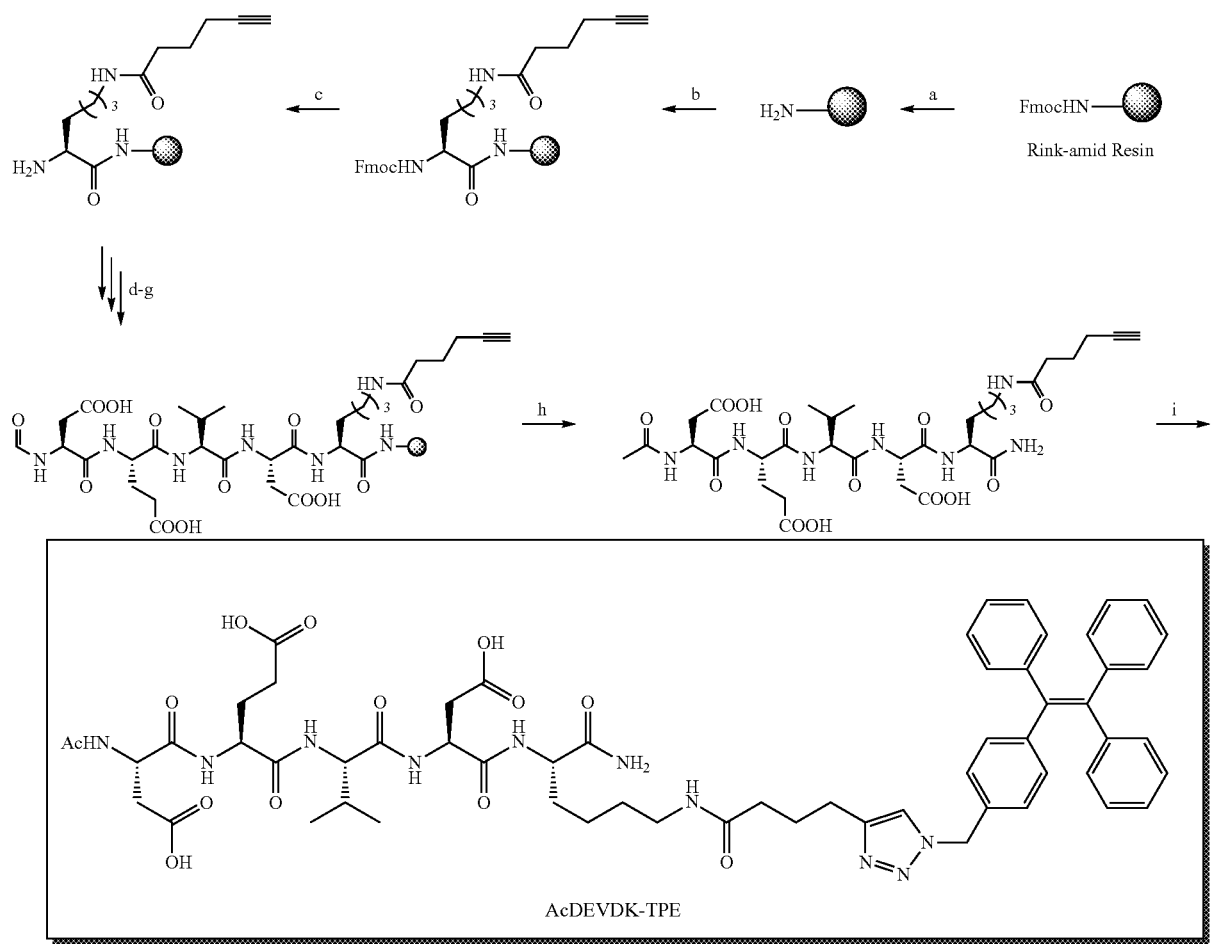

AcDEVDK-TPE

Synthesis of AcDEVDk-TPE:

The alkyne-containing DEVD peptide (1.6 mg, 2.0 μmol) and TPE-N$_3$ (0.7 mg, 1.8 μmol) were dissolved in 50 μL DMSO. A mixture of DMSO/H$_2$O solution (1:1; 0.5 mL) was subsequently added and the reaction was shaken for a few minutes to obtain a clear solution. The "click" reaction was initiated by sequential addition of catalytic amounts of sodium ascorbate (0.16 mg, 0.8 μmol) and CuSO$_4$ (0.06 mg, 0.4 μmol). The reaction was continued with shaking at room temperature for another 12 h. The reaction product was then directly analyzed by LC-MS. The final probe was subsequently purified by prep-HPLC and further characterized/confirmed by LC-MS. IT-TOF m/z M$^+$ calcd: 1127.25. found 1127.32.

Example 26

Titration Different Proteins with TPS-2cRGD

5 μL of the protein stock solution was diluted with 40 μL of 1×PBS buffer (pH 7.4). 5 μL of TPS-2cRGD (10 μM) was then added and the reaction mixture was incubated at room temperature for 30 min. The reaction mixture was then diluted to a total of 300 μL with deionized water for photoluminescence measurement. The solution was excited at 356 nm, and the emission was collected from 380 to 650 nm.

Example 27

Caspase-3/Caspase-7 Turn-on Assay

Cleavage of the peptide substrates AcDEVDK-TPE by caspase-3 or caspase-7 was monitored in quartz cells or in black flatbottom polypropylene 384-well plates (Nunc, USA). The corresponding concentrations of substrate and enzymes were used for each assay. Enzymatic cleavage of the substrates was monitored by fluorescence increase (excitation and emission wavelengths at 312 nm and 480 nm respectively) with on a Perkin-Elmer LS 55 spectrofluorometer or a Synergy TM 2 multi-mode microplate reader (Biotek Instruments).

Example 28

Cell Culture

The human carcinoma epithelial carcinoma cell line HeLa and HT-29 colon cancer cells were cultured (37° C., 5%

CO$_2$) in DMEM medium containing 10% fetal bovine serum. MCF-7 breast cancer cells were cultured (37° C., 5% CO$_2$) in RPMI 1640 medium containing 10% fetal bovine serum and 1% penicillin/streptomycin. Before experiment, the cells were pre-cultured until confluence was reached.

Example 29

Confocal Imaging at 4° C.

Before the detection of integrin $\alpha_v\beta_3$, HT-29 and MCF-7 cells were cultured in the chambers (LAB-TEK, Chambered Coverglass System) at 37° C., respectively. After 80% confluence, the adherent cells were washed twice with 1×PBS buffer. The TPS-2cRGD solution (2 μM, 0.3 mL) was then added to the chamber. After incubation for 30 min at 4° C., cells were washed two times with 1×PBS buffer and then treated with membrane tracker for 10 min and further washed twice with 1×PBS buffer. The cells were then imaged immediately by confocal laser scanning microscope (CLSM, Zeiss LSM 410, Jena, Germany) with imaging software (Fluoview FV500). The images are analyzed by ImageJ 1.43× program (developed by NIH). The images were taken upon excitation at 405 nm (5% laser power) with a band pass 505-525 nm filter for the probe, and 543 nm (5% laser power) with a band pass 575-635 nm filter for the membrane tracker. See FIG. 30.

Example 30

Real-Time Uptake Imaging of TPS-2cRGD

HT-29 cells were cultured in the 8-wells chambers (LAB-TEK, Chambered Coverglass System) at 37° C. After 80% confluence, the adherent cells were washed twice with 1×PBS buffer. The TPS-2cRGD solution (2 μM, 0.3 mL) and a small amount of membrane tracker were then added to the chamber. The chambers were placed on the microscope platform immediately and the microscope focused on a collection of cells. The fluorescence images (405 nm excitation and with a band pass 505-525 nm filter for the probe, and 543 nm excitation with a band pass 575-635 nm filter for the membrane tracker) acquired every 5 min.

Example 31

Cytotoxicity of TPS-2cRGD

Methylthiazolyldiphenyl-tetrazolium (MTT) assays were used to assess the metabolic activity of HT-29 cancer cells to study the cytotoxicity of TPS-2cRGD. HT-29 cells were seeded in 96-well plates (Costar, Ill., USA) at an intensity of $4\times10^4$ cells mL$^{-1}$. After 24 h incubation, the medium was replaced by the TPS-2cRGD suspension at concentrations of 2, 5, and 10 μM, and the cells were then incubated for 12, 24 and 48 h, respectively. After the designated time intervals, the wells were washed twice with 1×PBS buffer and 100 μL of freshly prepared MTT (0.5 mg mL$^{-1}$) solution in culture medium was added into each well. The MTT medium solution was carefully removed after 3 h incubation in the incubator at 37° C. DMSO (100 μL) was then added into each well and the plate was gently shaken to dissolve all the precipitates formed. The absorbance of MTT at 570 nm was monitored by the microplate reader (Genios Tecan). Cell viability was expressed by the ratio of absorbance of the cells incubated with TPS-2cRGD suspension to that of the cells incubated with culture medium only.

Example 32

Apoptosis Imaging in Live Cells with AcDEVD-TPE

The cells were cultured in the chambers (LAB-TEK, Chambered Coverglass System) at 37° C., respectively. After 80% confluence, the adherent cells were washed twice with 1×PBS buffer. The AcDEVD-TPE solution (5 μM, 0.3 mL) was then added to the chamber. After incubation for 2 h at 37° C., cells were washed two times with 1×PBS buffer. To induce apoptosis, cells were incubated with 1.0 μM of staurosporine for 1 hr and then imaged immediately by confocal laser scanning microscope (CLSM, Zeiss LSM 410, Jena, Germany) with imaging software (Fluoview FV500). The images are analyzed by ImageJ 1.43× program (developed by NIH).

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

Example 33

Synthesis of c-RGD-TPS-DEVD

As shown in the reaction scheme below, the asymmetric probe c-RGD-TPS-DEVD was synthesized by two step "Click" reactions. First, coupling between TPS-2N$_3$ (5.0 eqv) and DEVD-alknye (1.0 eqv) via Cu(I)-catalyzed "Click" reaction using CuSO$_4$/sodium ascorbate as the catalyst and DMSO/H$_2$O as the solvent to afford TPS-DEVD in 80% yield after HPLC purification. Pure TPS-DEVD was then reacted with alkyne functionalized cyclic RGD (c-RGD) using CuSO$_4$/sodium ascorbate as catalyst and DMSO/H$_2$O as the solvent to afford c-RGD-TPS-DEVD in 90% yield after HPLC purification. The HPLC condition is: 10-100% B for 10 min, then 100% B for 2 min, 10% B for 5 min (Solvent A: 100% H$_2$O with 0.1% TFA; Solvent B: 100% CH$_3$CN with 0.1% TFA).

DEVD-alkyne (1.8 mg, 3 μmol) and azide-functionalized tetraphenylsilole (TPS-2N$_3$) (7.9 mg, 15 μmol) were dissolved in 50 μL of DMSO. A mixture of DMSO/H$_2$O solution (v/v=1/1; 0.5 mL) was subsequently added and the reaction was shaken for a few minutes to obtain a clear solution. The "click" reaction was initiated by sequential addition of catalytic amounts of sodium ascorbate (0.4 mg, 2.0 μmol) and CuSO$_4$ (1.6 mg, 1.0 μmol). The reaction was continued with shaking at 4° C. overnight. The final product was purified by prep-HPLC and characterized by LC-MS. LC-MS (IT-TOF): m/z 1137.3952 ([M+H]$^+$, calcd 1137.4536).

The purified TPS-DEVD (5.5 mg, 5 μmol) and alkyne-functionalized cyclic RGD (c-RGD) (2.9 mg, 5 μmol) were dissolved in 50 μL of DMSO. A mixture of DMSO/H$_2$O solution (v/v=1/1; 0.5 mL) was subsequently added and the reaction was shaken for a few minutes to obtain a clear solution. The "click" reaction was initiated by sequential addition of catalytic amounts of sodium ascorbate (0.4 mg, 2.0 μmol) and CuSO$_4$ (1.6 mg, 1.0 μmol). The reaction was continued with shaking at room temperature for 24 h. The final probe was purified by HPLC and characterized by LC-MS. LC-MS (IT-TOF): m/z 1706.7069 ([M], calcd 1706.7086).

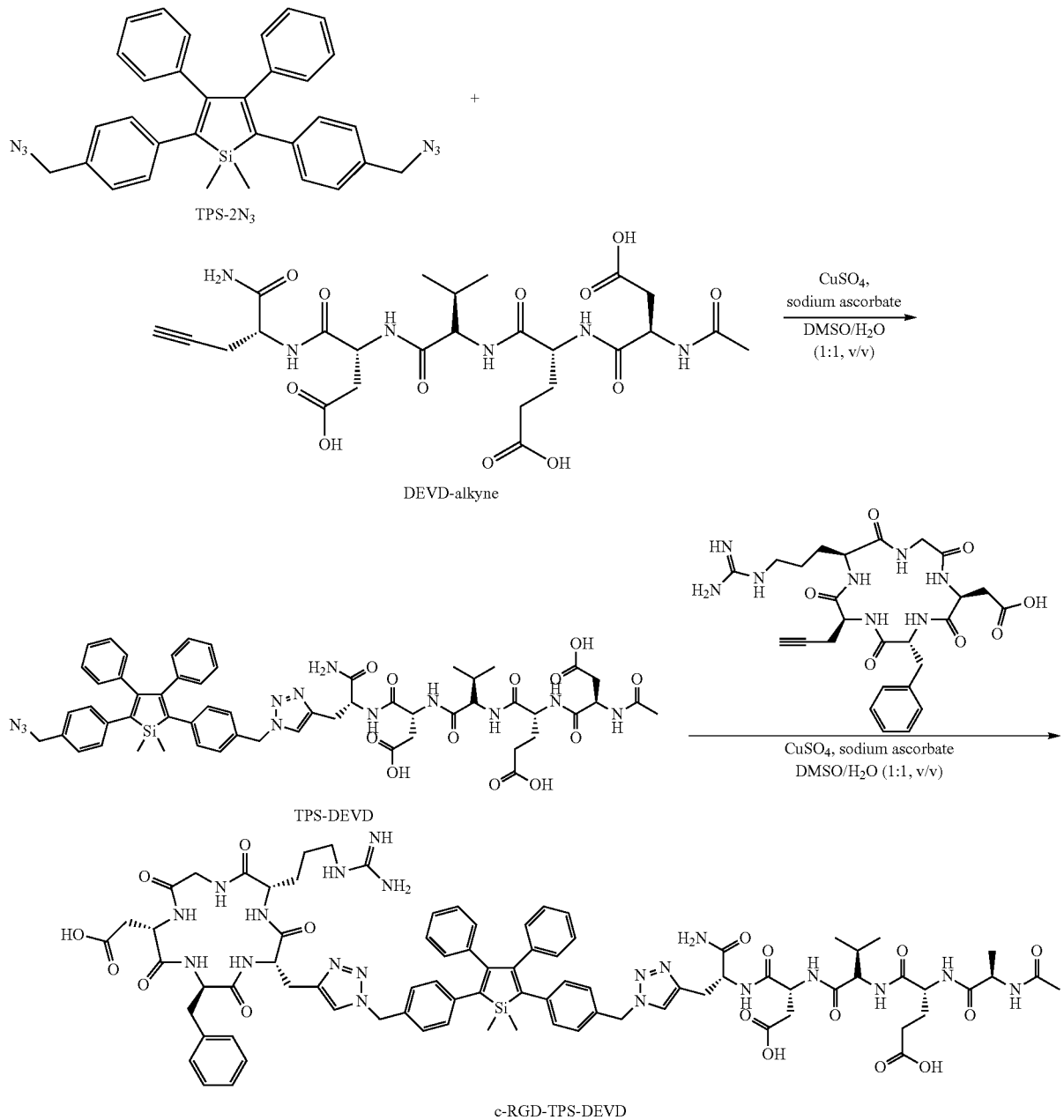

Example 34

Cellular Imaging

The application of DEVD-TPS-RGD and DEVD-TPS in living apoptotic cell imaging was conducted with confocal laser scanning microscopy (CLSM). U87MG glioblastoma cells with overexpressed integrin $\alpha_v\beta_3$ expression and MCF-7 breast cancer cells with low integrin $\alpha_v\beta_3$ expression on the cell membrane were used to demonstrate the utility of RGD-TPS-DEVD in targeted apoptotic cancer cell imaging.

U87MG glioblastoma cells were cultured in confocal imaging chambers (LAB-TEK, Chambered Coverglass System) at 37° C. After 80% confluence, the medium was removed and the adherent cells were washed twice with 1×PBS buffer. The DEVD-TPS and DEVD-TPS-RGD in FBS-free DMEM medium at the concentration of 5 μM were then added to the chamber, respectively. After incubation at 37° C. for 2 h, the cells were washed three times with 1×PBS buffer and then incubated with staurosporine (5 μM) in FBS-free DMEM medium for 3 h to induce cell apoptosis, which were further washed twice with 1×PBS buffer. The cell monolayer was then imaged by confocal laser scanning microscope (CLSM, Zeiss LSM 410, Jena, Germany) with imaging software (Olympus Fluoview FV1000). The fluorescent signal from the probes was collected upon excitation at 405 nm (1 mW) with a 505 nm longpass barrier filter. MCF-7 breast cancer cells incubated with DEVD-TPS-RGD were also studied following the same procedures.

Figure 45:
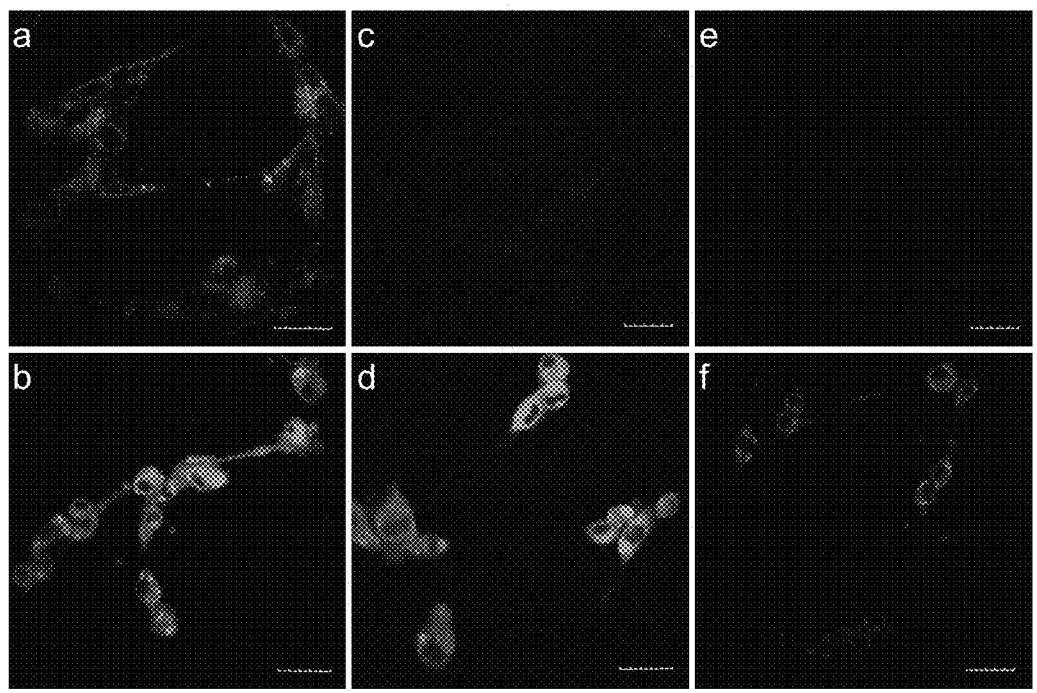
FIG. 45 illustrates CLSM images of DEVD-TPS-stained U87MG glioblastoma cells (a) before and (b) after staurosporine induced cell apoptosis. CLSM images of DEVD-TPS-RGD-stained U87MG glioblastoma cells (c) before and (d) after staurosporine induced cell apoptosis. CLSM images of DEVD-TPS-RGD-stained MCF-7 cancer cells (e) before and (f) after staurosporine induced cell apoptosis. Scale bar: 30 µm for all the images.

The CLSM images of U87MG glioblastoma cells incubated with DEVD-TPS and DEVD-TPS-RGD for 2 h at 37° C. are shown in FIGS. 45(*a*) and (*c*), respectively. Obvious green fluorescence can be observed for DEVD-TPS-stained U87MG cells (FIG. 45(*a*)) while negligible fluorescence is detected for DEVD-TPS-RGD-stained U87MG cells (FIG. 45(*c*)). This result reveals that the hydrophilic RGD peptide conjugation to the DEVD-TPS is able to improve probe solubility and reduce the background probe fluorescence. After the U87MG glioblastoma cells were incubated with DEVD-TPS and DEVD-TPS-RGD for 2 h at 37° C., respectively, the cells were subsequently treated with staurosporine to induce cell apoptosis, and the activated caspase-3 is able to trigger the digestion of the DEVD. As shown in FIGS. 45(*b*) and (*d*), upon inducing the apoptosis, intense fluorescence with similar fluorescence intensities is observed for DEVD-TPS-stained and DEVD-TPS-RGD-stained U87MG cells, which is much higher than that of corresponding probe-stained U87MG cells without drug treatment. This result suggests that the cleavage of DEVD from the probes results in the aggregation of TPS or TPS-RGD, making the fluorescence turn on. In addition, this result also indicates that DEVD-TPS-RGD has better sensitivity to image living apoptotic U87MG cell as compared to DEVD-TPS, which may result from the RGD peptide that favors more DEVD-TPS-RGD internalized into the U87MG cells.

The specific targeting ability of DEVD-TPS-RGD to U87MG glioblastoma cells was evaluated using MCF-7 breast cancer cells with low integrin $\alpha_v\beta_3$ expression on the cell membrane as a control. FIGS. 45(*e*) and (*f*) show the CLSM images of DEVD-TPS-RGD-stained MCF-7 cancer cells before and after staurosporine induced cell apoptosis. No fluorescence from DEVD-TPS-RGD-stained MCF-7 cells without drug inducing apoptosis is observed (FIG. 45(*e*)). Moreover, as shown in FIG. 45(*f*), although green fluorescence from DEVD-TPS-RGD-stained apoptotic MCF-7 cells is observed, the fluorescence intensity of these cells in much lower than that from DEVD-TPS-RGD-stained apoptotic U87MG cells (FIG. 45(*d*)). This result demonstrates the specific targeting ability of DEVD-TPS-RGD to the integrin receptor-overexpressed cancer cells.

Example 35

Synthesis of E/Z-TPE-2DEVD

As shown in the reaction scheme below, the probes of E/Z-TPE-2DEVD were synthesized by coupling between TPE-2N$_3$ and DEVD-P via Cu(I)-catalyzed "Click" reaction using CuSO$_4$/sodium ascorbate as the catalyst and DMSO/H$_2$O as the solvent in 80% yield.

DEVD-P (3.1 mg, 5 μmol) and azide-functionalized tetraphenyl (TPE-2N$_3$) (2.7 mg, 6 μmol) were dissolved in 50 μL of DMSO. A mixture of DMSO/H$_2$O solution (v/v=1/1; 0.5 mL) was subsequently added and the reaction was shaken for a few minutes to obtain a clear solution. The "click" reaction was initiated by sequential addition of catalytic amounts of sodium ascorbate (0.4 mg, 2.0 μmol) and CuSO$_4$ (1.6 mg, 1.0 μmol). The reaction was continued with shaking at room temperature for another 24 h. The final product was purified by prep-HPLC.HRMS (MALDI-TOF): m/z 1666.5101 ([M], calcd 1666.6688). The HPLC condition is: 10-100% B for 10 min, then 100% B for 2 min, 10% B for 5 min (Solvent A: 100% H$_2$O with 0.1% TFA; Solvent B: 100% CH$_3$CN with 0.1% TFA).

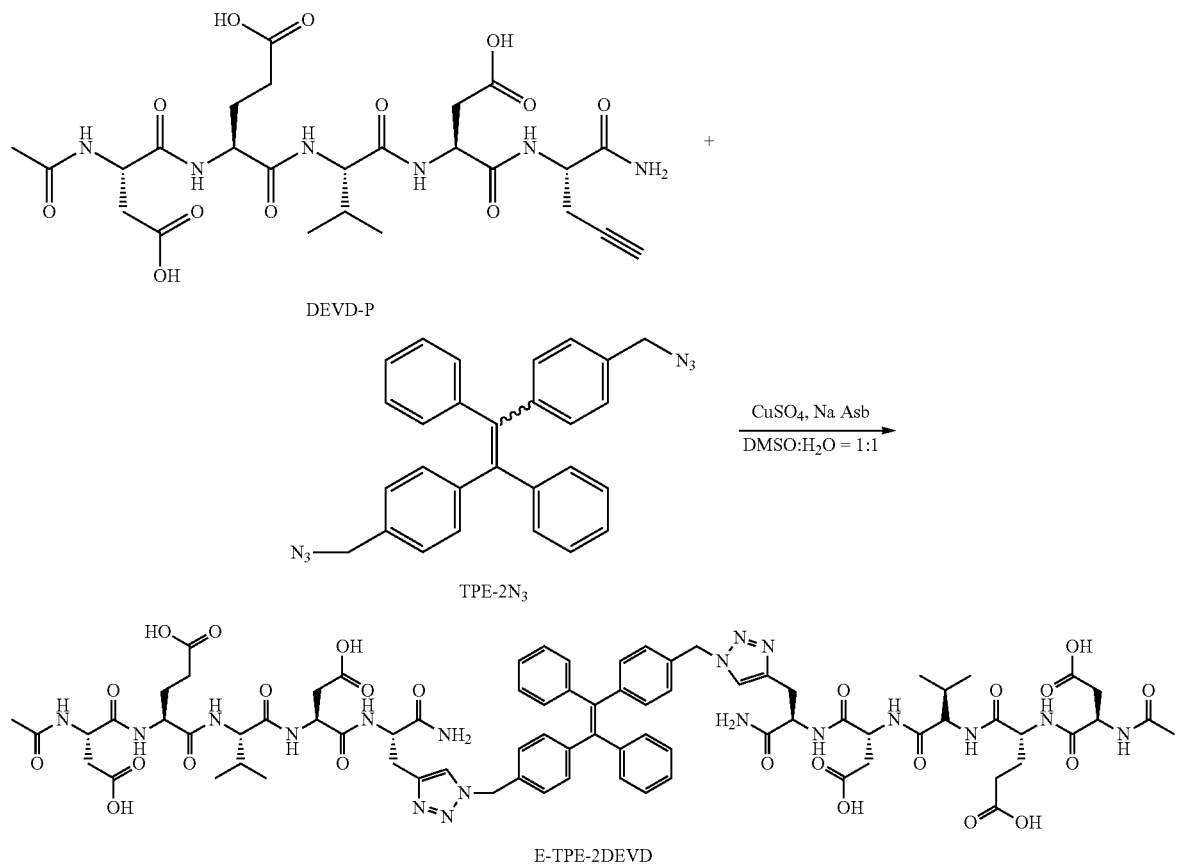

-continued

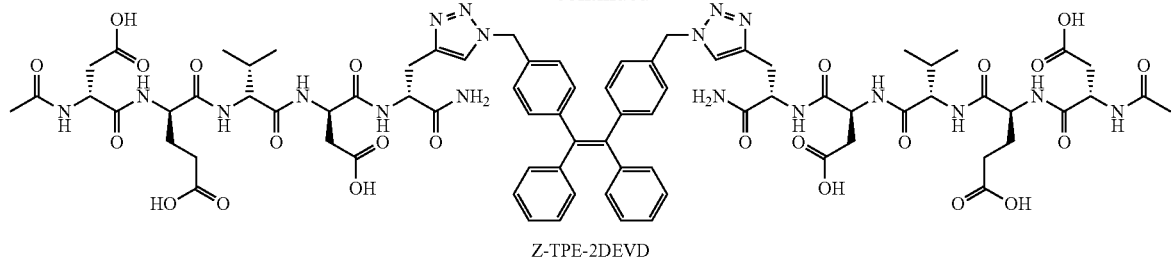

Z-TPE-2DEVD

Figure 46:
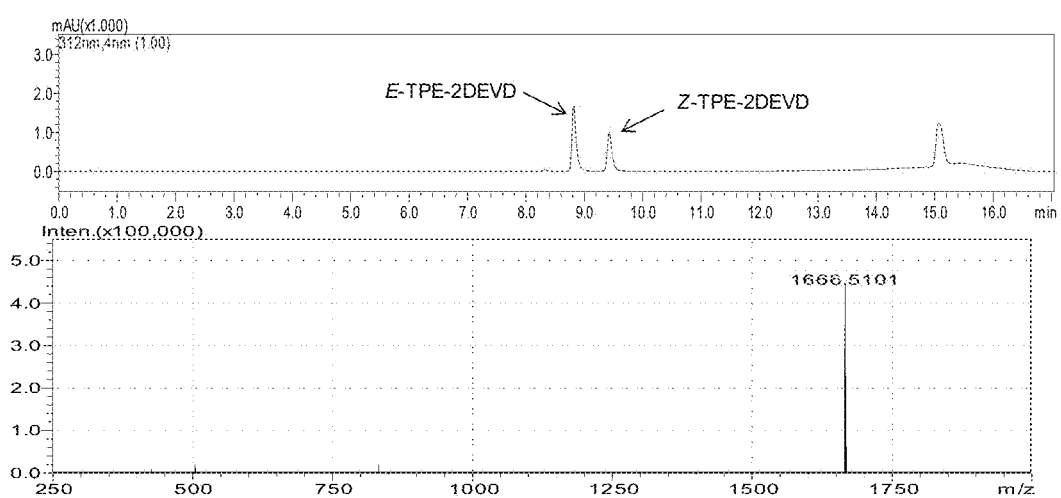
FIG. 46 illustrates an LC-MS spectra of E/Z-TPE-2DEVD.

HPLC spectrum analysis shows that the obtained probes contain two isomers, namely E-TPE-2DEVD and Z-TPE-2DEVD. Both isomers have been separated and further confirmed by LC-MS (FIG. 46). The HPLC condition is: 10-100% B for 10 min, then 100% B for 2 min, 10% B for 5 min (Solvent A: 100% $H_2O$ with 0.1% TFA; Solvent B: 100% $CH_3CN$ with 0.1% TFA).

Figure 47:
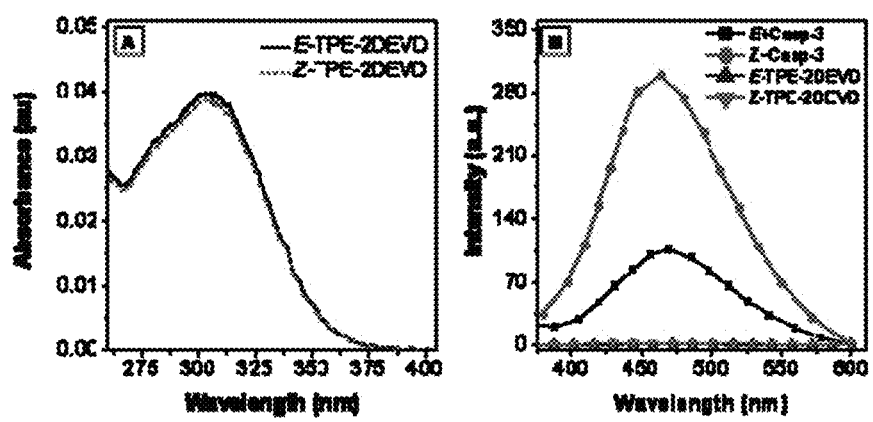
FIG. 47 illustrates (A) UV-vis absorption spectra of E/Z-TPE-2DEVD in DMSO/water (v/v=1:199). [E-TPE-2DEVD]=[Z-TPE-2DEVD]=10 µM. (B) Photoluminescence (PL) spectra E/Z-TPE-2DEVD with and without caspase-3 in PIPES buffer. [E-TPE-2DEVD]=[Z-TPE-2DEVD]=10 µM, [caspase-3]=3 µg mL$^{-1}$.
Figure 48:
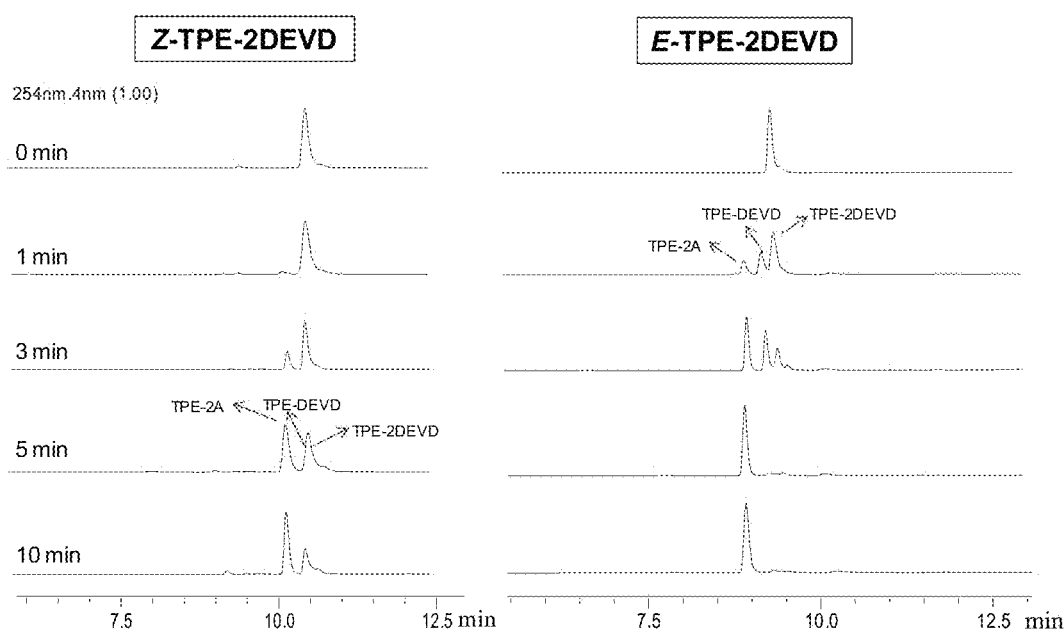
FIG. 48 illustrates the hydrolysis of E/Z-TPE-2DEVD monitored by LC-MS.

The UV-vis absorption spectra of E-TPE-2DEVD and Z-TPE-2DEVD in DMSO/water (v/v=1/199) are shown in FIG. 47(A). Both have a similar absorption profile with an obvious absorbance in the 270-380 nm range. Both probes are almost non-fluorescent in piperazine-N,N'-bis(2-ethane-sulfonic acid)(PIPES) buffer due to its good solubility in water. However, when they are treated with recombinant caspase-3(100 pM) at 37° C., strong fluorescence signals are recorded for both assays (FIG. 47(B)). However, the two isomerous probes show distinct "turn-on" features: Z-TPE-2DEVD apparently has stronger fluorescence enhancement than E-TPE-2DEVD.

The enzyme kinetic studies by incubating recombinant caspase-3 with E/Z-TPE-2DEVD in buffer at 37° C. were subsequently performed, and the changes in probe hydrolysis were monitored with HPLC. DMSO stock solutions of TPE-2DEVD were diluted with caspase-3assay buffer (50 mM PIPES, 100 mM NaCl, 1 mM EDTA, 0.1% w/v CHAPS, 25% w/v sucrose, pH=7.2) to make 10 μM working solutions. 5 μL of the recombinant caspase-3 (~0.04 μg/μL stock solution in assay buffer) was added into the above working solution. The reaction mixture was incubated at room temperature for 60 min and was then diluted to a total of 300 μL with deionized water for photoluminescence measurement. The solution was excited at 312 nm, and the emission was collected from 360 to 600 nm. The results indicate that the E-TPE-2DEVD underwent enzyme activated hydrolysis faster than that for Z-TPE-2DEVD.

Figure 49:
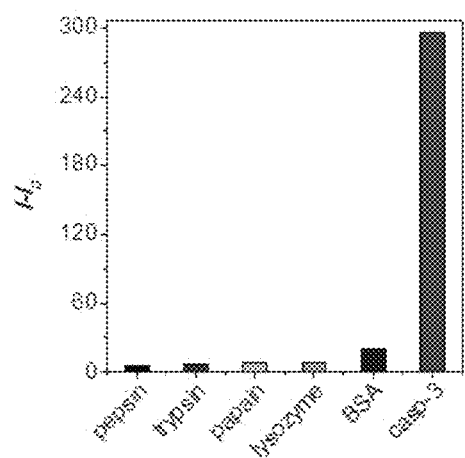
FIG. 49 illustrates Plot of $(I-I_0)/I_0$ with respect to different proteins, where I and $I_0$ are the PL intensities at protein concentrations of 100 and 0 pM, respectively.

To further investigate the probe selectivity, Z-TPE-2DEVD was treated with several proteins, such as caspase-3, pepsin, BSA, trypsin, papain and lysozyme, under identical conditions. As shown in FIG. 49, caspase-3 displays apparent higher changes in $(I-I_0)/I_0$ than the other five proteins. This substantiates that Z-TPE-2DEVD is indeed a specific probe for caspase-3.

To study the interaction between caspase-3 and the probe, we also performed the modeling experiments with Z/E-TPE-2DEVD and X-ray structures of caspase-3 (PDB ID 2CNO). The docking results confirm that E-TPE-2DEVD bound tightly to the active site of caspase-3 in a manner that was closely matched that of the known inhibitor DEVD-CHO. This result further demonstrates that the hydrolysis of E-TPE-2DEVD is faster than Z-TPE-2DEVD.

We claim:

1. A fluorescent bioprobe comprising fluorogen-loaded nanoparticles comprising a fluorogen that exhibits aggregation induced emission properties, wherein the fluorogen comprises one or more chromophores conjugated with one or more aggregation induced emission fluorophores; wherein the fluorogen-loaded nanoparticles have a fluorescence emission; and wherein the fluorogen comprises a backbone structure and the backbone structure is:

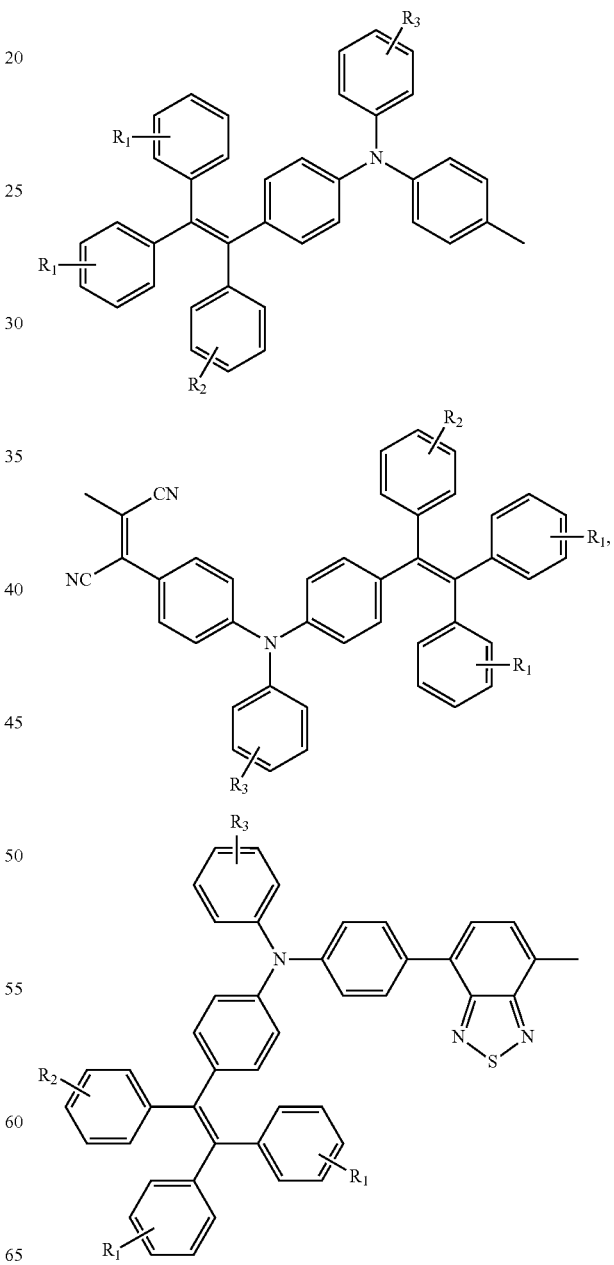

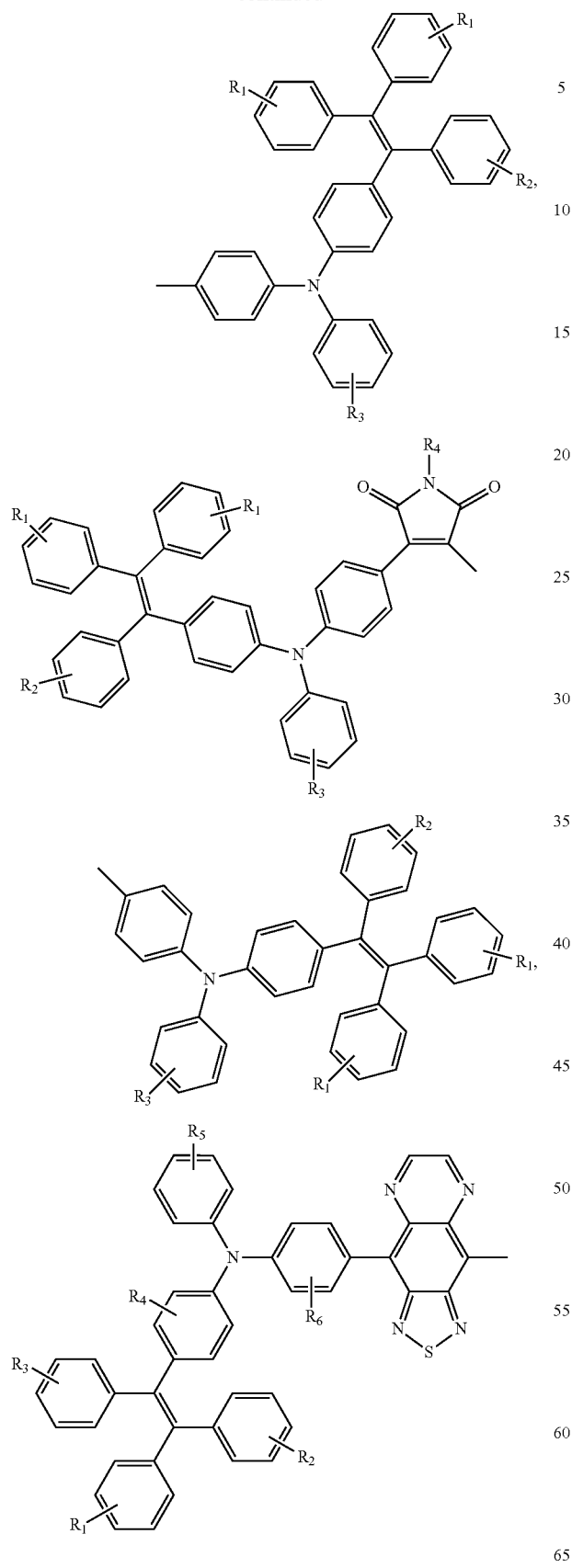

-continued

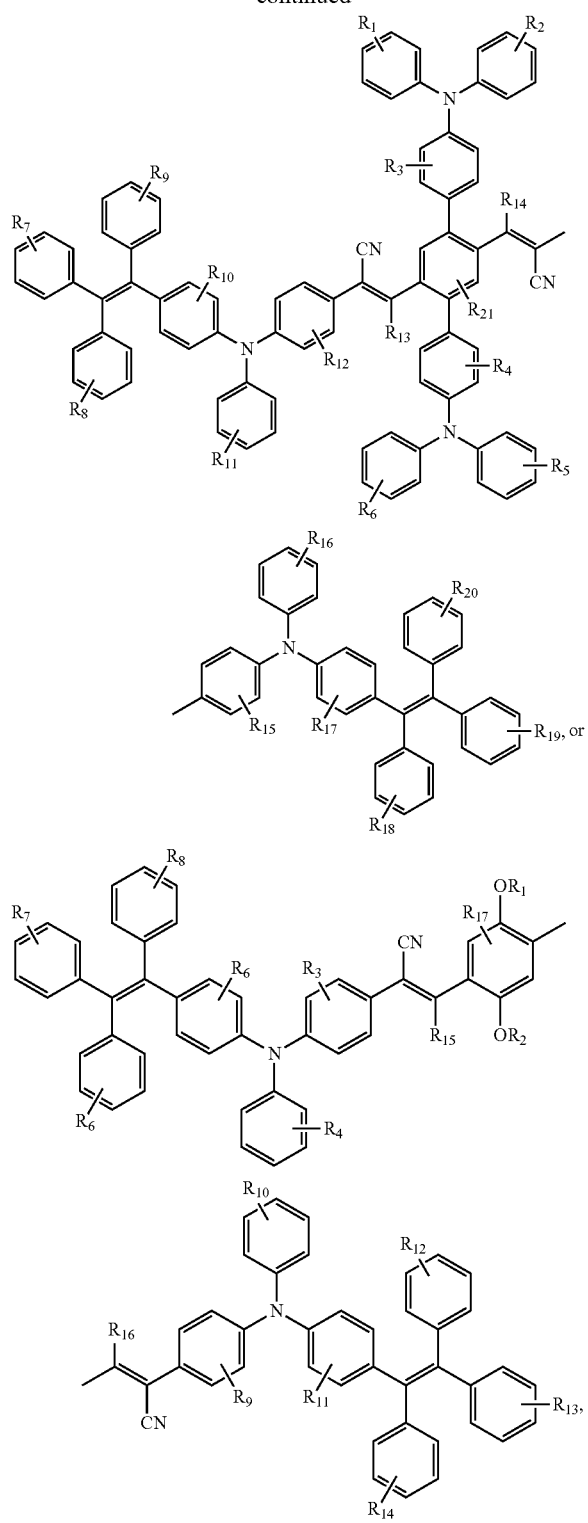

wherein each $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$ is independently H, alkyl, unsaturated alkyl, heteroalkyl, cycloalkyl, heterocycloalkyl, aryl, heteroaryl, or alkoxy.

2. The fluorescent bioprobe of claim 1, wherein any one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, and $R_{21}$ further comprises a terminal functional group independently selected from $N_3$, $NH_2$, COOH, NCS, SH, alkyne, N-Hydroxysuccinimide ester, a maleimide, a hydrazide, a nitrone group, —CHO, —OH, a halide, or a charged ionic group; wherein a peptide independently selected from a biorecognition peptide or a cell penetrating peptide is conjugated to the terminal functional group.

3. The fluorescent bioprobe of claim 1, wherein the fluorogen-loaded nanoparticles further comprise a biocompatible polymer matrix.

4. The fluorescent bioprobe of claim 3, wherein the biocompatible polymer matrix is animal serum albumin, 1,2-distearoyle-sn-glycero-3-phosphoethanolamine, polyethylene glycol, or polyfluorene vinylene, or mixtures thereof.

5. The fluorescent bioprobe of any claim 4, wherein the biocompatible polymer matrix is BSA, DSPE-PEG, or DSPE-PEG-Folate.

6. The fluorescent bioprobe of claim 1, wherein the fluorescence emission of the fluorogen loaded nanoparticles is further amplified by applying one or more of: (a) a conjugated polymer as a fluorescence resonance energy transfer donor or (b) an arginine-glycine-aspartic acid peptide as a bio-recognition reagent functionalized on a surface of the nanoparticle.

7. A fluorescent bioprobe of claim 1, wherein the fluorogen-loaded nanoparticles are 1 nm to 100,000 nm in size.

8. The fluorescent bioprobe of claim 3, wherein the fluorogen-loaded nanoparticles are BSA, DSPE-PEG, DSPE-PEG-Folate or DSPE-PEG-$NH_2$ encapsulated nanoparticles.

9. A method for preparing the fluorescent bioprobe of claim 3 comprising loading the fluorogen with the biocompatible polymer matrix by:
 (a) preparing a solution comprising an organic solvent and the fluorogen;
 (b) preparing an aqueous solution of a biocompatible polymer;
 (c) mixing the solution comprising the organic solvent and the fluorogen with the aqueous solution together and sonicating; and
 (d) removing the organic solvent to form the fluorogen-loaded nanoparticles.

10. The method of claim 9, wherein the fluorogen-loaded nanoparticles are fabricated with any molecule that can specifically target cancer cells or can amplify the fluorescence imaging.

11. A method of cellular imaging comprising contacting target cells with the fluorescent bioprobe of claim 1 and detecting the fluorescent bioprobe by cellular imaging.

12. The method of claim 11, further comprising determining whether a tumor or cancer cells are present.

13. The method of claim 12, wherein in vitro cellular imaging is conducted using biological imaging samples selected from MCF-7 cells, HT-29 cancer cells, or HeLa cancer cells; or wherein in vivo cellular imaging is conducted using ICR mice bearing tumors as the biological imaging sample.

14. The fluorescent bioprobe of claim 1, wherein the fluorogen comprises the following backbone structure:

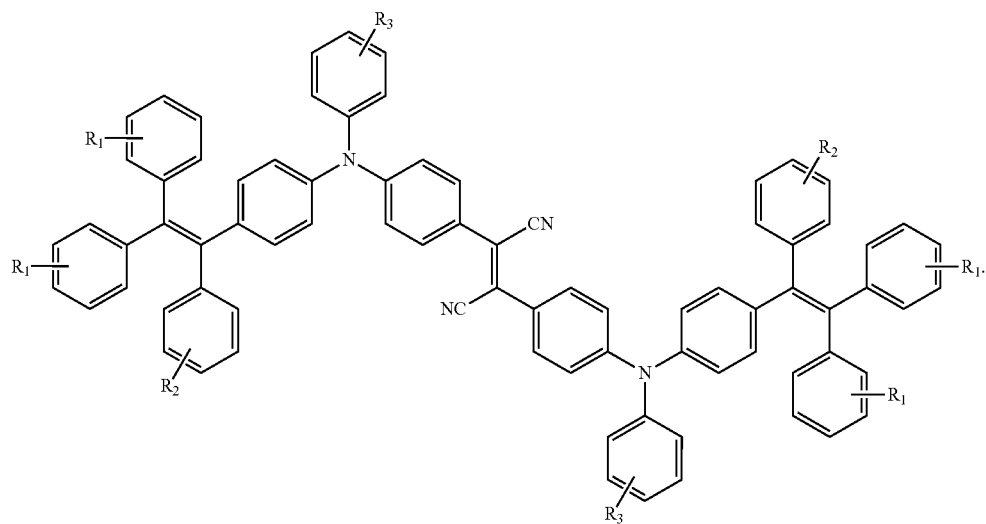
15. The fluorescent bioprobe of claim 14, wherein $R_1$, $R_2$ and $R_3$ are each hydrogen.
* * * * *